United States Patent
Lin et al.

(10) Patent No.: US 12,247,010 B2
(45) Date of Patent: *Mar. 11, 2025

(54) TUBULIN INHIBITORS

(71) Applicant: LIN BIOSCIENCE PTY LTD., Collingwood (AU)

(72) Inventors: Tom Lin, San Diego, CA (US); Cheng-Chi Irene Wang, San Diego, CA (US); Jason Olejniczak, San Diego, CA (US); Jessica Crisp, San Diego, CA (US); Richard Truong, San Diego, CA (US)

( * ) Notice: Subject to any disclaimer, the term of this patent is extended or adjusted under 35 U.S.C. 154(b) by 762 days.

This patent is subject to a terminal disclaimer.

(21) Appl. No.: 17/244,767

(22) Filed: Apr. 29, 2021

(65) Prior Publication Data

US 2022/0089539 A1 Mar. 24, 2022

Related U.S. Application Data

(63) Continuation of application No. 16/211,051, filed on Dec. 5, 2018, now Pat. No. 11,040,945.

(60) Provisional application No. 62/595,530, filed on Dec. 6, 2017.

(51) Int. Cl.
| | |
|---|---|
| C07D 213/75 | (2006.01) |
| A61P 35/04 | (2006.01) |
| C07D 401/12 | (2006.01) |
| C07D 403/12 | (2006.01) |
| C07D 405/12 | (2006.01) |
| C07D 409/12 | (2006.01) |
| C07D 413/12 | (2006.01) |
| C07D 413/14 | (2006.01) |
| C07D 417/04 | (2006.01) |
| C07D 471/04 | (2006.01) |
| C07D 487/04 | (2006.01) |

(52) U.S. Cl.
CPC ............ *C07D 213/75* (2013.01); *A61P 35/04* (2018.01); *C07D 401/12* (2013.01); *C07D 403/12* (2013.01); *C07D 405/12* (2013.01); *C07D 409/12* (2013.01); *C07D 413/12* (2013.01); *C07D 413/14* (2013.01); *C07D 417/04* (2013.01); *C07D 471/04* (2013.01); *C07D 487/04* (2013.01)

(58) Field of Classification Search
CPC ...... C07D 213/75; C07D 401/12; A61P 35/04
See application file for complete search history.

(56) References Cited

U.S. PATENT DOCUMENTS

| | | | |
|---|---|---|---|
| 3,859,338 A | 1/1975 | Engel et al. | |
| 3,868,380 A | 2/1975 | Molteni et al. | |
| 5,196,543 A | 3/1993 | Jarreau et al. | |
| 5,756,507 A | 5/1998 | Goulet et al. | |
| 10,745,355 B2 | 8/2020 | Munoz et al. | |
| 2007/0254913 A1 | 11/2007 | Dunn et al. | |
| 2011/0124643 A1 | 5/2011 | Bellevergue et al. | |
| 2013/0267712 A1 | 10/2013 | Klumpp et al. | |
| 2015/0079154 A1 | 3/2015 | Zender et al. | |
| 2015/0272947 A1* | 10/2015 | Zeitlmann | A61P 29/00 514/342 |

FOREIGN PATENT DOCUMENTS

| | | | |
|---|---|---|---|
| AT | 336594 B | 5/1977 | |
| AU | 2020205331 A1 | 8/2020 | |
| JP | 2009-185010 A | 8/2009 | |
| WO | WO-9119730 A1 | 12/1991 | |
| WO | WO-0112189 A1 | 2/2001 | |
| WO | WO-0114353 A1 | 3/2001 | |
| WO | WO-03000694 A1 | 1/2003 | |
| WO | WO-2005054199 A1 | 6/2005 | |
| WO | WO-2005116009 A1 | 12/2005 | |
| WO | WO-2006060108 A1 | 6/2006 | |
| WO | WO-2008005457 A2 | 1/2008 | |
| WO | WO-2011022473 A1 * | 2/2011 | ............ A61K 31/42 |
| WO | WO-2011113606 A1 | 9/2011 | |
| WO | WO-2013007708 A1 | 1/2013 | |
| WO | WO-2014142755 A1 | 9/2014 | |
| WO | WO2015/078800 A1 | 6/2015 | |
| WO | WO-2016067009 A1 | 5/2016 | |
| WO | WO-2016119017 A1 | 8/2016 | |
| WO | WO-2016193939 A1 | 12/2016 | |

OTHER PUBLICATIONS

Datta S, Grant DJ. Crystal structures of drugs: advances in determination, prediction and engineering. Nat Rev Drug Discov. Jan. 2004;3(1):42-57. doi: 10.1038/nrd1280. (Year: 2004).*
Abbassi et al.: Lower Tubulin Expression in Glioblastoma Stem Cells Attenuates Efficacy of Microtubule-Targeting Agents. ACS Pharmacology & Translational Science. 2:402-413 (2019).
Brocklehurst et l.: Discovery, optimisation and in vivo evaluation of novel GPR119 agonists, Bioorganic & medicinal chemistry letters, 21(24) pp. 7310-7316 (2011).
CAS Registry No. 1607369-88-9; Entered STN May 21, 2014; 3-Pyrrolidinecarboxamide, N-ethyl-3-fluoro-N-[[4-(4-methoxy-1-piperidinyl)phenyl]methyl]-,hydrochloride (1:2) Whole document.
CAS Registry No. 1841021-36-0; Entered STN Jan. 7, 2016; 2-Propenamide, N-(6-amino-1,3-benzodioxol-5-yl)-3-[4-(1H-imidazol-1-yl)phynyl]-,hydrochloride (1:2).
CAS Registry No. 2040740-98-3; Entered STN Nov. 30, 2016; 2H-Pyran-4-carboxamide, 4-(aminomethyl)tetrahydro-N-methyl-N-[[2-(1pyrrollidinyl)phenyl]methyl].
CAS RN: 1088716-89-5, STN entry date Dec. 22, 2008, Chemical name: Benzeneacetamide, N-[2-(1-β-D-ribofuranosyl-1H-imidazol-4-yl)ethyl].
CAS RN: 1329340-85-3, STN entry date Sep. 7, 2011, Chemical name: Carbamic acid, N-[2-[4-(4-morpholinyl)phenyl]ethyl]-, phenyl ester.

(Continued)

*Primary Examiner* — Erich A Leeser

(57) ABSTRACT

Provided herein are compounds, pharmaceutical compositions, and methods of treatment for various diseases, such as cancer. In one aspect, the method comprises the treatment of brain cancers or metastatic cancers that spread to the brain.

20 Claims, No Drawings

(56) References Cited

OTHER PUBLICATIONS

CAS RN: 1444316-73-7, STN entry date Jul. 16, 2013, Chemical name: Benzeneacetamide, N-[2-(2-bromophenyl)ethyl]-4-hydroxy.
CAS RN: 1457495-24-7, STN entry date Oct. 14, 2013, Chemical name: Carbamic acid, N-[2-3(3-fluorophenyl)ethyl]-, phenyl ester.
CAS RN: 1458569-90-8, STN entry date Oct. 16, 2014, Chemical name: Guanidine, N-[2-(3-fluorophenyl)ethyl]-N'-phenyl.
CAS RN: 1579392-33-8, STN entry date Apr. 4, 2014, Chemical name: Benzeneacetamide, 4-amino-N-[2-[4-(1H-pyrazol-1-yl)phenyl]ethyl].
CAS RN: 1580673-62-6, STN entry date Apr. 6, 2014, Chemical name: Benzeneacetamide, 2-amino-N-(2-[1, 1'-biphenyl]-4-ylethyl).
CAS RN: 1582519-57-0, STN entry date Apr. 11, 2014, Chemical name: Benzeneacetamide, 2-amino-N-[2-[1-(4-fluorophenyl)-IH-pyrazol-3-yl]ethyl].
CAS RN: 1583024-75-2, STN entry date Apr. 12, 2014, Chemical name: Benzenebutanamide, N-(4-aminophenyl)-3-bromo.
CAS RN: 1583495-90-2, STN entry date Apr. 13, 2014, Chemical name: Benzeneacetamide, 4-amino-N-[2-[4-(2-methyl-4-thiazolyl)phenyl]ethyl].
Datta et al.: Crystal structures of drugs: Advances in determination, prediction, and engineering. Nature Reviews. vol. 3:42-57 (2004).
Davidson W, et al. Discovery and characterization of a substrate selective p38alpha inhibitor. Biochemistry. 2004;43(37): 11658-71.
Den et al.: A Phase I Study of the Combination of Sorafenib With Temozolomide and Radiation Therapy for the Treatment of Primary and Recurrent High-Grade Gliomas; International Journal of Radiation: Oncology Biology Physics; 85(2); 321-328 (2013).
Döbber et al.: Development and Biological Evaluation of a Photoactivatable Small Molecule Microtubule-Targeting Agent. ACS Medicinal Chemistry Letters. 8:395-400 (2017).
European Patent Application No. 007683105 Extended European Search Report dated May 6, 2021.
European Patent Application No. 16742584.2 Communication dated Jun. 28, 2019.
European Patent Application No. 2016212701 First Examination Report dated Jul. 18, 2019.
Fang et al.: Selective Palladium-Catalyzed Aminocarbonylation of Olefins with Aromatic Amines and Nitroarenes; Angew. Cham. Int. Ed.; 52; 14089-14093 (2013).
Gurgis et al.: Cytotoxic activity of the MK2 inhibitor CMPD1 in glioblastoma cells is independent of MK2. Cell Death Discovery. 15028 | doi:10.1038/cddiscovery.2015.28 (2015).
International Application No. PCT/AU2019/050073 Written Opinion dated Apr. 1, 2019.
International Application No. PCT/US2018/064114 International Search Report and Written Opinion dated Mar. 27, 2019.
International Application No. PCT/US2018/064114 PCT Invitation to Pay Additional Fees dated Jan. 25, 2019.
Kher et al.: 2-Aryl-N-acyl indole derivatives as liver X receptor (LXR) agonists; Bioorganic & Medicinal Chemistry Letters; 17; 4442-4446 (2007).
Mustafa et al.: Chain length-dependent effects of alkylmaltosides on nasal absorption of enoxaparin. J. pharm. Sci. 39(3):674-683 (2004).
Ooguri et al.: Chemi-, Regio- and Stereoselective Preparation of Silyl Enol Ethers from Thiol Esters and Bis(iodozincio)alkane; Chemical Communications, vol. 45, pp. 4761-4763 (2000).
PCT/US2018/064114 International Preliminary Report on Patentability dated Jun. 9, 2020.
Phoa et al.: Pharmacology of novel small-molecule tubulin inhibitors in glioblastoma cells with enhanced EGFR signalling. Biochemical Pharmacology. 98:587-601 (2015).
Pubmed Compound Summary for CID 118388845, 'Zafyypbzkfzvks-Uhfffaoysa-N', U.S. National Library of Medicine, p. 1-12 (2016) (https://pubchem.ncbi.nlm.nih.gov/compound/118388845).
Pubmed Compound Summary for CID 68973598, 'Iiqzammjldiqhg-Uhfffaoysa-N', U.S. National Library of Medicine, p. 1-12 (2012) (https://pubchem.ncbi.nlm.nih.gov/compound/68973598).
U.S. Appl. No. 16/211,051 Final Office Action dated Feb. 28, 2020.
U.S. Appl. No. 16/211,051 Non-final Office Action dated Sep. 30, 2020.
U.S. Appl. No. 16/211,051 Restriction Requirement dated Jun. 27, 2019.
Chen et al.: Aluminium Chloride-Catalyzed Intermolecular vs. Intramolecular Friedel-Crafts Reaction of Acrylanilides and 3-Chloropropanamides; JCCS; 47 155-162 (2000).
International Application No. PCT/AU2016/050044 Written Opinion of the International Searching Authority dated Mar. 2, 2016.

\* cited by examiner

TUBULIN INHIBITORS

CROSS-REFERENCE

This application is a continuation of U.S. application Ser. No. 16/211,051 filed Dec. 5, 2018, which claims the benefit of U.S. Provisional Application No. 62/595,530, filed on Dec. 6, 2017, which is incorporated herein by reference in its entirety.

BACKGROUND

A need exists in the medicinal arts for the effective treatment of cancer with small molecules, especially compounds for the treatment of brain cancers. Additionally, compounds capable of crossing the blood-brain barrier are needed.

BRIEF SUMMARY OF THE INVENTION

Described herein are compounds and methods for the treatment of proliferative diseases, such as cancer. In some embodiments, the cancer is a brain cancer. In some embodiments, the cancer is a metastatic cancer.

Described herein are compounds of Formula (VIIIa), or a pharmaceutically acceptable salt, solvate, or stereoisomer thereof:

Formula (VIIIa)

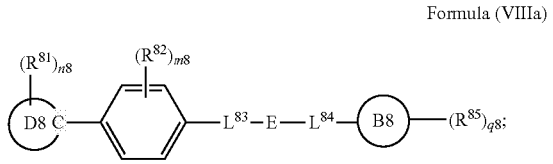

wherein:
$L^{83}$ is —C($R^{83}$)$_2$C($R^{83}$)$_2$C($R^{83}$)$_2$—;
E is —C(=O)N$R^{84}$— or —N$R^{84}$C(=O)—;
$L^{84}$ is a bond or —C$R^{86}R^{87}$—;
Rings D8 and B8 are independently heteroaryl or $C_2$-$C_8$ heterocyclyl;
each $R^{81}$ is independently hydrogen, halogen, —CN, —O$R^a$, —S$R^a$, —S(=O)$R^b$, —NO$_2$, —N$R^cR^d$, —S(=O)$_2R^d$, —N$R^aS$(=O)$_2R^d$, —S(=O)$_2NR^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^aC$(=O) N$R^cR^d$, —N$R^aC$(=O)$R^b$, —N$R^aC$(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —O$R^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;
each $R^{82}$ is independently hydrogen, halogen, —CN, —O$R^a$, —S$R^a$, —S(=O)$R^b$, —NO$_2$, —N$R^cR^d$, —S(=O)$_2R^d$, —N$R^aS$(=O)$_2R^d$, —S(=O)$_2NR^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^aC$(=O) N$R^cR^d$, —N$R^aC$(=O)$R^b$, —N$R^aC$(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;
each $R^{83}$ is independently hydrogen, halogen, —CN, —O$R^a$, —S$R^a$, —S(=O)$R^b$, —NO$_2$, —N$R^cR^d$, —S(=O)$_2R^d$, —N$R^aS$(=O)$_2R^d$, —S(=O)$_2NR^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^aC$(=O) $R^b$, —N$R^aC$(=O)O$R^a$, (—N$R^aC$(=O)N$R^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —O$R^a$, or —N$R^cR^d$; and the cycloalkyl, and heteroaryl is optionally substituted with one, two, or three of halogen, $C_1$-$C_6$ alkyl, $C_1$-$C_6$ haloalkyl-O$R^a$, or —N$R^cR^d$;
$R^{84}$ is hydrogen, —S(=O)$R^b$, —S(=O)$_2R^d$, —S(=O)$_2$ N$R^cR^d$, —C(=O)$R^b$, —CO$_2R^a$, —C(=O)N$R^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;
each $R^{85}$ is independently hydrogen, halogen, —CN, —O$R^a$, —S$R^a$, —S(=O)$R^b$, (—S(=O)$_2R^d$), —NO$_2$, —N$R^cR^d$, —N$R^aS$(=O)$_2R^d$, —S(=O)$_2NR^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^aC$(=O) N$R^cR^d$, —N$R^aC$(=O)$R^b$, —N$R^aC$(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;
or two $R^{85}$ substituents on the same carbon are taken together to form an oxo;
$R^{86}$ and $R^{87}$ are independently hydrogen, halogen, —CN, —O$R^a$, —S$R^a$, —S(=O)$R^b$, —NO$_2$, —N$R^cR^d$, —S(=O)$_2R^d$, —N$R^aS$(=O)$_2R^d$, —S(=O)$_2NR^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^aC$(=O) N$R^cR^d$, —N$R^aC$(=O)$R^b$, —N$R^aC$(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$.
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;

m8 is 1-4; and q8 is 1-5.

In some embodiments of a compound of Formula (VIIIa), $L^{84}$ is a bond. In some embodiments of a compound of Formula (VIIIa), $L^{84}$ is —$CR^{86}R^{87}$, wherein: $R^{86}$ and $R^{87}$ are independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$. In some embodiments of a compound of Formula (VIIIa), E is —$C(=O)NR^{84}$—. In some embodiments of a compound of Formula (VIIIa), E is —$NR^{84}C(=O)$—. In some embodiments of a compound of Formula (VIIIa), Ring D8 is $C_3$-$C_9$ heteroaryl. In some embodiments of a compound of Formula (VIIIa), Ring D8 is aryl. In some embodiments of a compound of Formula (VIIIa), Ring D8 is a fused bicyclic ring. In some embodiments of a compound of Formula (VIIIa), Ring D8 comprises at least one nitrogen atom in the ring. In some embodiments of a compound of Formula (VIIIa), Ring D8 comprises at least two nitrogen atoms in the ring. In some embodiments of a compound of Formula (VIIIa), Ring D8 is selected from the group consisting of indolyl, isoindolyl, indazolyl, quinolinyl, purinyl, indolizinyl, isoquinolinyl, quinazolinyl, and pteridinyl. In some embodiments of a compound of Formula (VIIIa), Ring D8 is selected from the group consisting of:

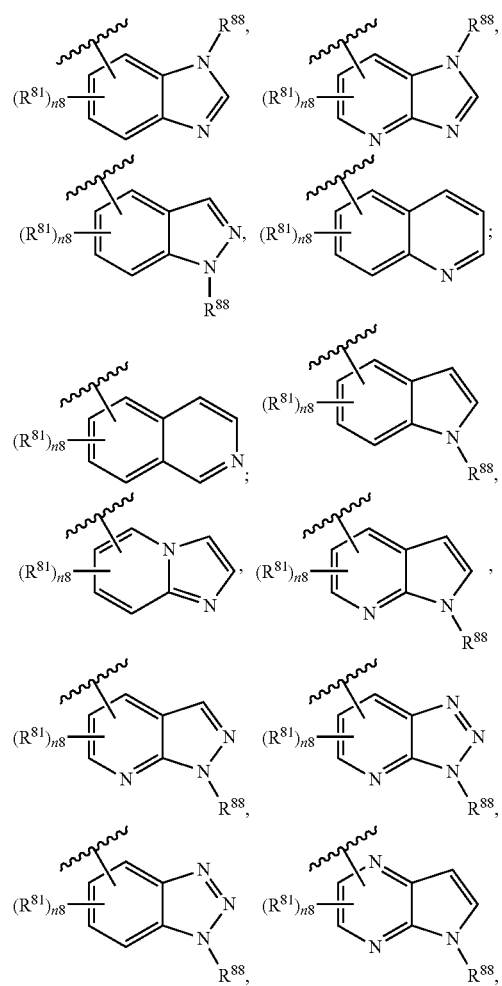

wherein: each $R^{88}$ is independently hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$; and n8 is 0-2.

In some embodiments of a compound of Formula (VIIIa), Ring B8 is heteroaryl. In some embodiments of a compound of Formula (VIIIa), Ring B8 is aryl. In some embodiments of a compound of Formula (VIIIa), Ring B8 is a 6-membered heteroaryl. In some embodiments of a compound of Formula (VIIIa), Ring B8 is pyridyl, pyrimidinyl, or pyrazinyl. In some embodiments of a compound of Formula (VIIIa), Ring B8 is pyridyl. In some embodiments of a compound of Formula (VIIIa), Ring B8 is a 5-membered heteroaryl. In some embodiments of a compound of Formula (VIIIa), Ring B8 is thiophenyl, furanyl, pyrrolyl, thiazolyl, oxazolyl, isoxazolyl, imidazolyl, pyrazolyl, thiadiazolyl, or oxadiazolyl. In some embodiments of a compound of Formula (VIIIa), Ring B8 is isoxazolyl. In some embodiments of a compound of Formula (VIIIa), Ring B8 is pyrazolyl. In some embodiments of a compound of Formula (VIIIa), each $R^{81}$ is independently halogen, $C_1$-$C_6$ alkyl, or $C_1$-$C_6$ haloalkyl. In some embodiments of a compound of Formula (VIIIa), each $R^{81}$ is independently fluoro. In some embodiments of a compound of Formula (VIIIa), n8 is 1. In some embodiments of a compound of Formula (VIIIa), each $R^{82}$ is independently hydrogen, halogen, $C_1$-$C_6$ alkyl, or $C_1$-$C_6$ haloalkyl. In some embodiments of a compound of Formula (VIIIa), each $R^{82}$ is hydrogen. In some embodiments of a compound of Formula (VIIIa), m8 is 1. In some embodiments of a compound of Formula (VIIIa), each $R^{83}$ is independently hydrogen, halogen, $C_1$-$C_6$ alkyl, or $C_1$-$C_6$ haloalkyl. In some embodiments of a compound of Formula (VIIIa), each $R^{83}$ is hydrogen. In some embodiments of a compound of Formula (VIIIa), $R^{84}$ is hydrogen or $C_1$-$C_6$ alkyl. In some embodiments of a compound of Formula (VIIIa), $R^{84}$ is hydrogen. In some embodiments of a compound of Formula (VIIIa), each $R^{85}$ is independently hydrogen, halogen, amino, —$NH_2$, $C_1$-$C_6$ alkyl, or $C_1$-$C_6$ haloalkyl. In some embodiments of a compound of Formula (VIIIa), each $R^{85}$ is independently hydrogen, —$NH_2$, —OH, or Me. In some embodiments of a compound of Formula (VIIIa), q8 is 1 or 2.

Described herein are compounds of Formula (VIIIb), or a pharmaceutically acceptable salt, solvate, or stereoisomer thereof:

Formula (VIIIb)

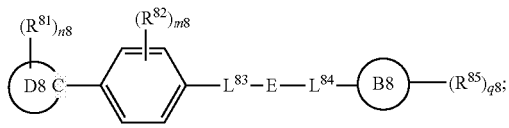

wherein:
$L^{83}$ is —$C(R^{83})_2C(R^{83})_2C(R^{83})_2$—;
E is —C(=O)$NR^{84}$— or —$NR^{84}$C(=O)—;
$L^{84}$ is a bond or —$CR^{86}R^{87}$—;
Ring D8 and B8 are independently aryl, heteroaryl, or $C_2$-$C_8$ heterocyclyl, provided that at least one of D8 or B8 is heteroaryl or $C_2$-$C_8$ heterocyclyl;
each $R^{81}$ is independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O) $NR^cR^d$, —$NR^aC$(=O)$R^b$, —$NR^aC$(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —$OR^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
each $R^{82}$ is independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O) $NR^cR^d$, —$NR^aC$(=O)$R^b$, —$NR^aC$(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
each $R^{83}$ is independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O) $R^b$, —$NR^aC$(=O)$OR^a$, (—$NR^aC$(=O)$NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_6$ heterocycloalkyl, or heteroaryl; wherein the alkyl, alkenyl, alkynyl, and heteroalkyl is optionally substituted with one, two, or three of halogen, —$OR^a$, or —$NR^cR^d$; and the cycloalkyl, and heteroaryl is optionally substituted with one, two, or three of halogen, $C_1$-$C_6$ alkyl, $C_1$-$C_6$ haloalkyl-$OR^a$, or —$NR^cR^d$;
$R^{84}$ is hydrogen, —S(=O)$R^b$, —S(=O)$_2R^d$, —S(=O)$_2$ $NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;
each $R^{85}$ is independently hydrogen, halogen, —CN, —$OR^a$, —$SR^a$, —S(=O)$R^b$, (—S(=O)$_2R^d$), —$NO_2$, —$NR^cR^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O) $NR^cR^d$, —$NR^aC$(=O)$R^b$, —$NR^aC$(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$; or two $R^{85}$ substituents on the same carbon are taken together to form an oxo;
$R^{86}$ and $R^{87}$ are independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O) $NR^cR^d$, —$NR^aC$(=O)$R^b$, —$NR^aC$(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$.
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;
m8 is 1-4; and
q8 is 1-5;

provided that when D8 is heteroaryl and $L^{84}$ is a bond, then B8 is heteroaryl or $C_2$-$C_8$ heterocyclyl; or when D8 is phenyl, n is 1, $R^{81}$ is fluoro at the ortho position of the phenyl ring, and $L^{84}$ is a bond, then B8 is $C_2$-$C_8$ heterocyclyl.

In some embodiments of a compound of Formula (VIIIb), $L^{84}$ is a bond. In some embodiments of a compound of Formula (VIIIb), $L^{84}$ is —CR$^{86}$R$^{87}$, wherein: $R^{86}$ and $R^{87}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$. In some embodiments of a compound of Formula (VIIIb), B8 is a monocyclic heteroaryl or monocyclic heterocyclyl ring. In some embodiments of a compound of Formula (VIIIb), Ring B8 is heteroaryl. In some embodiments of a compound of Formula (VIIIb), Ring B8 is a 6-membered heteroaryl. In some embodiments of a compound of Formula (VIIIb), Ring B8 is pyridyl, pyrimidinyl, or pyrazinyl. In some embodiments of a compound of Formula (VIIIb), Ring B8 is pyridyl. In some embodiments of a compound of Formula (VIIIb), Ring B8 is a 5-membered heterocycle comprising at least one substituent selected from the group consisting of $C_1$-$C_6$ alkyl, $C_1$-$C_6$ haloalkyl, amino, hydroxy, acyl, $C_1$-$C_6$ alkoxy, and aryl. In some embodiments of a compound of Formula (VIIIb), Ring B8 is a 5-membered heteroaryl. In some embodiments of a compound of Formula (VIIIb), Ring B8 is thiophenyl, furanyl, pyrrolyl, thiazolyl, oxazolyl, isoxazolyl, imidazolyl, pyrazolyl, thiadiazolyl, or oxadiazolyl. In some embodiments of a compound of Formula (VIIIb), Ring B8 is isoxazolyl. In some embodiments of a compound of Formula (VIIIb), Ring B8 is pyrazolyl. In some embodiments of a compound of Formula (VIIIb), B8 is a heterobicycle comprising at least one nitrogen atom. In some embodiments of a compound of Formula (VIIIb), B8 is a heterobicycle comprising at least two nitrogen atoms. In some embodiments of a compound of Formula (VIIIb), Ring D8 is selected from the group consisting of:

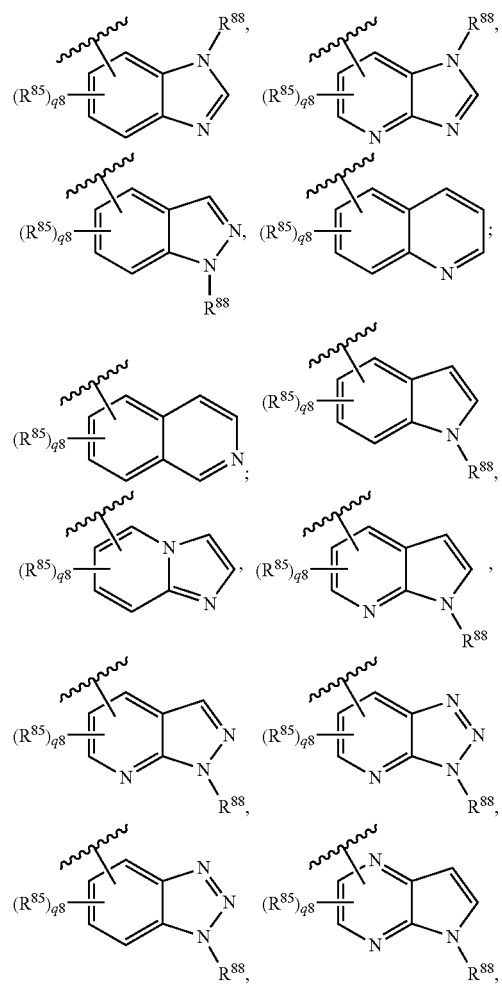

wherein: each $R^{88}$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$; and q8 is 0-2. In some embodiments of a compound of Formula (VIIIb), B8 is phenyl and $L^{84}$ is not a bond. In some embodiments of a compound of Formula (VIIIb), B8 is cycloalkyl. In some embodiments of a compound of Formula (VIIIb), B8 is cyclopropyl cyclobutyl, cyclopentyl, or cyclohexyl. In some embodiments of a compound of Formula (VIIIb), each $R^{81}$ is independently halogen, $C_1$-$C_6$ alkyl, or $C_1$-$C_6$ haloalkyl. In some embodiments of a compound of Formula (VIIIb), n8 is 1. In some embodiments of a compound of Formula (VIIIb), each $R^{82}$ is independently hydrogen, halogen, $C_1$-$C_6$ alkyl, or $C_1$-$C_6$ haloalkyl. In some embodiments of a compound of Formula (VIIIb), each $R^{82}$ is hydrogen. In some embodiments of a compound of Formula (VIIIb), m8 is 1. In some embodiments of a compound of Formula (VIIIb), each $R^{83}$ is independently hydrogen, halogen, $C_1$-$C_6$ alkyl, or $C_1$-$C_6$ haloalkyl. In some embodiments of a compound of Formula (VIIIb), each $R^{83}$ is hydrogen. In some embodiments of a compound of Formula (VIIIb), $R^{84}$ is hydrogen or $C_1$-$C_6$ alkyl. In some embodiments of a compound of Formula (VIIIb), $R^{84}$ is hydrogen. In some embodiments of a compound of Formula (VIIIb), each $R^{85}$ is independently hydrogen, halogen, amino, hydroxyl, acyl, $C_1$-$C_6$ alkyl, $C_1$-$C_6$ alkoxy, aryl, or $C_1$-$C_6$ haloalkyl. In some embodiments of a compound of Formula (VIIIb), each $R^{85}$ is independently halogen, —$NH_2$, hydroxyl, $C_1$-$C_6$ alkyl, or $C_1$-$C_6$ haloalkyl. In some embodiments of a compound of Formula (VIIIb), each $R^{85}$ is independently hydrogen, —$NH_2$, —OH, $CF_3$, OMe, or Me. In some embodiments of a compound of Formula (VIIIb), q8 is 1 or 2.

Described herein are compounds of Formula (VIIIc), or a pharmaceutically acceptable salt, solvate, or stereoisomer thereof:

Formula (VIIIc)

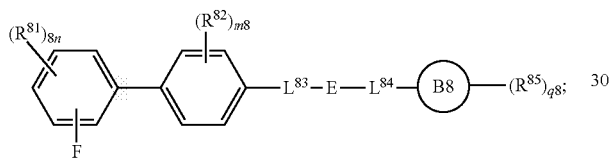

wherein:
$L^{83}$ is —$C(R^{83})_2C(R^{83})_2C(R^{83})_2$—;
$L^{84}$ is a bond or —$CR^{83}R^{83}$—;
E is —$NR^{84}C(=O)$—;
Ring B8 is selected from the group consisting of:
  (a) a bicyclic ring comprising at least one nitrogen atom;
  (b) a 5-membered ring comprising at least one nitrogen atom;
  (c) cycloalkyl;
  (d) a monocyclic heteroaryl or monocyclic $C_2$-$C_8$ heterocyclyl ring, wherein at least one $R^{85}$ is selected from the group consisting of $C_1$-$C_6$ alkyl, $C_1$-$C_6$ haloalkyl, amino, hydroxy, $C_1$-$C_6$ N-acylamino, acyl, $C_1$-$C_6$ alkoxy, $C_2$-$C_8$ heterocycloalkyl, and aryl; and
  (f) monocyclic aryl, monocyclic heteroaryl, or monocyclic heterocyclyl ring, provided that $L^{84}$ is not a bond;
each $R^{81}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)$ $NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, or —$OR^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$; each $R^{82}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)$ $NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{83}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)$ $R^b$, —$NR^aC(=O)OR^a$, (—$NR^aC(=O)NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —$OR^a$, or —$NR^cR^d$; and the cycloalkyl, and heteroaryl is optionally substituted with one, two, or three of halogen, $C_1$-$C_6$ alkyl, $C_1$-$C_6$ haloalkyl-$OR^a$, or —$NR^cR^d$;

$R^{84}$ is hydrogen, —$S(=O)R^b$, —$S(=O)_2R^d$, —$S(=O)_2$ $NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c$ $R^d$;

or two $R^{83}$ substituents are taken together to form a ring;
each $R^{85}$ is independently hydrogen, halogen, —CN, —$OR^a$, —$SR^a$, —$S(=O)R^b$, (—$S(=O)_2R^d$), —$NO_2$, —$NR^cR^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)$ $NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{85}$ substituents on the same carbon are taken together to form an oxo;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n8 is 1-5;
m8 is 1-4; and
q8 is 1-5.

In some embodiments of a compound of Formula (VIIIc), $L^{84}$ is a bond. In some embodiments of a compound of Formula (VIIIc), $L^{84}$ is —$CR^{86}R^{87}$, wherein: $R^{86}$ and $R^{87}$ are independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$. In some embodiments of a compound of Formula (VIIIc), B8 is a monocyclic heteroaryl or monocyclic heterocyclyl ring. In some embodiments of a compound of Formula (VIIIc), Ring B8 is heteroaryl. In some embodiments of a compound of Formula (VIIIc), Ring B8 is a 6-membered heteroaryl. In some embodiments of a compound of Formula (VIIIc), Ring B8 is pyridyl, pyrimidinyl, or pyrazinyl. In some embodiments of a compound of Formula (VIIIc), Ring B8 is pyridyl. In some embodiments of a compound of Formula (VIIIc), Ring B8 is a 5-membered heterocycle comprising at least one substituent selected from the group consisting of $C_1$-$C_6$ alkyl, $C_1$-$C_6$ haloalkyl, amino, hydroxy, acyl, $C_1$-$C_6$ alkoxy, and aryl. In some embodiments of a compound of Formula (VIIIc), Ring B8 is a 5-membered heteroaryl. In some embodiments of a compound of Formula (VIIIc), Ring B8 is thiophenyl, furanyl, pyrrolyl, thiazolyl, oxazolyl, isoxazolyl, imidazolyl, pyrazolyl, thiadiazolyl, or oxadiazolyl. In some embodiments of a compound of Formula (VIIIc), Ring B8 is isoxazolyl. In some embodiments of a compound of Formula (VIIIc), Ring B8 is pyrazolyl. In some embodiments of a compound of Formula (VIIIc), B8 is a heterobicycle comprising at least one nitrogen atom. In some embodiments of a compound of Formula (VIIIc), B8 is a heterobicycle comprising at least two nitrogen atoms. In some embodiments of a compound of Formula (VIIIc), Ring D8 is selected from the group consisting of:

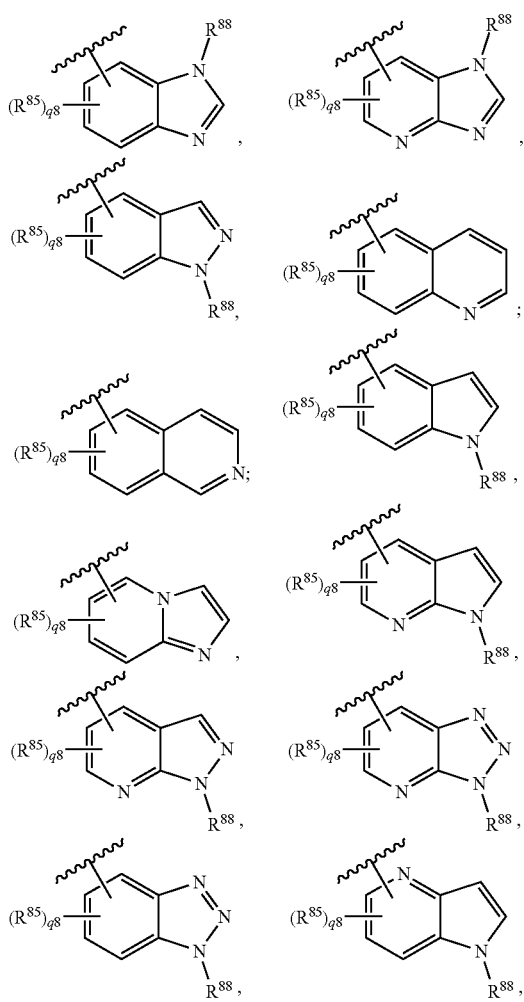

wherein: each $R^{88}$ is independently hydrogen, —S(=O)$R^b$, —S(=O)$_2R^d$, —S(=O)$_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$; and q8 is 0-2. In some embodiments of a compound of Formula (VIIIc), B8 is phenyl and $L^{84}$ is not a bond. In some embodiments of a compound of Formula (VIIIc), B8 is cycloalkyl. In some embodiments of a compound of Formula (VIIIc), B8 is cyclopropyl cyclobutyl, cyclopentyl, or cyclohexyl. In some embodiments of a compound of Formula (VIIIc), each $R^{81}$ is independently halogen, $C_1$-$C_6$ alkyl, or $C_1$-$C_6$ haloalkyl. In some embodiments of a compound of Formula (VIIIc), n8 is 1. In some embodiments of a compound of Formula (VIIIc), each $R^{82}$ is independently hydrogen, halogen, $C_1$-$C_6$ alkyl, or $C_1$-$C_6$ haloalkyl. In some embodiments of a compound of Formula (VIIIc), each $R^{82}$ is hydrogen. In some embodiments of a compound of Formula (VIIIc), m8 is 1. In some embodiments of a compound of Formula (VIIIc), each $R^{83}$ is independently hydrogen, halogen, $C_1$-$C_6$ alkyl, or $C_1$-$C_6$ haloalkyl. In some embodiments of a compound of Formula (VIIIc), each $R^{83}$ is hydrogen. In some embodiments of a compound of Formula (VIIIc), $R^{84}$ is hydrogen or $C_1$-$C_6$ alkyl. In some embodiments of a compound of Formula (VIIIc), $R^{84}$ is hydrogen. In some embodiments of a compound of Formula (VIIIc), each $R^{85}$ is independently hydrogen, halogen, amino, hydroxyl, acyl, $C_1$-$C_6$ alkyl, $C_1$-$C_6$ alkoxy, aryl, or $C_1$-$C_6$ haloalkyl. In some embodiments of a compound of Formula (VIIIc), each $R^{85}$ is independently halogen, —$NH_2$, hydroxyl, $C_1$-$C_6$ alkyl, or $C_1$-$C_6$ haloalkyl. In some embodiments of a compound of Formula (VIIIc), each $R^{85}$ is independently hydrogen, —$NH_2$, —OH, $CF_3$, OMe, or Me. In some embodiments of a compound of Formula (VIIIc), q8 is 1 or 2.

Described herein are compounds of Formula (V), or a pharmaceutically acceptable salt, solvate, or stereoisomer thereof:

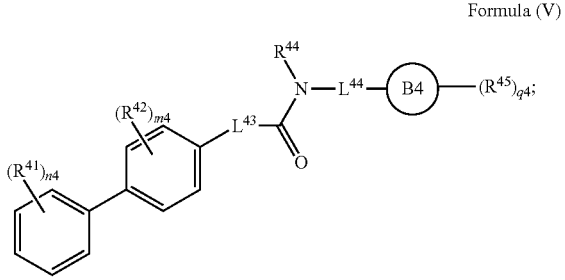

Formula (V)

wherein:

$L^{43}$ is —$C(R^{43})_2C(R^{43})_2C(R^{43})_2$—;

$L^{44}$ is a bond or —$CR^{46}R^{47}$—;

Ring B4 is heteroaryl or $C_2$-$C_8$ heterocycloalkyl;

each $R^{41}$ is independently halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{42}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{43}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)OR^a$, (—$NR^aC(=O)NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, aryl, and heteroaryl is optionally substituted with one, two, or three of halogen, $C_1$-$C_6$ alkyl, $C_1$-$C_6$ haloalkyl-$OR^a$, or —$NR^cR^d$;

$R^{44}$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{45}$ is independently hydrogen, halogen, —CN, —$OR^a$, —$SR^a$, —$S(=O)R^b$, (—$S(=O)_2R^d$), —$NO_2$, —$NR^cR^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{45}$ substituents on the same carbon are taken together to form an oxo;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n4 is 1-5;

m4 is 1-4; and q4 is 1-5.

In some embodiments of a compound of Formula (V), $L^{44}$ is a bond. In some embodiments of a compound of Formula (V), $L^{44}$ is —$CR^{46}R^{47}$—, wherein: $R^{46}$ and $R^{47}$ are independently hydrogen, halogen, —CN, —$OR^a$, —$SR^a$, —S(=O)$R^b$, —NO$_2$, —$NR^cR^d$, —S(=O)$_2R^d$, —$NR^a$S(=O)$_2R^d$, —S(=O)$_2NR^cR^d$, —C(=O)$R^b$, —OC(=O)$R^b$, —CO$_2R^a$, —OCO$_2R^a$, —C(=O)$NR^cR^d$, —OC(=O)$NR^c$$R^d$, —$NR^a$C(=O)$NR^cR^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$. In some embodiments of a compound of Formula (V), Ring B4 is heteroaryl. In some embodiments of a compound of Formula (V), Ring B4 is a 6-membered heteroaryl. In some embodiments of a compound of Formula (V), Ring B4 is pyridyl, pyrimidinyl, or pyrazinyl. In some embodiments of a compound of Formula (V), Ring B4 is pyridyl. In some embodiments of a compound of Formula (V), Ring B4 is a 5-membered heteroaryl. In some embodiments of a compound of Formula (V), Ring B4 is thiophenyl, furanyl, pyrrolyl, thiazolyl, oxazolyl, isoxazolyl, imidazolyl, pyrazolyl, thiadiazolyl, or oxadiazolyl. In some embodiments of a compound of Formula (V), Ring B4 is pyrrolyl. In some embodiments of a compound of Formula (V), Ring B4 is $C_7$-$C_9$ heteroaryl. In some embodiments of a compound of Formula (V), Ring B4 is indolyl, indazolyl, or benzofuranyl. In some embodiments of a compound of Formula (V), Ring B4 is a fused bicyclic ring. In some embodiments of a compound of Formula (V), each $R^{41}$ is independently halogen, $C_1$-$C_6$ alkyl, or $C_1$-$C_6$ haloalkyl. In some embodiments of a compound of Formula (V), each $R^{41}$ is independently fluoro. In some embodiments of a compound of Formula (V), n4 is 1. In some embodiments of a compound of Formula (V), each $R^{42}$ is independently hydrogen, halogen, $C_1$-$C_6$ alkyl, or $C_1$-$C_6$ haloalkyl. In some embodiments of a compound of Formula (V), each $R^{42}$ is hydrogen. In some embodiments of a compound of Formula (V), m4 is 1. In some embodiments of a compound of Formula (V), each $R^{43}$ is independently hydrogen, halogen, $C_1$-$C_6$ alkyl, or $C_1$-$C_6$ haloalkyl. In some embodiments of a compound of Formula (V), each $R^{43}$ is hydrogen. In some embodiments of a compound of Formula (V), each $R^{43}$ is halogen. In some embodiments of a compound of Formula (V), $R^{44}$ is hydrogen or $C_1$-$C_6$ alkyl. In some embodiments of a compound of Formula (V), $R^{44}$ is hydrogen. In some embodiments of a compound of Formula (V), each $R^{45}$ is independently hydrogen, halogen, —OH, $C_1$-$C_6$ alkyl, or $C_1$-$C_6$ haloalkyl. In some embodiments of a compound of Formula (V), each $R^{45}$ is hydrogen, —OH, or Me. In some embodiments of a compound of Formula (V), q4 is 1.

Described herein are pharmaceutical compositions comprising a compound of Formula (V), Formula (VIII), Formula (VIIIa), Formula (VIIIb), Formula (VIIIc), or a pharmaceutically acceptable salt, solvate, or stereoisomer thereof, and a pharmaceutically acceptable excipient.

Described herein are methods of treating a proliferative disease or disorder in a subject in need thereof, the method comprising administering to the subject a compound of Formula (V), Formula (VIII), Formula (VIIIa), Formula (VIIIb), Formula (VIIIc), or a pharmaceutically acceptable salt, solvate, or stereoisomer thereof, or administering to the subject a composition comprising Formula (V), Formula (VIII), Formula (VIIIa), Formula (VIIIb), or Formula (VIIIc). In some embodiments of a method described herein, the disease or disorder is cancer. In some embodiments of a method described herein, the disease or disorder is cancer of the central nervous system. In some embodiments of a method described herein, the disease or disorder is brain cancer. In some embodiments of a method described herein, the disease or disorder is primary brain cancer. In some embodiments of a method described herein, the primary brain cancer is a glioma. In some embodiments of a method described herein, the glioma is an astrocytoma, oligodendroglioma, or ependymoma. In some embodiments of a method described herein, the primary brain cancer is meningioma, Schwannoma, craniopharyngioma, germinoma, or pineal tumor. In some embodiments of a method described herein, the disease or disorder is metastatic cancer. In some embodiments of a method described herein, the metastatic cancer originates from primary lung cancer. In some embodiments of a method described herein, the metastatic cancer originates from primary breast cancer.

In some embodiments of a method described herein, the method further comprises surgery or radiation therapy.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_8$ alkyl). In other embodiments, the alkyl group is selected from methyl, ethyl, 1-propyl (n-propyl), 1-methylethyl (iso-propyl). 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, w-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_8$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An A-heterocyclyl radical is optionally substituted as described above for heterocyclyl radicals. Examples of such A-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) К-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[6][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An A-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

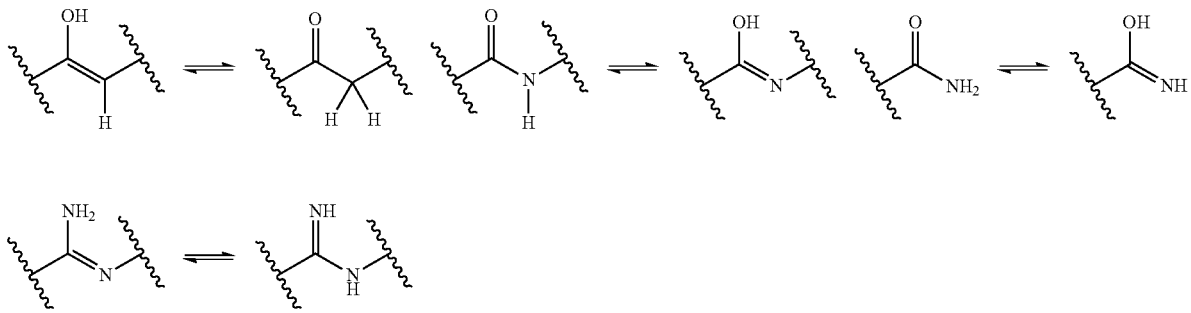

-continued

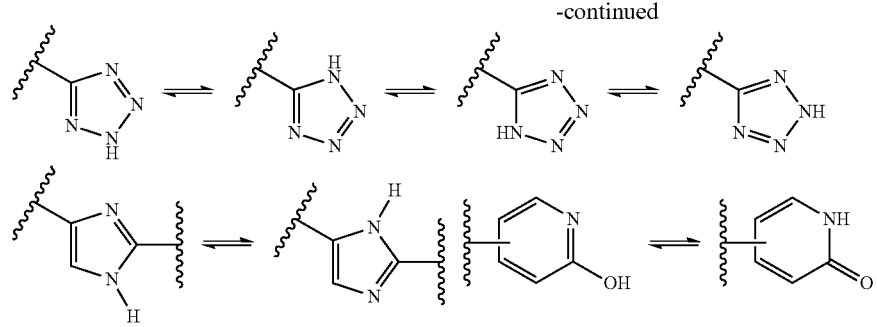

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^3H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

"Pharmaceutically acceptable salt" includes both acid and base addition salts. A pharmaceutically acceptable salt of any one of the compounds described herein is intended to encompass any and all pharmaceutically suitable salt forms.

Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as alginates, gluconates, and galacturonates (see, for example, Beige S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N A-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

Provided herein in some embodiments are compounds and pharmaceutical compositions comprising said compounds.

Some embodiments provided herein describe a compound, or a pharmaceutically acceptable salt, solvate, or stereoisomer thereof, having the structure of Formula (I):

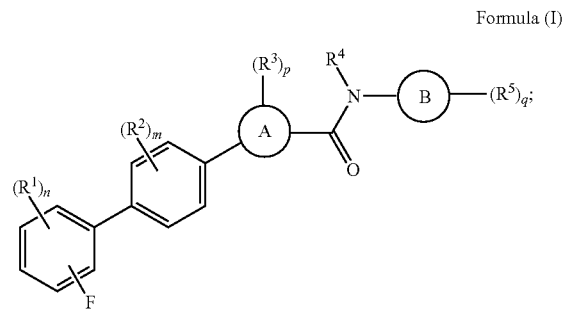

Formula (I)

wherein:

Ring A is aryl, partially unsaturated cycloalkyl or heterocycloalkyl, heteroaryl, $C_2$-$C_{10}$ heterocycloalkyl, or $C_3$-$C_8$ cycloalkyl;

Ring B is aryl or heteroaryl;

each $R^1$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^2$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^3$ is independently hydrogen, halogen, —CN, —$OR^a$, —$SR^a$, two $R^3$ on the same carbon are taken together to form an oxo, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)R^b$, —$NR^aC(=O)OR^a$, —$NR^aC(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-$OR^a$, or —$NR^cR^d$;

$R^4$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^5$ is independently hydrogen, halogen, —CN, —$OR^a$, —$SR^a$, —$S(=O)R^b$, —$NO_2$, —$NR^cR^d$, —$NR^aS(=O)_2R^d$, —$S(=O)_2NR^cR^d$, —$S(=O)_2R^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n is 1-4;

m is 1-4;

p is 1-4; and q is 1-5.

Some embodiments provided herein describe a compound, or a pharmaceutically acceptable salt, solvate, or stereoisomer thereof, having the structure of Formula (I):

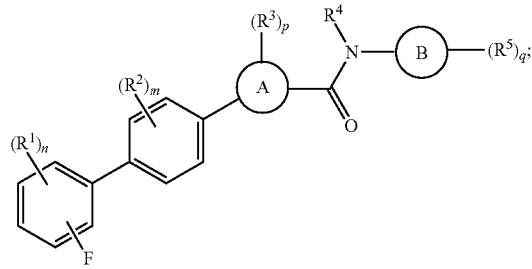

Formula (I)

wherein:

Ring A is heteroaryl, $C_2$-$C_8$ heterocycloalkyl, or $C_3$-$C_8$ cycloalkyl;

Ring B is aryl or heteroaryl;

each $R^1$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^2$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^3$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-$OR^a$, or —$NR^cR^d$;

$R^4$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^5$ is independently hydrogen, halogen, —CN, —OR$^a$, —SR$^a$, —S(=O)R$^b$, —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n is 1-4;

m is 1-4;

p is 1-4; and q is 1-5.

In some embodiments of a compound of Formula (I), Ring A is heteroaryl. In some embodiments of a compound of Formula (I), Ring A is a 6-membered heteroaryl. In some embodiments of a compound of Formula (I), Ring A is pyridyl. In some embodiments of a compound of Formula (I), Ring A is pyrimidinyl. In some embodiments of a compound of Formula (I), Ring A is pyrazinyl. In some embodiments of a compound of Formula (I), Ring A is a 5-membered heteroaryl. In some embodiments of a compound of Formula (I), Ring A is tetrazolyl. In some embodiments of a compound of Formula (I), Ring A is thiazolyl. In some embodiments of a compound of Formula (I), Ring A is furanyl. In some embodiments of a compound of Formula (I), Ring A is thiophenyl. In some embodiments of a compound of Formula (I), Ring A is oxazolyl. In some embodiments of a compound of Formula (I), Ring A is oxadiazolyl. In some embodiments of a compound of Formula (I), Ring A is thiadiazolyl. In some embodiments of a compound of Formula (I), Ring A is pyrazolyl. In some embodiments of a compound of Formula (I), Ring A is imidazolyl. In some embodiments of a compound of Formula (I), Ring A is triazolyl. In some embodiments of a compound of Formula (I), Ring A is triazolyl.

In some embodiments of a compound of Formula (I), Ring A is $C_2$-$C_8$ heterocycloalkyl. In some embodiments of a compound of Formula (I), Ring A is pyrrolidinyl. In some embodiments of a compound of Formula (I), Ring A is piperidinyl. In some embodiments of a compound of Formula (I), Ring A is piperazinyl. In some embodiments of a compound of Formula (I), Ring A is pyranyl. In some embodiments of a compound of Formula (I), Ring A1 is tetrahydrofuranyl. In some embodiments of a compound of Formula (I), Ring A is morpholinyl. In some embodiments of a compound of Formula (I), Ring A is azetidinyl.

In some embodiments of a compound of Formula (I), Ring A is $C_3$-$C_8$ cycloalkyl. In some embodiments of a compound of Formula (I), Ring A is cyclopropyl. In some embodiments of a compound of Formula (I), Ring A is cyclobutyl. In some embodiments of a compound of Formula (I), Ring A is cyclohexyl. In some embodiments of a compound of Formula (I), Ring A is cyclopentyl.

In some embodiments of a compound of Formula (I), Ring B is aryl. In some embodiments of a compound of Formula (I), Ring B is phenyl. In some embodiments of a compound of Formula (I), Ring B is naphthyl.

In some embodiments of a compound of Formula (I), Ring B is heteroaryl. In some embodiments of a compound of Formula (I), Ring B is fused heteroaryl. In some embodiments of a compound of Formula (I), Ring B is 6-membered heteroaryl. In some embodiments of a compound of Formula (I), Ring B is pyridyl. In some embodiments of a compound of Formula (I), Ring B is pyrimidinyl. In some embodiments of a compound of Formula (I), Ring B is pyrazinyl. In some embodiments of a compound of Formula (I), Ring B is a 5-membered heteroaryl. In some embodiments of a compound of Formula (I), Ring B is thiophenyl. In some embodiments of a compound of Formula (I), Ring B is furanyl. In some embodiments of a compound of Formula (I), Ring B is pyrrolyl. In some embodiments of a compound of Formula (I), Ring B is thiazolyl. In some embodiments of a compound of Formula (I), Ring B is oxazolyl. In some embodiments of a compound of Formula (I), Ring B is isoxazolyl. In some embodiments of a compound of Formula (I), Ring B is imidazolyl. In some embodiments of a compound of Formula (I), Ring B is pyrazolyl. In some embodiments of a compound of Formula (I), Ring B is thiadiazolyl. In some embodiments of a compound of Formula (I), Ring B is oxadiazolyl.

In some embodiments of a compound of Formula (I), each R$^1$ is independently hydrogen. In some embodiments of a compound of Formula (I), each R$^1$ is independently halogen. In some embodiments of a compound of Formula (I), each R$^1$ is independently $C_1$-$C_6$ alkyl. In some embodiments of a compound of Formula (I), each R$^1$ is independently $C_1$-$C_6$ haloalkyl. In some embodiments of a compound of Formula (I), each R$^1$ is independently fluoro.

In some embodiments of a compound of Formula (I), n is 1. In some embodiments of a compound of Formula (I), n is 2. In some embodiments of a compound of Formula (I), n is 3. In some embodiments of a compound of Formula (I), n is 4.

In some embodiments of a compound of Formula (I), each $R^2$ is independently halogen. In some embodiments of a compound of Formula (I), each $R^2$ is independently $C_1$-$C_6$ alkyl. In some embodiments of a compound of Formula (I), each $R^2$ is independently $C_1$-$C_6$ haloalkyl. In some embodiments of a compound of Formula (I), each $R^2$ is hydrogen.

In some embodiments of a compound of Formula (I), m is 1. In some embodiments of a compound of Formula (I), m is 2. In some embodiments of a compound of Formula (I), m is 3. In some embodiments of a compound of Formula (I), m is 4.

In some embodiments of a compound of Formula (I), each $R^3$ is independently halogen. In some embodiments of a compound of Formula (I), each $R^3$ is independently $C_1$-$C_6$ alkyl. In some embodiments of a compound of Formula (I), each $R^3$ is independently $C_1$-$C_6$ haloalkyl. In some embodiments of a compound of Formula (I), each $R^3$ is hydrogen.

In some embodiments of a compound of Formula (I), p is 1. In some embodiments of a compound of Formula (I), p is 2. In some embodiments of a compound of Formula (I), p is 3. In some embodiments of a compound of Formula (I), p is 4.

In some embodiments of a compound of Formula (I), $R^4$ is hydrogen or $C_1$-$C_6$ alkyl. In some embodiments of a compound of Formula (I), $R^4$ is $C_1$-$C_6$ alkyl. In some embodiments of a compound of Formula (I), $R^4$ is hydrogen.

In some embodiments of a compound of Formula (I), each $R^5$ is independently hydrogen. In some embodiments of a compound of Formula (I), each $R^5$ is independently halogen. In some embodiments of a compound of Formula (I), each $R^5$ is independently —OH. In some embodiments of a compound of Formula (I), each $R^5$ is independently $C_1$-$C_6$ alkyl. In some embodiments of a compound of Formula (I), each $R^5$ is independently $C_1$-$C_6$ haloalkyl. In some embodiments of a compound of Formula (I), each $R^5$ is Me.

In some embodiments of a compound of Formula (I), q is 1. In some embodiments of a compound of Formula (I), q is 2. In some embodiments of a compound of Formula (I), q is 3. In some embodiments of a compound of Formula (I), q is 4. In some embodiments of a compound of Formula (I), q is 5.

Some embodiments provided herein describe a compound, or a pharmaceutically acceptable salt, solvate, or stereoisomer thereof, having the structure of Formula (Ia):

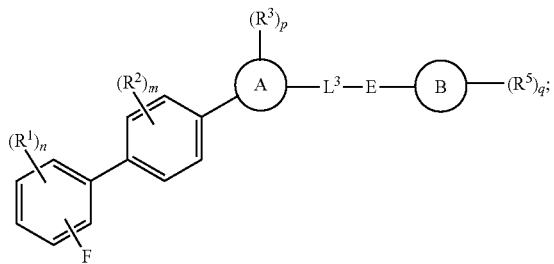

Formula (Ia)

wherein:
Ring A is heteroaryl, $C_2$-$C_8$ heterocycloalkyl, or $C_3$-$C_8$ cycloalkyl;

E is —C(=O)NR$^4$— or —NR$^4$C(=O)—;
L$^3$ is a bond or —CR$^6$R$^7$—;
Ring B is aryl or heteroaryl;
each R$^1$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^3$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

R$^4$ is hydrogen, —S(=O)R$^b$, —S(=O)$_2$R$^d$, —S(=O)$_2$ NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$ R$^d$;

each R$^5$ is independently hydrogen, halogen, —CN, —OR$^a$, —SR$^a$, —S(=O)R$^b$, —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$ R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^6$ and R$^7$ are independently hydrogen, taken together to form an oxo, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n is 1-4;
m is 1-4;
p is 1-4; and
q is 1-5.

In some embodiments of a compound of Formula (Ia), E is —NR$^4$C(=O)—. In some embodiments of a compound of Formula (Ia), E is —C(=O)NR$^4$—. In some embodiments of a compound of Formula (Ia), L$^3$ is a bond. In some embodiments of a compound of Formula (Ia), L$^3$ is —CR$^6$R$^7$—.

In some embodiments of a compound of Formula (Ia), Ring A is heteroaryl. In some embodiments of a compound of Formula (Ia), Ring A is a 6-membered heteroaryl. In some embodiments of a compound of Formula (Ia), Ring A is pyridyl. In some embodiments of a compound of Formula (Ia), Ring A is pyrimidinyl. In some embodiments of a compound of Formula (Ia), Ring A is pyrazinyl. In some embodiments of a compound of Formula (Ia), Ring A is a 5-membered heteroaryl. In some embodiments of a compound of Formula (Ia), Ring A is tetrazolyl. In some embodiments of a compound of Formula (Ia), Ring A is thiazolyl. In some embodiments of a compound of Formula (Ia), Ring A is furanyl. In some embodiments of a compound of Formula (Ia), Ring A is thiophenyl. In some embodiments of a compound of Formula (Ia), Ring A is oxazolyl. In some embodiments of a compound of Formula (Ia), Ring A is oxadiazolyl. In some embodiments of a compound of Formula (Ia), Ring A is thiadiazolyl. In some embodiments of a compound of Formula (Ia), Ring A is pyrazolyl. In some embodiments of a compound of Formula (Ia), Ring A is imidazolyl. In some embodiments of a compound of Formula (Ia), Ring A is triazolyl. In some embodiments of a compound of Formula (Ia), Ring A is triazolyl.

In some embodiments of a compound of Formula (Ia), Ring A is $C_2$-$C_8$ heterocycloalkyl. In some embodiments of a compound of Formula (Ia), Ring A is pyrrolidinyl. In some embodiments of a compound of Formula (Ia), Ring A is piperidinyl. In some embodiments of a compound of Formula (Ia), Ring A is piperazinyl. In some embodiments of a compound of Formula (Ia), Ring A is pyranyl. In some embodiments of a compound of Formula (Ia), Ring A1 is tetrahydrofuranyl. In some embodiments of a compound of Formula (Ia), Ring A is morpholinyl. In some embodiments of a compound of Formula (Ia), Ring A is azetidinyl.

In some embodiments of a compound of Formula (Ia), Ring A is $C_3$-$C_8$ cycloalkyl. In some embodiments of a compound of Formula (Ia), Ring A is cyclopropyl. In some embodiments of a compound of Formula (Ia), Ring A is cyclobutyl. In some embodiments of a compound of Formula (Ia), Ring A is cyclohexyl. In some embodiments of a compound of Formula (Ia), Ring A is cyclopentyl.

In some embodiments of a compound of Formula (Ia), Ring B is aryl. In some embodiments of a compound of Formula (Ia), Ring B is phenyl. In some embodiments of a compound of Formula (Ia), Ring B is naphthyl.

In some embodiments of a compound of Formula (Ia), Ring B is heteroaryl. In some embodiments of a compound of Formula (Ia), Ring B is fused heteroaryl. In some embodiments of a compound of Formula (Ia), Ring B is 6-membered heteroaryl. In some embodiments of a compound of Formula (Ia), Ring B is pyridyl. In some embodiments of a compound of Formula (Ia), Ring B is pyrimidinyl. In some embodiments of a compound of Formula (Ia), Ring B is pyrazinyl. In some embodiments of a compound of Formula (Ia), Ring B is a 5-membered heteroaryl. In some embodiments of a compound of Formula (Ia), Ring B is thiophenyl. In some embodiments of a compound of Formula (Ia), Ring B is furanyl. In some embodiments of a compound of Formula (Ia), Ring B is pyrrolyl. In some embodiments of a compound of Formula (Ia), Ring B is thiazolyl. In some embodiments of a compound of Formula (Ia), Ring B is oxazolyl. In some embodiments of a compound of Formula (Ia), Ring B is isoxazolyl. In some embodiments of a compound of Formula (Ia), Ring B is imidazolyl. In some embodiments of a compound of Formula (Ia), Ring B is pyrazolyl. In some embodiments of a compound of Formula (Ia), Ring B is thiadiazolyl. In some embodiments of a compound of Formula (Ia), Ring B is oxadiazolyl.

In some embodiments of a compound of Formula (Ia), each R$^1$ is independently hydrogen. In some embodiments of a compound of Formula (Ia), each R$^1$ is independently halogen. In some embodiments of a compound of Formula (Ia), each R$^1$ is independently $C_1$-$C_6$ alkyl. In some embodiments of a compound of Formula (Ia), each R$^1$ is independently $C_1$-$C_6$ haloalkyl. In some embodiments of a compound of Formula (Ia), each $R^1$ is independently fluoro.

In some embodiments of a compound of Formula (Ia), n is 1. In some embodiments of a compound of Formula (Ia), n is 2. In some embodiments of a compound of Formula (Ia), n is 3. In some embodiments of a compound of Formula (Ia), n is 4.

In some embodiments of a compound of Formula (Ia), each $R^2$ is independently halogen. In some embodiments of a compound of Formula (Ia), each $R^2$ is independently $C_1$-$C_6$ alkyl. In some embodiments of a compound of Formula (Ia), each $R^2$ is independently $C_1$-$C_6$ haloalkyl. In some embodiments of a compound of Formula (Ia), each $R^2$ is hydrogen.

In some embodiments of a compound of Formula (Ia), m is 1. In some embodiments of a compound of Formula (Ia), m is 2. In some embodiments of a compound of Formula (Ia), m is 3. In some embodiments of a compound of Formula (Ia), m is 4.

In some embodiments of a compound of Formula (Ia), each $R^3$ is independently halogen. In some embodiments of a compound of Formula (Ia), each $R^3$ is independently $C_1$-$C_6$ alkyl. In some embodiments of a compound of Formula (Ia), each $R^3$ is independently $C_1$-$C_6$ haloalkyl. In some embodiments of a compound of Formula (Ia), each $R^3$ is hydrogen.

In some embodiments of a compound of Formula (Ia), p is 1. In some embodiments of a compound of Formula (Ia), p is 2. In some embodiments of a compound of Formula (Ia), p is 3. In some embodiments of a compound of Formula (Ia), p is 4.

In some embodiments of a compound of Formula (Ia), $R^4$ is hydrogen or $C_1$-$C_6$ alkyl. In some embodiments of a compound of Formula (Ia), $R^4$ is $C_1$-$C_6$ alkyl. In some embodiments of a compound of Formula (Ia), $R^4$ is hydrogen.

In some embodiments of a compound of Formula (Ia), each $R^5$ is independently hydrogen. In some embodiments of a compound of Formula (Ia), each $R^5$ is independently halogen. In some embodiments of a compound of Formula (Ia), each $R^5$ is independently —OH. In some embodiments of a compound of Formula (Ia), each $R^5$ is independently $C_1$-$C_6$ alkyl. In some embodiments of a compound of Formula (Ia), each $R^5$ is independently $C_1$-$C_6$ haloalkyl. In some embodiments of a compound of Formula (Ia), each $R^5$ is Me.

In some embodiments of a compound of Formula (Ia), q is 1. In some embodiments of a compound of Formula (Ia), q is 2. In some embodiments of a compound of Formula (Ia), q is 3. In some embodiments of a compound of Formula (Ia), q is 4. In some embodiments of a compound of Formula (Ia), q is 5.

Some embodiments provided herein describe a compound, or a pharmaceutically acceptable salt, solvate, or stereoisomer thereof, having the structure of Formula (II):

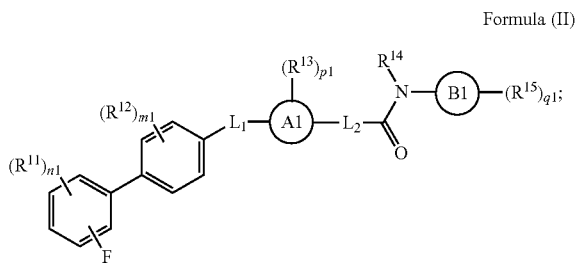

Formula (II)

wherein:
$L_1$ is —$CR^{16}R^{17}$— and $L_2$ is a bond, or
$L_1$ is a bond and $L_2$ is —$CR^{18}R^{19}$—;
provided that $L_1$ and $L_2$ are not on the same carbon;
Ring A1 is aryl, heteroaryl, $C_2$-$C_8$ heterocycloalkyl, or $C_3$-$C_8$ cycloalkyl;
Ring B1 is cycloalkyl, heterocycloalkyl, aryl or heteroaryl;
each $R^{11}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
each $R^{12}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
each $R^{13}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
$R^{14}$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
each $R^{15}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^{16}$ and $R^{17}$ are independently hydrogen, taken together to form an oxo, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^{18}$ and $R^{19}$ are independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n1 is 1-4;
m1 is 1-4;
p1 is 1-4; and
q1 is 1-5.

Some embodiments provided herein describe a compound, or a pharmaceutically acceptable salt, solvate, or stereoisomer thereof, having the structure of Formula (II):

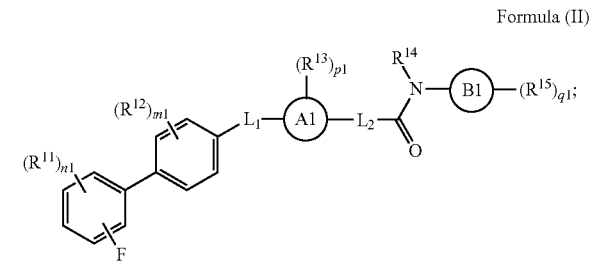

Formula (II)

wherein:
$L_1$ is —$CR^{16}R^{17}$— and $L_2$ is a bond, or
$L_1$ is a bond and $L_2$ is —$CR^{18}R^{19}$—;
provided that $L_1$ and $L_2$ are not on the same carbon;
Ring A1 is aryl, heteroaryl, $C_2$-$C_8$ heterocycloalkyl, or $C_3$-$C_8$ cycloalkyl;
Ring B1 is aryl or heteroaryl;
each $R^{11}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{12}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{13}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^{14}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{15}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^{16}$ and R$^{17}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^{18}$ and R$^{19}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n1 is 1-4;
m1 is 1-4;
p1 is 1-4; and
q1 is 1-5.

In some embodiments of a compound of Formula (II), $L_1$ is a bond and $L_2$ is a bond. In some embodiments of a compound of Formula (II), one of $L_1$ or $L_2$ is not a bond.

In some embodiments of a compound of Formula (II), $L_1$ is a bond and $L_2$ is —CR$^{18}$R$^{19}$—. In some embodiments of a compound of Formula (II), R$^1$ s and R$_{19}$ are hydrogen. In some embodiments of a compound of Formula (II), $L_1$ is —CR$^{16}$R$^{17}$— and $L_2$ is a bond. In some embodiments of a compound of Formula (II), R$_{16}$ and R$_{17}$ are hydrogen.

In some embodiments of a compound of Formula (II), Ring A1 is heteroaryl. In some embodiments of a compound of Formula (II), Ring A1 is a 6-membered heteroaryl. In some embodiments of a compound of Formula (II), Ring A1 is pyrimidinyl. In some embodiments of a compound of Formula (II), Ring A1 is pyrazinyl. In some embodiments of a compound of Formula (II), Ring A1 is pyridyl. In some embodiments of a compound of Formula (II), Ring A1 is a 5-membered heteroaryl. In some embodiments of a compound of Formula (II), Ring B is thiophenyl. In some embodiments of a compound of Formula (II), Ring B is furanyl. In some embodiments of a compound of Formula (II), Ring B is pyrrolyl. In some embodiments of a compound of Formula (II), Ring B is thiazolyl. In some embodiments of a compound of Formula (II), Ring B is oxazolyl. In some embodiments of a compound of Formula (II), Ring B is isoxazolyl. In some embodiments of a compound of Formula (II), Ring B is imidazolyl. In some embodiments of a compound of Formula (II), Ring B is pyrazolyl. In some embodiments of a compound of Formula (II), Ring B is thiadiazolyl. In some embodiments of a compound of Formula (II), Ring B is oxadiazolyl.

In some embodiments of a compound of Formula (II), Ring A1 is $C_2$-$C_8$ heterocycloalkyl. In some embodiments of a compound of Formula (II), Ring A1 is pyrrolidinyl. In some embodiments of a compound of Formula (II), Ring A1 is piperidinyl. In some embodiments of a compound of Formula (II), Ring A1 is piperazinyl. In some embodiments of a compound of Formula (II), Ring A1 is pyranyl. In some embodiments of a compound of Formula (II), Ring A1 is tetrahydrofuranyl. In some embodiments of a compound of Formula (II), Ring A1 is morpholinyl.

In some embodiments of a compound of Formula (II), Ring A1 is $C_3$-$C_8$ cycloalkyl. In some embodiments of a compound of Formula (II), Ring A1 is cyclopropyl. In some embodiments of a compound of Formula (II), Ring A1 is cyclobutyl. In some embodiments of a compound of Formula (II), Ring A1 is cyclopentyl. In some embodiments of a compound of Formula (II), Ring A1 is cyclohexyl.

In some embodiments of a compound of Formula (II), Ring B1 is aryl. In some embodiments of a compound of Formula (II), Ring B1 is phenyl. In some embodiments, B1 is biphenyl.

In some embodiments of a compound of Formula (II), Ring B1 is heteroaryl. In some embodiments of a compound of Formula (II), Ring B1 is fused bicyclic heteroaryl. In some embodiments of a compound of Formula (II), Ring B1 is a 6-membered heteroaryl. In some embodiments of a compound of Formula (II), Ring B1 is pyrimidinyl. In some embodiments of a compound of Formula (II), Ring B1 is pyrazinyl. In some embodiments of a compound of Formula (II), Ring B1 is pyridyl. In some embodiments of a compound of Formula (II), Ring B1 is a 5-membered heteroaryl. In some embodiments of a compound of Formula (II), Ring B1 is thiophenyl. In some embodiments of a compound of Formula (II), Ring B1 is furanyl. In some embodiments of a compound of Formula (II), Ring B1 is pyrrolyl. In some embodiments of a compound of Formula (II), Ring B1 is thiazolyl. In some embodiments of a compound of Formula (II), Ring B1 is oxazolyl. In some embodiments of a compound of Formula (II), Ring B1 is isoxazolyl. In some embodiments of a compound of Formula (II), Ring B1 is imidazolyl. In some embodiments of a compound of Formula (II), Ring B1 is thiadiazolyl. In some embodiments of a compound of Formula (II), Ring B1 is oxadiazolyl. In some embodiments of a compound of Formula (II), Ring B1 is pyrazolyl.

In some embodiments of a compound of Formula (II), each $R^{11}$ is independently halogen. In some embodiments of a compound of Formula (II), each $R^{11}$ is independently $C_1$-$C_6$ alkyl. In some embodiments of a compound of Formula (II), each $R^{11}$ is independently $C_1$-$C_6$ haloalkyl. In some embodiments of a compound of Formula (II), each $R^{11}$ is hydrogen.

In some embodiments of a compound of Formula (II), n1 is 1. In some embodiments of a compound of Formula (II), n1 is 2. In some embodiments of a compound of Formula (II), n1 is 3. In some embodiments of a compound of Formula (II), n1 is 4.

In some embodiments of a compound of Formula (II), each $R^{12}$ is independently halogen. In some embodiments of a compound of Formula (II), each $R^{12}$ is independently $C_1$-$C_6$ alkyl. In some embodiments of a compound of Formula (II), each $R^{12}$ is independently $C_1$-$C_6$ haloalkyl. In some embodiments of a compound of Formula (II), each $R^{12}$ is hydrogen.

In some embodiments of a compound of Formula (II), m1 is 1. In some embodiments of a compound of Formula (II), m1 is 2. In some embodiments of a compound of Formula (II), m1 is 3. In some embodiments of a compound of Formula (II), m1 is 4.

In some embodiments of a compound of Formula (II), each $R^{13}$ is independently halogen. In some embodiments of a compound of Formula (II), each $R^{13}$ is independently $C_1$-$C_6$ alkyl. In some embodiments of a compound of Formula (II), each $R^{13}$ is independently $C_1$-$C_6$ haloalkyl. In some embodiments of a compound of Formula (II), each $R^{13}$ is hydrogen.

In some embodiments of a compound of Formula (II), p1 is 1. In some embodiments of a compound of Formula (II), p1 is 2. In some embodiments of a compound of Formula (II), p1 is 3. In some embodiments of a compound of Formula (II), p1 is 4.

In some embodiments of a compound of Formula (II), $R^{14}$ is hydrogen or $C_1$-$C_6$ alkyl. In some embodiments of a compound of Formula (II), $R^{14}$ is $C_1$-$C_6$ alkyl. In some embodiments of a compound of Formula (II), $R^{14}$ is hydrogen.

In some embodiments of a compound of Formula (II), each $R^{15}$ is independently hydrogen. In some embodiments of a compound of Formula (II), each $R^{15}$ is independently halogen. In some embodiments of a compound of Formula (II), each $R^{15}$ is independently —OH. In some embodiments of a compound of Formula (II), each $R^{15}$ is independently $C_1$-$C_6$ alkyl. In some embodiments of a compound of Formula (II), each $R^{15}$ is independently $C_1$-$C_6$ haloalkyl. In some embodiments of a compound of Formula (II), each $R^{15}$ is Me.

In some embodiments of a compound of Formula (II), q1 is 1. In some embodiments of a compound of Formula (II), q1 is 2. In some embodiments of a compound of Formula (II), q1 is 3. In some embodiments of a compound of Formula (II), q1 is 4. In some embodiments of a compound of Formula (II), q1 is 5.

Described herein are compounds of Formula (III), or a pharmaceutically acceptable salt, solvate, or stereoisomer thereof:

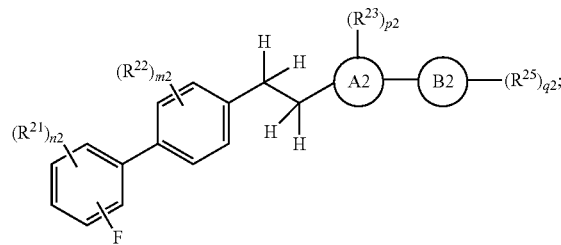

Formula (III)

wherein:
Ring A2 is heteroaryl;
Ring B2 is cycloalkyl, heterocycloalkyl, aryl or heteroaryl;
each $R^{21}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{22}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{23}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{25}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n2 is 1-4;
m2 is 1-4;
p2 is 1-4; and
q2 is 1-5.

Described herein are compounds of Formula (III), or a pharmaceutically acceptable salt, solvate, or stereoisomer thereof:

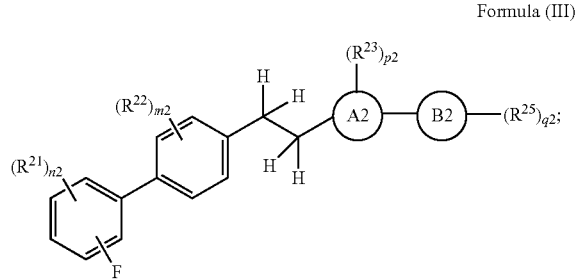

Formula (III)

wherein:
Ring A2 is heteroaryl;
Ring B2 is aryl or heteroaryl;
each $R^{21}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{22}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{23}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{25}$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)$ $NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n2 is 1-4;
m2 is 1-4;
p2 is 1-4; and
q2 is 1-5.

In some embodiments of a compound of Formula (III), Ring A2 is a 6-membered heteroaryl. In some embodiments of a compound of Formula (III), Ring A2 is pyrimidinyl. In some embodiments of a compound of Formula (III), Ring A2 is pyrazinyl. In some embodiments of a compound of Formula (III), Ring A2 is pyridyl. In some embodiments of a compound of Formula (III), Ring A2 is a 5-membered heteroaryl. In some embodiments of a compound of Formula (III), Ring A2 is thiophenyl. In some embodiments of a compound of Formula (III), Ring A2 is furanyl. In some embodiments of a compound of Formula (III), Ring A2 is pyrrolyl. In some embodiments of a compound of Formula (III), Ring A2 is thiazolyl. In some embodiments of a compound of Formula (III), Ring A2 is oxazolyl. In some embodiments of a compound of Formula (III), Ring A2 is isoxazolyl. In some embodiments of a compound of Formula (III), Ring A2 is imidazolyl. In some embodiments of a compound of Formula (III), Ring A2 is pyrazolyl. In some embodiments of a compound of Formula (III), Ring A2 is thiadiazolyl. In some embodiments of a compound of Formula (III), Ring A2 is oxadiazolyl.

In some embodiments of a compound of Formula (III), Ring B2 is aryl. In some embodiments of a compound of Formula (III), Ring B2 is phenyl. In some embodiments of a compound of Formula (III), Ring B2 is biphenyl.

In some embodiments of a compound of Formula (III), Ring B2 is heteroaryl. In some embodiments of a compound of Formula (III), Ring B2 is a 6-membered heteroaryl. In some embodiments of a compound of Formula (III), Ring B2 is pyrimidinyl. In some embodiments of a compound of Formula (III), Ring B2 is pyrazinyl. In some embodiments of a compound of Formula (III), Ring B2 is pyridyl. In some embodiments of a compound of Formula (III), Ring B2 is a 5-membered heteroaryl. In some embodiments of a compound of Formula (III), Ring B2 is thiophenyl. In some embodiments of a compound of Formula (III), Ring B2 is furanyl. In some embodiments of a compound of Formula (III), Ring B2 is pyrrolyl. In some embodiments of a compound of Formula (III), Ring B2 is thiazolyl. In some embodiments of a compound of Formula (III), Ring B2 is oxazolyl. In some embodiments of a compound of Formula (III), Ring B2 is isoxazolyl. In some embodiments of a compound of Formula (III), Ring B2 is imidazolyl. In some embodiments of a compound of Formula (III), Ring B2 is thiadiazolyl. In some embodiments of a compound of Formula (III), Ring B2 oxadiazolyl. In some embodiments of a compound of Formula (III), Ring B2 is pyrazolyl.

In some embodiments of a compound of Formula (III), each $R^{21}$ is independently halogen. In some embodiments of a compound of Formula (III), each $R^{21}$ is independently $C_1$-$C_6$ alkyl. In some embodiments of a compound of Formula (III), each $R^{21}$ is independently $C_1$-$C_6$ haloalkyl. In some embodiments of a compound of Formula (III), each $R^{21}$ is hydrogen.

In some embodiments of a compound of Formula (III), n2 is 1. In some embodiments of a compound of Formula (III), n2 is 2. In some embodiments of a compound of Formula (III), n2 is 3. In some embodiments of a compound of Formula (III), n2 is 4.

In some embodiments of a compound of Formula (III), each $R^{22}$ is independently halogen. In some embodiments of a compound of Formula (III), each $R^{22}$ is independently $C_1$-$C_6$ alkyl. In some embodiments of a compound of Formula (III), each $R^{22}$ is independently $C_1$-$C_6$ haloalkyl. In some embodiments of a compound of Formula (III), each $R^{22}$ is hydrogen.

In some embodiments of a compound of Formula (III), m2 is 1. In some embodiments of a compound of Formula (III), m2 is 2. In some embodiments of a compound of Formula (III), m2 is 3. In some embodiments of a compound of Formula (III), m2 is 4.

In some embodiments of a compound of Formula (III), each $R^{23}$ is independently halogen. In some embodiments of a compound of Formula (III), each $R^{23}$ is independently $C_1$-$C_6$ alkyl. In some embodiments of a compound of Formula (III), each $R^{23}$ is independently $C_1$-$C_6$ haloalkyl. In some embodiments of a compound of Formula (III), each $R^{23}$ is hydrogen.

In some embodiments of a compound of Formula (III), p2 is 1. In some embodiments of a compound of Formula (III), p2 is 2. In some embodiments of a compound of Formula (III), p2 is 3. In some embodiments of a compound of Formula (III), p2 is 4.

In some embodiments of a compound of Formula (III), each $R^{25}$ is independently hydrogen. In some embodiments of a compound of Formula (III), each $R^{25}$ is independently halogen. In some embodiments of a compound of Formula (III), each $R^{25}$ is independently —OH. In some embodiments of a compound of Formula (III), each $R^{25}$ is independently $C_1$-$C_6$ alkyl. In some embodiments of a compound of Formula (III), each $R^{25}$ is independently $C_1$-$C_6$ haloalkyl. In some embodiments of a compound of Formula (III), each $R^{25}$ is independently methyl.

In some embodiments of a compound of Formula (III), q2 is 1. In some embodiments of a compound of Formula (III), q2 is 2. In some embodiments of a compound of Formula (III), q2 is 3. In some embodiments of a compound of Formula (III), q2 is 4. In some embodiments of a compound of Formula (III), q2 is 5.

Described herein are compounds of Formula (IV), or a pharmaceutically acceptable salt, solvate, or stereoisomer thereof:

Formula (IV)

wherein:
Ring B3 is $C_3$-$C_8$ cycloalkyl, $C_2$-$C_8$ heterocycloalkyl, aryl, or heteroaryl;
each $R^{31}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
each $R^{32}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
$R^{34}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
each $R^{35}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
$R^{36}$ and $R^{37}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n3 is 1-4;
m3 is 1-4; and
q3 is 1-5.

In some embodiments of a compound of Formula (IV), Ring B3 is aryl. In some embodiments of a compound of Formula (IV), Ring B3 is phenyl. In some embodiments of a compound of Formula (IV), Ring B3 is naphthyl.

In some embodiments of a compound of Formula (IV), Ring B3 is heteroaryl. In some embodiments of a compound of Formula (IV), Ring B3 is a 6-membered heteroaryl. In some embodiments of a compound of Formula (IV), Ring B3 is pyrimidinyl. In some embodiments of a compound of Formula (IV), Ring B3 is pyrazinyl. In some embodiments of a compound of Formula (IV), Ring B3 is pyridyl. In some embodiments of a compound of Formula (IV), Ring B3 is a 5-membered heteroaryl. In some embodiments of a compound of Formula (IV), Ring B3 is thiophenyl. In some embodiments of a compound of Formula (IV), Ring B3 is furanyl. In some embodiments of a compound of Formula (IV), Ring B3 is pyrrolyl. In some embodiments of a compound of Formula (IV), Ring B3 is thiazolyl. In some embodiments of a compound of Formula (IV), Ring B3 is oxazolyl. In some embodiments of a compound of Formula (IV), Ring B3 is isoxazolyl. In some embodiments of a compound of Formula (IV), Ring B3 is imidazolyl. In some embodiments of a compound of Formula (IV), Ring B3 is thiadiazolyl. In some embodiments of a compound of Formula (IV), Ring B3 is oxadiazolyl. In some embodiments of a compound of Formula (IV), Ring B3 is pyrazolyl.

In some embodiments of a compound of Formula (IV), each $R^{31}$ is independently halogen. In some embodiments of a compound of Formula (IV), each $R^{31}$ is independently $C_1$-$C_6$ alkyl. In some embodiments of a compound of Formula (IV), each $R^{31}$ is independently $C_1$-$C_6$ haloalkyl. In some embodiments of a compound of Formula (IV), each $R^{31}$ is hydrogen.

In some embodiments of a compound of Formula (IV), n3 is 1. In some embodiments of a compound of Formula (IV), n3 is 2. In some embodiments of a compound of Formula (IV), n3 is 3. In some embodiments of a compound of Formula (IV), n3 is 4.

In some embodiments of a compound of Formula (IV), each $R^{32}$ is independently halogen. In some embodiments of a compound of Formula (IV), each $R^{32}$ is independently $C_1$-$C_6$ alkyl. In some embodiments of a compound of Formula (IV), each $R^{32}$ is independently $C_1$-$C_6$ haloalkyl. In some embodiments of a compound of Formula (IV), each $R^{32}$ is hydrogen.

In some embodiments of a compound of Formula (IV), m3 is 1. In some embodiments of a compound of Formula (IV), m3 is 2. In some embodiments of a compound of Formula (IV), m3 is 3. In some embodiments of a compound of Formula (IV), m3 is 4.

In some embodiments of a compound of Formula (IV), $R^{34}$ is hydrogen or $C_1$-$C_6$ alkyl. In some embodiments of a compound of Formula (IV), $R^{34}$ is $C_1$-$C_6$ alkyl. In some embodiments of a compound of Formula (IV), $R^{34}$ is hydrogen.

In some embodiments of a compound of Formula (IV), each $R^{35}$ is independently hydrogen. In some embodiments of a compound of Formula (IV), each $R^{35}$ is independently halogen. In some embodiments of a compound of Formula (IV), each $R^{35}$ is independently —OH. In some embodiments of a compound of Formula (IV), each $R^{35}$ is independently $C_1$-$C_6$ alkyl. In some embodiments of a compound of Formula (IV), each $R^{35}$ is independently $C_1$-$C_6$ haloalkyl. In some embodiments of a compound of Formula (IV), each $R^{35}$ is Me.

In some embodiments of a compound of Formula (IV), q3 is 1. In some embodiments of a compound of Formula (IV), q3 is 2. In some embodiments of a compound of Formula (IV), q3 is 3. In some embodiments of a compound of Formula (IV), q3 is 4. In some embodiments of a compound of Formula (IV), q3 is 5.

In some embodiments of a compound of Formula (IV), $R^{36}$ and $R^{37}$ is independently hydrogen, halogen, $C_1$-$C_6$ alkyl, or $C_1$-$C_6$ haloalkyl. In some embodiments of a compound of Formula (IV), $R^{36}$ and $R^{37}$ are hydrogen.

Described herein are compounds of Formula (V), or a pharmaceutically acceptable salt, solvate, or stereoisomer thereof:

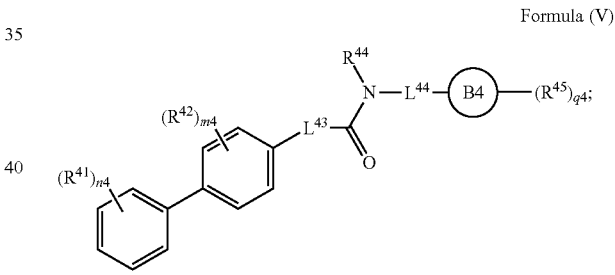

Formula (V)

wherein:
$L^{43}$ is —C($R^{43}$)$_2$C($R^{43}$)$_2$C($R^{43}$)$_2$—;
$L^{44}$ is a bond or —C$R^{46}R^{47}$—;
Ring B4 is heteroaryl or $C_2$-$C_8$ heterocycloalkyl;
each $R^{41}$ is independently hydrogen, halogen, —CN, —OR$^a$, —SR$^a$, —S(=O)R$^b$, —NO$_2$, —NR$^cR^d$, —S(=O)$_2$R$^d$, —NR$^a$S(=O)$_2$R$^d$, —S(=O)$_2$NR$^cR^d$, —C(=O)R$^b$, —OC(=O)R$^b$, —CO$_2$R$^a$, —OCO$_2$R$^a$, —C(=O)NR$^cR^d$, —OC(=O)NR$^cR^d$, —NR$^a$C(=O)NR$^cR^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^cR^d$;

each $R^{42}$ is independently hydrogen, halogen, —CN, —OR$^a$, —SR$^a$, —S(=O)R$^b$, —NO$_2$, —NR$^cR^d$, —S(=O)$_2$R$^d$, —NR$^a$S(=O)$_2$R$^d$, —S(=O)$_2$NR$^cR^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{43}$ is independently hydrogen, halogen, two R$^{43}$ on the same carbon are taken together to form an oxo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), C$_1$-C$_6$ alkyl, C$_2$-C$_6$ alkenyl, C$_2$-C$_6$ alkynyl, C$_1$-C$_6$ heteroalkyl, C$_3$-C$_{10}$ heterocycloalkyl, C$_3$-C$_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl-OR$^a$, or —NR$^c$R$^d$;

R$^{44}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{45}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_{56}$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

or two R$^{45}$ substituents on the same carbon are taken together to form an oxo;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ are independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

n4 is 1-5;
m4 is 1-4; and
q4 is 1-5.

Described herein are compounds of Formula (V), or a pharmaceutically acceptable salt, solvate, or stereoisomer thereof:

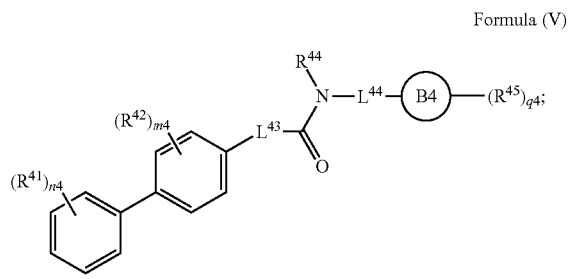

Formula (V)

wherein:
L$^{43}$ is —C(R$^{43}$)$_2$C(R$^{43}$)$_2$C(R$^{43}$)$_2$—;
L$^{44}$ is a bond or —CR$^{46}$R$^{47}$—;
Ring B4 is heteroaryl or C$_2$-C$_8$ heterocycloalkyl;
each R$^{41}$ is independently halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{42}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{43}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

R$^{44}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{45}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

or two R$^{45}$ substituents on the same carbon are taken together to form an oxo;

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n4 is 1-5;

m4 is 1-4; and q4 is 1-5.

In some embodiments of a compound of Formula (V), L$^{44}$ is a bond. In some embodiments of a compound of Formula (V), L$^{44}$ is —CR$^{46}$R$^{47}$—. In some embodiments of a compound of Formula (V), R$^{46}$ and R$^{47}$ are independently hydrogen. In some embodiments of a compound of Formula (V), R$^{46}$ and R$^{47}$ are independently halogen. In some embodiments of a compound of Formula (V), R$^{46}$ and R$^{47}$ are independently fluoro. In some embodiments of a compound of Formula (V), R$^{46}$ and R$^{47}$ are independently aryl. In some embodiments of a compound of Formula (V), R$^{46}$ and R$^{47}$ are independently heteroaryl. In some embodiments of a compound of Formula (V), R$^{46}$ and R$^{47}$ are independently —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl; wherein the alkyl, alkenyl, alkynyl, and heteroalkyl is optionally substituted with one, two, or three of halogen, —OR$^a$, or —NR$^c$R$^d$; In some embodiments of a compound of Formula (V), R$^{46}$ and R$^{47}$ are independently $C_3$-$C_8$cycloalkyl, $C_2$-$C_8$ heterocycloalkyl; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

In some embodiments of a compound of Formula (V), Ring B4 is heterocycloalkyl. In some embodiments of a compound of Formula (V), Ring B4 is $C_2$-$C_8$ heterocycloalkyl. In some embodiments of a compound of Formula (V), Ring B4 is pyrrolidinyl. In some embodiments of a compound of Formula (V), Ring B4 is piperidinyl. In some embodiments of a compound of Formula (V), Ring B4 is piperazinyl. In some embodiments of a compound of Formula (V), Ring B4 is pyranyl. In some embodiments of a compound of Formula (V), Ring B4 is tetrahydrofuranyl. In some embodiments of a compound of Formula (V), Ring B4 is morpholinyl.

In some embodiments of a compound of Formula (V), Ring B4 is heteroaryl.

In some embodiments of a compound of Formula (V), Ring B4 is a 6-membered heteroaryl. In some embodiments of a compound of Formula (V), Ring B4 is pyrimidinyl. In some embodiments of a compound of Formula (V), Ring B4 is pyrazinyl. In some embodiments of a compound of Formula (V), Ring B4 is pyridyl. In some embodiments of a compound of Formula (V), Ring B4 is a 5-membered heteroaryl. In some embodiments of a compound of Formula (V), Ring B4 is thiophenyl. In some embodiments of a compound of Formula (V), Ring B4 is furanyl. In some embodiments of a compound of Formula (V), Ring B4 is pyrrolyl. In some embodiments of a compound of Formula (V), Ring B4 is thiazolyl. In some embodiments of a compound of Formula (V), Ring B4 is oxazolyl. In some embodiments of a compound of Formula (V), Ring B4 is isoxazolyl. In some embodiments of a compound of Formula (V), Ring B4 is imidazolyl. In some embodiments of a compound of Formula (V), Ring B4 is pyrazolyl. In some embodiments of a compound of Formula (V), Ring B4 is thiadiazolyl. In some embodiments of a compound of Formula (V), Ring B4 is oxadiazolyl. In some embodiments of a compound of Formula (V), Ring B4 is $C_7$-$C_9$ heteroaryl. In some embodiments of a compound of Formula (V), Ring B4 is indolyl. In some embodiments of a compound of Formula (V), Ring B4 is indazolyl. In some embodiments of a compound of Formula (V), Ring B4 is benzofuranyl. In some embodiments of a compound of Formula (V), Ring B4 is a fused bicyclic ring.

In some embodiments of a compound of Formula (V), the compound has the Formula (Va), or a pharmaceutically acceptable salt, solvate, or stereoisomer thereof:

Formula (Va)

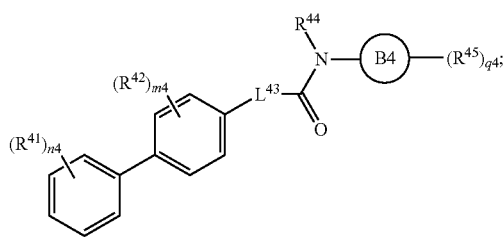

wherein:

$L^{43}$ is —C($R^{43}$)$_2$C($R^{43}$)$_2$C($R^{43}$)$_2$—;

Ring B4 is fused bicyclic heteroaryl comprising at least two nitrogen atoms in the rings, or fused heteroaryl comprising at least one non-aromatic ring;

each $R^{41}$ is independently halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{42}$ is independently hydrogen, halogen, —CN, —$OR^a$, —$SR^a$, —S(=O)$R^b$, —$NO_2$, —$NR^cR^d$, —S(=O)$_2R^a$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)$ $NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{43}$ is independently hydrogen, halogen, two $R^{43}$ on the same carbon are taken together to form an oxo, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)$ $R^b$, —$NR^aC(=O)OR^a$, (—$NR^aC(=O)NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_3$-$C_{10}$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-$OR^a$, or —$NR^cR^d$;

$R^{44}$ is hydrogen, —S(=O)$R^b$, —S(=O)$_2R^a$, —S(=O)$_2$ $NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c$ $R^d$;

each $R^{45}$ is independently hydrogen, halogen, —CN, —$OR^a$, —$SR^a$, —S(=O)$R^b$, (—S(=O)$_2R^d$), —$NO_2$, —$NR^cR^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)$ $NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{45}$ substituents on the same carbon are taken together to form an oxo;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n4 is 1-5;

m4 is 1-4; and q4 is 1-5.

In some embodiments of a compound of Formula (V), the compound has the Formula (Va), or a pharmaceutically acceptable salt, solvate, or stereoisomer thereof:

Formula (Va)

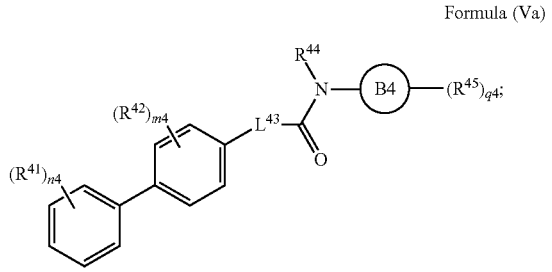

wherein:

$L^{43}$ is —$C(R^{43})_2 C(R^{43})_2 C(R^{43})_2$—;

Ring B4 is fused bicyclic heteroaryl comprising at least two nitrogen atoms in the rings, or fused heteroaryl comprising at least one non-aromatic ring;

each $R^{41}$ is independently halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{42}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{43}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)R^b$, —$NR^aC(=O)OR^a$, (—$NRaC(=O)NRcRd$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, aryl, and heteroaryl is optionally substituted with one, two, or three of halogen, $C_1$-$C_6$ alkyl, $C_1$-$C_6$ haloalkyl-$OR^a$, or —$NR^cR^d$;

$R^{44}$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{45}$ is independently hydrogen, halogen, —CN, —$OR^a$, —$SR^a$, —$S(=O)R^b$, (—$S(=O)_2R^d$), —$NO_2$, —$NR^cR^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{45}$ substituents on the same carbon are taken together to form an oxo;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n4 is 1-5;

m4 is 1-4; and q4 is 1-5.

In some embodiments of a compound of Formula (V) or Formula (Va), each $R^{41}$ is independently halogen. In some embodiments of a compound of Formula (V) or Formula (Va), each $R^{41}$ is independently fluoro. In some embodiments of a compound of Formula (V) or Formula (Va), each $R^{41}$ is independently $C_1$-$C_6$ alkyl. In some embodiments of a compound of Formula (V) or Formula (Va), each $R^{41}$ is independently $C_1$-$C_6$ haloalkyl.

In some embodiments of a compound of Formula (V) or Formula (Va), n4 is 1. In some embodiments of a compound of Formula (V) or Formula (Va), n4 is 2. In some embodiments of a compound of Formula (V) or Formula (Va), n4 is 3. In some embodiments of a compound of Formula (V) or Formula (Va), n4 is 4. In some embodiments of a compound of Formula (V) or Formula (Va), n4 is 5.

In some embodiments of a compound of Formula (V) or Formula (Va), each $R^{42}$ is independently halogen. In some embodiments of a compound of Formula (V) or Formula (Va), each $R^{42}$ is independently $C_1$-$C_6$ alkyl. In some embodiments of a compound of Formula (V) or Formula (Va), each $R^{42}$ is independently $C_1$-$C_6$ haloalkyl. In some embodiments of a compound of Formula (V) or Formula (Va), each $R^{42}$ is hydrogen.

In some embodiments of a compound of Formula (V) or Formula (Va), m4 is 1. In some embodiments of a compound of Formula (V) or Formula (Va), m4 is 2. In some embodiments of a compound of Formula (V) or Formula (Va), m4 is 3. In some embodiments of a compound of Formula (V) or Formula (Va), m4 is 4.

In some embodiments of a compound of Formula (V) or Formula (Va), each $R^{43}$ is independently halogen. In some embodiments of a compound of Formula (V) or Formula (Va), each $R^{43}$ is independently $C_1$-$C_6$ alkyl. In some embodiments of a compound of Formula (V) or Formula (Va), each $R^{43}$ is independently $C_1$-$C_6$ haloalkyl. In some embodiments of a compound of Formula (V) or Formula (Va), each $R^{43}$ is hydrogen.

In some embodiments of a compound of Formula (V) or Formula (Va), $R^{44}$ is hydrogen or $C_1$-$C_6$ alkyl. In some embodiments of a compound of Formula (V) or Formula (Va), $R^{44}$ is $C_1$-$C_6$ alkyl. In some embodiments of a compound of Formula (V) or Formula (Va), $R^{44}$ is hydrogen. In some embodiments of a compound of Formula (V) or Formula (Va), $R^{44}$ is methyl.

In some embodiments of a compound of Formula (V) or Formula (Va), q4 is 1. In some embodiments of a compound of Formula (V) or Formula (Va), q4 is 2. In some embodiments of a compound of Formula (V) or Formula (Va), q4 is 3. In some embodiments of a compound of Formula (V) or Formula (Va), q4 is 4. In some embodiments of a compound of Formula (V) or Formula (Va), q4 is 5.

In some embodiments of a compound of Formula (V) or Formula (Va), Ring B4 is fused bicyclic heteroaryl comprising at least two nitrogen atoms in the rings. In some embodiments of a compound of Formula (V) or Formula (Va), Ring B4 is cinnolinyl. In some embodiments of a compound of Formula (V) or Formula (Va), Ring B4 is quinazolinyl. In some embodiments of a compound of Formula (V) or Formula (Va), Ring B4 is quinoxalinyl. In some embodiments of a compound of Formula (V) or Formula (Va), Ring B4 is indazolyl. In some embodiments of a compound of Formula (V) or Formula (Va), Ring B4 is benzoimidazolyl.

In some embodiments of a compound of Formula (V) or Formula (Va), Ring B4 is selected from the group consisting of:

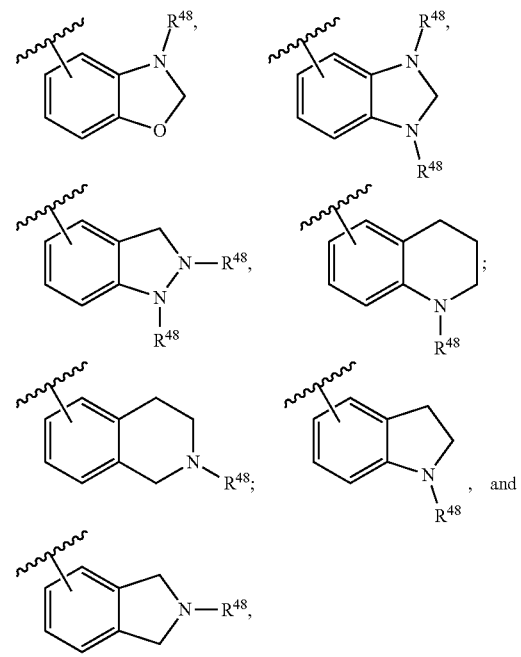

each optionally substituted with one or more $R^{45}$;
wherein:
each $R^{48}$ is independently hydrogen, —S(=O)$R^b$, —S(=O)$_2R^d$, —S(=O)$_2$NR$^c$R$^d$, —C(=O)$R^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

In some embodiments of a compound of Formula (V) or Formula (Va), Ring B4 is

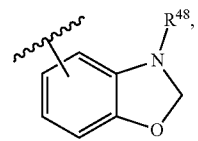

optionally substituted with at least one $R^{45}$. In some embodiments of a compound of Formula (V) or Formula (Va), Ring B4 is

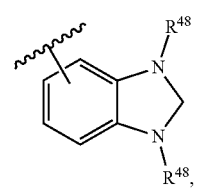

optionally substituted with at least one $R^{45}$. In some embodiments of a compound of Formula (V) or Formula (Va), Ring B4 is

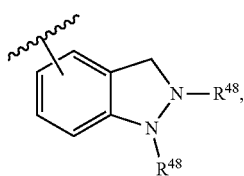

optionally substituted with at least one $R^{45}$. In some embodiments of a compound of Formula (V) or Formula (Va), Ring B4 is

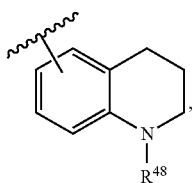

optionally substituted with at least one $R^{45}$. In some embodiments of a compound of Formula (V) or Formula (Va), Ring B4 is

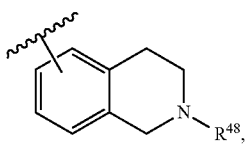

optionally substituted with at least one $R^{45}$. In some embodiments of a compound of Formula (V) or Formula (Va), Ring B4 is

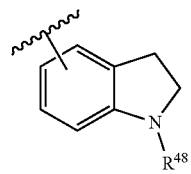

optionally substituted with at least one $R^{45}$. In some embodiments of a compound of Formula (V) or Formula (Va), Ring B4 is

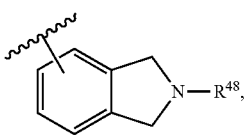

each optionally substituted with one or more $R^{45}$.

In some embodiments of a compound of Formula (V) or Formula (Va), each $R^{45}$ is independently hydrogen. In some embodiments of a compound of Formula (V) or Formula (Va), each $R^{45}$ is independently —S(=O)$R^b$, —S(=O)$_2R^d$, —S(=O)$_2$NR$^c R^d$, —C(=O)$R^b$, —CO$_2R^a$, —C(=O)NR$^c$ R$^d$. In some embodiments of a compound of Formula (V) or Formula (Va), $R^{45}$ is independently $C_1$-$C_6$ alkyl, $C_2$-$C_6$ alkenyl, $C_2$-$C_6$ alkynyl, $C_1$-$C_6$ heteroalkyl; wherein the alkyl, alkenyl, alkynyl, and heteroalkyl is optionally substituted with one, two, or three of halogen, —OR$^a$, or —NR$^c$R$^d$. In some embodiments of a compound of Formula (V) or Formula (Va), each $R^{45}$ is independently $C_3$-$C_8$ cycloalkyl, $C_2$-$C_8$ heterocycloalkyl, aryl, or heteroaryl; wherein the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$. In some embodiments of a compound of Formula (V) or Formula (Va), two $R^{45}$ on the same carbon are taken together to form an oxo. In some embodiments of a compound of Formula (V) or Formula (Va), $R^{45}$ is hydrogen or $C_1$-$C_5$ alkyl.

In some embodiments of a compound of Formula (V) or Formula (Va), each $R^{48}$ is independently hydrogen. In some embodiments of a compound of Formula (V) or Formula (Va), each $R^{48}$ is independently halogen. In some embodiments of a compound of Formula (V) or Formula (Va), each $R^{48}$ is independently taken together to form an oxo. In some embodiments of a compound of Formula (V) or Formula (Va), each $R^{48}$ is independently —CN, —OR$^a$, —SR$^a$, —S(=O)$R^b$, —NO$_2$. In some embodiments of a compound of Formula (V) or Formula (Va), each $R^{48}$ is independently —NR$^c$R$^d$, —S(=O)$_2R^d$, —NR$^a$S(=O)$_2R^d$, —S(=O)$_2$NR$^c$R$^d$, —C(=O)$R^b$, —OC(=O)$R^b$, —CO$_2R^a$, —OCO$_2R^a$, —C(=O)NR$^c$R$^d$, —OC(=O)NR$^c$R$^d$, —NR$^a$C(=O)$R^b$, —NR$^a$C(=O)OR$^a$, (—NR$^a$C(=O)NR$^c$R$^d$). In some embodiments of a compound of Formula (V) or Formula (Va), each $R^{48}$ is independently $C_1$-$C_6$ alkyl, $C_2$-$C_6$ alkenyl, $C_2$-$C_6$ alkynyl, $C_1$-$C_6$ heteroalkyl; wherein the alkyl, alkenyl, alkynyl, and heteroalkyl is optionally substituted with one, two, or three of halogen, —OR$^a$, or —NR$^c$R$^d$. In some embodiments of a compound of Formula (V) or Formula (Va), each $R^{48}$ is independently $C_1$-$C_6$ heterocyclyl, $C_2$-$C_8$ heterocycloalkyl, $C_3$-$C_8$ cycloalkyl, aryl, or heteroaryl; wherein the cycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$.

Described herein are compounds of Formula (VI), or a pharmaceutically acceptable salt, solvate, or stereoisomer thereof:

Formula (VI)

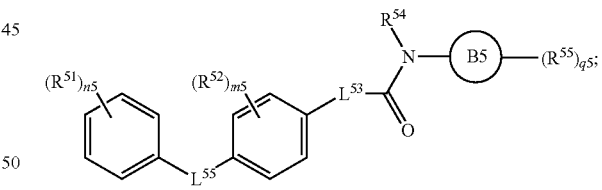

wherein:
$L^{53}$ is —C(R$^{53}$)$_2$C(R$^{53}$)$_2$C(R$^{53}$)$_2$—;
$L^{55}$ is O;
Ring B5 is aryl, heteroaryl, or $C_2$-$C_8$ heterocyclyl;
each $R^{51}$ is independently hydrogen, halogen, —CN, —OR$^a$, —SR$^a$, —S(=O)$R^b$, —NO$_2$, —NR$^c$R$^d$, —S(=O)$_2R^d$, —NR$^a$S(=O)$_2R^d$, —S(=O)$_2$NR$^c$R$^d$, —C(=O)$R^b$, —OC(=O)$R^b$, —CO$_2R^a$, —OCO$_2R^a$, —C(=O)NR$^c$R$^d$, —OC(=O)NR$^c$R$^d$, —NR$^a$C(=O) NR$^c$R$^d$, —NR$^a$C(=O)$R^b$, —NR$^a$C(=O)OR$^a$, —(C$_1$-C$_6$ alkyl)-NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

each $R^{52}$ is independently hydrogen, halogen, —CN, —$OR^a$, —$SR^a$, —S(=O)$R^b$, —$NO_2$, —$NR^c R^d$, —S(=O)$_2 R^d$, —$NR^a$S(=O)$_2 R^d$, —S(=O)$_2 NR^c R^d$, —C(=O)$R^b$, —OC(=O)$R^b$, —$CO_2 R^a$, —$OCO_2 R^a$, —C(=O)$NR^c R^d$, —OC(=O)$NR^c R^d$, —$NR^a$C(=O)$NR^c R^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_{56}$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

each $R^{53}$ is independently hydrogen, halogen, two $R^{53}$ on the same carbon are taken together to form an oxo, —CN, —$OR^a$, —$SR^a$, —S(=O)$R^b$, —$NO_2$, —$NR^c R^d$, —S(=O)$_2 R^d$, —$NR^a$S(=O)$_2 R^d$, —S(=O)$_2 NR^c R^d$, —C(=O)$R^b$, —OC(=O)$R^b$, —$CO_2 R^a$, —$OCO_2 R^a$, —C(=O)$NR^c R^d$, —OC(=O)$NR^c R^d$, —$NR^a$C(=O) $R^b$, —$NR^a$C(=O)$OR^a$, (—$NR^a$C(=O)$NR^c R^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, aryl, and heteroaryl is optionally substituted with one, two, or three $C_1$-$C_6$ alkyl, $C_1$-$C_6$ haloalkyl-$OR^a$, or —$NR^c R^d$;

$R^{54}$ is hydrogen, —S(=O)$R^b$, —S(=O)$_2 R^d$, —S(=O)$_2 NR^c R^d$, —C(=O)$R^b$, —$CO_2 R^a$, —C(=O)$NR^c R^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

each $R^{55}$ is independently hydrogen, halogen, —CN, —$OR^a$, —$SR^a$, —S(=O)$R^b$, (—S(=O)$_2 R^d$), —$NO_2$, —$NR^c R^d$, —$NR^a$S(=O)$_2 R^d$, —S(=O)$_2 NR^c R^d$, —C(=O)$R^b$, —OC(=O)$R^b$, —$CO_2 R^a$, —$OCO_2 R^a$, —C(=O)$NR^c R^d$, —OC(=O)$NR^c R^d$, —$NR^a$C(=O)$NR^c R^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n5 is 1-5;

m5 is 1-4;

q5 is 1-5.

Described herein are compounds of Formula (VI), or a pharmaceutically acceptable salt, solvate, or stereoisomer thereof:

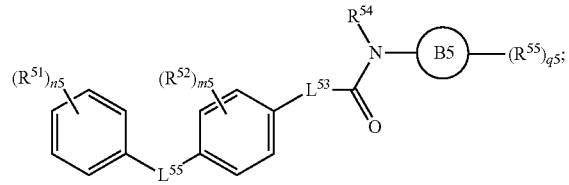

Formula (VI)

wherein:

$L^{53}$ is —C($R^{53}$)$_2$C($R^{53}$)$_2$C($R^{53}$)$_2$—;

$L^{55}$ is O;

Ring B5 is aryl, heteroaryl, or $C_2$-$C_8$ heterocyclyl;

each $R^{51}$ is independently halogen, —CN, —$OR^a$, —$SR^a$, —S(=O)$R^b$, —$NO_2$, —$NR^c R^d$, —S(=O)$_2 R^d$, —$NR^a$S(=O)$_2 R^d$, —S(=O)$_2 NR^c R^d$, —C(=O)$R^b$, —OC(=O)$R^b$, —$CO_2 R^a$, —$OCO_2 R^a$, —C(=O)$NR^c R^d$, —OC(=O)$NR^c R^d$, —$NR^a$C(=O)$NR^c R^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —$OR^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

each $R^{52}$ is independently hydrogen, halogen, —CN, —$OR^a$, —$SR^a$, —S(=O)$R^b$, —$NO_2$, —$NR^c R^d$, —S(=O)$_2 R^d$, —$NR^a$S(=O)$_2 R^d$, —S(=O)$_2 NR^c R^d$, —C(=O)$R^b$, —OC(=O)$R^b$, —$CO_2 R^a$, —$OCO_2 R^a$, —C(=O)$NR^c R^d$, —OC(=O)$NR^c R^d$, —$NR^a$C(=O)$NR^c R^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{53}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, and heteroaryl is optionally substituted with one, two, or three of halogen, $C_1$-$C_6$ alkyl, $C_1$-$C_6$ haloalkyl-OR$^a$, or —NR$^c$R$^d$;

R$^{54}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{55}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n5 is 1-5;

m5 is 1-4; and q5 is 1-5.

In some embodiments of a compound of Formula (VI), Ring B5 is aryl. In some embodiments of a compound of Formula (VI), Ring B5 is phenyl. In some embodiments of a compound of Formula (VI), Ring B5 is naphthyl.

In some embodiments of a compound of Formula (VI), Ring B5 is heterocycloalkyl. In some embodiments of a compound of Formula (VI), Ring B5 is $C_2$-$C_8$ heterocycloalkyl. In some embodiments of a compound of Formula (VI), Ring B5 is pyrrolidinyl. In some embodiments of a compound of Formula (VI), Ring B5 is piperidinyl. In some embodiments of a compound of Formula (VI), Ring B5 is piperazinyl. In some embodiments of a compound of Formula (VI), Ring B5 is pyranyl. In some embodiments of a compound of Formula (VI), Ring B5 is tetrahydrofuranyl. In some embodiments of a compound of Formula (VI), Ring B5 is morpholinyl.

In some embodiments of a compound of Formula (VI), Ring B5 is a 6-membered heteroaryl. In some embodiments of a compound of Formula (VI), Ring B5 is pyrimidinyl. In some embodiments of a compound of Formula (VI), Ring B5 is pyrazinyl. In some embodiments of a compound of Formula (VI), Ring B5 is pyridyl. In some embodiments of a compound of Formula (VI), Ring B5 is a 5-membered heteroaryl. In some embodiments of a compound of Formula (VI), Ring B5 is thiophenyl. In some embodiments of a compound of Formula (VI), Ring B5 is furanyl. In some embodiments of a compound of Formula (VI), Ring B5 is pyrrolyl. In some embodiments of a compound of Formula (VI), Ring B5 is thiazolyl. In some embodiments of a compound of Formula (VI), Ring B5 is oxazolyl. In some embodiments of a compound of Formula (VI), Ring B5 is isoxazolyl. In some embodiments of a compound of Formula (VI), Ring B5 is imidazolyl. In some embodiments of a compound of Formula (VI), Ring B5 is thiadiazolyl. In some embodiments of a compound of Formula (VI), Ring B5 is oxadiazolyl. In some embodiments of a compound of Formula (VI), Ring B5 is pyrazolyl.

In some embodiments of a compound of Formula (VI), each R$^{51}$ is independently halogen, In some embodiments of a compound of Formula (VI), each R$^{51}$ is independently $C_1$-$C_6$ alkyl. In some embodiments of a compound of Formula (VI), each R$^{51}$ is independently $C_1$-$C_6$ haloalkyl. In some embodiments of a compound of Formula (VI), each R$^{51}$ is independently fluoro.

In some embodiments of a compound of Formula (VI), n5 is 1. In some embodiments of a compound of Formula (VI), n5 is 2. In some embodiments of a compound of Formula (VI), n5 is 3. In some embodiments of a compound of Formula (VI), n5 is 4. In some embodiments of a compound of Formula (VI), n5 is 5.

In some embodiments of a compound of Formula (VI), each R$^{52}$ is independently halogen. In some embodiments of a compound of Formula (VI), each $R^{52}$ is independently $C_1$-$C_6$ alkyl. In some embodiments of a compound of Formula (VI), each $R^{52}$ is independently $C_1$-$C_6$ haloalkyl. In some embodiments of a compound of Formula (VI), each $R^{52}$ is hydrogen.

In some embodiments of a compound of Formula (VI), m5 is 1. In some embodiments of a compound of Formula (VI), m5 is 2. In some embodiments of a compound of Formula (VI), m5 is 3. In some embodiments of a compound of Formula (VI), m5 is 4.

In some embodiments of a compound of Formula (VI), each $R^{53}$ is independently halogen. In some embodiments of a compound of Formula (VI), each $R^{53}$ is independently $C_1$-$C_6$ alkyl. In some embodiments of a compound of Formula (VI), each $R^{53}$ is independently $C_1$-$C_6$ haloalkyl. In some embodiments of a compound of Formula (VI), each $R^{53}$ is hydrogen.

In some embodiments of a compound of Formula (VI), $R^{54}$ is hydrogen or $C_1$-$C_6$ alkyl. In some embodiments of a compound of Formula (VI), $R^{54}$ is $C_1$-$C_6$ alkyl. In some embodiments of a compound of Formula (VI), $R^{54}$ is hydrogen.

In some embodiments of a compound of Formula (VI), each $R^{55}$ is independently hydrogen. In some embodiments of a compound of Formula (VI), each $R^{55}$ is independently halogen. In some embodiments of a compound of Formula (VI), each $R^{55}$ is independently —OH. In some embodiments of a compound of Formula (VI), each $R^{55}$ is independently $C_1$-$C_6$ alkyl. In some embodiments of a compound of Formula (VI), each $R^{55}$ is independently $C_1$-$C_6$ haloalkyl. In some embodiments of a compound of Formula (VI), each $R^{55}$ is independently methyl.

In some embodiments of a compound of Formula (VI), q5 is 1. In some embodiments of a compound of Formula (VI), q5 is 2. In some embodiments of a compound of Formula (VI), q5 is 3. In some embodiments of a compound of Formula (VI), q5 is 4. In some embodiments of a compound of Formula (VI), q5 is 5.

Described herein are compounds of Formula (VII), or a pharmaceutically acceptable salt, solvate, or stereoisomer thereof:

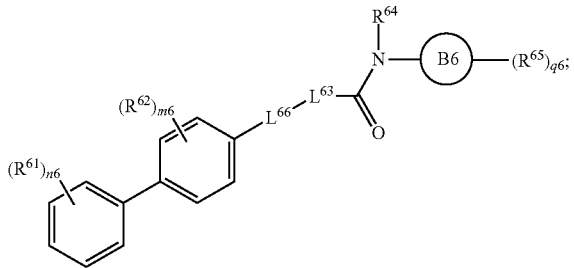

Formula (VII)

wherein:
$L^{63}$ is —C($R^{63}$)$_2$C($R^{63}$)$_2$—;
$L^{66}$ is O, NR$^{66}$, S, SO, or SO$_2$;
Ring B6 is aryl, heteroaryl, or $C_2$-$C_8$ heterocyclyl;
each $R^{61}$ is independently hydrogen, fluoro, chloro, bromo, iodo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O) NR$^c$R$^d$, —NR$^a$C(=O)NR$^c$R$^d$, —NR$^a$C(=O)R$^b$, —NR$^a$C(=O)OR$^a$, —N=CR$^a$R$^b$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{62}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{63}$ is independently hydrogen, halogen, two $R^{63}$ are taken together to form an oxo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_2$-$C_8$ heterocycloalkyl, $C_3$-$C_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

$R^{64}$ and $R^{66}$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{65}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_{56}$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ are independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

n6 is 1-5;
m6 is 1-4; and
q6 is 1-5.

Described herein are compounds of Formula (VII), or a pharmaceutically acceptable salt, solvate, or stereoisomer thereof:

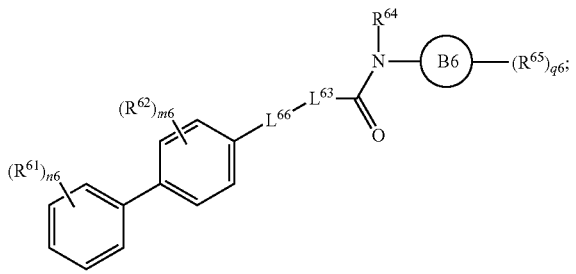

Formula (VII)

wherein:
L$^{63}$ is —C(R$^{63}$)$_2$C(R$^{63}$)$_2$—;
L$^{66}$ is O, NR$^{66}$, S, SO, or SO$_2$;
Ring B6 is aryl, heteroaryl, or C$_2$-C$_8$ heterocyclyl;
each R$^{61}$ is independently fluoro, bromo, iodo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{62}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{63}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), C$_1$-C$_6$ alkyl, C$_2$-C$_6$ alkenyl, C$_2$-C$_6$ alkynyl, C$_1$-C$_6$ heteroalkyl, C$_2$-C$_8$ heterocycloalkyl, C$_3$-C$_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, aryl, and heteroaryl is optionally substituted with one, two, or three of halogen, C$_1$-C$_6$ alkyl, C$_1$-C$_6$ haloalkyl-OR$^a$, or —NR$^c$R$^d$;

R$^{64}$ and R$^{66}$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{65}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_{56}$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n6 is 1-5;
m6 is 1-4; and
q6 is 1-5.

In some embodiments of a compound of Formula (VII), $L^{66}$ is O, NR$^{66}$, or S. In some embodiments of a compound of Formula (VII), $L^{66}$ is O or NR$^{66}$. In some embodiments of a compound of Formula (VII), $L^{66}$ is O.

In some embodiments of a compound of Formula (VII), the compound has the Formula (VIIa), or a pharmaceutically acceptable salt, solvate, or stereoisomer thereof:

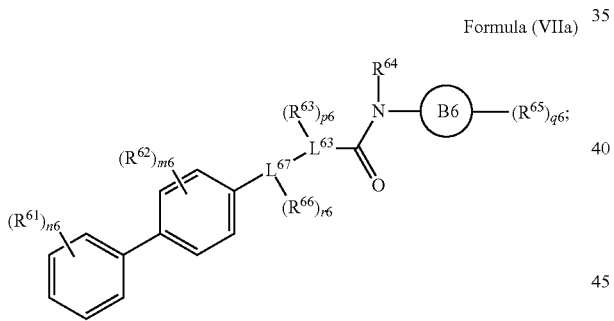

Formula (VIIa)

wherein:
$L^{63}$ is —C(R$^{63}$)$_2$C(R$^{63}$)$_2$—;
$L^{67}$ is NR$^{66}$, S, SO, or SO$_2$;
Ring B6 is aryl, heteroaryl, or $C_2$-$C_8$ heterocyclyl;
each $R^{61}$ is independently fluoro, bromo, iodo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, —N=CR$^a$R$^b$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{62}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_{56}$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{63}$ is independently hydrogen, halogen, two $R^{63}$ are taken together to form an oxo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_2$-$C_8$ heterocycloalkyl, $C_3$-$C_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

$R^{64}$ and $R^{66}$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{65}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ are independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

n6 is 1-4;
m6 is 1-4; and
q6 is 1-5.

In some embodiments of a compound of Formula (VII), the compound has the Formula (VIIa), or a pharmaceutically acceptable salt, solvate, or stereoisomer thereof:

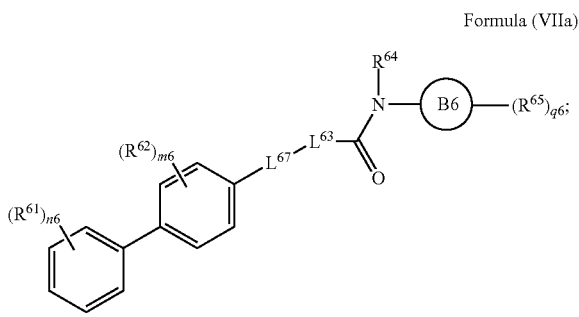

Formula (VIIa)

wherein:
L$^{63}$ is —C(R$^{53}$)$_2$C(R$^{53}$)$_2$—;
L$^{67}$ is NR$^{66}$, S, SO, or SO$_2$;
Ring B6 is aryl, heteroaryl, or C$_2$-C$_8$ heterocyclyl;

each R$^{61}$ is independently fluoro, bromo, iodo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{62}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{63}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), C$_1$-C$_6$ alkyl, C$_2$-C$_6$ alkenyl, C$_2$-C$_6$ alkynyl, C$_1$-C$_6$ heteroalkyl, C$_2$-C$_8$ heterocycloalkyl, C$_3$-C$_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, aryl, and heteroaryl is optionally substituted with one, two, or three of halogen, C$_1$-C$_6$ alkyl, C$_1$-C$_6$ haloalkyl- OR$^a$, or —NR$^c$R$^d$;

R$^{64}$ and R$^{66}$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^{65}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ are independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n6 is 1-4;

m6 is 1-4; and q6 is 1-5.

In some embodiments of a compound of Formula (VIIa), L$^{67}$ is NR$^{66}$ or S. In some embodiments of a compound of Formula (VIIa), L$^{66}$ is NR$^{66}$.

In some embodiments of a compound of Formula (VII) or Formula (VIIa), Ring B6 is aryl. In some embodiments of a compound of Formula (VII) or Formula (VIIa), Ring B6 is phenyl. In some embodiments of a compound of Formula (VII) or Formula (VIIa), Ring B6 is napthyl.

In some embodiments of a compound of Formula (VII) or Formula (VIIa), Ring B6 is heterocycloalkyl. In some embodiments of a compound of Formula (VII) or Formula (VIIa), Ring B6 is $C_2$-$C_8$ heterocycloalkyl. In some embodiments of a compound of Formula (VII) or Formula (VIIa), Ring B6 is pyrrolidinyl. In some embodiments of a compound of Formula (VII) or Formula (VIIa), Ring B6 is piperidinyl. In some embodiments of a compound of Formula (VII) or Formula (VIIa), Ring B6 is piperazinyl. In some embodiments of a compound of Formula (VII) or Formula (VIIa), Ring B6 is pyranyl. In some embodiments of a compound of Formula (VII) or Formula (VIIa), Ring B6 is tetrahydrofuranyl. In some embodiments of a compound of Formula (VII) or Formula (VIIa), Ring B6 is morpholinyl.

In some embodiments of a compound of Formula (VII) or Formula (VIIa), Ring B6 is heteroaryl. In some embodiments of a compound of Formula (VII) or Formula (VIIa), Ring B6 is a 6-membered heteroaryl. In some embodiments of a compound of Formula (VII) or Formula (VIIa), Ring B6 is pyrimidinyl. In some embodiments of a compound of Formula (VII) or Formula (VIIa), Ring B6 is pyrazinyl. In some embodiments of a compound of Formula (VII) or Formula (VIIa), Ring B6 is pyridyl. In some embodiments of a compound of Formula (VII) or Formula (VIIa), Ring B6 is a 5-membered heteroaryl. In some embodiments of a compound of Formula (VII) or Formula (VIIa), Ring B6 is thiophenyl. In some embodiments of a compound of Formula (VII) or Formula (VIIa), Ring B6 is furanyl. In some embodiments of a compound of Formula (VII) or Formula (VIIa), Ring B6 is pyrrolyl. In some embodiments of a compound of Formula (VII) or Formula (VIIa), Ring B6 is thiazolyl. In some embodiments of a compound of Formula (VII) or Formula (VIIa), Ring B6 is oxazolyl. In some embodiments of a compound of Formula (VII) or Formula (VIIa), Ring B6 is isoxazolyl. In some embodiments of a compound of Formula (VII) or Formula (VIIa), Ring B6 is imidazolyl. In some embodiments of a compound of Formula (VII) or Formula (VIIa), Ring B6 is thiadiazolyl. In some embodiments of a compound of Formula (VII) or Formula (VIIa), Ring B6 is oxadiazolyl. In some embodiments of a compound of Formula (VII) or Formula (VIIa), Ring B6 is pyrazolyl.

In some embodiments of a compound of Formula (VII) or Formula (VIIa), each R$^{61}$ is independently halogen. In some embodiments of a compound of Formula (VII) or Formula (VIIa), each R$^{61}$ is independently $C_1$-$C_6$ alkyl. In some embodiments of a compound of Formula (VII) or Formula (VIIa), each R$^{61}$ is independently $C_1$-$C_6$ haloalkyl. In some embodiments of a compound of Formula (VII) or Formula (VIIa), each R$^{61}$ is independently fluoro.

In some embodiments of a compound of Formula (VII) or Formula (VIIa), n6 is 1. In some embodiments of a compound of Formula (VII) or Formula (VIIa), n6 is 2. In some embodiments of a compound of Formula (VII) or Formula (VIIa), n6 is 3. In some embodiments of a compound of Formula (VII) or Formula (VIIa), n6 is 4.

In some embodiments of a compound of Formula (VII) or Formula (VIIa), each R$^{62}$ is independently hydrogen. In some embodiments of a compound of Formula (VII) or Formula (VIIa), each R$^{62}$ is independently halogen. In some embodiments of a compound of Formula (VII) or Formula (VIIa), each R$^{62}$ is independently $C_1$-$C_6$ alkyl. In some embodiments of a compound of Formula (VII) or Formula (VIIa), each R$^{62}$ is independently $C_1$-$C_6$ haloalkyl.

In some embodiments of a compound of Formula (VII) or Formula (VIIa), m6 is 1. In some embodiments of a compound of Formula (VII) or Formula (VIIa), m6 is 2. In some embodiments of a compound of Formula (VII) or Formula (VIIa), m6 is 3. In some embodiments of a compound of Formula (VII) or Formula (VIIa), m6 is 4.

In some embodiments of a compound of Formula (VII) or Formula (VIIa), each R$^{63}$ is independently halogen. In some embodiments of a compound of Formula (VII) or Formula (VIIa), each R$^{63}$ is independently $C_1$-$C_6$ alkyl. In some embodiments of a compound of Formula (VII) or Formula (VIIa), each R$^{63}$ is independently $C_1$-$C_6$ haloalkyl. In some embodiments of a compound of Formula (VII) or Formula (VIIa), each R$^{63}$ is hydrogen.

In some embodiments of a compound of Formula (VII) or Formula (VIIa), R$^{64}$ is hydrogen or $C_1$-$C_6$ alkyl. In some embodiments of a compound of Formula (VII) or Formula (VIIa), R$^{64}$ is $C_1$-$C_6$ alkyl. In some embodiments of a compound of Formula (VII) or Formula (VIIa), R$^{64}$ is hydrogen.

In some embodiments of a compound of Formula (VII) or Formula (VIIa), each R$^{65}$ is independently hydrogen. In some embodiments of a compound of Formula (VII) or Formula (VIIa), each R$^{65}$ is independently halogen. In some embodiments of a compound of Formula (VII) or Formula (VIIa), each R$^{65}$ is independently —OH. In some embodiments of a compound of Formula (VII) or Formula (VIIa), each R$^{65}$ is independently $C_1$-$C_6$ alkyl. In some embodiments of a compound of Formula (VII) or Formula (VIIa), each R$^{65}$ is independently hydrogen or $C_1$-$C_6$ haloalkyl. In some embodiments of a compound of Formula (VII) or Formula (VIIa), each R$^{65}$ is independently methyl.

In some embodiments of a compound of Formula (VII) or Formula (VIIa), q6 is 1. In some embodiments of a compound of Formula (VII) or Formula (VIIa), q6 is 2. In some embodiments of a compound of Formula (VII) or Formula (VIIa), q6 is 3. In some embodiments of a compound of Formula (VII) or Formula (VIIa), q6 is 4.

Described herein are compounds of Formula (VIII), or a pharmaceutically acceptable salt, solvate, or stereoisomer thereof:

Formula (VIII)

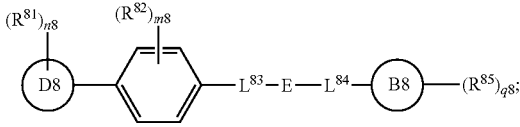

wherein:
$L^{83}$ is —C($R^{83}$)$_2$C($R^{83}$)$_2$C($R^{83}$)$_2$—, —C($R^{83}$)$_2$C($R^{83}$)$_2$—, —OC($R^{83}$)$_2$C($R^{83}$)—, or —SC($R^{83}$)$_2$C($R^{83}$)—;

E is —C(=O)N$R^{84}$—, —N$R^{84}$C(=O)—, —S(=O)$_2$N$R^{84}$—, —N$R^{84}$S(=O)$_2$—, —N$R^{84}$C(=O)O—, —OC(=O) N$R^{84}$—, —N$R^{84}$C(=O) N$R^{84}$—, oxadiazole, thiadiazole, or sulfonamide;

$L^{84}$ is a bond or —C$R^{86}R^{87}$—;

Rings D8 and B8 are independently aryl, heteroaryl, $C_2$-$C_8$ heterocyclyl, or $C_3$-$C_8$ cycloalkyl; wherein D8 is C-linked or N-linked;

each $R^{81}$ is independently hydrogen, halogen, —CN, —O$R^a$, —S$R^a$, —S(=O)$R^b$, —NO$_2$, —N$R^cR^d$, —S(=O)$_2R^d$, —N$R^a$S(=O)$_2R^d$, —S(=O)$_2$N$R^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^a$C(=O) N$R^cR^d$, —N$R^a$C(=O)$R^b$, —N$R^a$C(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —O$R^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;

each $R^{82}$ is independently hydrogen, halogen, —CN, —O$R^a$, —S$R^a$, —S(=O)$R^b$, —NO$_2$, —N$R^cR^d$, —S(=O)$_2R^d$, —N$R^a$S(=O)$_2R^d$, —S(=O)$_2$N$R^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^a$C(=O) N$R^cR^d$, —N$R^a$C(=O)$R^b$, —N$R^a$C(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;

each $R^{83}$ is independently hydrogen, halogen, —CN, —O$R^a$, —S$R^a$, —S(=O)$R^b$, —NO$_2$, —N$R^cR^d$, —S(=O)$_2R^d$, —N$R^a$S(=O)$_2R^d$, —S(=O)$_2$N$R^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^a$C(=O) $R^b$, —N$R^a$C(=O)O$R^a$, (—N$R^a$C(=O)N$R^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —O$R^a$, or —N$R^cR^d$; and the cycloalkyl, and heteroaryl is optionally substituted with one, two, or three of halogen, $C_1$-$C_6$ alkyl, $C_1$-$C_6$ haloalkyl-O$R^a$, or —N$R^cR^d$;

$R^{84}$ is hydrogen, —S(=O)$R^b$, —S(=O)$_2R^b$, —S(=O)$_2$N$R^cR^d$, —C(=O)$R^b$, —CO$_2R^a$, —C(=O)N$R^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;

each $R^{85}$ is independently hydrogen, halogen, —CN, —O$R^a$, —S$R^a$, —S(=O)$R^b$, (—S(=O)$_2R^d$), —NO$_2$, —N$R^cR^d$, —N$R^a$S(=O)$_2R^d$, —S(=O)$_2$N$R^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^a$C(=O) N$R^cR^d$, —N$R^a$C(=O)$R^b$, —N$R^a$C(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$;

or two $R^{85}$ substituents on the same carbon are taken together to form an oxo;

$R^{86}$ and $R^{87}$ are independently hydrogen, halogen, —CN, —O$R^a$, —S$R^a$, —S(=O)$R^b$, —NO$_2$, —N$R^cR^d$, —S(=O)$_2R^d$, —N$R^a$S(=O)$_2R^d$, —S(=O)$_2$N$R^cR^d$, —C(=O)$R^b$, —OC(=O)$R^b$, —CO$_2R^a$, —OCO$_2R^a$, —C(=O)N$R^cR^d$, —OC(=O)N$R^cR^d$, —N$R^a$C(=O) N$R^cR^d$, —N$R^a$C(=O)$R^b$, —N$R^a$C(=O)O$R^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —O$R^a$, or —N$R^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —O$R^a$, or —N$R^cR^d$.

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;

m8 is 1-4;

q8 is 1-5.

Described herein are compounds of Formula (VIII), or a pharmaceutically acceptable salt, solvate, or stereoisomer thereof:

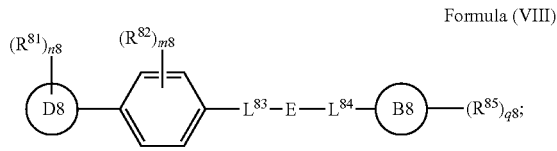

Formula (VIII)

wherein:

$L^{83}$ is —C(R$^{83}$)$_2$C(R$^{83}$)$_2$C(R$^{83}$)$_2$—, —C(R$^{83}$)$_2$C(R$^{83}$)$_2$—, —OC(R$^{83}$)$_2$C(R$^{83}$)—, or —SC(R$^{83}$)$_2$C(R$^{83}$)—;

E is —C(=O)NR$^{84}$—, —NR$^{84}$C(=O)—, —S(=O)$_2$NR$^{84}$—, —NR$^{84}$S(=O)$_2$—, —NR$^{84}$C(=O)O—, —OC(=O)NR$^{84}$—, —NR$^{84}$C(=O)NR$^{84}$—, oxadiazole, thiadiazole, or sulfonamide;

$L^{84}$ is a bond or —CR$^{86}$R$^{87}$—;

Rings D8 and B8 are independently heteroaryl, $C_2$-$C_8$ heterocyclyl, or cycloalkyl; wherein D8 is C-linked or N-linked;

each $R^{81}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{82}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{83}$ is independently hydrogen, halogen, two $R^{83}$ on the same carbon are taken together to form an oxo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_{10}$ heterocycloalkyl, $C_3$-$C_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

or two $R^{83}$ substituents on the same carbon are taken together to form a $C_3$-$C_8$ cycloalkyl;

$R^{84}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{85}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

or two $R^{85}$ substituents on the same carbon are taken together to form an oxo;

$R^{86}$ and $R^{87}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;

m8 is 1-4;

q8 is 1-5.

In some embodiments of a compound of Formula (VIII), $L^{83}$ is a bond. In some embodiments of a compound of Formula (VIII), $L^{83}$ is —CR$^{83}$R$^{83}$—. In some embodiments of a compound of Formula (V), $L^{83}$ is —C(R$^{83}$)$_2$C(R$^{83}$)$_2$C(R$^{83}$)$_2$—. In some embodiments of a compound of Formula (V), $L^{83}$ is —OC(R$^{83}$)$_2$C(R$^{83}$)—. In some embodiments of a compound of Formula (VIII), $L^{83}$ is —SC(R$^{83}$)$_2$C(R$^{83}$)—. $R^{83}$ is independently hydrogen. In some embodiments of a compound of Formula (VIII), $R^{83}$ is independently halogen. In some embodiments of a compound of Formula (VIII), $R^{83}$ is independently fluoro. In some embodiments of a compound of Formula (VIII), $R^{83}$ is independently aryl. In some embodiments of a compound of Formula (VIII), $R^{83}$ is independently heteroaryl. In some embodiments of a compound of Formula (VIII), $R^{83}$ is independently —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl; wherein the alkyl, alkenyl, alkynyl, and heteroalkyl is optionally substituted with one, two, or three of halogen, —OR$^a$, or —NR$^c$R$^d$; In some embodiments of a compound of Formula (VIII), $R^{83}$ is independently $C_3$-$C_8$ cycloalkyl, $C_2$-$C_8$ heterocycloalkyl; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

In some embodiments of a compound of Formula (VIII), $L^{83}$ is a bond. In some embodiments of a compound of Formula (VIII), $L^{83}$ is —CR$^{83}$R$^{83}$—. In some embodiments of a compound of Formula (V), $L^{83}$ is —C(R$^{83}$)$_2$C(R$^{83}$)$_2$C(R$^{83}$)$_2$—. In some embodiments of a compound of Formula (VIII), D8 is aryl and B8 is heterocyclyl. In some embodiments of a compound of Formula (VIII), D8 is aryl and B8 is heteroaryl. In some embodiments of a compound of Formula (VIII), D8 is heteroaryl and B8 is heterocyclyl. In some embodiments of a compound of Formula (VIII), D8 is heteroaryl and B8 is aryl. In some embodiments of a compound of Formula (VIII), D8 is aryl and B8 is aryl. In some embodiments of a compound of Formula (VIII), D8 is heteroaryl and B8 is heteroaryl. In some embodiments of a compound of Formula (VIII), $R^{81}$ is halogen. In some embodiments of a compound of Formula (VIII), E is —C(=O)NR$^{84}$—. In some embodiments of a compound of Formula (VIII), E is —NR$^{84}$C(=O)—. In some embodiments of a compound of Formula (VIII), $R^{84}$ is hydrogen or $C_1$-$C_6$ alkyl. In some embodiments of a compound of Formula (VIII), $L^{84}$ is a bond. In some embodiments of a compound of Formula (VIII), $L^{84}$ is —CR$^{86}$R$^{87}$—. In some embodiments of a compound of Formula (VIII), $R^{86}$ and $R^{87}$ are hydrogen or $C_1$-$C_6$ alkyl.

In some embodiments of a compound of Formula (VIII), $L^{84}$ is a bond. In some embodiments of a compound of Formula (VIII), $L^{84}$ is —CR$^{86}$R$^{87}$—. In some embodiments of a compound of Formula (VIII), $R^{86}$ and $R^{87}$ are independently hydrogen. In some embodiments of a compound of Formula (VIII), $R^{86}$ and $R^{87}$ are independently halogen. In some embodiments of a compound of Formula (VIII), $R^{86}$ and $R^{87}$ are independently fluoro. In some embodiments of a compound of Formula (VIII), $R^{86}$ and $R^{87}$ are independently aryl. In some embodiments of a compound of Formula (VIII), $R^{86}$ and $R^{87}$ are independently heteroaryl. In some embodiments of a compound of Formula (VIII), $R^{86}$ and $R^{87}$ are independently —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl; wherein the alkyl, alkenyl, alkynyl, and heteroalkyl is optionally substituted with one, two, or three of halogen, —OR$^a$, or —NR$^c$R$^d$; In some embodiments of a compound of Formula (VIII), $R^{46}$ and $R^{47}$ are independently $C_3$-$C_8$ cycloalkyl, $C_2$-$C_8$ heterocycloalkyl; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

In some embodiments of a compound of Formula (VIII), Rings D8 and B8 are independently heterocycloalkyl. In some embodiments of a compound of Formula (VIII), Rings D8 and B8 are independently $C_2$-$C_8$ heterocycloalkyl. In some embodiments of a compound of Formula (VIII), Rings D8 and B8 are independently pyrrolidinyl. In some embodiments of a compound of Formula (VIII), Rings D8 and B8 are independently piperidinyl. In some embodiments of a compound of Formula (VIII), Rings D8 and B8 are independently piperazinyl. In some embodiments of a compound of Formula (VIII), Rings D8 and B8 are independently pyranyl. In some embodiments of a compound of Formula (VIII), Rings D8 and B8 are independently tetrahydrofuranyl. In some embodiments of a compound of Formula (VIII), Rings D8 and B8 are independently morpholinyl.

In some embodiments of a compound of Formula (VIII), Rings D8 and B8 are independently aryl. In some embodiments of a compound of Formula (VIII), Rings D8 and B8 are independently phenyl.

In some embodiments of a compound of Formula (VIII), Rings D8 and B8 are independently heteroaryl.

In some embodiments of a compound of Formula (VIII), Rings D8 and B8 are independently a 6-membered heteroaryl. In some embodiments of a compound of Formula (VIII), Rings D8 and B8 are independently pyrimidinyl. In some embodiments of a compound of Formula (VIII), Rings D8 and B8 are independently pyrazinyl. In some embodiments of a compound of Formula (VIII), Rings D8 and B8 are independently pyridyl. In some embodiments of a compound of Formula (VIII), Rings D8 and B8 are independently a 5-membered heteroaryl. In some embodiments of a compound of Formula (VIII), Rings D8 and B8 are independently thiophenyl. In some embodiments of a compound of Formula (VIII), Rings D8 and B8 are independently furanyl. In some embodiments of a compound of Formula (VIII), Rings D8 and B8 are independently pyrrolyl. In some embodiments of a compound of Formula (VIII), Rings D8 and B8 are independently thiazolyl. In some embodiments of a compound of Formula (VIII), Rings D8 and B8 are independently oxazolyl. In some embodiments of a compound of Formula (VIII), Rings D8 and B8 are independently isoxazolyl. In some embodiments of a compound of Formula (VIII), Rings D8 and B8 are independently imidazolyl. In some embodiments of a compound of Formula (VIII), Rings D8 and B8 are independently pyrazolyl. In some embodiments of a compound of Formula (VIII), Rings D8 and B8 are independently thiadiazolyl. In some embodiments of a compound of Formula (VIII), Rings D8 and B8 are independently oxadiazolyl. In some embodiments of a compound of Formula (VIII), Rings D8 and B8 are independently $C_7$-$C_9$ heteroaryl. In some embodiments of a compound of Formula (VIII), Rings D8 and B8 are independently indolyl. In some embodiments of a compound of Formula (VIII), Rings D8 and B8 are independently indazolyl. In some embodiments of a compound of Formula (VIII), Rings D8 and B8 are independently benzofuranyl. In some embodiments of a compound of Formula (VIII), Rings D8 and B8 are independently a fused bicyclic ring.

Described herein are compounds of Formula (VIII), or a pharmaceutically acceptable salt, solvate, or stereoisomer thereof:

Formula (VIIIa)

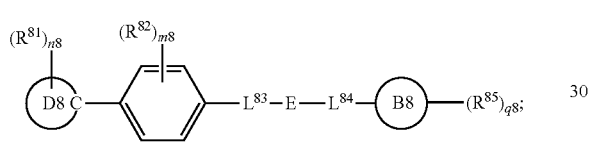

wherein:
$L^{83}$ is —C($R^{83}$)$_2$C($R^{83}$)$_2$C($R^{83}$)$_2$—;
E is —C(=O)NR$^{84}$— or —NR$^{84}$C(=O)—;
$L^{84}$ is a bond or —CR$^{86}$R$^{87}$—;
Rings D8 and B8 are independently heteroaryl or $C_2$-$C_8$ heterocyclyl;
each $R^{81}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
each $R^{82}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{83}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, and heteroaryl is optionally substituted with one, two, or three of halogen, $C_1$-$C_6$ alkyl, $C_1$-$C_6$ haloalkyl-OR$^a$, or —NR$^c$R$^d$;
$R^{84}$ is hydrogen, —S(=O)R$^b$, —S(=O)$_2$R$^d$, —S(=O)$_2$ NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
each $R^{85}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
or two $R^{85}$ substituents on the same carbon are taken together to form an oxo;
$R^{86}$ and $R^{87}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each R$^c$ and R$^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;
m8 is 1-4;
q8 is 1-5.

Described herein are compounds of Formula (VIIIb), or a pharmaceutically acceptable salt, solvate, or stereoisomer thereof:

Formula (VIIIb)

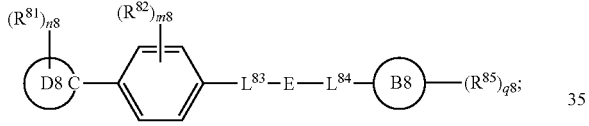

wherein:
L$^{83}$ is —C(R$^{83}$)$_2$C(R$^{83}$)$_2$C(R$^{83}$)$_2$—;
E is —C(=O)NR$^{84}$— or —NR$^{84}$C(=O)—;
L$^{84}$ is a bond or —CR$^{86}$R$^{87}$—;
Ring D8 and B8 are independently aryl, heteroaryl, or $C_2$-$C_8$ heterocyclyl, provided that at least one of D8 or B8 is heteroaryl or $C_2$-$C_8$ heterocyclyl;

each R$^{81}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{82}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{83}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, and heteroaryl is optionally substituted with one, two, or three of halogen, $C_1$-$C_6$ alkyl, $C_1$-$C_6$ haloalkyl-OR$^a$, or —NR$^c$R$^d$;

R$^{84}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^{85}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

or two R$^{85}$ substituents on the same carbon are taken together to form an oxo;

R$^{86}$ and R$^{87}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$.

R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n8 is 1-5;
m8 is 1-4;
q8 is 1-5; and
provided that when D8 is heteroaryl and $L^{84}$ is a bond, then B8 is heteroaryl or $C_2$-$C_8$ heterocyclyl; or
when D8 is phenyl, n is 1, $R^{81}$ is fluoro at the ortho position of the phenyl ring, and $L^{84}$ is a bond, then B8 is $C_2$-$C_8$ heterocyclyl.

Described herein are compounds of Formula (VIIIb), or a pharmaceutically acceptable salt, solvate, or stereoisomer thereof:

Formula (VIIIc)

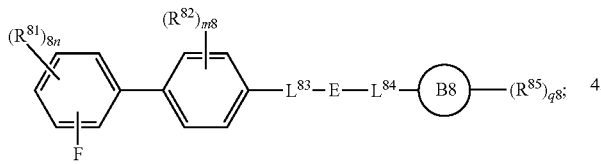

wherein:
$L^{83}$ is —$C(R^{83})_2C(R^{83})_2C(R^{83})_2$—;
$L^{84}$ is a bond or —$CR^{83}R^{83}$—;
E is —$NR^{84}C(=O)$—;
Ring B8 is selected from the group consisting of:
a bicyclic ring comprising at least one nitrogen atom;
a 5-membered ring comprising at least one nitrogen atom;
cycloalkyl;
a monocyclic heteroaryl or monocyclic $C_2$-$C_8$ heterocyclyl ring, wherein at least one $R^{85}$ is selected from the group consisting of $C_1$-$C_6$ alkyl, $C_1$-$C_6$ haloalkyl, amino, hydroxy, $C_1$-$C_6$ N-acylamino, acyl, $C_1$-$C_6$ alkoxy, and aryl; and
monocyclic aryl, monocyclic heteroaryl, or monocyclic heterocyclyl ring, provided that $L^{84}$ is not a bond;
each $R^{81}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —$OR^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$; each $R^{82}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{83}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)R^b$, —$NR^aC(=O)OR^a$, (—$NR^aC(=O)NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —$OR^a$, or —$NR^cR^d$; and the cycloalkyl, and heteroaryl is optionally substituted with one, two, or three of halogen, $C_1$-$C_6$ alkyl, $C_1$-$C_6$ haloalkyl-$OR^a$, or —$NR^cR^d$;

$R^{84}$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{83}$ substituents are taken together to form a ring;
each $R^{85}$ is independently hydrogen, halogen, —CN, —$OR^a$, —$SR^a$, —$S(=O)R^b$, (—$S(=O)_2R^d$), —$NO_2$, —$NR^cR^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or two $R^{85}$ substituents on the same carbon are taken together to form an oxo;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

each $R^c$ and $R^d$ are independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$;

n8 is 1-5;
m8 is 1-4; and
q8 is 1-5.

Described herein are compounds of Formula (IX), or a pharmaceutically acceptable salt, solvate, or stereoisomer thereof:

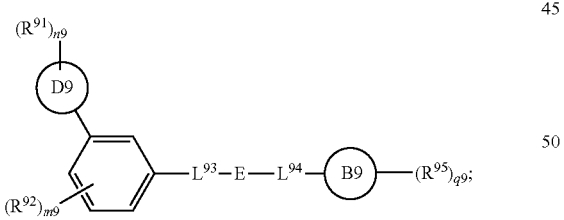

Formula (IX)

wherein:
$L^{93}$ is —C($R^{93}$)$_2$C($R^{93}$)$_2$C($R^{93}$)$_2$—, —C($R^{93}$)$_2$C($R^{93}$)$_2$—, —OC($R^{93}$)$_2$C($R^{93}$)—, or —SC($R^{93}$)$_2$C($R^{93}$)—;

E is —C(=O)NR$^{94}$—, —NR$^{94}$C(=O)—, —S(=O)$_2$NR$^{94}$—, —NR$^{94}$S(=O)$_2$—, —NR$^{94}$C(=O)O—, —OC(=O)NR$^{94}$—, —NR$^{94}$C(=O)NR$^{94}$—, oxadiazole, thiadiazole, or sulfonamide;

$L^{94}$ is a bond or —CR$^{96}$R$^{97}$—;

Rings D9 and B9 are independently heteroaryl, $C_2$-$C_8$ heterocyclyl, or cycloalkyl;

each $R^{91}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{92}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{93}$ is independently hydrogen, halogen, two $R^{83}$ on the same carbon are taken together to form an oxo, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) R$^b$, —NR$^a$C(=O)OR$^a$, (—NR$^a$C(=O)NR$^c$R$^d$), $C_1$-$C_6$ alkyl, $C_2$-$C_6$ alkenyl, $C_2$-$C_6$ alkynyl, $C_1$-$C_6$ heteroalkyl, $C_3$-$C_{10}$ heterocycloalkyl, $C_3$-$C_8$ cycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl-OR$^a$, or —NR$^c$R$^d$;

or two $R^{93}$ substituents on the same carbon are taken together to form a $C_3$-$C_8$ cycloalkyl ring;

$R^{94}$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{95}$ is independently hydrogen, halogen, —CN, —OR$^a$, —SR$^a$, —S(=O)R$^b$, (—S(=O)$_2$R$^d$), —NO$_2$, —NR$^c$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

or two R$^{95}$ substituents on the same carbon are taken together to form an oxo;

R$^{96}$ and R$^{97}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$.

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ are independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

n9 is 1-5;
m9 is 1-4;
q9 is 1-5.

In some embodiments of a compound of Formula (IX), L$^{93}$ is —C(R$^{93}$)$_2$C(R$^{93}$)$_2$C(R$^{93}$)$_2$—. In some embodiments of a compound of Formula (IX), L$^{93}$ is —C(R$^{93}$)$_2$C(R$^{93}$)$_2$—. In some embodiments of a compound of Formula (IX), L$^{93}$ is —OC(R$^{93}$)$_2$C(R$^{93}$)—. In some embodiments of a compound of Formula (IX), L$^{93}$ is —SC(R$^{93}$)$_2$C(R$^{93}$)—.

In some embodiments of a compound of Formula (IX), E is —C(=O)NR$^{94}$—. In some embodiments of a compound of Formula (IX), E is —NR$^{94}$C(=O)—. In some embodiments of a compound of Formula (IX), E is —S(=O)$_2$NR$^{94}$—. In some embodiments of a compound of Formula (IX), E is —NR$^{94}$S(=O)$_2$—. In some embodiments of a compound of Formula (IX), E is —NR$^{94}$C(=O)O—. In some embodiments of a compound of Formula (IX), E is —OC(=O)NR$^{94}$—. In some embodiments of a compound of Formula (IX), E is —NR$^{94}$C(=O)NR$^{94}$—. In some embodiments of a compound of Formula (IX), E is oxadiazole. In some embodiments of a compound of Formula (IX), E is thiadiazole. In some embodiments of a compound of Formula (IX), E is sulfonamide.

In some embodiments of a compound of Formula (IX), L$^{94}$ is —CR$^{96}$R$^{97}$—. In some embodiments of a compound of Formula (IX), L$^{94}$ is a bond.

In some embodiments, the compounds disclosed herein are provided in Table 1.

TABLE 1

| Compound No. | Name | Structure |
|---|---|---|
| 1 | N-(1H-benzo[d]imidazol-5-yl)-4-(2'-fluoro-[1,1'-biphenyl]-4-yl)butanamide | 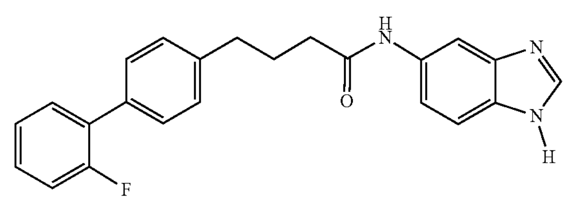 [SMILES: O=C(CCCc1ccc(-c2ccccc2F)cc1)Nc1ccc2[nH]cnc2c1] |
| 2 | 4-(2'-fluoro-[1,1'-biphenyl]-4-yl)-N-(2-oxo-2,3-dihydrobenzo[d]oxazol-6-yl)butanamide | 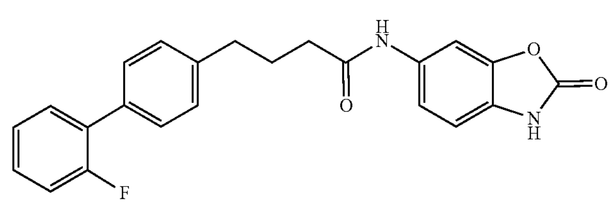 [SMILES: O=C(CCCc1ccc(-c2ccccc2F)cc1)Nc1ccc2[nH]c(=O)oc2c1] |

TABLE 1-continued

| Compound No. | Name | Structure |
|---|---|---|
| 3 | 4-(2'-fluoro-[1,1'-biphenyl]-4-yl)-N-(3-methyl-2-oxo-2,3-dihydro-1H-benzo[d]imidazol-5-yl)butanamide | 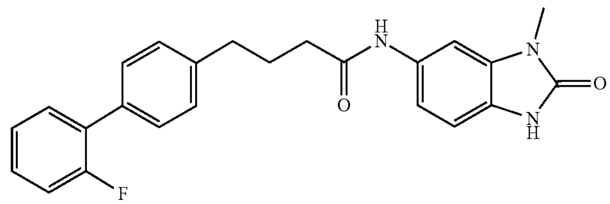 [SMILES: Cn1c(=O)[nH]c2ccc(NC(=O)CCCc3ccc(-c4ccccc4F)cc3)cc21] |
| 4 | 4-(2'-fluoro-[1,1'-biphenyl]-4-yl)-N-(1H-indazol-5-yl)butanamide | 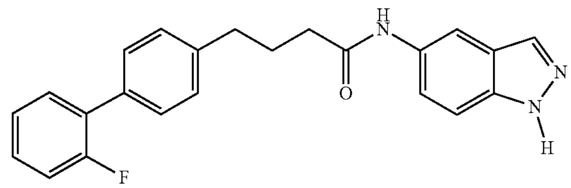 [SMILES: O=C(CCCc1ccc(-c2ccccc2F)cc1)Nc1ccc2[nH]ncc2c1] |
| 5 | 4-(2'-fluoro-[1,1'-biphenyl]-4-yl)-N-(1H-indazol-5-yl)butanamide | 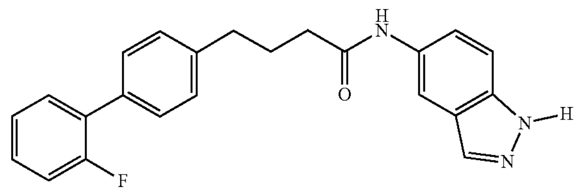 [SMILES: O=C(CCCc1ccc(-c2ccccc2F)cc1)Nc1ccc2[nH]ncc2c1] |
| 6 | 4-(2'-fluoro-[1,1'-biphenyl]-4-yl)-N-(1H-indol-5-yl)butanamide | 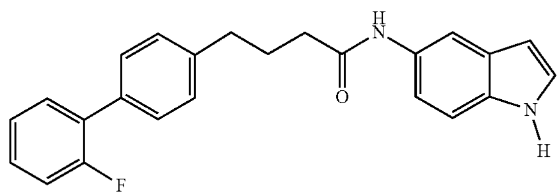 [SMILES: O=C(CCCc1ccc(-c2ccccc2F)cc1)Nc1ccc2[nH]ccc2c1] |
| 7 | 4-(2'-fluoro-[1,1'-biphenyl]-4-yl)-N-(2-oxo-1,2,3,4-tetrahydroquinolin-6-yl)butanamide | 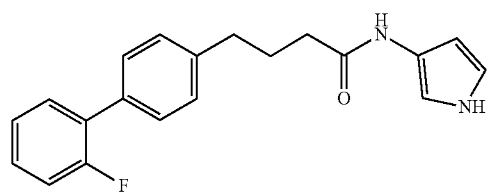 |
| 8 | 4-(2'-fluoro-[1,1'-biphenyl]-4-yl)-N-(6-hydroxypyridin-3-yl)butanamide | 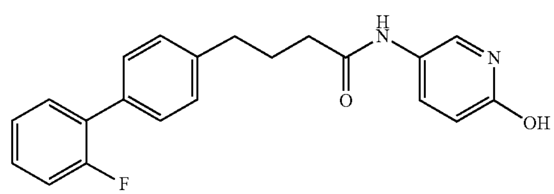 [SMILES: O=C(CCCc1ccc(-c2ccccc2F)cc1)Nc1ccc(O)nc1] |
| 9 | 4-(2'-fluoro-[1,1'-biphenyl]-4-yl)-N-(1H-pyrrol-3-yl)butanamide | 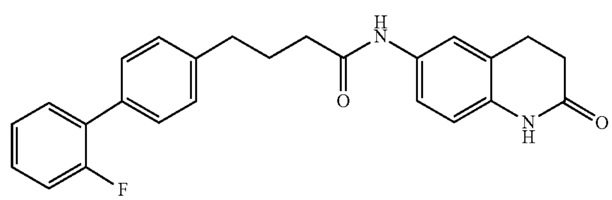 [SMILES: O=C(CCCc1ccc(-c2ccccc2F)cc1)Nc1ccc2c(c1)CCC(=O)N2] |
| 10 | 4-(4-(2-fluorophenoxy)phenyl)-N-(4-hydroxyphenyl)butanamide | 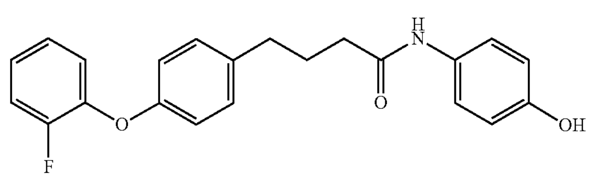 [SMILES: O=C(CCCc1ccc(Oc2ccccc2F)cc1)Nc1ccc(O)cc1] |

TABLE 1-continued

| Compound No. | Name | Structure |
|---|---|---|
| 11 | 3-((2'-fluoro-[1,1'-biphenyl]-4-yl)oxy)-N-(4-hydroxyphenyl)propanamide | 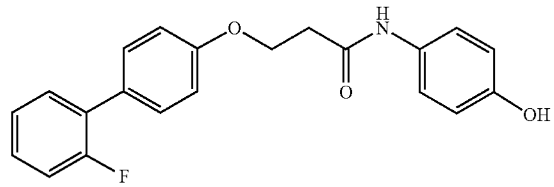 [SMILES: O=C(CCOc1ccc(-c2ccccc2F)cc1)Nc1ccc(O)cc1] |
| 12 | N-((1H-pyrrol-3-yl)methyl)-4-(2'-fluoro-[1,1'-biphenyl]-4-yl)butanamide | 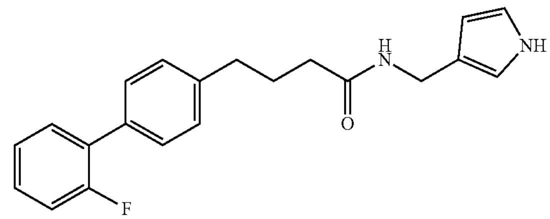 [SMILES: O=C(CCCc1ccc(-c2ccccc2F)cc1)NCc1cc[nH]c1] |
| 13 | 3-(2'-fluoro-[1,1'-biphenyl]-4-yl)-N-(4-hydroxyphenyl)cyclopentane-1-carboxamide | 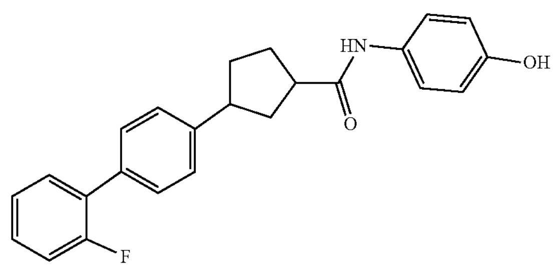 [SMILES: O=C(Nc1ccc(O)cc1)C1CCC(c2ccc(-c3ccccc3F)cc2)C1] |
| 14 | 4-(2'-fluoro[1,1'-biphenyl]-4-yl)-N-(4-hydroxyphenyl)piperazine-1-carboxamide | 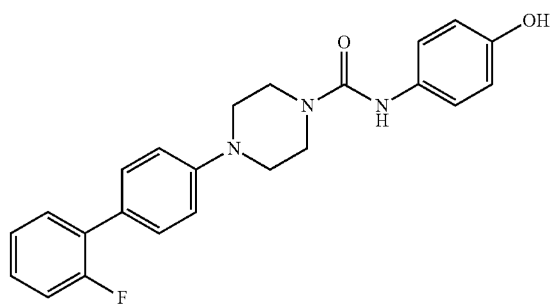 [SMILES: O=C(Nc1ccc(O)cc1)N1CCN(c2ccc(-c3ccccc3F)cc2)CC1] |
| 15 | 2-(2'-fluoro[1,1'-biphenyl]-4-yl)-N-(4-hydroxyphenyl)isonicotinamide | 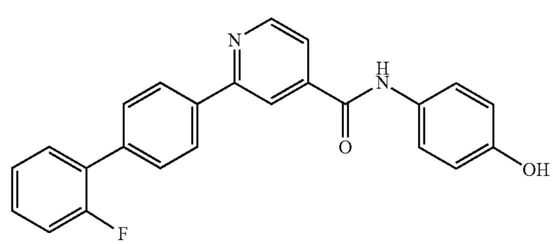 [SMILES: O=C(Nc1ccc(O)cc1)c1ccnc(-c2ccc(-c3ccccc3F)cc2)c1] |
| 16 | 4-(2'-fluoro[1,1'-biphenyl]-4-yl)-N-(4-hydroxyphenyl)picolinamide | 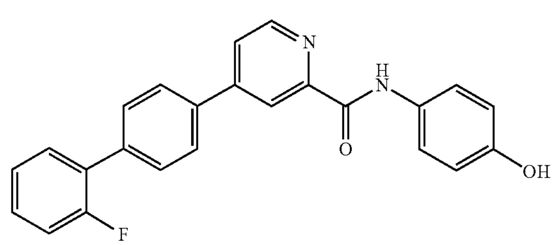 [SMILES: O=C(Nc1ccc(O)cc1)c1cc(-c2ccc(-c3ccccc3F)cc2)ccn1] |

TABLE 1-continued

| Compound No. | Name | Structure |
|---|---|---|
| 17 | 2-(4-(2'-fluoro[1,1'-biphenyl]-4-yl)piperazin-1-yl)-N-(4-hydroxyphenyl)acetamide | 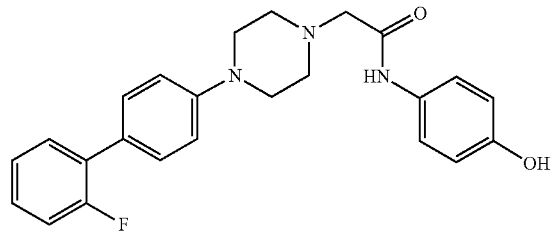 [SMILES: O=C(CN1CCN(c2ccc(-c3ccccc3F)cc2)CC1)Nc1ccc(O)cc1] |
| 18 | 4-((2'-fluoro-[1,1'-biphenyl]-4-yl)methyl)-N-(4-hydroxyphenyl)piperazine-1-carboxamide | 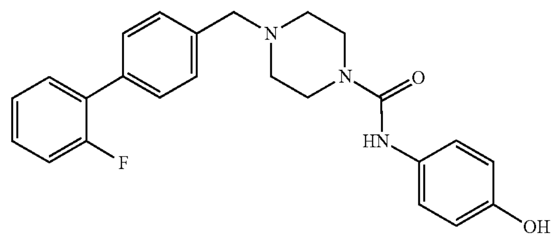 [SMILES: O=C(Nc1ccc(O)cc1)N1CCN(Cc2ccc(-c3ccccc3F)cc2)CC1] |
| 19 | 4-(3-(2-(2'-fluoro-[1,1'-biphenyl]-4-yl)ethyl)-1,2,4-oxadiazol-5-yl)phenol | 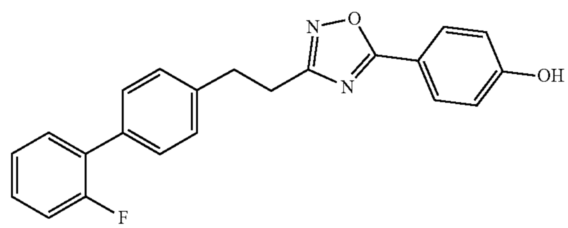 [SMILES: Oc1ccc(-c2nc(CCc3ccc(-c4ccccc4F)cc3)no2)cc1] |
| 20 | 4-(5-(2-(2'-fluoro-[1,1'-biphenyl]-4-yl)ethyl)-1,3,4-oxadiazol-2-yl)phenol | 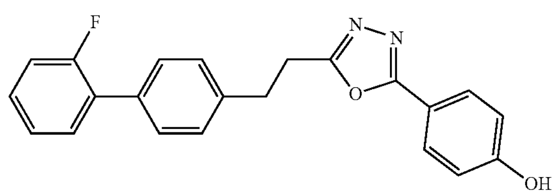 [SMILES: Oc1ccc(-c2nnc(CCc3ccc(-c4ccccc4F)cc3)o2)cc1] |
| 21 | 2-(2-(2'-fluoro-[1,1'-biphenyl]-4-yl)ethyl)-5-(pyridin-3-yl)-1,3,4-oxadiazole | 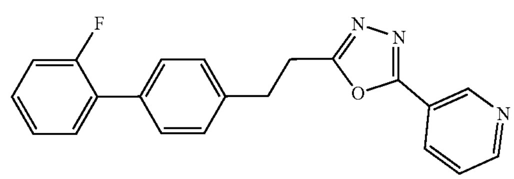 [SMILES: Fc1ccccc1-c1ccc(CCc2nnc(-c3cccnc3)o2)cc1] |
| 22 | 3-(2'-fluoro-[1,1'-biphenyl]-4-yl)-4-(4-hydroxyphenyl)pyrrolidine-2,5-dione | 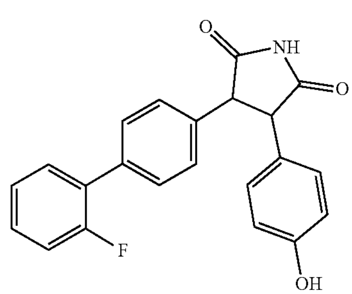 [SMILES: O=C1NC(=O)C(c2ccc(-c3ccccc3F)cc2)C1c1ccc(O)cc1] |

TABLE 1-continued

| Compound No. | Name | Structure |
|---|---|---|
| 23 | 3-(2'-fluoro-[1,1'-biphenyl]-4-yl)-4-(pyridin-3-yl)pyrrolidine-2,5-dione | 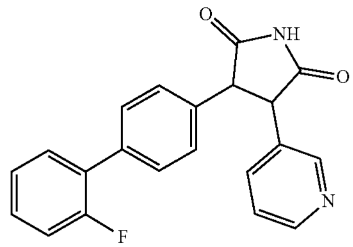 [SMILES: O=C1NC(=O)C(c2cccnc2)C1c1ccc(-c2ccccc2F)cc1] |
| 24 | 4,4-difluoro-4-(2'-fluoro-[1,1'-biphenyl]-4-yl)-N-(4-hydroxyphenyl)butanamide | 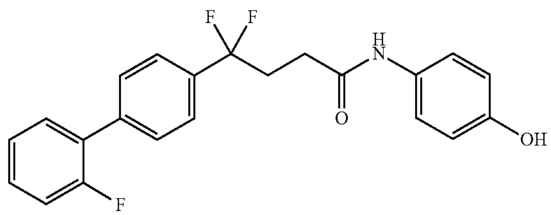 [SMILES: O=C(CCC(F)(F)c1ccc(-c2ccccc2F)cc1)Nc1ccc(O)cc1] |
| 25 | 4-(4-(tert-butyl)phenyl)-N-(4-hydroxyphenyl)butanamide | 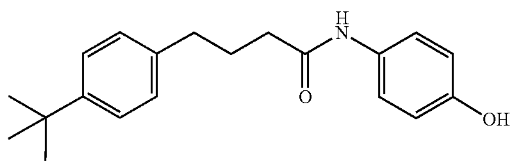 [SMILES: CC(C)(C)c1ccc(CCCC(=O)Nc2ccc(O)cc2)cc1] |
| 26 | N-(4-hydroxyphenyl)-4-(4-(trifluoromethyl)phenyl)butanamide | 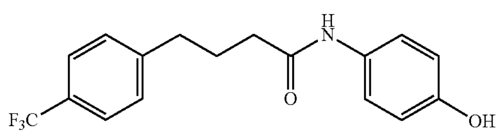 [SMILES: O=C(CCCc1ccc(C(F)(F)F)cc1)Nc1ccc(O)cc1] |
| 27 | N-(4-hydroxyphenyl)-4-(1H-indol-6-yl)butanamide | 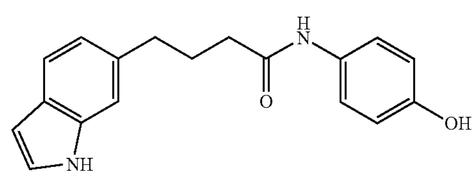 [SMILES: O=C(CCCc1ccc2cc[nH]c2c1)Nc1ccc(O)cc1] |
| 28 | N-(4-hydroxyphenyl)-4-(2-oxoindolin-6-yl)butanamide | 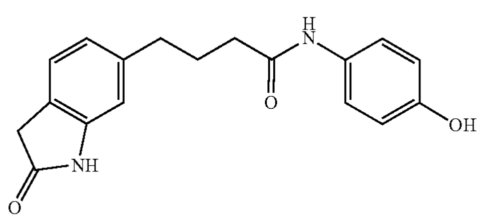 [SMILES: O=C(CCCc1ccc2c(c1)NC(=O)C2)Nc1ccc(O)cc1] |
| 29 | 4-(9H-carbazol-2-yl)-N-(4-hydroxyphenyl)butanamide | 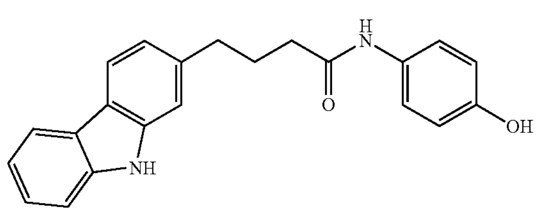 [SMILES: O=C(CCCc1ccc2c(c1)[nH]c1ccccc12)Nc1ccc(O)cc1] |
| 30 | 4-(2'-fluoro-[1,1'-biphenyl]-4-yl)-N-(4-hydroxyphenyl)-2,2-dimethylbutanamide | 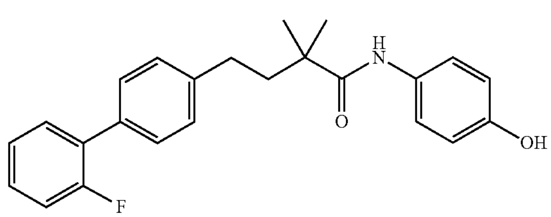 [SMILES: CC(C)(CCc1ccc(-c2ccccc2F)cc1)C(=O)Nc1ccc(O)cc1] |

TABLE 1-continued

| Compound No. | Name | Structure |
|---|---|---|
| 31 | 4-(2'-fluoro-[1,1'-biphenyl]-4-yl)-N-(3-hydroxybicyclo[1.1.1]pentan-1-yl)butanamide | 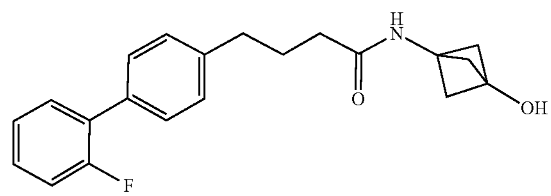 [SMILES: O=C(CCCc1ccc(-c2ccccc2F)cc1)NC12CC(O)(C1)C2] |
| 32 | 2-(2-(2'-fluoro-[1,1'-biphenyl]-4-yl)ethyl)benzo[d]oxazol-5-ol | 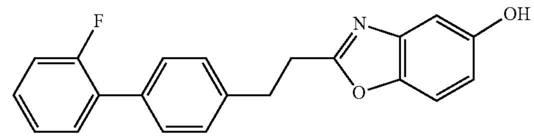 [SMILES: Oc1ccc2oc(CCc3ccc(-c4ccccc4F)cc3)nc2c1] |
| 33 | 4-(8-fluoronaphthalen-2-yl)-N-(4-hydroxyphenyl)butanamide | 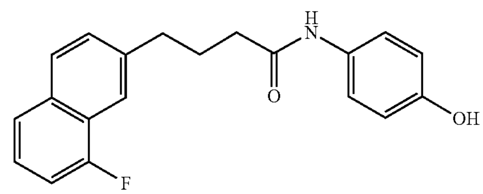 [SMILES: O=C(CCCc1ccc2cccc(F)c2c1)Nc1ccc(O)cc1] |
| 34 | 4-(4-(1H-pyrrol-2-yl)phenyl)-N-(4-hydroxyphenyl)butanamide | 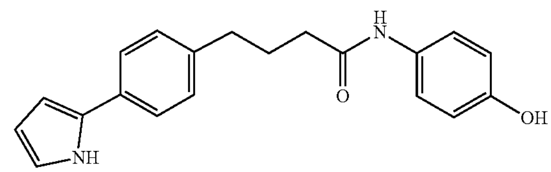 [SMILES: O=C(CCCc1ccc(-c2ccc[nH]2)cc1)Nc1ccc(O)cc1] |
| 35 | 4-(2'-fluoro-[1,1'-biphenyl]-4-yl)-N-(4-hydroxyphenyl)-3,3-dimethylbutanamide | 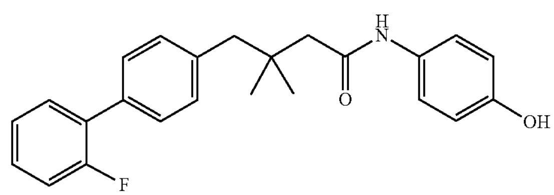 [SMILES: CC(C)(CC(=O)Nc1ccc(O)cc1)Cc1ccc(-c2ccccc2F)cc1] |
| 36 | 3-((2'-fluoro-[1,1'-biphenyl]-4-yl)amino)-N-(4-hydroxyphenyl)propanamide | 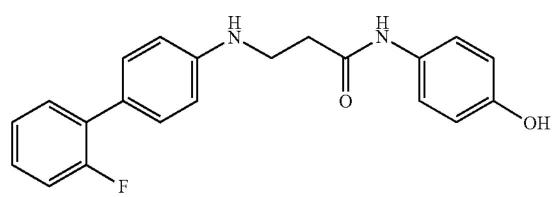 [SMILES: O=C(CCNc1ccc(-c2ccccc2F)cc1)Nc1ccc(O)cc1] |
| 37 | 4-(2'-fluoro-[1,1'-biphenyl]-4-yl)-N-(pyridin-3-yl)butanamide | 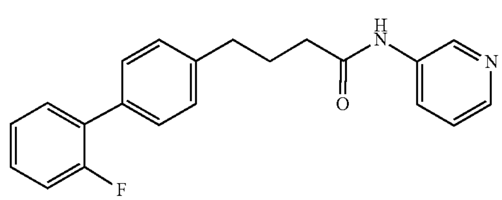 [SMILES: O=C(CCCc1ccc(-c2ccccc2F)cc1)Nc1cccnc1] |
| 38 | 4-(2'-fluoro-[1,1'-biphenyl]-4-yl)-N-(thiazol-2-yl)butanamide | 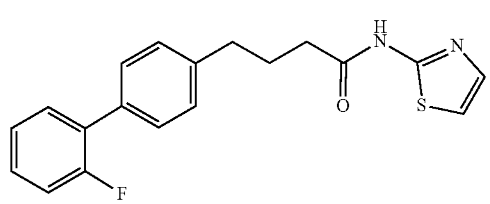 [SMILES: O=C(CCCc1ccc(-c2ccccc2F)cc1)Nc1nccs1] |

TABLE 1-continued

| Compound No. | Name | Structure |
|---|---|---|
| 39 | 4-(2'-fluoro-[1,1'-biphenyl]-4-yl)-N-(6-methoxypyridin-3-yl)butanamide | 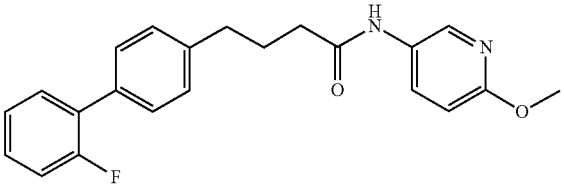 [SMILES: COc1ccc(NC(=O)CCCc2ccc(-c3ccccc3F)cc2)cn1] |
| 40 | 4-(2'-fluoro-[1,1'-biphenyl]-4-yl)-N-(pyridin-2-yl)butanamide | 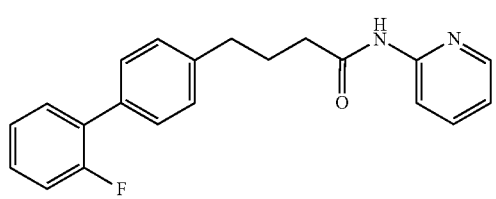 [SMILES: O=C(CCCc1ccc(-c2ccccc2F)cc1)Nc1ccccn1] |
| 41 | 4-(2'-fluoro-[1,1'-biphenyl]-4-yl)-N-(pyridin-3-ylmethyl)butanamide | 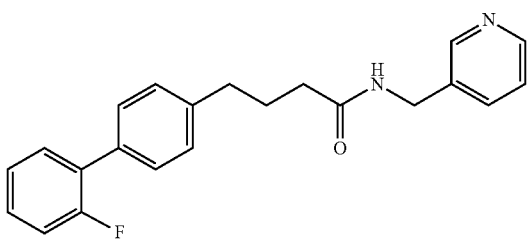 [SMILES: O=C(CCCc1ccc(-c2ccccc2F)cc1)NCc1cccnc1] |
| 42 | 4-(2'-fluoro-[1,1'-biphenyl]-4-yl)-N-(pyridin-4-ylmethyl)butanamide | 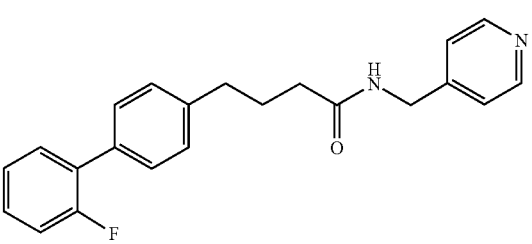 [SMILES: O=C(CCCc1ccc(-c2ccccc2F)cc1)NCc1ccncc1] |
| 43 | 4-(2'-fluoro-[1,1'-biphenyl]-4-yl)-N-(pyridin-2-ylmethyl)butanamide | 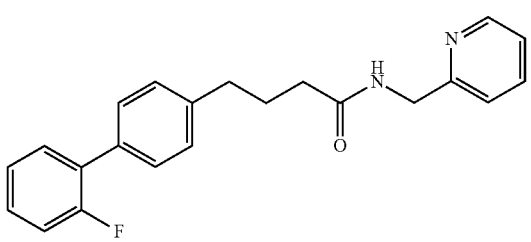 [SMILES: O=C(CCCc1ccc(-c2ccccc2F)cc1)NCc1ccccn1] |
| 44 | 4-(2'-fluoro-[1,1'-biphenyl]-4-yl)-N-(4-methoxybenzyl)butanamide | 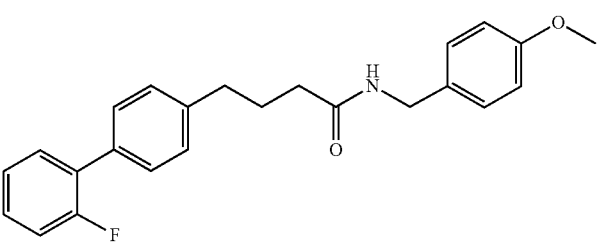 [SMILES: COc1ccc(CNC(=O)CCCc2ccc(-c3ccccc3F)cc2)cc1] |
| 45 | 4-(2'-fluoro-[1,1'-biphenyl]-4-yl)-N-(6-methylpyridin-3-yl)butanamide | 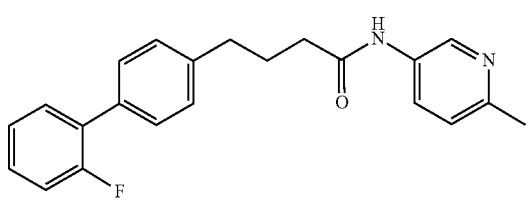 [SMILES: Cc1ccc(NC(=O)CCCc2ccc(-c3ccccc3F)cc2)cn1] |

TABLE 1-continued

| Compound No. | Name | Structure |
|---|---|---|
| 46 | N-(benzo[d]oxazol-6-yl)-4-(2'-fluoro-[1,1'-biphenyl]-4-yl)butanamide | 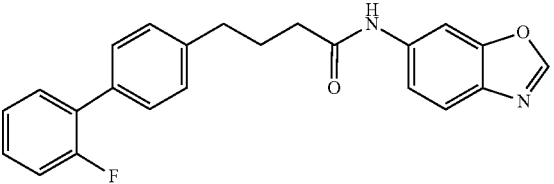 [SMILES: O=C(CCCc1ccc(-c2ccccc2F)cc1)Nc1ccc2ncoc2c1] |
| 47 | 4-(2'-fluoro-[1,1'-biphenyl]-4-yl)-N-(1H-pyrazol-4-yl)butanamide | 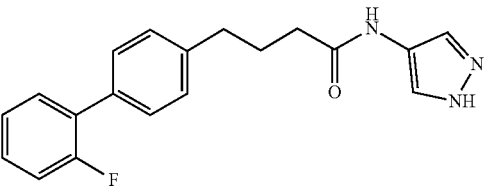 [SMILES: O=C(CCCc1ccc(-c2ccccc2F)cc1)Nc1cn[nH]c1] |
| 48 | 4-(2'-fluoro-[1,1'-biphenyl]-4-yl)-N-((1-methyl-1H-pyrazol-4-yl)methyl)butanamide | 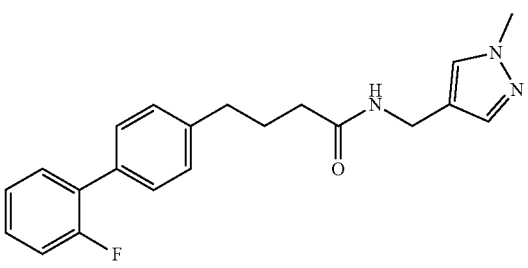 [SMILES: Cn1cc(CNC(=O)CCCc2ccc(-c3ccccc3F)cc2)cn1] |
| 49 | N-(1-acetylpiperidin-4-yl)-4-(2'-fluoro-[1,1'-biphenyl]-4-yl)butanamide | 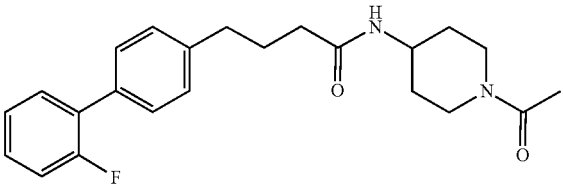 [SMILES: CC(=O)N1CCC(NC(=O)CCCc2ccc(-c3ccccc3F)cc2)CC1] |
| 50 | N-(cyclopropylmethyl)-4-(2'-fluoro-[1,1'-biphenyl]-4-yl)butanamide | 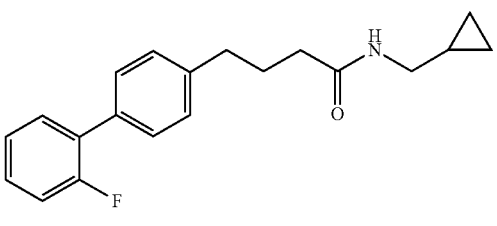 [SMILES: O=C(CCCc1ccc(-c2ccccc2F)cc1)NCC1CC1] |
| 51 | 4-(2'-fluoro-[1,1'-biphenyl]-4-yl)-N-(6-(trifluoromethyl)pyridin-3-yl)butanamide | 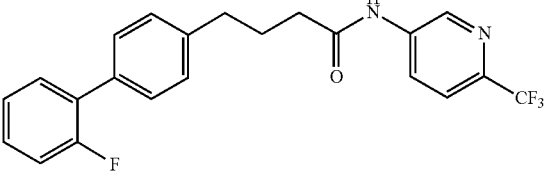 |
| 52 | 4-(2'-fluoro-[1,1'-biphenyl]-4-yl)-N-methyl-N-(pyridin-3-yl)butanamide | 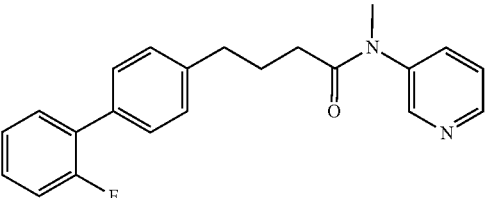 |

TABLE 1-continued

| Compound No. | Name | Structure |
|---|---|---|
| 53 | 4-(2'-fluoro-[1,1'-biphenyl]-4-yl)-N-(3-oxo-3,4-dihydro-2H-benzo[b][1,4]oxazin-7-yl)butanamide | 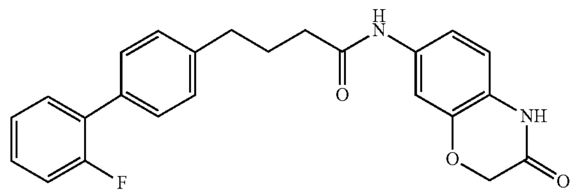 [SMILES: O=C(CCCc1ccc(-c2ccccc2F)cc1)Nc1ccc2c(c1)OCC(=O)N2] |
| 54 | N-(4,4-difluorocyclohexyl)-4-(2'-fluoro-[1,1'-biphenyl]-4-yl)butanamide | 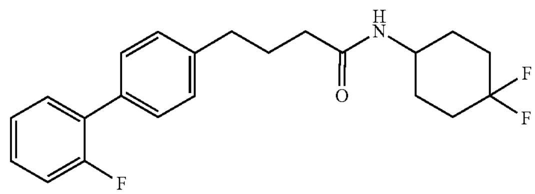 [SMILES: O=C(CCCc1ccc(-c2ccccc2F)cc1)NC1CCC(F)(F)CC1] |
| 55 | 4-(2'-fluoro-[1,1'-biphenyl]-4-yl)-N-(oxetan-3-yl)butanamide | 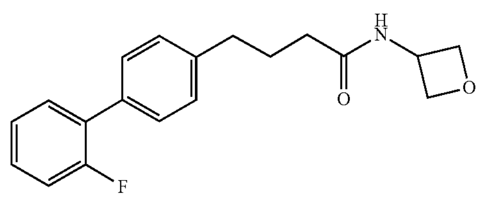 [SMILES: O=C(CCCc1ccc(-c2ccccc2F)cc1)NC1COC1] |
| 56 | 4-(2'-fluoro-[1,1'-biphenyl]-4-yl)-N-(tetrahydro-2H-pyran-4-yl)butanamide | 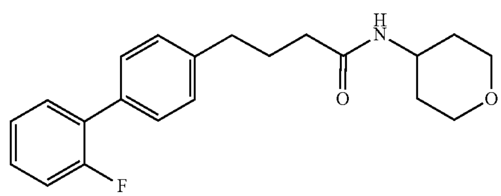 [SMILES: O=C(CCCc1ccc(-c2ccccc2F)cc1)NC1CCOCC1] |
| 57 | 4-(2'-fluoro-[1,1'-biphenyl]-4-yl)-N-(1H-pyrrolo[2,3-b]pyridin-5-yl)butanamide | 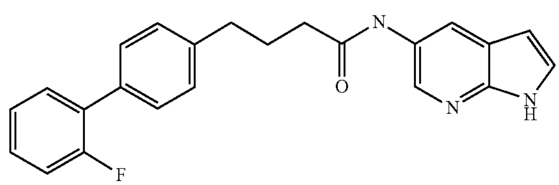 |
| 58 | 4-(2'-fluoro-[1,1'-biphenyl]-4-yl)-N-(2-oxo-2,3-dihydro-1H-benzo[d]imidazol-5-yl)butanamide | 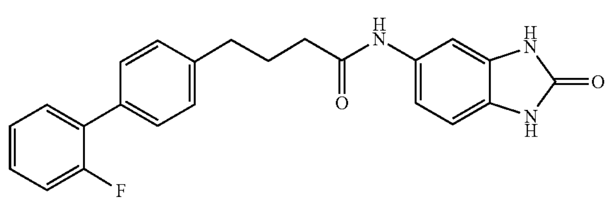 [SMILES: O=C(CCCc1ccc(-c2ccccc2F)cc1)Nc1ccc2[nH]c(=O)[nH]c2c1] |
| 59 | 4-(2'-fluoro-[1,1'-biphenyl]-4-yl)-N-(1-oxoisoindolin-5-yl)butanamide | 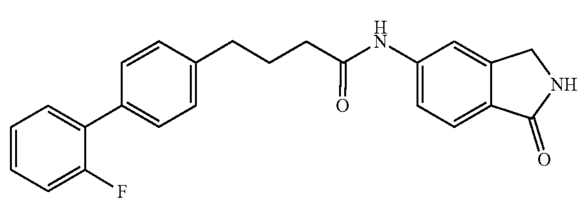 [SMILES: O=C(CCCc1ccc(-c2ccccc2F)cc1)Nc1ccc2c(c1)CNC2=O] |

TABLE 1-continued

| Compound No. | Name | Structure |
|---|---|---|
| 60 | 4-(2'-fluoro-[1,1'-biphenyl]-4-yl)-1-morpholinobutan-1-one | 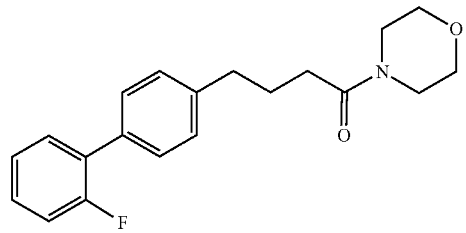 [SMILES: O=C(CCCc1ccc(-c2ccccc2F)cc1)N1CCOCC1] |
| 61 | N-(1,1-dioxidotetmhydro-2H-thiopyran-4-yl)-4-(2'-fluoro-[1,1'-biphenyl]-4-yl)butanamide | 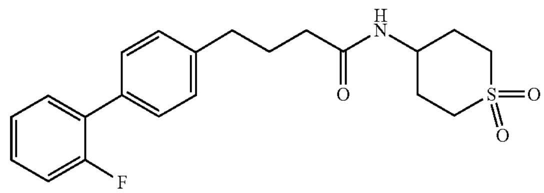 [SMILES: O=C(CCCc1ccc(-c2ccccc2F)cc1)NC1CCS(=O)(=O)CC1] |
| 62 | 4-(2'-fluoro-[1,1'-biphenyl]-4-yl)-N-(4-hydroxycyclohexyl)butanamide | 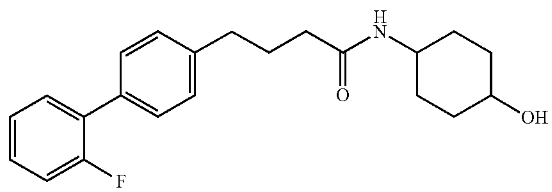 [SMILES: O=C(CCCc1ccc(-c2ccccc2F)cc1)NC1CCC(O)CC1] |
| 63 | 4-(2'-fluoro-[1,1'-biphenyl]-4-yl)-N-(isoxazol-3-yl)butanamide | 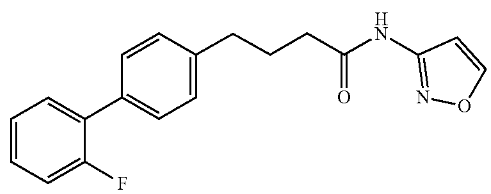 [SMILES: O=C(CCCc1ccc(-c2ccccc2F)cc1)Nc1ccon1] |
| 64 | N-(3-(2'-fluoro-[1,1'-biphenyl]-4-yl)propyl)nicotinamide | 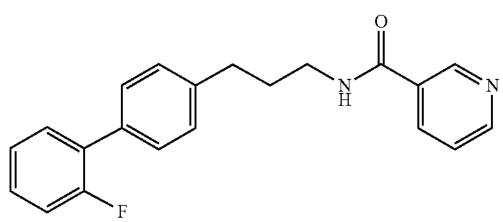 [SMILES: O=C(NCCCc1ccc(-c2ccccc2F)cc1)c1cccnc1] |
| 65 | N-(3-(2'-fluoro-[1,1'-biphenyl]-4-yl)propyl)pyridazine-3-carboxamide | 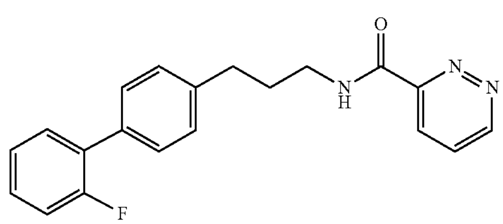 [SMILES: O=C(NCCCc1ccc(-c2ccccc2F)cc1)c1cccnn1] |
| 66 | N-(3-(2'-fluoro-[1,1'-biphenyl]-4-yl)propyl)-1H-pyrazole-4-carboxamide | 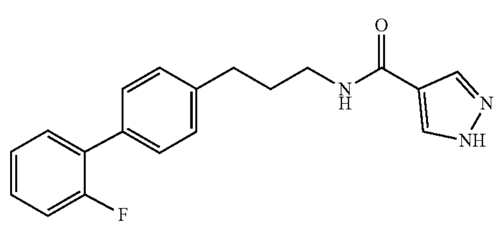 [SMILES: O=C(NCCCc1ccc(-c2ccccc2F)cc1)c1cn[nH]c1] |

TABLE 1-continued

| Compound No. | Name | Structure |
|---|---|---|
| 67 | N-(3-(2'-fluoro-[1,1'-biphenyl]-4-yl)propyl)pyrimidine-5-carboxamide | 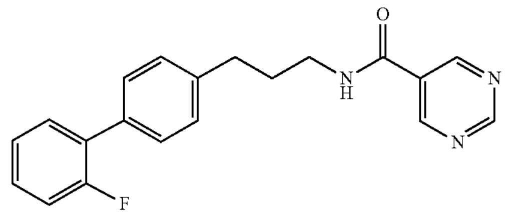 [SMILES: O=C(NCCCc1ccc(-c2ccccc2F)cc1)c1cncnc1] |
| 68 | N-(3-(2'-fluoro-[1,1'-biphenyl]-4-yl)propyl)-6-hydroxynicotinamide | 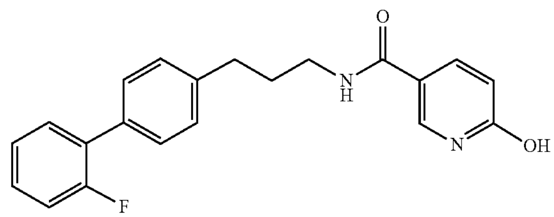 [SMILES: O=C(NCCCc1ccc(-c2ccccc2F)cc1)c1ccc(O)nc1] |
| 69 | N-(3-(2'-fluoro-[1,1'-biphenyl]-4-yl)propyl)-1H-indazole-3-carboxamide | 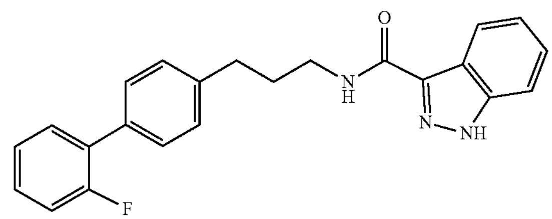 [SMILES: O=C(NCCCc1ccc(-c2ccccc2F)cc1)c1n[nH]c2ccccc12] |
| 70 | N-(3-(2'-fluoro-[1,1'-biphenyl]-4-yl)propyl)-1H-benzo[d][1,2,3]triazole-5-carboxamide | 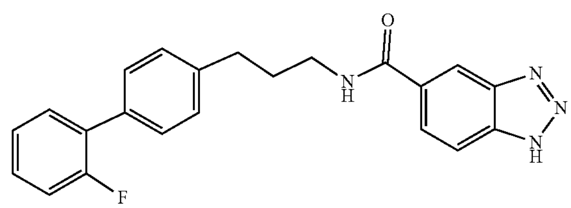 [SMILES: O=C(NCCCc1ccc(-c2ccccc2F)cc1)c1ccc2[nH]nnc2c1] |
| 71 | N-(3-(2'-fluoro-[1,1'-biphenyl]-4-yl)propyl)-6-methylnicotinamide | 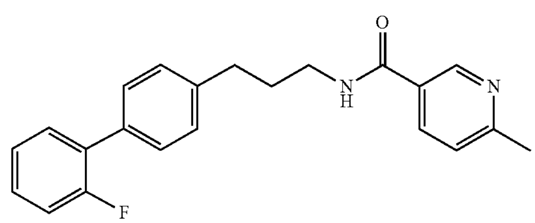 [SMILES: Cc1ccc(C(=O)NCCCc2ccc(-c3ccccc3F)cc2)cn1] |
| 72 | N-(3-(2'-fluoro-[1,1'-biphenyl]-4-yl)propyl)pyrimidine-2-carboxamide | 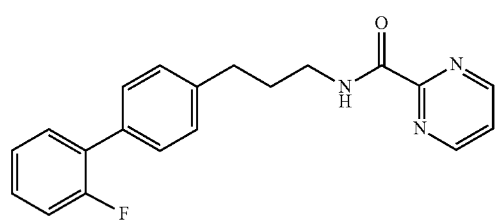 [SMILES: O=C(NCCCc1ccc(-c2ccccc2F)cc1)c1ncccn1] |
| 73 | N-(3-(2'-fluoro-[1,1'-biphenyl]-4-yl)propyl)-1H-indazole-5-carboxamide | 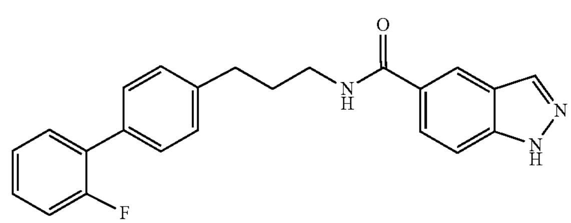 [SMILES: O=C(NCCCc1ccc(-c2ccccc2F)cc1)c1ccc2[nH]ncc2c1] |

TABLE 1-continued

| Compound No. | Name |
|---|---|
| 74 | N-(3-(2'-fluoro-[1,1'-biphenyl]-4-yl)propyl)-1H-indole-5-carboxamide |
| 75 | 3,3-difluoro-N-(3-(2'-fluoro-[1,1'-biphenyl]-4-yl)propyl)cyclobutane-1-carboxamide |
| 76 | N-(3-(2'-fluoro-[1,1'-biphenyl]-4-yl)propyl)pyrazine-2-carboxamide |
| 77 | (1s,3s)-N-(3-(2'-fluoro-[1,1'-biphenyl]-4-yl)propyl)-3-hydroxycyclobutane-1-carboxamide |
| 78 | N-(3-(2'-fluoro-[1,1'-biphenyl]-4-yl)propyl)-2-hydroxynicotinamide |
| 79 | N-(3-(2'-fluoro-[1,1'-biphenyl]-4-yl)propyl)-1H-indazole-6-carboxamide |
| 80 | N-(3-(2'-fluoro-[1,1'-biphenyl]-4-yl)propyl)-5-methylnicotinamide |

TABLE 1-continued

| Compound No. | Name | Structure |
|---|---|---|
| 81 | N-(3-(2'-fluoro-[1,1'-biphenyl]-4-yl)propyl)-2-methylnicotinamide | 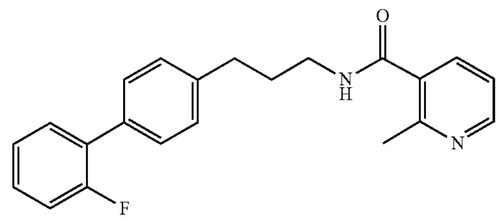 [SMILES: Cc1ncccc1C(=O)NCCCc1ccc(-c2ccccc2F)cc1] |
| 82 | N-(3-(2'-fluoro-[1,1'-biphenyl]-4-yl)propyl)-1,8a-dihydroimidazo[1,2-a]pyridine-6-carboxamide | 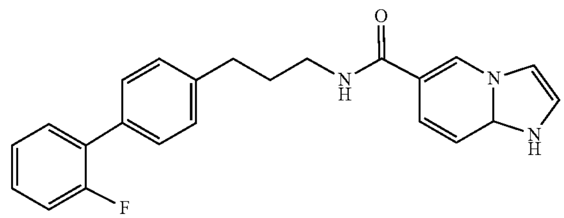 [SMILES: O=C(NCCCc1ccc(-c2ccccc2F)cc1)C1=CN2C=CNC2C=C1] |
| 83 | N-(3-(2'-fluoro-[1,1'-biphenyl]-4-yl)propyl)-6-(trifluoromethyl)nicotinamide | 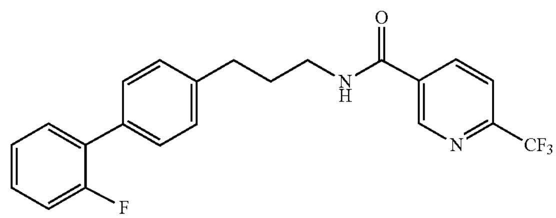 [SMILES: O=C(NCCCc1ccc(-c2ccccc2F)cc1)c1ccc(C(F)(F)F)nc1] |
| 84 | N-(3-(2'-fluoro-[1,1'-biphenyl]-4-yl)propyl)-1H-benzo[d]imidazole-2-carboxamide | 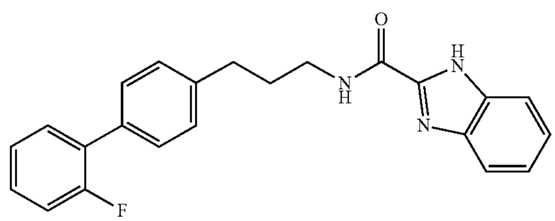 [SMILES: O=C(NCCCc1ccc(-c2ccccc2F)cc1)c1nc2ccccc2[nH]1] |
| 85 | N-(3-(2'-fluoro-[1,1'-biphenyl]-4-yl)propyl)-5-(trifluoromethyl)nicotinamide | 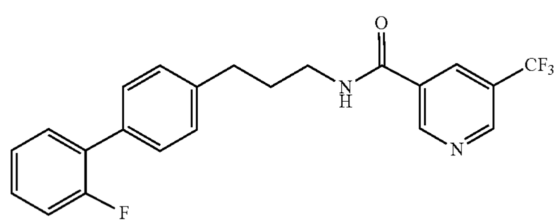 [SMILES: O=C(NCCCc1ccc(-c2ccccc2F)cc1)c1cncc(C(F)(F)F)c1] |
| 86 | N-(3-(2'-fluoro-[1,1'-biphenyl]-4-yl)propyl)imidazo[1,2-a]pyridine-8-carboxamide | 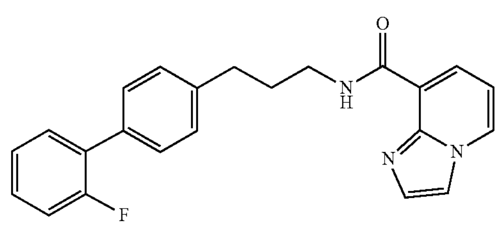 [SMILES: O=C(NCCCc1ccc(-c2ccccc2F)cc1)c1cccn2ccnc12] |
| 87 | N-(3-(2'-fluoro-[1,1'-biphenyl]-4-yl)propyl)-1-methylpiperidine-4-carboxamide | 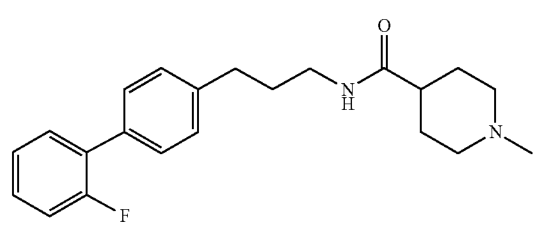 [SMILES: CN1CCC(C(=O)NCCCc2ccc(-c3ccccc3F)cc2)CC1] |

TABLE 1-continued

| Compound No. | Name | Structure |
|---|---|---|
| 88 | N-(3-(2'-fluoro-[1,1'-biphenyl]-4-yl)propyl)-1-methyl-1H-imidazole-4-carboxamide | 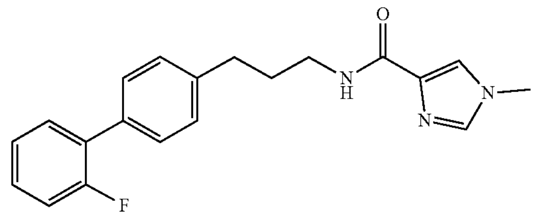 [SMILES: Cn1cnc(C(=O)NCCCc2ccc(-c3ccccc3F)cc2)c1] |
| 89 | N-(3-(2'-fluoro-[1,1'-biphenyl]-4-yl)propyl)-1,3-dimethyl-1H-pyrazole-5-carboxamide | 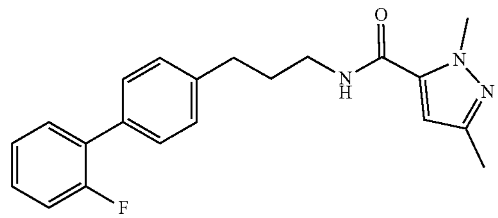 [SMILES: Cc1cc(C(=O)NCCCc2ccc(-c3ccccc3F)cc2)n(C)n1] |
| 90 | N-(3-(2'-fluoro-[1,1'-biphenyl]-4-yl)propyl)-5-methylisoxazole-3-carboxamide | 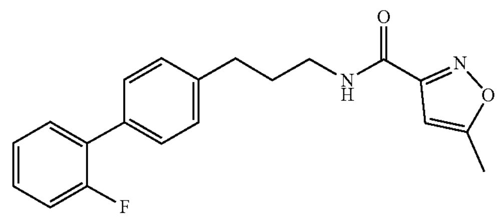 [SMILES: Cc1cc(C(=O)NCCCc2ccc(-c3ccccc3F)cc2)no1] |
| 91 | N-(3-(2'-fluoro-[1,1'-biphenyl]-4-yl)propyl)-2,3-dihydrobenzo[b][1,4]dioxine-6-carboxamide | 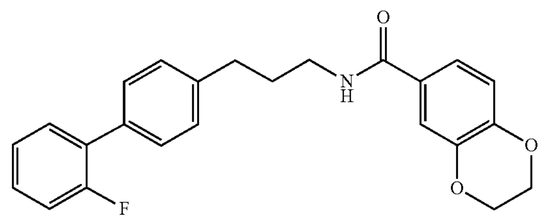 [SMILES: O=C(NCCCc1ccc(-c2ccccc2F)cc1)c1ccc2c(c1)OCCO2] |
| 92 | N-(3-(2'-fluoro-[1,1'-biphenyl]-4-yl)propyl)-1H-pyrrolo[3,2-c]pyridine-3-catboxamide | 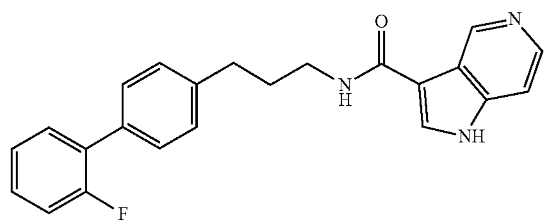 [SMILES: O=C(NCCCc1ccc(-c2ccccc2F)cc1)c1c[nH]c2ccncc12] |
| 93 | N-(3-(2'-fluoro-[1,1'-biphenyl]-4-yl)propyl)-5-methyl-1,3,4-oxadiazole-2-carboxamide | 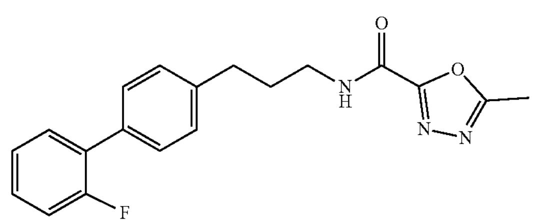 [SMILES: Cc1nnc(C(=O)NCCCc2ccc(-c3ccccc3F)cc2)o1] |
| 94 | N-(3-(2'-fluoro-[1,1'-biphenyl]-4-yl)propyl)-3-oxo-3,4-dihydro-2H-benzo[b][1,4]oxazine-7-carboxamide | 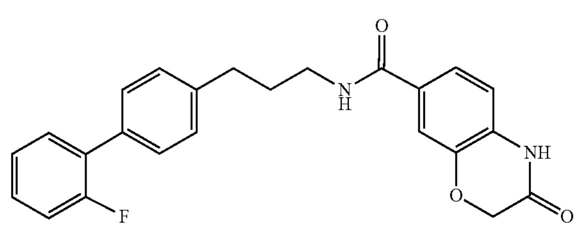 [SMILES: O=C1COc2cc(C(=O)NCCCc3ccc(-c4ccccc4F)cc3)ccc2N1] |

TABLE 1-continued

| Compound No. | Name | Structure |
|---|---|---|
| 95 | N-(3-(2'-fluoro-[1,1'-biphenyl]-4-yl)propyl)-3-methyl-3H-imidazo[4,5-b]pyridine-6-carboxamide | 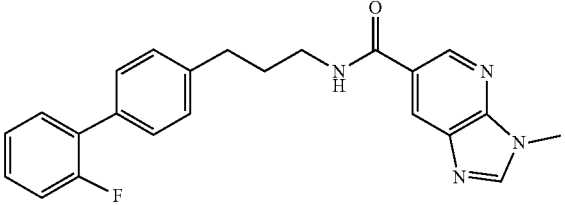 [SMILES: Cn1cnc2cc(C(=O)NCCCc3ccc(-c4ccccc4F)cc3)cnc21] |
| 96 | 2-amino-N-(3-(2'-fluoro-[1,1'-biphenyl]-4-yl)propyl)pyrimidine-5-carboxamide | 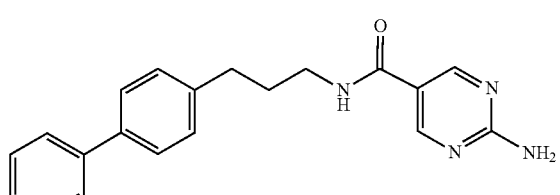 |
| 97 | N-(3-(2'-fluoro-[1,1'-biphenyl]-4-yl)propyl)-[1,2,4]triazolo[4,3-a]pyridine-6-carboxamide | 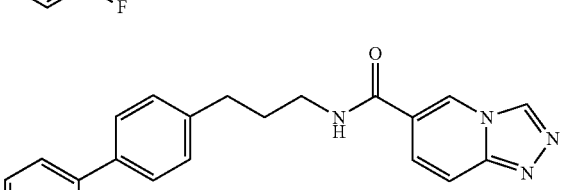 |
| 98 | N-(3-(2'-fluoro-[1,1'-biphenyl]-4-yl)propyl)pyridazine-4-carboxamide | 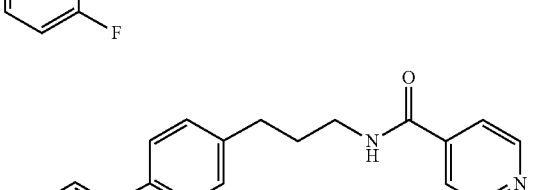 |
| 99 | N-(3-(2'-fluoro-[1,1'-biphenyl]-4-yl)propyl)-2,6-dimethylnicotinamide | 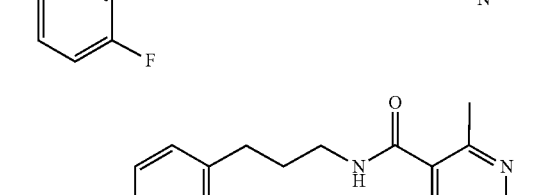 |
| 100 | N-(3-(2'-fluoro-[1,1'-biphenyl]-4-yl)propyl)-2-methyl-1H-benzo[d]imidazole-5-carboxamide | 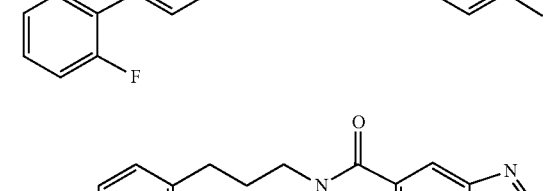 |
| 101 | N-(3-(2'-fluoro-[1,1'-biphenyl]-4-yl)propyl)-2-(4-methoxyphenyl)acetamide | 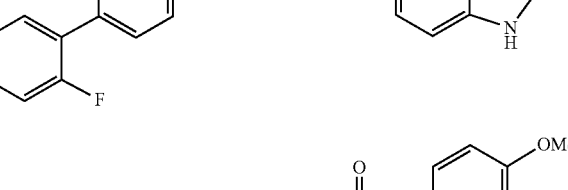 |

TABLE 1-continued

| Compound No. | Name | Structure |
|---|---|---|
| 102 | 2-(benzo[d]isoxazol-3-yl)-N-(3-(2'-fluoro-[1,1'-biphenyl]-4-yl)propyl)acetamide | 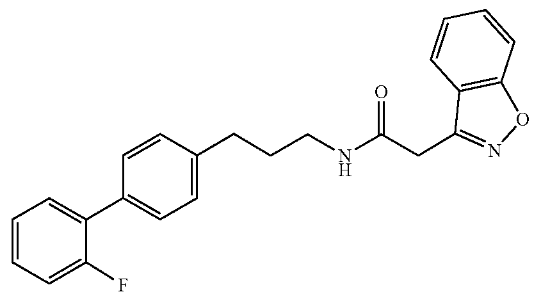 [SMILES: O=C(Cc1noc2ccccc12)NCCCc1ccc(-c2ccccc2F)cc1] |
| 103 | N-(3-(2'-fluoro-[1,1'-biphenyl]-4-yl)propyl)-3-methyloxetane-3-carboxamide | 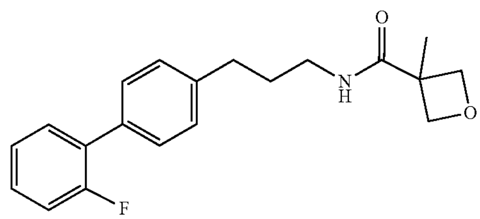 [SMILES: CC1(C(=O)NCCCc2ccc(-c3ccccc3F)cc2)COC1] |
| 104 | N-(3-(2'-fluoro-[1,1'-biphenyl]-4-yl)propyl)-2-oxoindoline-5-carboxamide | 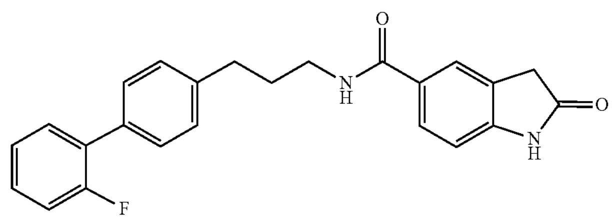 [SMILES: O=C1Cc2cc(C(=O)NCCCc3ccc(-c4ccccc4F)cc3)ccc2N1] |
| 105 | 6-amino-N-(3-(2'-fluoro-[1,1'-biphenyl]-4-yl)propyl)nicotinamide | 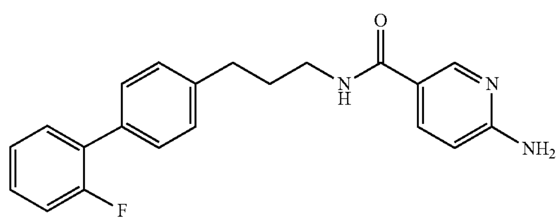 [SMILES: Nc1ccc(C(=O)NCCCc2ccc(-c3ccccc3F)cc2)cn1] |
| 106 | N-(3-(2'-fluoro-[1,1'-biphenyl]-4-yl)propyl)-1-methyl-1H-pyrazole-5-carboxamide | 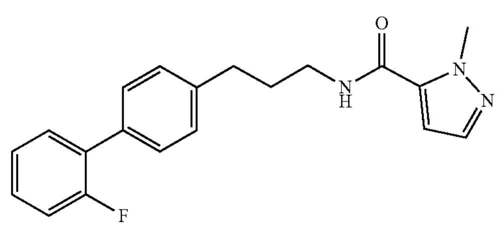 [SMILES: Cn1nccc1C(=O)NCCCc1ccc(-c2ccccc2F)cc1] |
| 107 | N-(3-(2'-fluoro-[1,1'-biphenyl]-4-yl)propyl)-1-methyl-3-(trifluoromethyl)-1H-pyrazole-5-carboxamide | 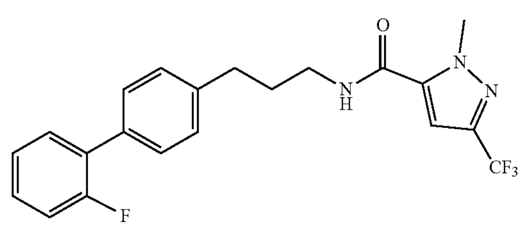 [SMILES: Cn1nc(C(F)(F)F)cc1C(=O)NCCCc1ccc(-c2ccccc2F)cc1] |

TABLE 1-continued

| Compound No. | Name | Structure |
|---|---|---|
| 108 | 2,2-difluoro-N-(3-(2'-fluoro-[1,1'-biphenyl]-4-yl)propyl)-2-phenylacetamide | 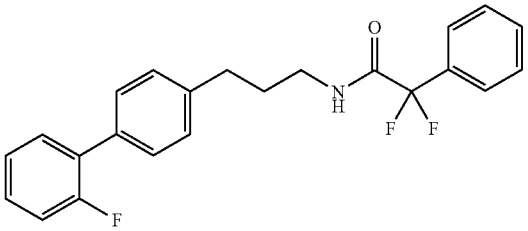 [SMILES: O=C(NCCCc1ccc(-c2ccccc2F)cc1)C(F)(F)c1ccccc1] |
| 109 | 1-ethyl-N-(3-(2'-fluoro-[1,1'-biphenyl]-4-yl)propyl)-3-methyl-1H-pyrazole-5-carboxamide | 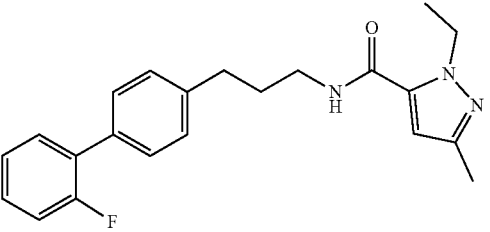 [SMILES: CCn1nc(C)cc1C(=O)NCCCc1ccc(-c2ccccc2F)cc1] |
| 110 | 2-(3,4-dimethoxyphenyl)-N-(3-(2'-fluoro-[1,1'-biphenyl]-4-yl)propyl)acetamide | 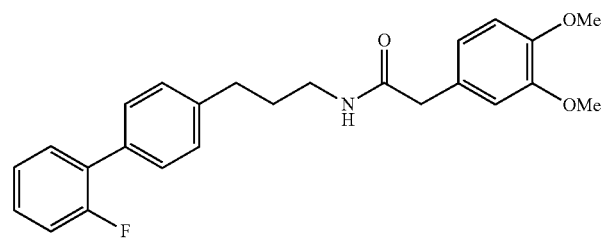 [SMILES: COc1ccc(CC(=O)NCCCc2ccc(-c3ccccc3F)cc2)cc1OC] |
| 111 | N-(3-(2'-fluoro-[1,1'-biphenyl]-4-yl)propyl)isoxazole-5-carboxamide | 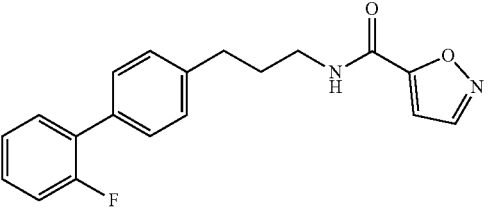 [SMILES: O=C(NCCCc1ccc(-c2ccccc2F)cc1)c1ccno1] |
| 112 | 2-(4-ethoxyphenyl)-N-(3-(2'-fluoro-[1,1'-biphenyl]-4-yl)propyl)acetamide | 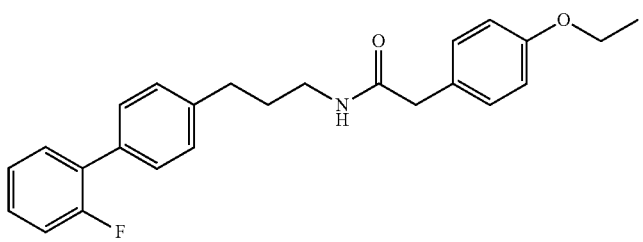 [SMILES: CCOc1ccc(CC(=O)NCCCc2ccc(-c3ccccc3F)cc2)cc1] |
| 113 | N-(3-(2'-fluoro-[1,1'-biphenyl]-4-yl)propyl)-1H-pyrazole-3-carboxamide | 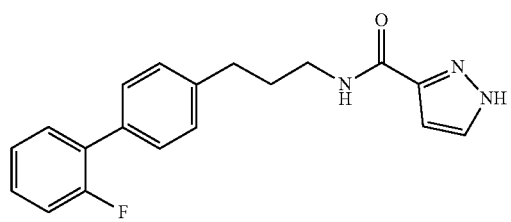 [SMILES: O=C(NCCCc1ccc(-c2ccccc2F)cc1)c1cc[nH]n1] |

TABLE 1-continued

| Compound No. | Name | Structure |
|---|---|---|
| 114 | 2-(2,4-dimethoxyphenyl)-N-(3-(2'-fluoro-[1,1'-biphenyl]-4-yl)propyl)acetamide | 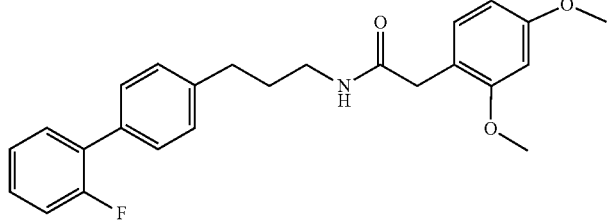 [SMILES: COc1ccc(CC(=O)NCCCc2ccc(-c3ccccc3F)cc2)c(OC)c1] |
| 115 | N-(3-(2'-fluoro-[1,1'-biphenyl]-4-yl)propyl)-3-methyl-4-oxo-3,4-dihydroquinazoline-7-carboxamide | 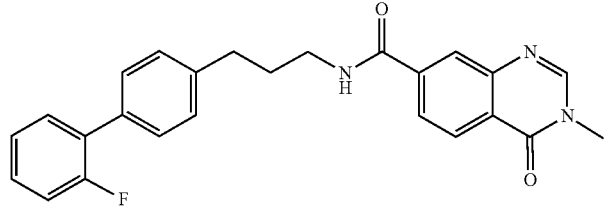 [SMILES: Cn1cnc2cc(C(=O)NCCCc3ccc(-c4ccccc4F)cc3)ccc2c1=O] |
| 116 | N-(3-(2'-fluoro-[1,1'-biphenyl]-4-yl)propyl)-2-oxo-1,2,3,4-terahydroquinoline-6-carboxamide | 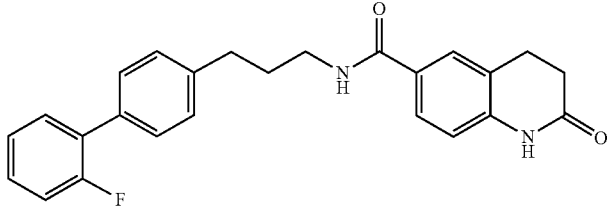 [SMILES: O=C1CCc2cc(C(=O)NCCCc3ccc(-c4ccccc4F)cc3)ccc2N1] |
| 117 | N-(3-(2'-fluoro-[1,1'-biphenyl]-4-yl)propyl)-1H-indole-3-carboxamide | 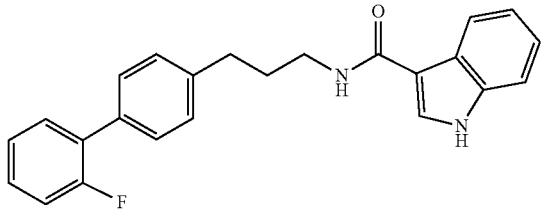 [SMILES: O=C(NCCCc1ccc(-c2ccccc2F)cc1)c1c[nH]c2ccccc12] |
| 118 | N-(3-(2'-fluoro-[1,1'-biphenyl]-4-yl)propyl)-1H-pyrrole-3-carboxamide | 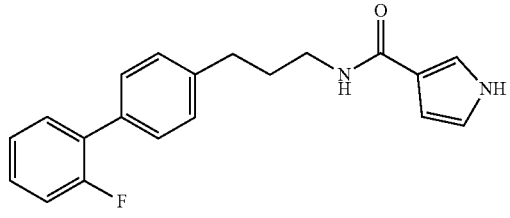 [SMILES: O=C(NCCCc1ccc(-c2ccccc2F)cc1)c1cc[nH]c1] |
| 119 | N-(3-(2'-fluoro-[1,1'-biphenyl]-4-yl)propyl)-1-(4-methoxyphenyl)cyclopropane-1-carboxamide | 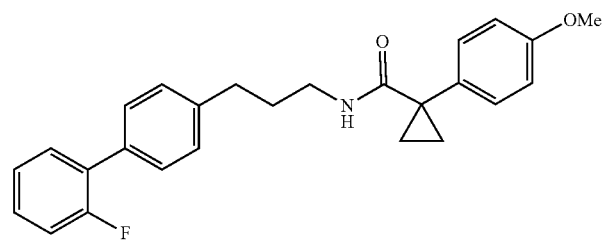 [SMILES: COc1ccc(C2(C(=O)NCCCc3ccc(-c4ccccc4F)cc3)CC2)cc1] |

TABLE 1-continued

| Compound No. | Name | Structure |
|---|---|---|
| 120 | N-(3-(2'-fluoro-[1,1'-biphenyl]-4-yl)propyl)-2-(4-(trifluoromethoxy)phenyl)acetamide | 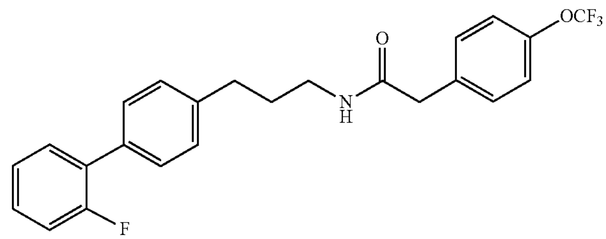 [SMILES: O=C(Cc1ccc(OC(F)(F)F)cc1)NCCCc1ccc(-c2ccccc2F)cc1] |
| 121 | 6-acetamido-N-(3-(2'-fluoro-[1,1'-biphenyl]-4-yl)propyl)nicotinamide | 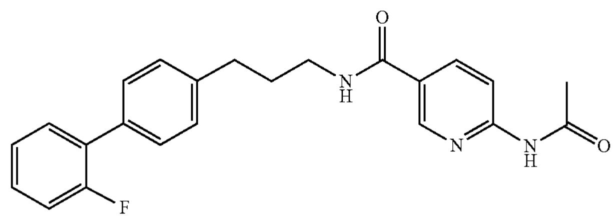 [SMILES: CC(=O)Nc1ccc(C(=O)NCCCc2ccc(-c3ccccc3F)cc2)cn1] |
| 122 | N-(3-(2'-fluoro-[1,1'-biphenyl]-4-yl)propyl)-1H-benzo[d]imidazole-4-carboxamide | 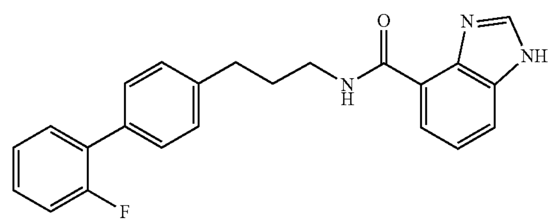 [SMILES: O=C(NCCCc1ccc(-c2ccccc2F)cc1)c1cccc2[nH]cnc12] |
| 123 | N-(3-(2'-fluoro-[1,1'-biphenyl]-4-yl)propyl)quinoxaline-6-carboxamide | 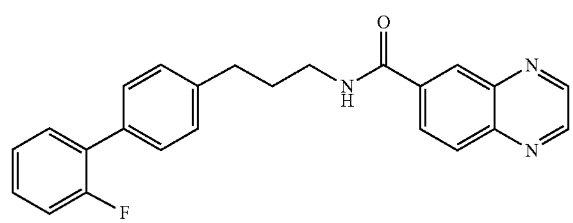 [SMILES: O=C(NCCCc1ccc(-c2ccccc2F)cc1)c1ccc2nccnc2c1] |
| 124 | N-(3-(2'-fluoro-[1,1'-biphenyl]-4-yl)propyl)-2-(1H-imidazol-1-yl)acetamide | 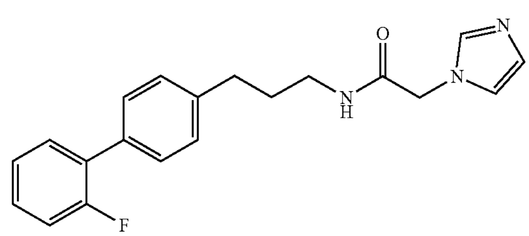 [SMILES: O=C(Cn1ccnc1)NCCCc1ccc(-c2ccccc2F)cc1] |
| 125 | N-(3-(2'-fluoro-[1,1'-biphenyl]-4-yl)propyl)-1,5-dimethyl-1H-pyrazole-3-carboxamide | 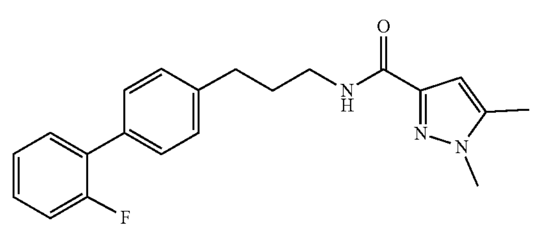 [SMILES: Cc1cc(C(=O)NCCCc2ccc(-c3ccccc3F)cc2)nn1C] |

TABLE 1-continued

| Compound No. | Name | Structure |
|---|---|---|
| 126 | 2-(3-fluoro-4-methoxyphenyl)-N-(3-(2'-fluoro-[1,1'-biphenyl]-4-yl)propyl)acetamide | 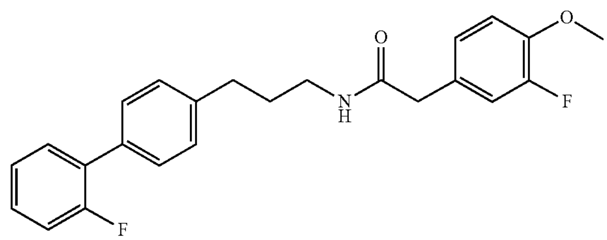 [SMILES: COc1ccc(CC(=O)NCCCc2ccc(-c3ccccc3F)cc2)cc1F] |
| 127 | N-(3-(2'-fluoro-[1,1'-biphenyl]-4-yl)propyl)-4-hydroxy-3,5-dimethylbenzamide | 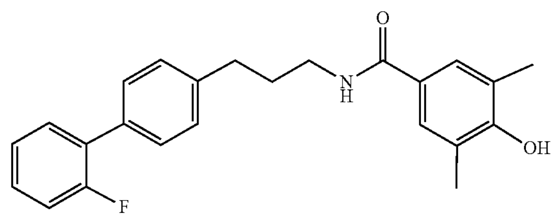 [SMILES: Cc1cc(C(=O)NCCCc2ccc(-c3ccccc3F)cc2)cc(C)c1O] |
| 128 | N-(3-(2'-fluoro-[1,1'-biphenyl]-4-yl)propyl)-3-methylisoxazole-5-carboxamide | 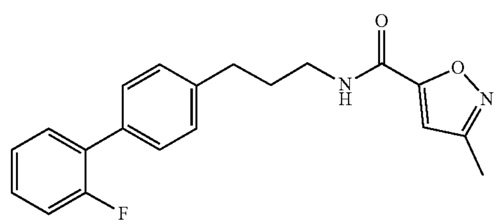 [SMILES: Cc1cc(C(=O)NCCCc2ccc(-c3ccccc3F)cc2)on1] |
| 129 | N-(3-(2'-fluoro-[1,1'-biphenyl]-4-yl)propyl)-1H-pyrrolo[2,3-b]pyridine-2-carboxamide | 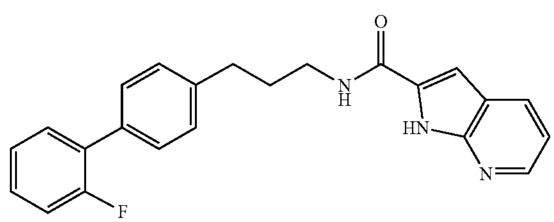 [SMILES: O=C(NCCCc1ccc(-c2ccccc2F)cc1)c1cc2cccnc2[nH]1] |
| 130 | N-(3-(2'-fluoro-[1,1'-biphenyl]-4-yl)propyl)-1-methyl-1H-imidazole-5-carboxamide | 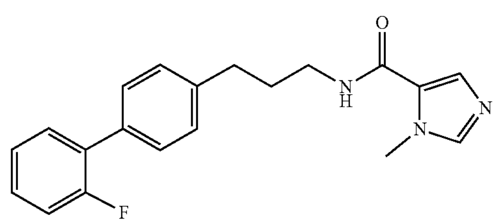 [SMILES: Cn1cncc1C(=O)NCCCc1ccc(-c2ccccc2F)cc1] |
| 131 | N-(3-(2'-fluoro-[1,1'-biphenyl]-4-yl)propyl)oxazole-5-carboxamide | 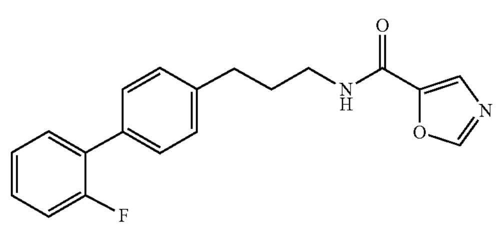 [SMILES: O=C(NCCCc1ccc(-c2ccccc2F)cc1)c1cnco1] |
| 132 | N-(3-(2'-fluoro-[1,1'-biphenyl]-4-yl)propyl)-5-methylthiazole-2-carboxamide | 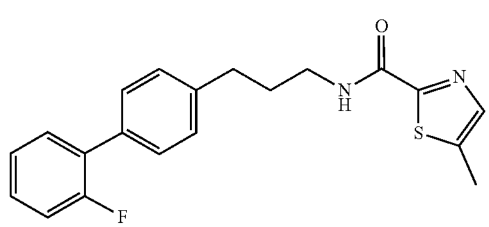 [SMILES: Cc1cnc(C(=O)NCCCc2ccc(-c3ccccc3F)cc2)s1] |

TABLE 1-continued

| Compound No. | Name | Structure |
|---|---|---|
| 133 | N-(3-(2'-fluoro-[1,1'-biphenyl]-4-yl)propyl)-1,3-dimethyl-1H-pyrazole-4-carboxamide | 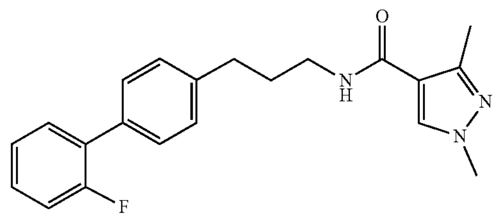 [SMILES: Cc1nn(C)cc1C(=O)NCCCc1ccc(-c2ccccc2F)cc1] |
| 134 | N-(3-(2'-fluoro-[1,1'-biphenyl]-4-yl)propyl)-1H-pyrrole-2-carboxamide | 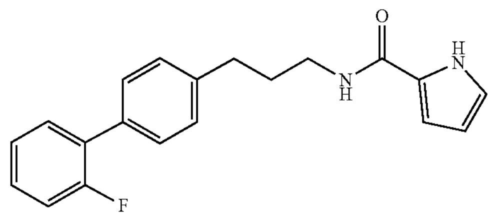 [SMILES: O=C(NCCCc1ccc(-c2ccccc2F)cc1)c1ccc[nH]1] |
| 135 | (S)-1-acetyl-N-(3-(2'-fluoro-[1,1'-biphenyl]-4-yl)propyl)pyrrolidine-2-carboxamide | 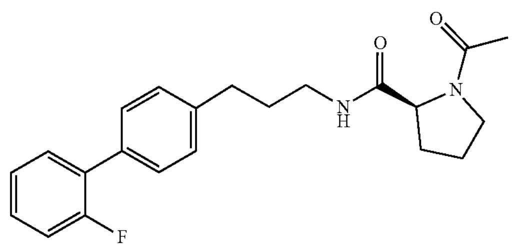 [SMILES: CC(=O)N1CCC[C@H]1C(=O)NCCCc1ccc(-c2ccccc2F)cc1] |
| 136 | N-(3-(2'-fluoro-[1,1'-biphenyl]-4-yl)propyl)-1H-benzo[d]imidazole-5-carboxamide | 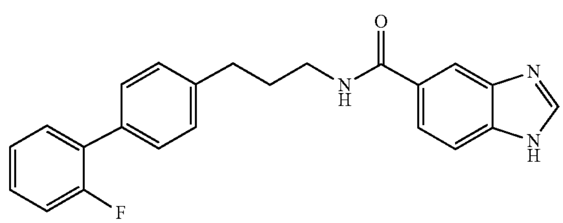 [SMILES: O=C(NCCCc1ccc(-c2ccccc2F)cc1)c1ccc2[nH]cnc2c1] |
| 137 | N-(3-(2'-fluoro-[1,1'-biphenyl]-4-yl)propyl)imidazo[1,2-a]pyridine-3-carboxamide | 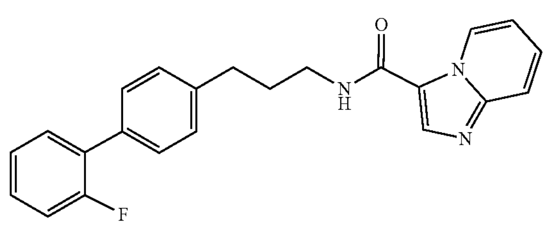 [SMILES: O=C(NCCCc1ccc(-c2ccccc2F)cc1)c1cnc2ccccn12] |
| 138 | N-(3-(2'-fluoro-[1,1'-biphenyl]-4-yl)propyl)-2-methylthiazole-5-carboxamide | 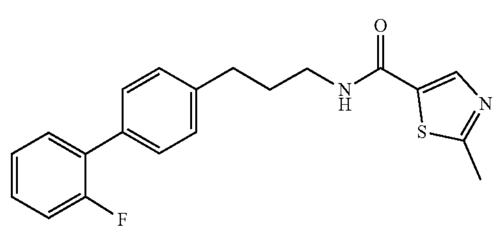 [SMILES: Cc1ncc(C(=O)NCCCc2ccc(-c3ccccc3F)cc2)s1] |

TABLE 1-continued

| Compound No. | Name | Structure |
|---|---|---|
| 139 | N-(3-(2'-fluoro-[1,1'-biphenyl]-4-yl)propyl)-3-methyl-1H-pyrazole-5-carboxamide | 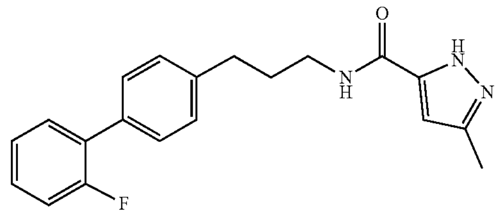 [SMILES: Cc1cc(C(=O)NCCCc2ccc(-c3ccccc3F)cc2)[nH]n1] |
| 140 | N-(3-(2'-fluoro-[1,1'-biphenyl]-4-yl)propyl)-2-(p-tolyl)acetamide | 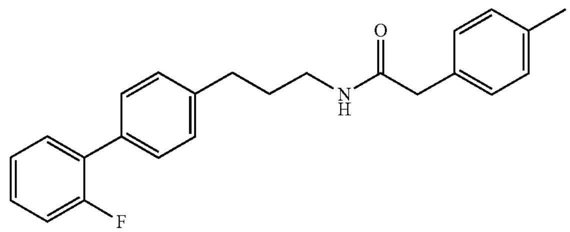 [SMILES: Cc1ccc(CC(=O)NCCCc2ccc(-c3ccccc3F)cc2)cc1] |
| 141 | N-(3-(2'-fluoro-[1,1'-biphenyl]-4-yl)propyl)-2-methylthiazole-4-carboxamide | 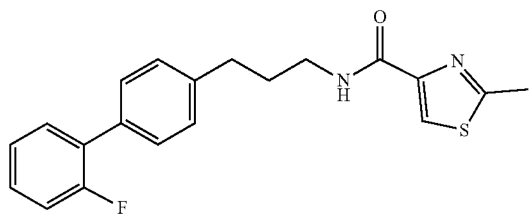 [SMILES: Cc1nc(C(=O)NCCCc2ccc(-c3ccccc3F)cc2)cs1] |
| 142 | N-(3-(2'-fluoro-[1,1'-biphenyl]-4-yl)propyl)-3-isopropyl-1-methyl-1H-pyrazole-5-carboxamide | 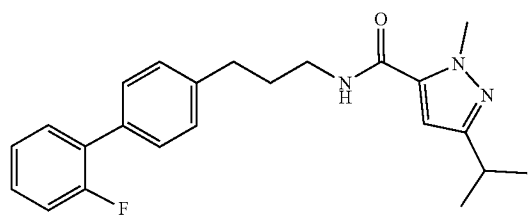 [SMILES: CC(C)c1cc(C(=O)NCCCc2ccc(-c3ccccc3F)cc2)n(C)n1] |
| 143 | N-(3-(2'-fluoro-[1,1'-biphenyl]-4-yl)propyl)-2-methyl-2H-indazole-3-carboxamide | 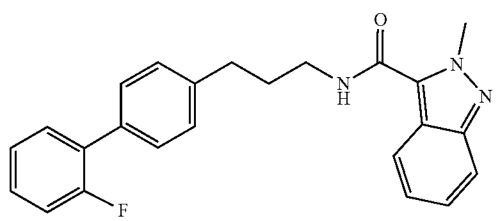 [SMILES: Cn1nc2ccccc2c1C(=O)NCCCc1ccc(-c2ccccc2F)cc1] |
| 144 | N-(3-(2'-fluoro-[1,1'-biphenyl]-4-yl)propyl)-3,5-dimethylisoxazole-4-carboxamide | 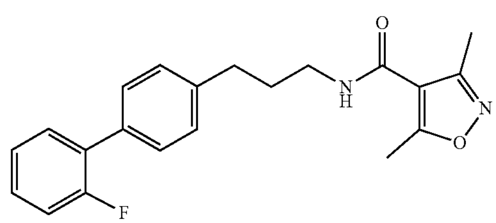 [SMILES: Cc1noc(C)c1C(=O)NCCCc1ccc(-c2ccccc2F)cc1] |
| 145 | N-(3-(2'-fluoro-[1,1'-biphenyl]-4-yl)propyl)-4-methylisoxazole-5-carboxamide | 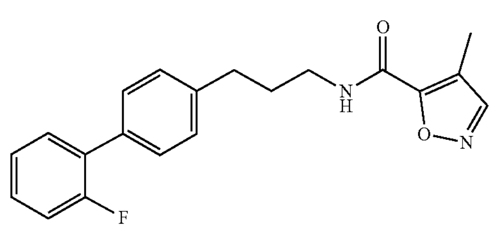 [SMILES: Cc1cnoc1C(=O)NCCCc1ccc(-c2ccccc2F)cc1] |

TABLE 1-continued

| Compound No. | Name | Structure |
|---|---|---|
| 146 | N-(3-(2'-fluoro-[1,1'-biphenyl]-4-yl)propyl)-1-methyl-1H-pyrazole-4-carboxamide | 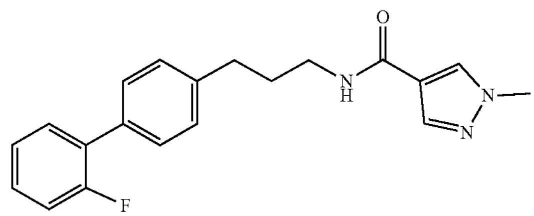 [SMILES: Cn1cc(C(=O)NCCCc2ccc(-c3ccccc3F)cc2)cn1] |
| 147 | N-(3-(2'-fluoro-[1,1'-biphenyl]-4-yl)propyl)-5-phenylisoxazole-3-carboxamide | 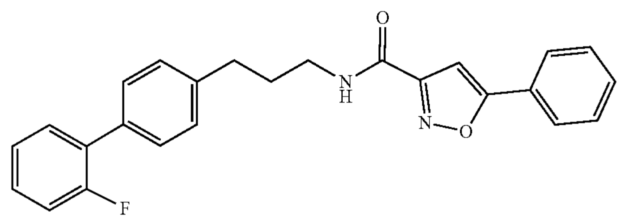 [SMILES: O=C(NCCCc1ccc(-c2ccccc2F)cc1)c1cc(-c2ccccc2)on1] |
| 148 | 4-(4-(1-methyl-1H-indazol-5-yl)phenyl)-N-(pyridin-3-yl)butanamide | 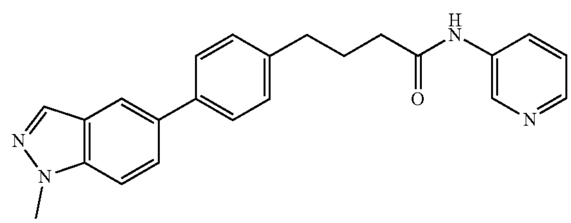 |
| 149 | 4-(2',3'-difluoro-[1,1'-biphenyl]-4-yl)-N-(pyridin-3-yl)butanamide | 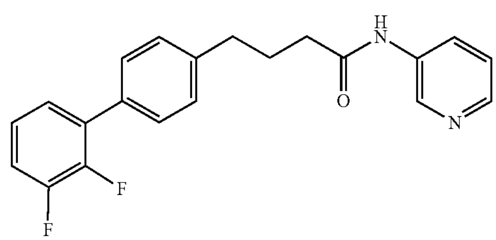 [SMILES: O=C(CCCc1ccc(-c2cccc(F)c2F)cc1)Nc1cccnc1] |
| 150 | 4-(4-cyclopropylphenyl)-N-(pyridin-3-yl)butanamide | 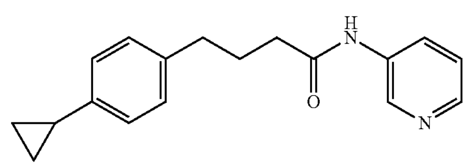 [SMILES: O=C(CCCc1ccc(C2CC2)cc1)Nc1cccnc1] |
| 151 | 4-([1,1'-biphenyl]-4-yl)-N-(pyridin-3-yl)butanamide | 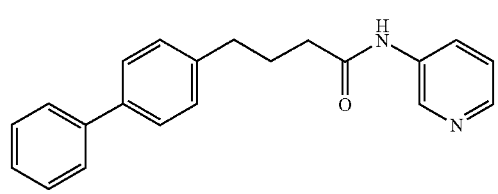 [SMILES: O=C(CCCc1ccc(-c2ccccc2)cc1)Nc1cccnc1] |
| 152 | 4-(2'-methyl-[1,1'-biphenyl]-4-yl)-N-(pyridin-3-yl)butanamide | 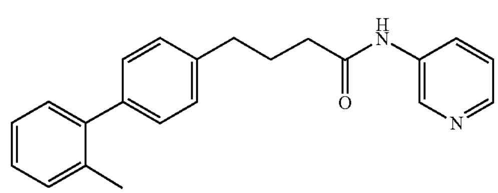 [SMILES: Cc1ccccc1-c1ccc(CCCC(=O)Nc2cccnc2)cc1] |

TABLE 1-continued

| Compound No. | Name | Structure |
|---|---|---|
| 153 | 4-(4-(6-methylpyridin-3-yl)phenyl)-N-(pyridin-3-yl)butanamide | 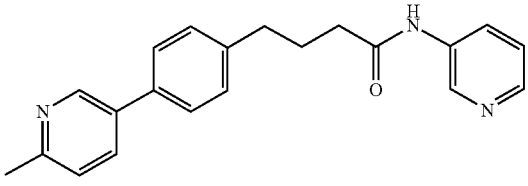 [SMILES: Cc1ccc(-c2ccc(CCCC(=O)Nc3cccnc3)cc2)cn1] |
| 154 | N-(pyridin-3-yl)-4-(2'-(trifluoromethoxy)-[1,1'-biphenyl]-4-yl)butanamide | 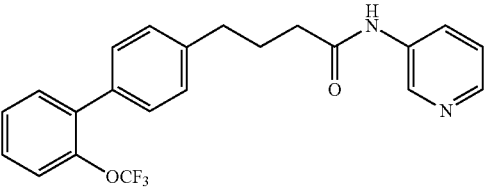 |
| 155 | N-(pyridin-3-yl)-4-(4-(6-(trifluoromethyl)pyridin-3-yl)phenyl)butanamide | 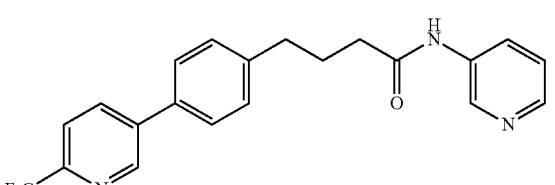 |
| 156 | 4-(4-(2-methylpyridin-4-yl)phenyl)-N-(pyridin-3-yl)butanamide | 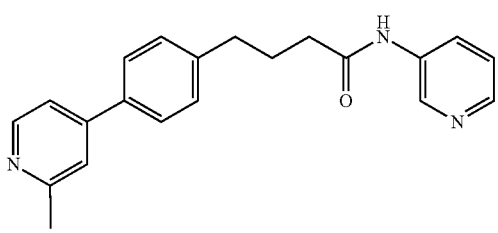 [SMILES: Cc1cc(-c2ccc(CCCC(=O)Nc3cccnc3)cc2)ccn1] |
| 157 | 4-(2',4'-difluoro-[1,1'-biphenyl]-4-yl)-N-(pyridin-3-yl)butanamide | 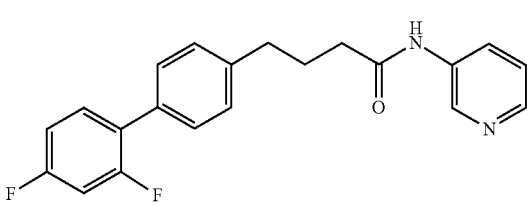 [SMILES: O=C(CCCc1ccc(-c2ccc(F)cc2F)cc1)Nc1cccnc1] |
| 158 | N-(pyridin-3-yl)-4-(4-(pyridin-3-yl)phenyl)butanamide | 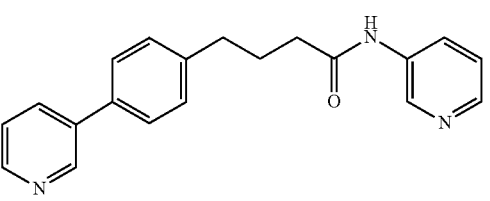 [SMILES: O=C(CCCc1ccc(-c2cccnc2)cc1)Nc1cccnc1] |
| 159 | 4-(2',6'-difluoro-[1,1'-biphenyl]-4-yl)-N-(pyridin-3-yl)butanamide | 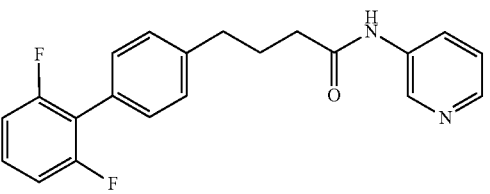 [SMILES: O=C(CCCc1ccc(-c2c(F)cccc2F)cc1)Nc1cccnc1] |

TABLE 1-continued

| Compound No. | Name | Structure |
|---|---|---|
| 160 | 4-(2'-chloro-[1,1'-biphenyl]-4-yl)-N-(pyridin-3-yl)butanamide | 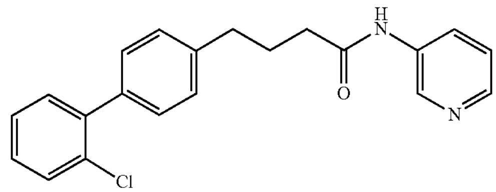 [SMILES: O=C(CCCc1ccc(-c2ccccc2Cl)cc1)Nc1cccnc1] |
| 161 | 4-(4-(benzo[c][1,2,5]oxadiazol-5-yl)phenyl)-N-(pyridin-3-yl)butanamide | 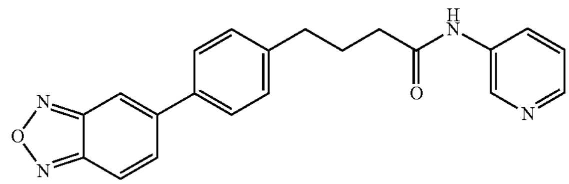 [SMILES: O=C(CCCc1ccc(-c2ccc3nonc3c2)cc1)Nc1cccnc1] |
| 162 | 4-(4-(2,3-dihydrobenzo[b][1,4]dioxin-6-yl)phenyl)-N-(pyridin-3-yl)butanamide | 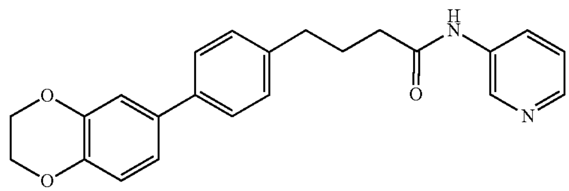 [SMILES: O=C(CCCc1ccc(-c2ccc3c(c2)OCCO3)cc1)Nc1cccnc1] |
| 163 | N-(pyridin-3-yl)-4-(4-(quinolin-6-yl)phenyl)butanamide | 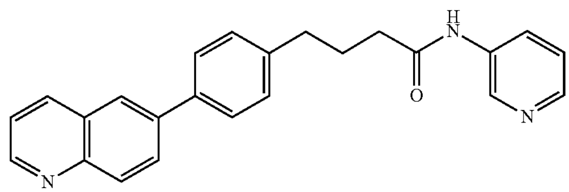 [SMILES: O=C(CCCc1ccc(-c2ccc3ncccc3c2)cc1)Nc1cccnc1] |
| 164 | 4-(4-(2-methyl-2H-indazol-5-yl)phenyl)-N-(pyridin-3-yl)butanamide | 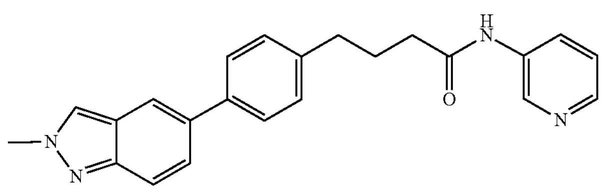 [SMILES: Cn1cc2cc(-c3ccc(CCCC(=O)Nc4cccnc4)cc3)ccc2n1] |
| 165 | 4-(4-(2-methyl-2H-indazol-4-yl)phenyl)-N-(pyridin-3-yl)butanamide | 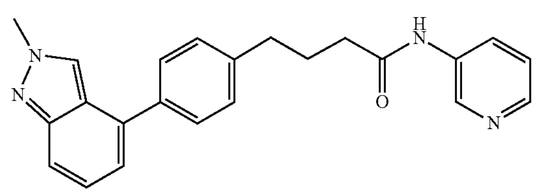 [SMILES: Cn1cc2c(-c3ccc(CCCC(=O)Nc4cccnc4)cc3)cccc2n1] |
| 166 | 4-(4-(1-methyl-1H-indazol-6-yl)phenyl)-N-(pyridin-3-yl)butanamide | 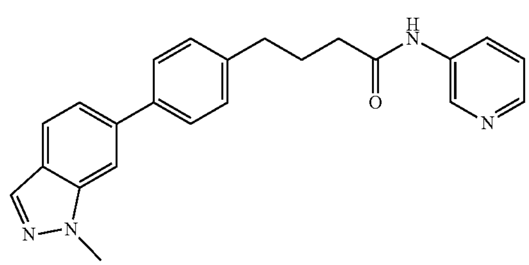 [SMILES: Cn1ncc2ccc(-c3ccc(CCCC(=O)Nc4cccnc4)cc3)cc21] |

TABLE 1-continued

| Compound No. | Name |
|---|---|
| 167 | 4-(4-(6-methoxypyridin-3-yl)phenyl)-N-(pyridin-3-yl)butanamide |
| 168 | 4-(3',4'-dimethoxy-[1,1'-biphenyl]-4-yl)-N-(pyridin-3-yl)butanamide |
| 169 | 4-(4-(1-methyl-1H-indol-5-yl)phenyl)-N-(pyridin-3-yl)butanamide |
| 170 | 4-(4-phenoxyphenyl)-N-(pyridin-3-yl)butanamide |
| 171 | 4-(4-(4-methoxyphenoxy)phenyl)-N-(pyridin-3-yl)butanamide |
| 172 | 4-(4-(3,5-dimethylisoxazol-4-yl)phenyl)-N-(pyridin-3-yl)butanamide |
| 173 | 4-(4-(benzo[d]oxazol-5-yl)phenyl)-N-(pyridin-3-yl)butanamide |
| 174 | N-(pyridin-3-yl)-4-(4-(pyrimidin-5-yl)phenyl)butanamide |

TABLE 1-continued

| Compound No. | Name | Structure |
|---|---|---|
| 175 | 4-(2'-fluoro-5'-methoxy-[1,1'-biphenyl]-4-yl)-N-(pyridin-3-yl)butanamide | 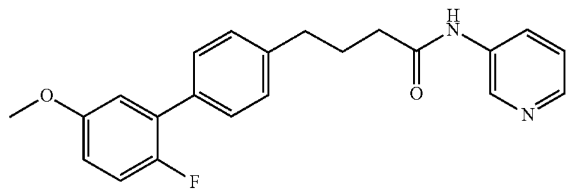 [SMILES: COc1ccc(F)c(-c2ccc(CCCC(=O)Nc3cccnc3)cc2)c1] |
| 176 | 4-(4-(1H-pyrazol-4-yl)phenyl)-N-(pyridin-3-yl)butanamide | 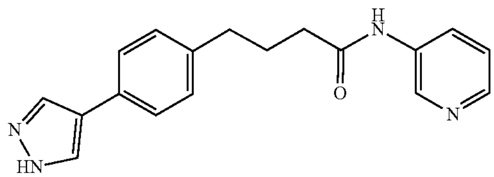 [SMILES: O=C(CCCc1ccc(-c2cn[nH]c2)cc1)Nc1cccnc1] |
| 177 | 4-(4-(2-oxoindolin-6-yl)phenyl)-N-(pyridin-3-yl)butanamide | 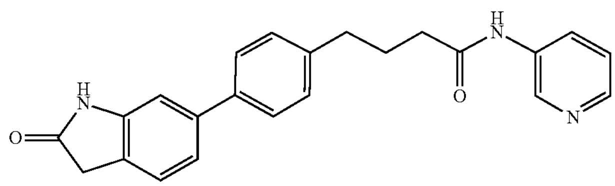 [SMILES: O=C(CCCc1ccc(-c2ccc3c(c2)NC(=O)C3)cc1)Nc1cccnc1] |
| 178 | 4-(4-(2-methoxypyridin-3-yl)phenyl)-N-(pyridin-3-yl)butanamide | 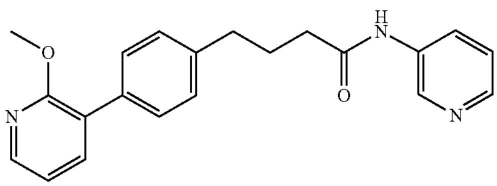 [SMILES: COc1ncccc1-c1ccc(CCCC(=O)Nc2cccnc2)cc1] |
| 179 | 4-(5'-chloro-2'-fluoro-[1,1'-biphenyl]-4-yl)-N-(pyridin-3-yl)butanamide | 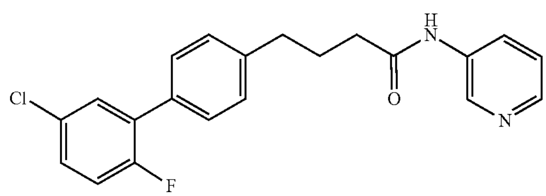 [SMILES: O=C(CCCc1ccc(-c2cc(Cl)ccc2F)cc1)Nc1cccnc1] |
| 180 | 4-(4-(4-methyl-1H-indazol-5-yl)phenyl)-N-(pyridin-3-yl)butanamide | 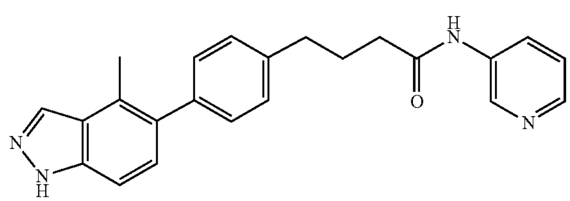 |
| 181 | 4-(4-(1H-pyrrolo[2,3-b]pyridin-5-yl)phenyl)-N-(pyridin-3-yl)butanamide | 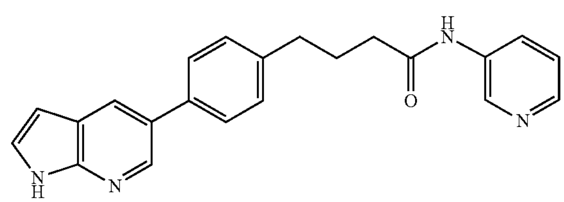 [SMILES: O=C(CCCc1ccc(-c2cnc3[nH]ccc3c2)cc1)Nc1cccnc1] |
| 182 | 4-(4-(1H-pyrazol-1-yl)phenyl)-N-(pyridin-3-yl)butanamide | 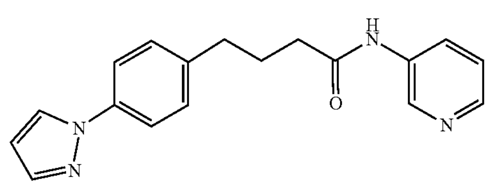 [SMILES: O=C(CCCc1ccc(-n2cccn2)cc1)Nc1cccnc1] |

TABLE 1-continued

| Compound No. | Name | Structure |
|---|---|---|
| 183 | N-(pyridin-3-yl)-4-(4-(quinolin-3-yl)phenyl)butanamide | 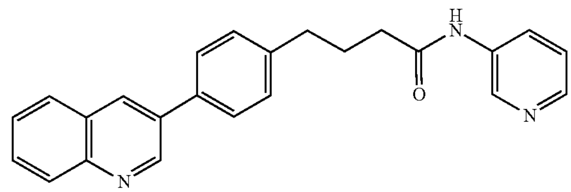 [SMILES: O=C(CCCc1ccc(-c2cnc3ccccc3c2)cc1)Nc1cccnc1] |
| 184 | 4-(2'-fluoro-3'-methoxy-[1,1'-biphenyl]-4-yl)-N-(pyridin-3-yl)butanamide | 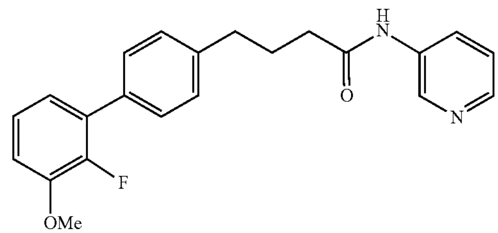 [SMILES: COc1cccc(-c2ccc(CCCC(=O)Nc3cccnc3)cc2)c1F] |
| 185 | 4-(3-(1H-pyrazol-1-yl)phenyl)-N-(pyridin-3-yl)butanamide | 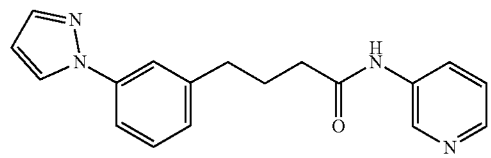 [SMILES: O=C(CCCc1cccc(-n2cccn2)c1)Nc1cccnc1] |
| 186 | 4-(4-benzylphenyl)-N-(pyridin-3-yl)butanamide | 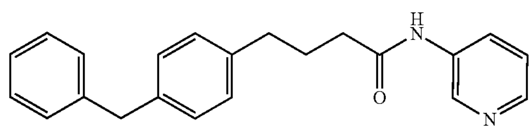 [SMILES: O=C(CCCc1ccc(Cc2ccccc2)cc1)Nc1cccnc1] |
| 187 | 4-(4-(1-methyl-6-oxo-1,6-dihydropyridin-3-yl)phenyl)-N-(pyridin-3-yl)butanamide | 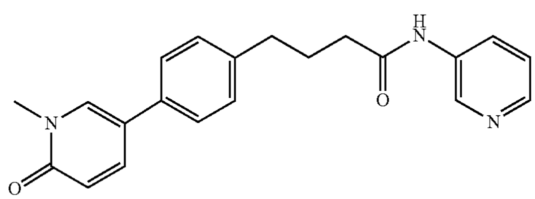 [SMILES: Cn1cc(-c2ccc(CCCC(=O)Nc3cccnc3)cc2)ccc1=O] |
| 188 | N-(pyridin-3-yl)-4-(2'-(trifluoromethyl)-[1,1'-biphenyl]-4-yl)butanamide | 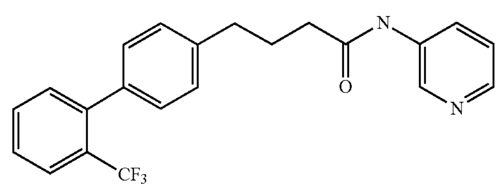 |
| 189 | 4-(2'-fluoro-4'-(trifluoromethyl)-[1,1'-biphenyl]-4-yl)-N-(pyridin-3-yl)butanamide | 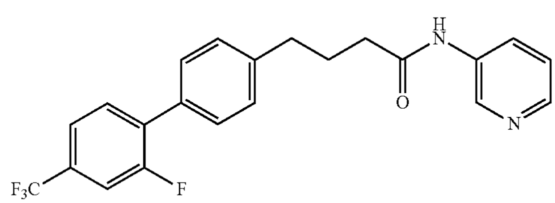 [SMILES: O=C(CCCc1ccc(-c2ccc(C(F)(F)F)cc2F)cc1)Nc1cccnc1] |
| 190 | 4-(4-(7-fluoroquinolin-6-yl)phenyl)-N-(pyridin-3-yl)butanamide | 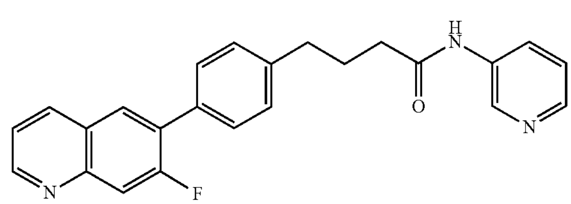 [SMILES: O=C(CCCc1ccc(-c2cc3cccnc3cc2F)cc1)Nc1cccnc1] |

TABLE 1-continued

| Compound No. | Name | Structure |
|---|---|---|
| 191 | 4-(4-(1,3-dimethyl-1H-indazol-5-yl)phenyl)-N-(pyridin-3-yl)butanamide | 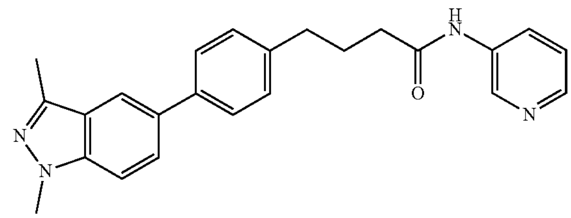 |
| 192 | N-(pyridin-3-yl)-4-(4-(quinoxalin-6-yl)phenyl)butanamide | 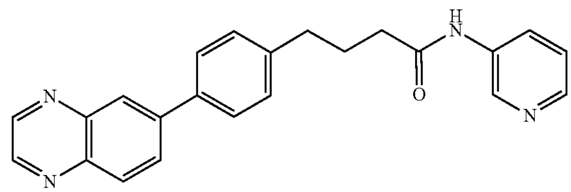 [SMILES: O=C(CCCc1ccc(-c2ccc3nccnc3c2)cc1)Nc1cccnc1] |
| 193 | 4-(4-(1-benzyl-1H-pyrazol-4-yl)phenyl)-N-(pyridin-3-yl)butanamide | 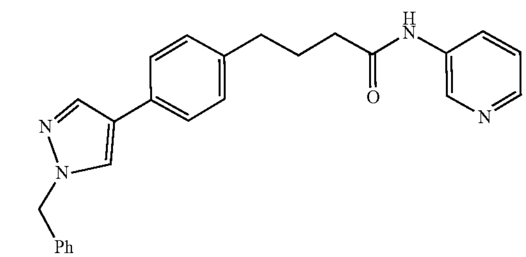 |
| 194 | 4-(4-(benzo[d]isoxazol-5-yl)phenyl)-N-(pyridin-3-yl)butanamide | 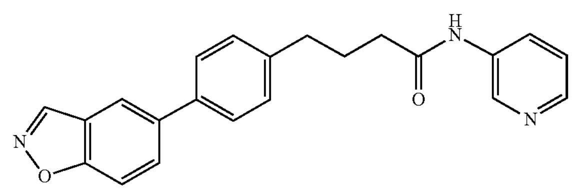 [SMILES: O=C(CCCc1ccc(-c2ccc3oncc3c2)cc1)Nc1cccnc1] |
| 195 | 4-(4-(1H-benzo[d]imidazol-5-yl)phenyl)-N-(pyridin-3-yl)butanamide | 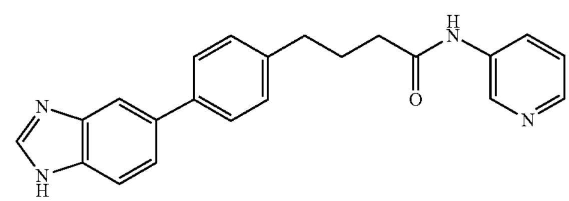 [SMILES: O=C(CCCc1ccc(-c2ccc3[nH]cnc3c2)cc1)Nc1cccnc1] |
| 196 | 4-(4-(2-oxo-1,2,3,4-tetrahydroquinolin-6-yl)phenyl)-N-(pyridin-3-yl)butanamide | 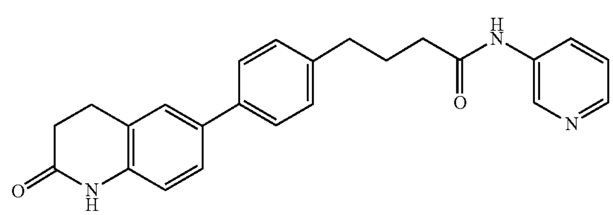 [SMILES: O=C(CCCc1ccc(-c2ccc3c(c2)CCC(=O)N3)cc1)Nc1cccnc1] |
| 197 | 4-(4-(imidazo[1,2-a]pyridin-6-yl)phenyl)-N-(pyridin-3-yl)butanamide | 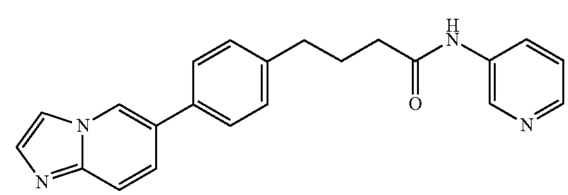 [SMILES: O=C(CCCc1ccc(-c2ccc3nccn3c2)cc1)Nc1cccnc1] |

TABLE 1-continued

| Compound No. | Name | Structure |
|---|---|---|
| 198 | 4-(4'-(1H-pyrazol-1-yl)-[1,1'-biphenyl]-4-yl)-N-(pyridin-3-yl)butanamide | 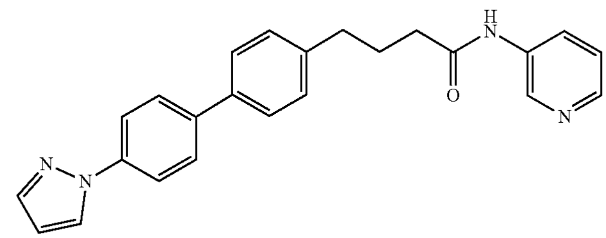 [SMILES: O=C(CCCc1ccc(-c2ccc(-n3cccn3)cc2)cc1)Nc1cccnc1] |
| 199 | 4-(4-(2-methylquinolin-6-yl)phenyl)-N-(pyridin-3-yl)butanamide | 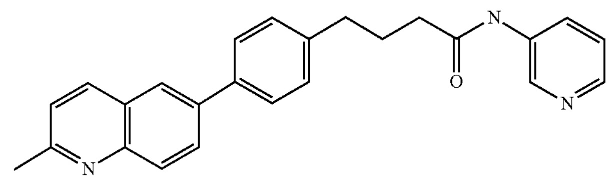 |
| 200 | 4-(2'-fluoro-5'-(morpholine-4-carbonyl)-[1,1'-biphenyl]-4-yl)-N-(pyridin-3-yl)butanamide | 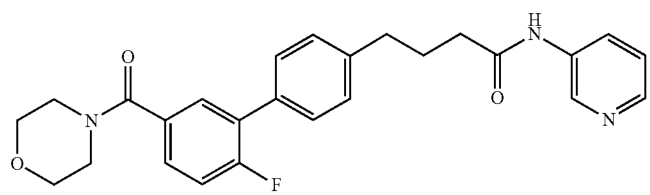 [SMILES: O=C(CCCc1ccc(-c2cc(C(=O)N3CCOCC3)ccc2F)cc1)Nc1cccnc1] |
| 201 | 4-(4-([1,2,4]triazolo[1,5-a]pyrimidin-6-yl)phenyl)-N-(pyridin-3-yl)butanamide | 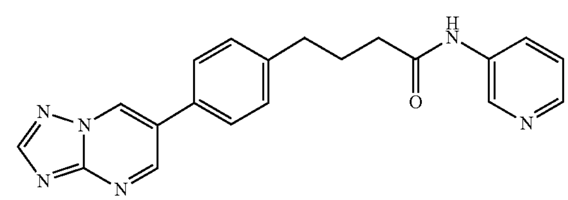 [SMILES: O=C(CCCc1ccc(-c2cnc3ncnn3c2)cc1)Nc1cccnc1] |
| 202 | N-(pyridin-3-yl)-4-(4-(pyridin-4-yl)phenyl)butanamide | 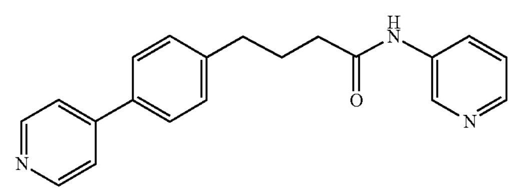 [SMILES: O=C(CCCc1ccc(-c2ccncc2)cc1)Nc1cccnc1] |
| 203 | 4-(4-(1,3-dimethyl-1H-pyrazol-4-yl)phenyl)-N-(pyridin-3-yl)butanamide | 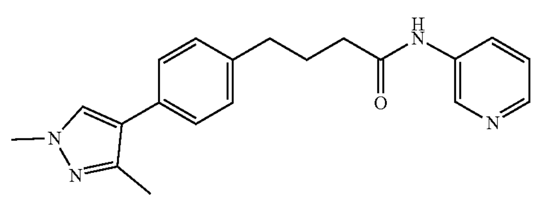 [SMILES: Cc1nn(C)cc1-c1ccc(CCCC(=O)Nc2cccnc2)cc1] |
| 204 | 4-(4-(1,3,4-oxadiazol-2-yl)phenyl)-N-(pyridin-3-yl)butanamide | 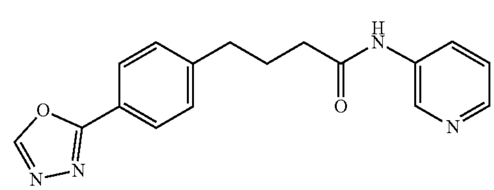 [SMILES: O=C(CCCc1ccc(-c2nnco2)cc1)Nc1cccnc1] |

TABLE 1-continued

| Compound No. | Name | Structure |
|---|---|---|
| 205 | 4-(4-(2-morpholinopyrimidin-5-yl)phenyl)-N-(pyridin-3-yl)butanamide | 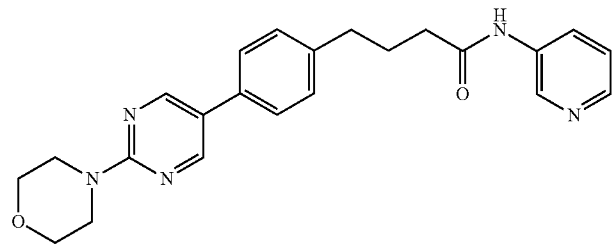 [SMILES: O=C(CCCc1ccc(-c2cnc(N3CCOCC3)nc2)cc1)Nc1cccnc1] |
| 206 | 4-(4-(1H-indazol-5-yl)phenyl)-N-(pyridin-3-yl)butanamide | 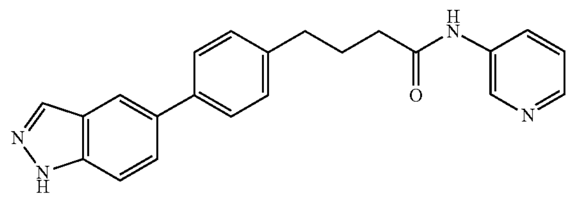 [SMILES: O=C(CCCc1ccc(-c2ccc3[nH]ncc3c2)cc1)Nc1cccnc1] |
| 207 | 4-(4-(2-oxo-1,2-dihydroquinolin-6-yl)phenyl)-N-(pyridin-3-yl)butanamide | 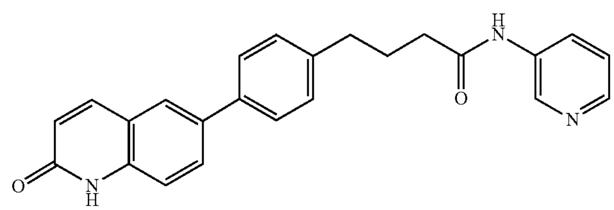 [SMILES: O=C(CCCc1ccc(-c2ccc3[nH]c(=O)ccc3c2)cc1)Nc1cccnc1] |
| 208 | 4-(4-(2-oxo-2,3-dihydrobenzo[d]floxazol-6-yl)phenyl)-N-(pyridin-3-yl)butanamide | 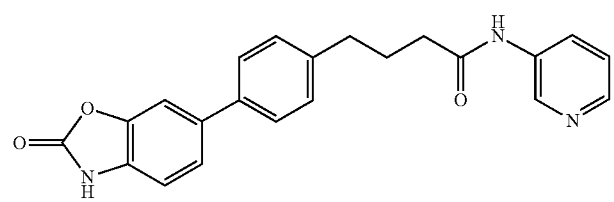 [SMILES: O=C(CCCc1ccc(-c2ccc3[nH]c(=O)oc3c2)cc1)Nc1cccnc1] |
| 209 | 4-(4-(6-fluoro-1H-indazol-5-yl)phenyl)-N-(pyridin-3-yl)butanamide | 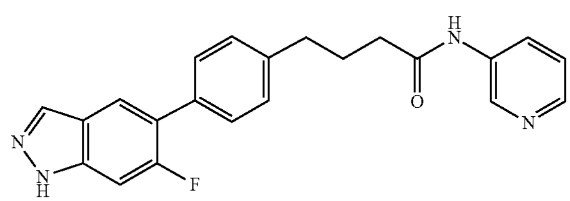 [SMILES: O=C(CCCc1ccc(-c2cc3cn[nH]c3cc2F)cc1)Nc1cccnc1] |
| 210 | 4-(4-(1H-pyrazolo[3,4-b]pyridin-5-yl)phenyl)-N-(pyridin-3-yl)butanamide | 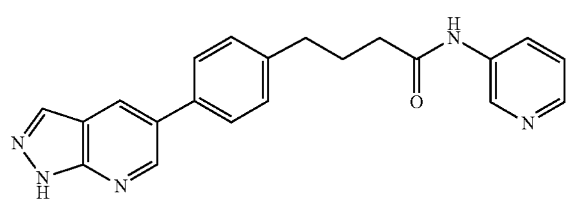 [SMILES: O=C(CCCc1ccc(-c2cnc3[nH]ncc3c2)cc1)Nc1cccnc1] |
| 211 | 4-(4-(7-oxo-5,6,7,8-tetrahydro-1,8-naphthyridin-3-yl)phenyl)-N-(pyridin-3-yl)butanamide | 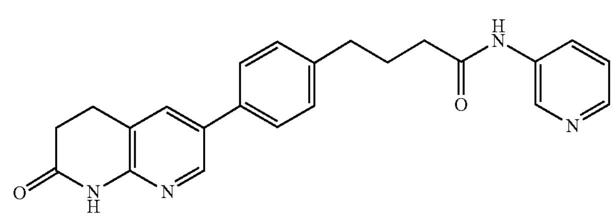 [SMILES: O=C(CCCc1ccc(-c2cnc3c(c2)CCC(=O)N3)cc1)Nc1cccnc1] |

TABLE 1-continued

| Compound No. | Name | Structure |
|---|---|---|
| 212 | 4-(4-(methyl(pyridin-3-yl)amino)phenyl)-N-(pyridin-3-yl)butanamide | 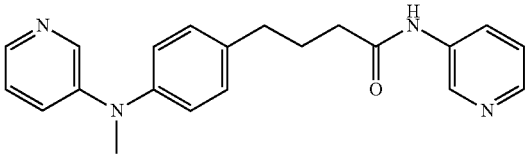 [SMILES: CN(c1ccc(CCCC(=O)Nc2cccnc2)cc1)c1cccnc1] |
| 213 | 4-(4-(1H-indol-5-yl)phenyl)-N-(pyridin-3-yl)butanamide | 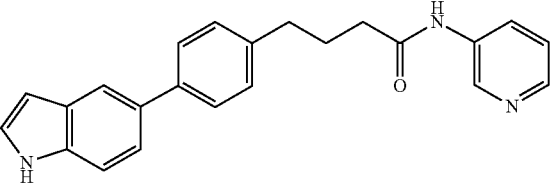 [SMILES: O=C(CCCc1ccc(-c2ccc3[nH]ccc3c2)cc1)Nc1cccnc1] |
| 214 | 4-(4-(isoquinolin-6-yl)phenyl)-N-(pyridin-3-yl)butanamide | 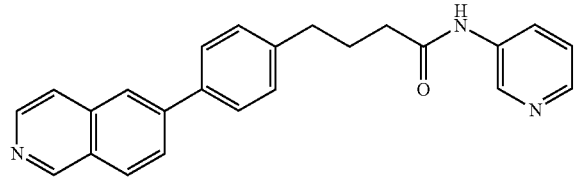 [SMILES: O=C(CCCc1ccc(-c2ccc3cnccc3c2)cc1)Nc1cccnc1] |
| 215 | 4-(4-(1-methyl-1H-imidazol-5-yl)phenyl)-N-(pyridin-3-yl)butanamide | 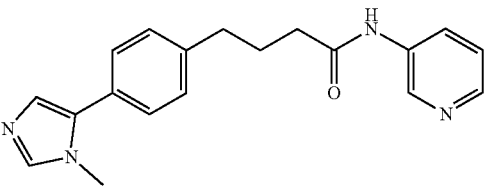 [SMILES: Cn1cncc1-c1ccc(CCCC(=O)Nc2cccnc2)cc1] |
| 216 | N-(pyridin-3-yl)-4-(4-(1,3,5-trimethyl-1H-pyrazol-4-yl)phenyl)butanamide | 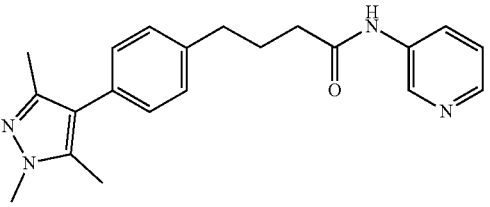 [SMILES: Cc1nn(C)c(C)c1-c1ccc(CCCC(=O)Nc2cccnc2)cc1] |
| 217 | N-(pyridin-3-yl)-4-(4-(thiazol-4-yl)phenyl)butanamide | 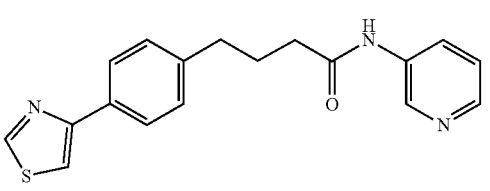 [SMILES: O=C(CCCc1ccc(-c2cscn2)cc1)Nc1cccnc1] |
| 218 | 4-(3'-ethoxy-2'-fluoro-[1,1'-biphenyl]-4-yl)-N-(pyridin-3-yl)butanamide | 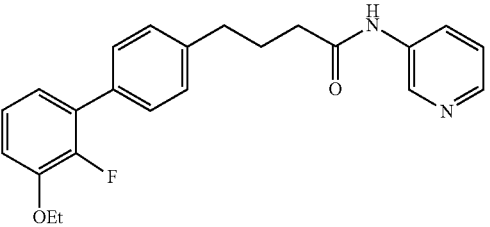 |

TABLE 1-continued

| Compound No. | Name | Structure |
|---|---|---|
| 219 | 4-(2'-fluoro-3'-methyl-[1,1'-biphenyl]-4-yl)-N-(pyridin-3-yl)butanamide | 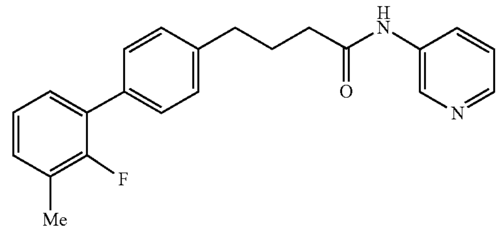 |
| 220 | 4-(2'-fluoro-3'-(trifluoromethyl)-[1,1'-biphenyl]-4-yl)-N-(pyridin-3-yl)butanamide | 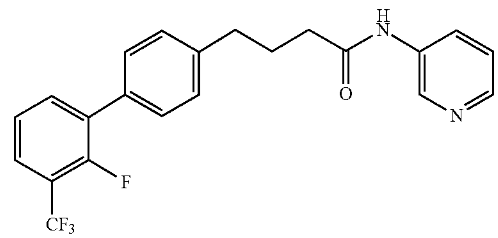 [SMILES: O=C(CCCc1ccc(-c2cccc(C(F)(F)F)c2F)cc1)Nc1cccnc1] |
| 221 | 4-(3'-cyano-2'-fluoro-[1,1'-biphenyl]-4-yl)-N-(pyridin-3-yl)butanamide | 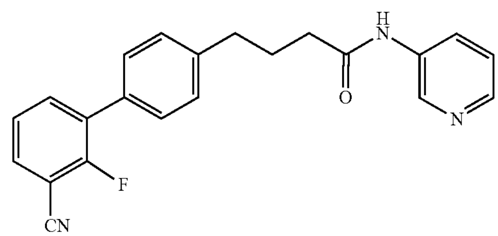 |
| 222 | 4-(4-(2-oxoindolin-5-yl)phenyl)-N-(pyridin-3-yl)butanamide | 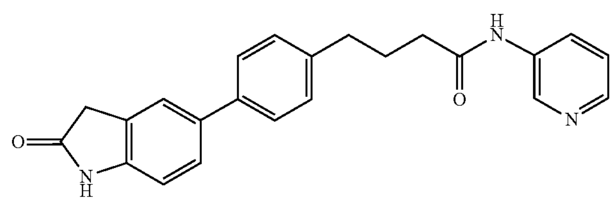 [SMILES: O=C(CCCc1ccc(-c2ccc3c(c2)CC(=O)N3)cc1)Nc1cccnc1] |
| 223 | 4-(4-(4-oxo-1,4-dihydroquinazolin-6-yl)phenyl)-N-(pyridin-3-yl)butanamide | 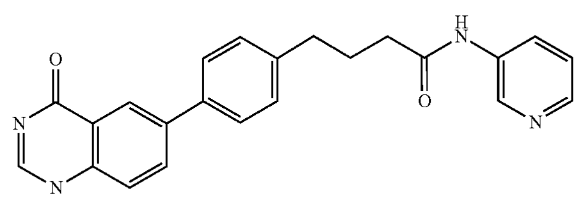 |
| 224 | 4-(4-(3-oxo-3,4-dihydro-2H-benzo[b][1,4]oxazin-7-triazoloyl)phenyl)-N-(pyridin-3-yl)butanamide | 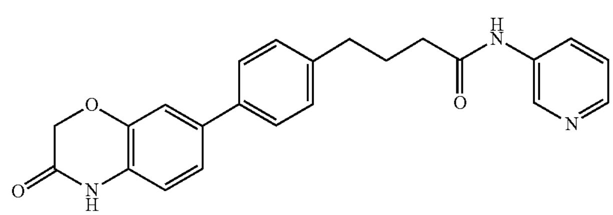 |
| 225 | 4-(3'-chloro-2'-fluoro-[1,1'-biphenyl]-4-yl)-N-(pyridin-3-yl)butanamide | 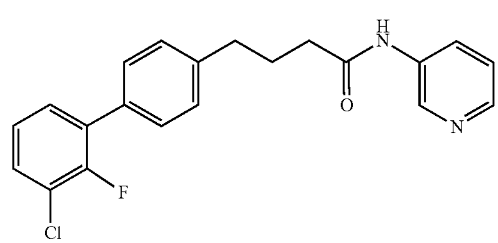 [SMILES: O=C(CCCc1ccc(-c2cccc(Cl)c2F)cc1)Nc1cccnc1] |

TABLE 1-continued

| Compound No. | Name | Structure |
|---|---|---|
| 226 | 6-methyl-N-(3-(4-(1-methyl-1H-indazol-5-yl)phenyl)propyl)nicotinamide | 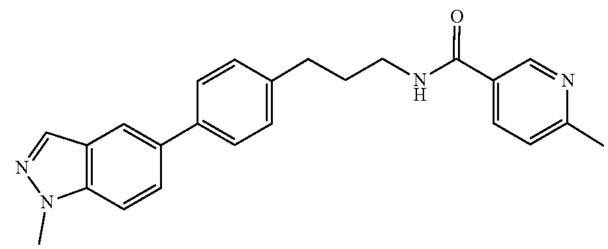 |
| 227 | 5-methyl-N-(3-(4-(1-methyl-1H-indazol-5-yl)phenyl)propyl)isoxazole-3-carboxamide | 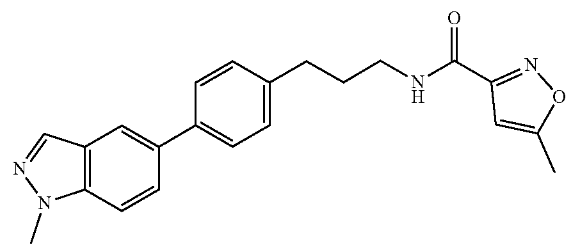 [SMILES: Cc1cc(C(=O)NCCCc2ccc(-c3ccc4c(cnn4C)c3)cc2)no1] |
| 228 | 1,3-dimethyl-N-(3-(4-(4-methyl-1H-indazol-5-yl)phenyl)propyl)-1H-pyrazole-5-carboxamide | 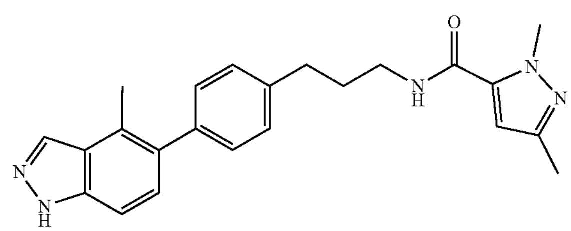 [SMILES: Cc1cc(C(=O)NCCCc2ccc(-c3ccc4[nH]ncc4c3C)cc2)n(C)n1] |
| 229 | N-(3-(4-(1H-pyrrolo[2,3-b]pyridin-5-yl)phenyl)propyl)-6-methylnicotinamide | 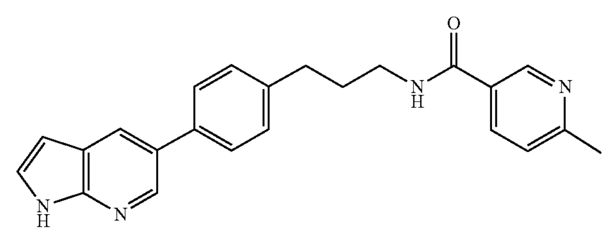 [SMILES: Cc1ccc(C(=O)NCCCc2ccc(-c3cnc4[nH]ccc4c3)cc2)cn1] |
| 230 | 5-methyl-N-(3-(4-(4-methyl-1H-indazol-5-yl)phenyl)propyl)isoxazole-3-carboxamide | 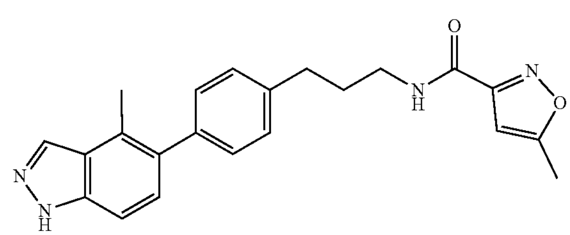 [SMILES: Cc1cc(C(=O)NCCCc2ccc(-c3ccc4[nH]ncc4c3C)cc2)no1] |
| 231 | N-(3-(4-(1-methyl-1H-indazol-5-yl)phenyl)propyl)pyrimidine-5-carboxamide | 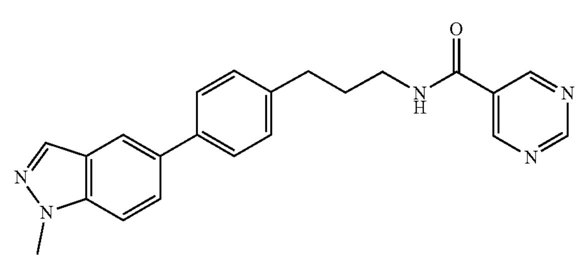 |

TABLE 1-continued

| Compound No. | Name | Structure |
|---|---|---|
| 232 | 2-amino-N-(3-(4-(1-methyl-1H-indazol-5-yl)phenyl)propyl)pyrimidine-5-carboxamide | 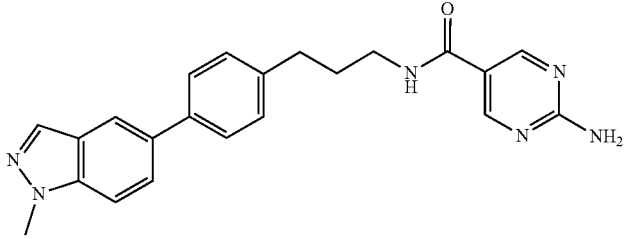 [SMILES: Cn1ncc2cc(-c3ccc(CCCNC(=O)c4cnc(N)nc4)cc3)ccc21] |
| 233 | N-(3-(4-(1H-pyrrolo[2,3-b]pyridin-5-yl)phenyl)propyl)-1,3-dimethyl-1H-pyrazole-5-carboxamide | 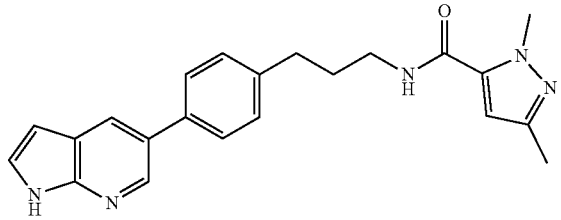 |
| 234 | N-(3-(2'-fluoro-3'-methoxy-[1,1'-biphenyl]-4-yl)propyl)-6-methylnicotinamide | 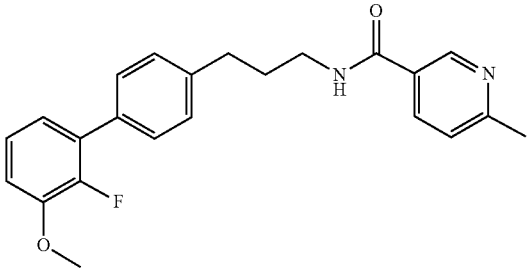 [SMILES: COc1cccc(-c2ccc(CCCNC(=O)c3ccc(C)nc3)cc2)c1F] |
| 235 | N-(3-(4-(1H-pyrrolo[2,3-b]pyridin-5-yl)phenyl)propyl)-5-methylisoxazole-3-carboxamide | 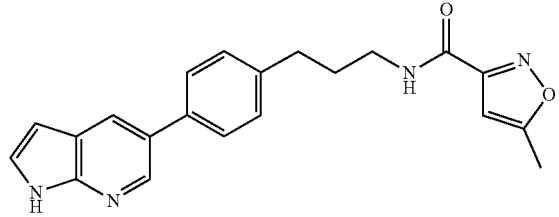 [SMILES: Cc1cc(C(=O)NCCCc2ccc(-c3cnc4[nH]ccc4c3)cc2)no1] |
| 236 | 1,3-dimethyl-N-(3-(4-(1-methyl-1H-indazol-5-yl)phenyl)propyl)-1H-pyrazole-5-carboxamide | 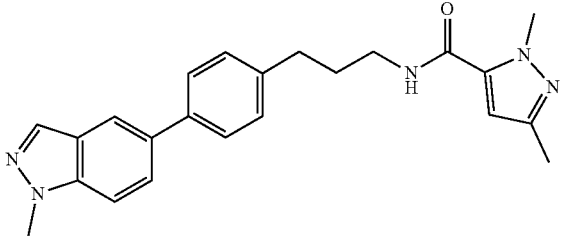 |
| 237 | 6-methyl-N-(3-(4-(quinolin-6-yl)phenyl)propyl)nicotinamide | 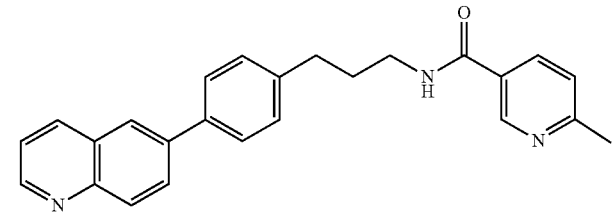 [SMILES: Cc1ccc(C(=O)NCCCc2ccc(-c3ccc4ncccc4c3)cc2)cn1] |

TABLE 1-continued

| Compound No. | Name | Structure |
|---|---|---|
| 238 | N-(3-(2'-fluoro-3'-methoxy-[1,1'-biphenyl]-4-yl)propyl)-1,3-dimethyl-1H-pyrazole-5-carboxamide | 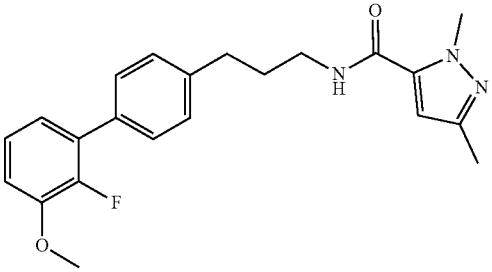 [SMILES: COc1cccc(-c2ccc(CCCNC(=O)c3cc(C)nn3C)cc2)c1F] |
| 239 | 5-methyl-N-(3-(4-(quinolin-6-yl)phenyl)propyl)isoxazole-3-carboxamide | 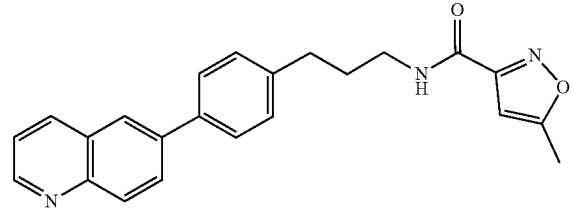 [SMILES: Cc1cc(C(=O)NCCCc2ccc(-c3ccc4ncccc4c3)cc2)no1] |
| 240 | N-(3-(2'-fluoro-3'-methoxy-[1,1'-biphenyl]-4-yl)propyl)-5-methylisoxazole-3-carboxamide | 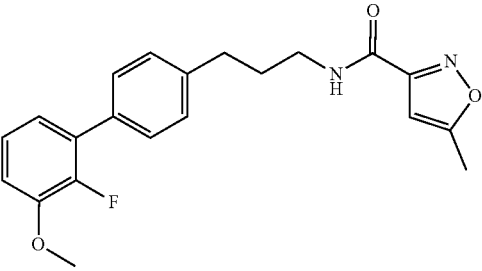 [SMILES: COc1cccc(-c2ccc(CCCNC(=O)c3cc(C)on3)cc2)c1F] |
| 241 | 2-methyl-N-(3-(4-(1-methyl-1H-indazol-5-yl)phenyl)propyl)nicotinamide | 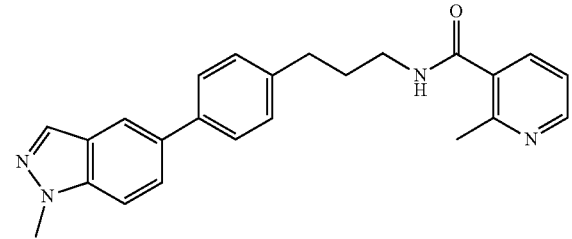 [SMILES: Cc1ncccc1C(=O)NCCCc1ccc(-c2ccc3c(cnn3C)c2)cc1] |
| 242 | 1,3-dimethyl-N-(3-(4-(quinolin-6-yl)phenyl)propyl)-1H-pyrazole-5-carboxamide | 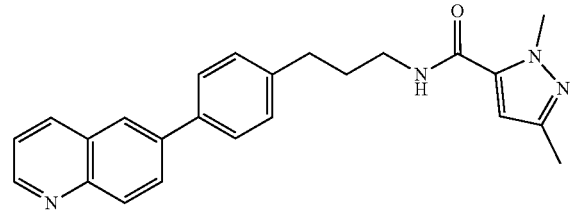 [SMILES: Cc1cc(C(=O)NCCCc2ccc(-c3ccc4ncccc4c3)cc2)n(C)n1] |
| 243 | 6-methyl-N-(3-(4-(4-methyl-1H-indazol-5-yl)phenyl)propyl)nicotinamide | 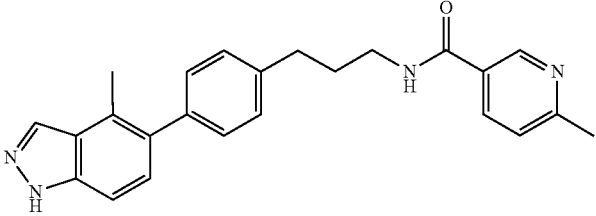 [SMILES: Cc1ccc(C(=O)NCCCc2ccc(-c3ccc4[nH]ncc4c3C)cc2)cn1] |

TABLE 1-continued

| Compound No. | Name |
|---|---|
| 244 | 2-(4-methoxyphenyl)-N-(3-(4-(1-methyl-1H-indazol-5-yl)phenyl)propyl)acetamide |
| 245 | N-(3-(2'-fluoro-3'-methoxy-[1,1'-biphenyl]-4-yl)propyl)-2-(4-methoxyphenyl)acetamide |
| 246 | 2-(4-methoxyphenyl)-N-(3-(4-(quinolin-6-yl)phenyl)propyl)acetamide |
| 247 | 2-(4-methoxyphenyl)-N-(3-(4-(4-methyl-1H-indazol-5-yl)phenyl)propyl)acetamide |
| 248 | N-(3-(2'-fluoro-3'-methoxy-[1,1'-biphenyl]-4-yl)propyl)pyrimidine-5-carboxamide |
| 249 | 5-(3-(2'-fluoro-[1,1'-biphenyl]-4-yl)propyl)-3-(pyridin-3-yl)-1,2,4-oxadiazole |

TABLE 1-continued

| Compound No. | Name | Structure |
|---|---|---|
| 250 | 4-((5-(3-(2'-fluoro-[1,1'-biphenyl]-4-yl)propyl)-1,2,4-oxadiazol-3-yl)methyl)morpholine | 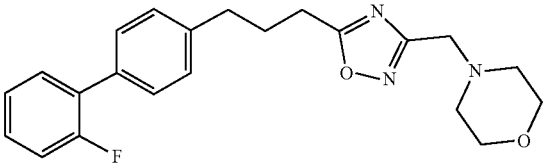 [SMILES: Fc1ccccc1-c1ccc(CCCc2nc(CN3CCOCC3)no2)cc1] |
| 251 | 5-(3-(2'-fluoro-[1,1'-biphenyl]-4-yl)propyl)-3-(1H-indol-6-yl)-1,2,4-oxadiazole | 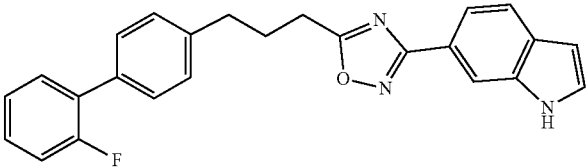 [SMILES: Fc1ccccc1-c1ccc(CCCc2nc(-c3ccc4cc[nH]c4c3)no2)cc1] |
| 252 | 5-(3-(2'-fluoro-[1,1'-biphenyl]-4-yl)propyl)-3-(pyridin-2-yl)-1,2,4-oxadiazole | 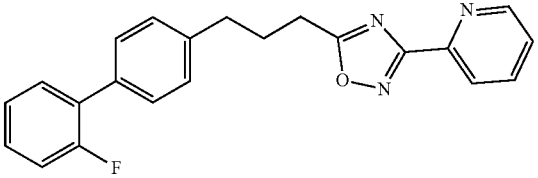 [SMILES: Fc1ccccc1-c1ccc(CCCc2nc(-c3ccccn3)no2)cc1] |
| 253 | 3-((1H-1,2,4-triazol-1-yl)methyl)-5-(3-(2'-fluoro-[1,1'-biphenyl]-4-yl)propyl)-1,2,4-oxadiazole | 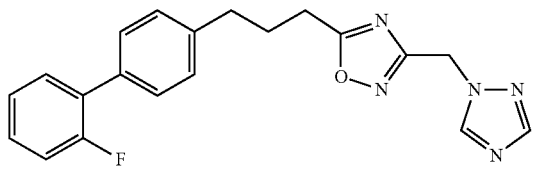 [SMILES: Fc1ccccc1-c1ccc(CCCc2nc(Cn3cncn3)no2)cc1] |
| 254 | 5-(3-(2'-fluoro-[1,1'-biphenyl]-4-yl)propyl)-3-(2-methoxypyridin-4-yl)-1,2,4-oxadiazole | 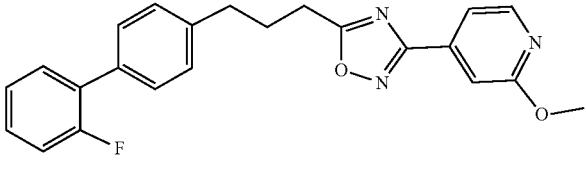 [SMILES: COc1cc(-c2noc(CCCc3ccc(-c4ccccc4F)cc3)n2)ccn1] |
| 255 | 3-cyclopropyl-5-(3-(2'-fluoro-[1,1'-biphenyl]-4-yl)propyl)-1,2,4-oxadiazole | 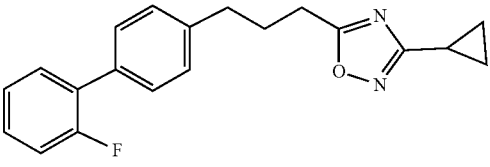 [SMILES: Fc1ccccc1-c1ccc(CCCc2nc(C3CC3)no2)cc1] |
| 256 | 5-(3-(2'-fluoro-[1,1'-biphenyl]-4-yl)propyl)-3-(tetrahydro-2H-pyran-4-yl)-1,2,4-oxadiazole | 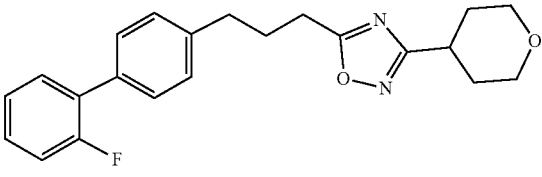 [SMILES: Fc1ccccc1-c1ccc(CCCc2nc(C3CCOCC3)no2)cc1] |
| 257 | 5-(3-(2'-fluoro-[1,1'-biphenyl]-4-yl)propyl)-3-(pyridin-4-yl)-1,2,4-oxadiazole | 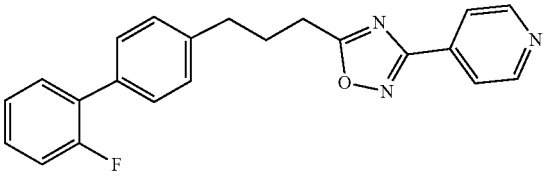 [SMILES: Fc1ccccc1-c1ccc(CCCc2nc(-c3ccncc3)no2)cc1] |

TABLE 1-continued

| Compound No. | Name | Structure |
|---|---|---|
| 258 | 2-(3-(2'-fluoro-[1,1'-biphenyl]-4-yl)propyl)-5-(pyridin-3-yl)-1,3,4-oxadiazole | 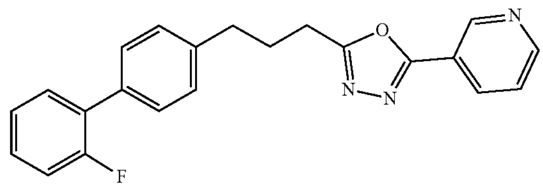 [SMILES: Fc1ccccc1-c1ccc(CCCc2nnc(-c3cccnc3)o2)cc1] |
| 259 | 2-(1,3-dimethyl-1H-pyrazol-5-yl)-5-(3-(2'-fluoro-[1,1'-biphenyl]-4-yl)propyl)-1,3,4-oxadiazole | 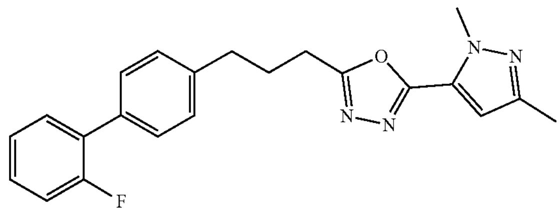 [SMILES: Cc1cc(-c2nnc(CCCc3ccc(-c4ccccc4F)cc3)o2)n(C)n1] |
| 260 | 2-(3-(2'-fluoro-[1,1'-biphenyl]-4-yl)propyl)-5-(1H-indol-5-yl)-1,3,4-oxadiazole | 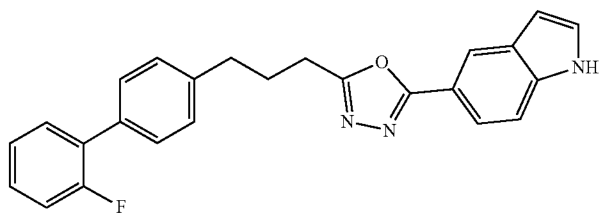 [SMILES: Fc1ccccc1-c1ccc(CCCc2nnc(-c3ccc4[nH]ccc4c3)o2)cc1] |
| 261 | 2-(3-(2'-fluoro-[1,1'-biphenyl]-4-yl)propyl)-5-(2-methylpyridin-3-yl)-1,3,4-oxadiazole | 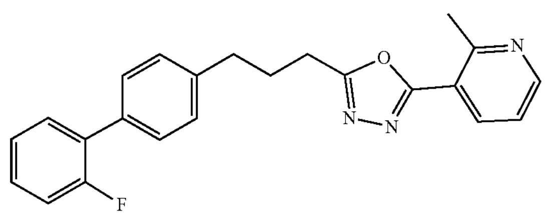 [SMILES: Cc1ncccc1-c1nnc(CCCc2ccc(-c3ccccc3F)cc2)o1] |
| 262 | N-(3-(2'-fluoro-[1,1'-biphenyl]-4-yl)propyl)pyridine-3-sulfonamide | 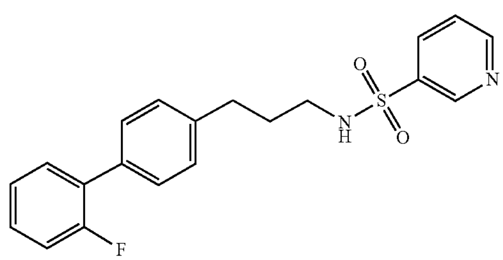 [SMILES: O=S(=O)(NCCCc1ccc(-c2ccccc2F)cc1)c1cccnc1] |
| 263 | N-(3-(2'-fluoro-[1,1'-biphenyl]-4-yl)propyl)-1-methyl-1H-imidazole-4-sulfonamide | 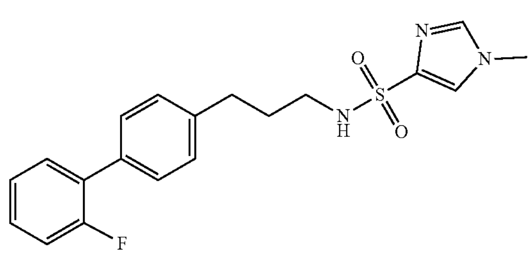 [SMILES: Cn1cnc(S(=O)(=O)NCCCc2ccc(-c3ccccc3F)cc2)c1] |

TABLE 1-continued

| Compound No. | Name | Structure |
|---|---|---|
| 264 | N-(3-(2'-fluoro-[1,1'-biphenyl]-4-yl)propyl)-1H-imidazole-4-sulfonamide | 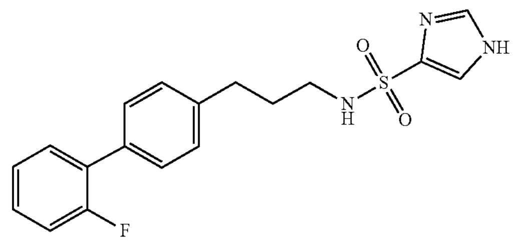 [SMILES: O=S(=O)(NCCCc1ccc(-c2ccccc2F)cc1)c1c[nH]cn1] |
| 265 | N-(3-(2'-fluoro-[1,1'-biphenyl]-4-yl)propyl)-3,5-dimethylisoxazole-4-sulfonamide | 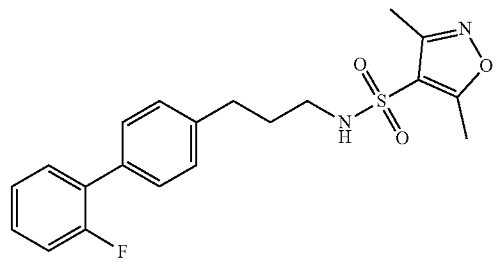 [SMILES: Cc1noc(C)c1S(=O)(=O)NCCCc1ccc(-c2ccccc2F)cc1] |
| 266 | N-(3-(2'-fluoro-[1,1'-biphenyl]-4-yl)propyl)-2-oxo-2,3-dihydrobenzo[d]oxazole-6-sulfonamide | 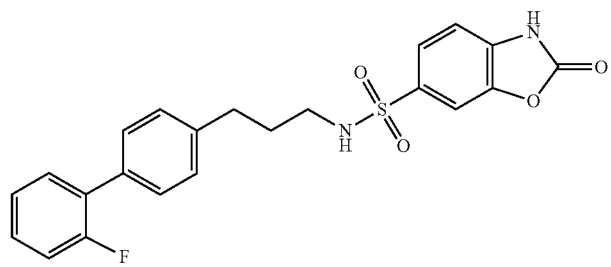 [SMILES: O=c1[nH]c2ccc(S(=O)(=O)NCCCc3ccc(-c4ccccc4F)cc3)cc2o1] |
| 267 | N-(3-(2'-fluoro-[1,1'-biphenyl]-4-yl)propyl)-1-methyl-2-oxoindoline-5-sulfonamide | 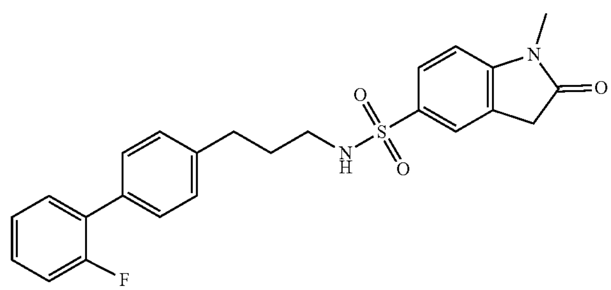 [SMILES: CN1C(=O)Cc2cc(S(=O)(=O)NCCCc3ccc(-c4ccccc4F)cc3)ccc21] |
| 268 | 3-(2-(2'-fluoro-[1,1'-biphenyl]-4-yl)ethyl)-5-(1H-indazol-7-yl)-1,2,4-oxadiazole | 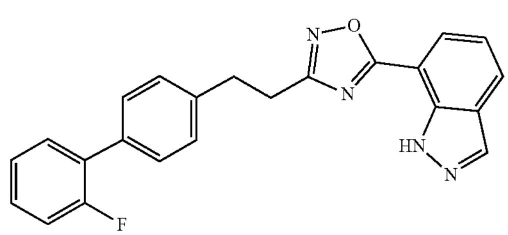 [SMILES: Fc1ccccc1-c1ccc(CCc2noc(-c3cccc4cn[nH]c34)n2)cc1] |
| 269 | 3-(2-(2'-fluoro-[1,1'-biphenyl]-4-yl)ethyl)-5-(pyridin-3-yl)-1,2,4-oxadiazole | 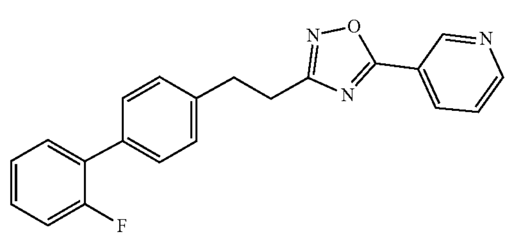 [SMILES: Fc1ccccc1-c1ccc(CCc2noc(-c3cccnc3)n2)cc1] |

TABLE 1-continued

| Compound No. | Name | Structure |
|---|---|---|
| 270 | (4-(2'-fluoro-[1,1'-biphenyl]-4-yl)pipemzin-1-yl)(6-methylpyridin-3-yl)methanone | 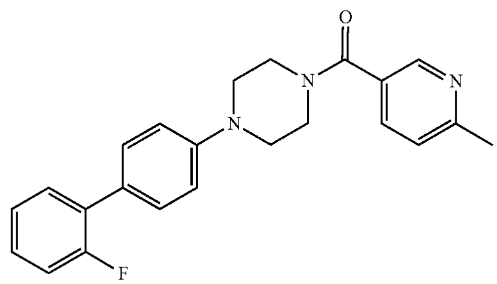 [SMILES: Cc1ccc(C(=O)N2CCN(c3ccc(-c4ccccc4F)cc3)CC2)cn1] |
| 271 | (4-(4-(1-methyl-1H-indazol-5-yl)phenyl)piperazin-1-yl)(6-methylpyridin-3-yl)methanone | 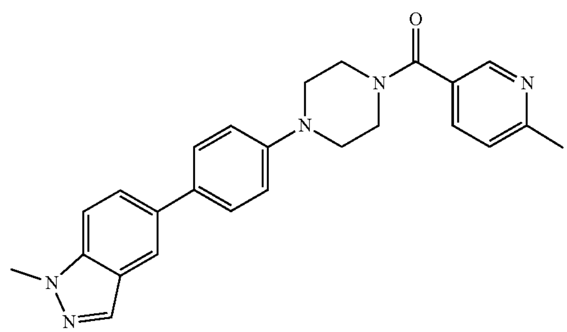 |
| 272 | 2-(2'-fluoro-[1,1'-biphenyl]-4-yl)ethyl (1H-indol-5-yl)carbamate | 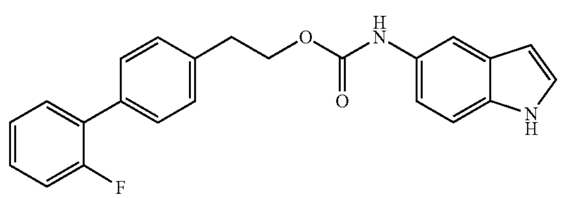 [SMILES: O=C(Nc1ccc2[nH]ccc2c1)OCCc1ccc(-c2ccccc2F)cc1] |
| 273 | 2-(2'-fluoro-[1,1'-biphenyl]-4-yl)ethyl (4-methoxybenzyl)carbamate | 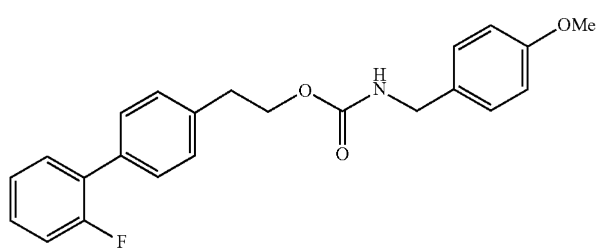 [SMILES: COc1ccc(CNC(=O)OCCc2ccc(-c3ccccc3F)cc2)cc1] |
| 274 | 2-(2'-fluoro-[1,1'-biphenyl]-4-yl)ethyl (6-methylpyridin-3-yl)carbamate | 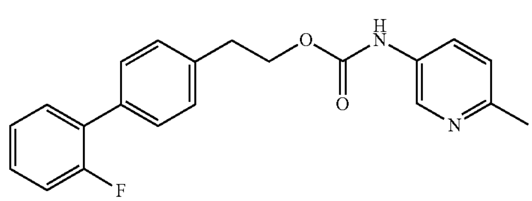 [SMILES: Cc1ccc(NC(=O)OCCc2ccc(-c3ccccc3F)cc2)cn1] |
| 275 | 2-(2'-fluoro-[1,1'-biphenyl]-4-yl)ethyl pyridin-3-ylcarbamate | 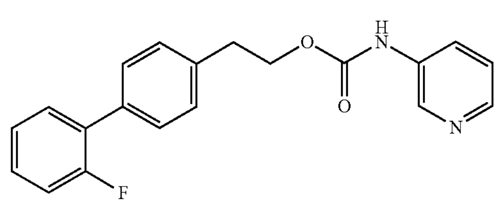 [SMILES: O=C(Nc1cccnc1)OCCc1ccc(-c2ccccc2F)cc1] |

TABLE 1-continued

| Compound No. | Name | Structure |
|---|---|---|
| 276 | N-(3-(2'-fluoro-3'-methoxy-[1,1'-biphenyl]-4-yl)-2,2-dimethylpropyl)-6-methylnicotinamide | 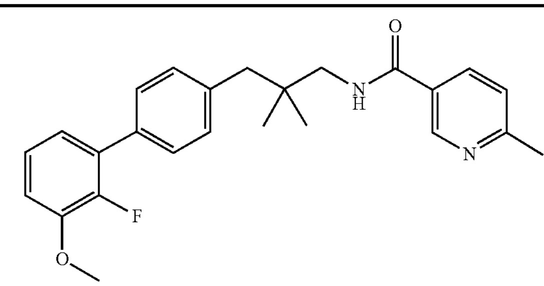 |
| 277 | N-(2,2-dimethyl-3-(4-(1-methyl-1H-indazol-5-yl)phenyl)propyl)-6-methylnicotinamide | 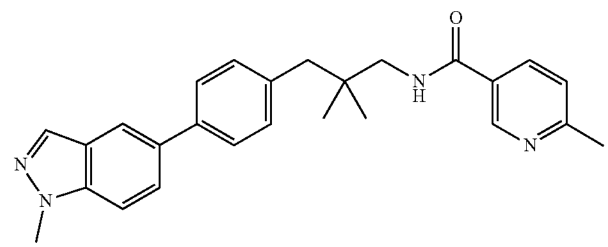 |
| 278 | 4-(2'-fluoro-[1,1'-biphenyl]-4-yl)-N-(pyridin-3-yl)piperazine-1-carboxamide | 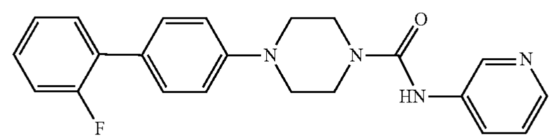 [SMILES: O=C(Nc1cccnc1)N1CCN(c2ccc(-c3ccccc3F)cc2)CC1] |
| 279 | 4-(2'-fluoro-[1,1'-biphenyl]-4-yl)-N-(6-methylpyridin-3-yl)piperazine-1-carboxamide | 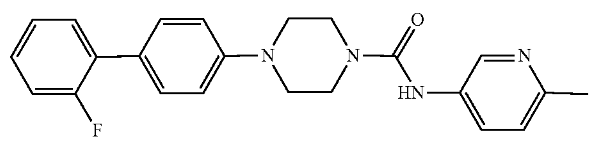 [SMILES: Cc1ccc(NC(=O)N2CCN(c3ccc(-c4ccccc4F)cc3)CC2)cn1] |
| 280 | 4-(2'-fluoro-[1,1'-biphenyl]-4-yl)-N-(1H-indol-5-yl)piperazine-1-carboxamide | 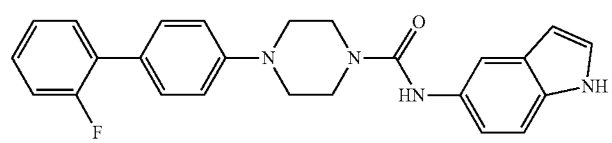 [SMILES: O=C(Nc1ccc2[nH]ccc2c1)N1CCN(c2ccc(-c3ccccc3F)cc2)CC1] |
| 281 | 4-(2'-fluoro-[1,1'-biphenyl]-4-yl)-N-(1H-pyrazol-4-yl)piperazine-1-carboxamide | 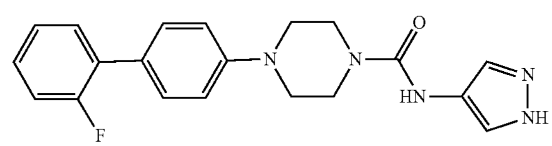 [SMILES: O=C(Nc1cn[nH]c1)N1CCN(c2ccc(-c3ccccc3F)cc2)CC1] |
| 282 | N-(2-((2'-fluoro-[1,1'-biphenyl]-4-yl)oxy)ethyl)-6-methylnicotinamide | 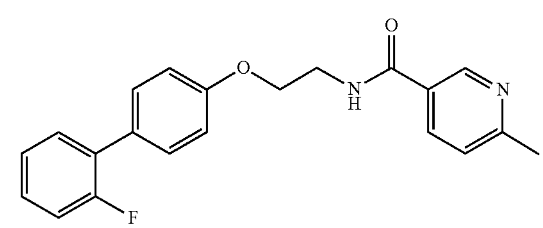 [SMILES: Cc1ccc(C(=O)NCCOc2ccc(-c3ccccc3F)cc2)cn1] |
| 283 | 6-methyl-N-(2-(4-(1-methyl-1H-indazol-5-yl)phenoxy)ethyl)nicotinamide | 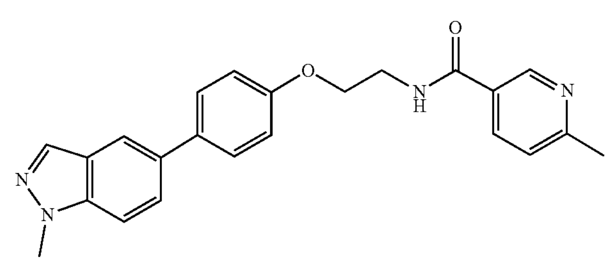 |

TABLE 1-continued

| Compound No. | Name | Structure |
|---|---|---|
| 284 | N-(3-(2'-fluoro-[1,1'-biphenyl]-4-yl)propyl)-2-(4-fluorophenyl)acetamide | 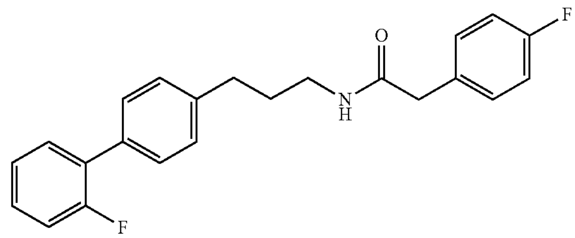 [SMILES: O=C(Cc1ccc(F)cc1)NCCCc1ccc(-c2ccccc2F)cc1] |
| 285 | N-(3-(2'-fluoro-[1,1'-biphenyl]-4-yl)propyl)-5-methylisoxazole-4-carboxamide | 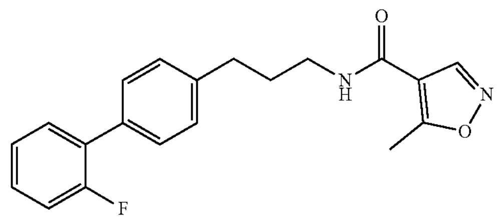 [SMILES: Cc1oncc1C(=O)NCCCc1ccc(-c2ccccc2F)cc1] |
| 286 | N-(3-(2'-fluoro-[1,1'-biphenyl]-4-yl)propyl)-2-methylpyrazolo[1,5-a]pyrimidine-6-carboxamide | 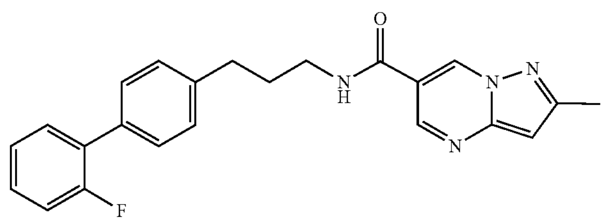 [SMILES: Cc1cc2ncc(C(=O)NCCCc3ccc(-c4ccccc4F)cc3)cn2n1] |
| 287 | N-(3-(2'-fluoro-[1,1'-biphenyl]-4-yl)propyl)-1-methyl-3-phenyl-1H-pyrazole-5-carboxamide | 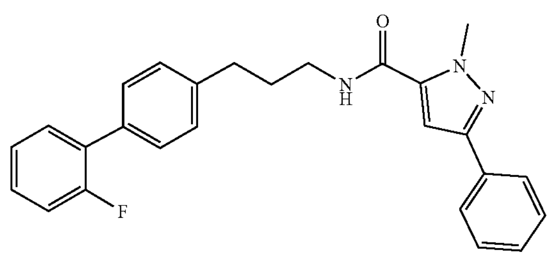 [SMILES: Cn1nc(-c2ccccc2)cc1C(=O)NCCCc1ccc(-c2ccccc2F)cc1] |
| 288 | N-(3-(2'-fluoro-[1,1'-biphenyl]-4-yl)propyl)-2,4-dimethylthiazole-5-carboxamide | 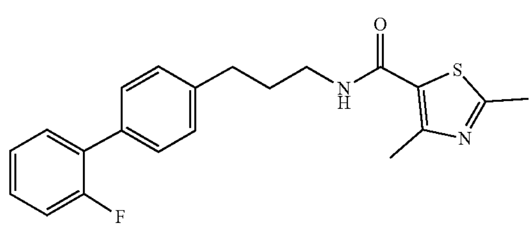 [SMILES: Cc1nc(C)c(C(=O)NCCCc2ccc(-c3ccccc3F)cc2)s1] |
| 289 | N-(3-(2'-fluoro-[1,1'-biphenyl]-4-yl)propyl)tetrahydro-2H-pyran-4-carboxamide | 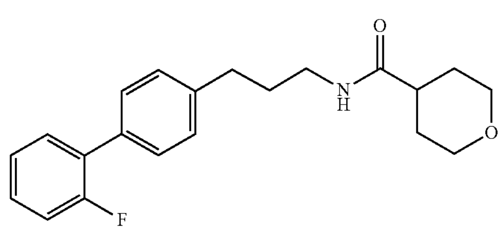 [SMILES: O=C(NCCCc1ccc(-c2ccccc2F)cc1)C1CCOCC1] |

TABLE 1-continued

| Compound No. | Name | Structure |
|---|---|---|
| 290 | N-(3-(2'-fluoro-[1,1'-biphenyl]-4-yl)propyl)-4-methyloxazole-5-carboxamide | 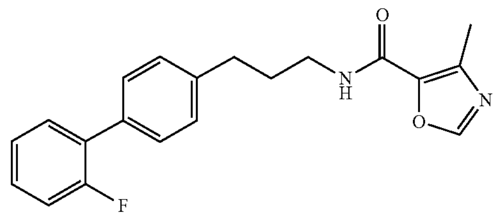 [SMILES: Cc1ncoc1C(=O)NCCCc1ccc(-c2ccccc2F)cc1] |
| 291 | N-(3-(2'-fluoro-[1,1'-biphenyl]-4-yl)propyl)-2-methylpyrimidine-5-carboxamide | 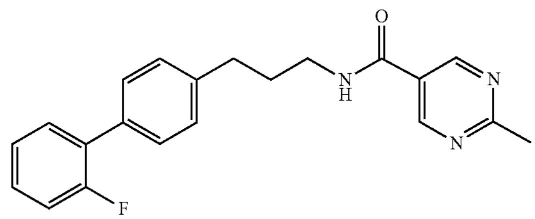 [SMILES: Cc1ncc(C(=O)NCCCc2ccc(-c3ccccc3F)cc2)cn1] |
| 292 | N-(3-(2'-fluoro-[1,1'-biphenyl]-4-yl)propyl)-2-methoxynicotinamide | 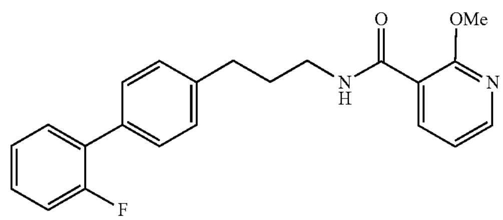 [SMILES: COc1ncccc1C(=O)NCCCc1ccc(-c2ccccc2F)cc1] |
| 293 | 2-(2,3-dihydrobenzo[b][1,4]dioxin-6-yl)-N-(3-(2'-fluoro-[1,1'-biphenyl]-4-yl)propyl)acetamide | 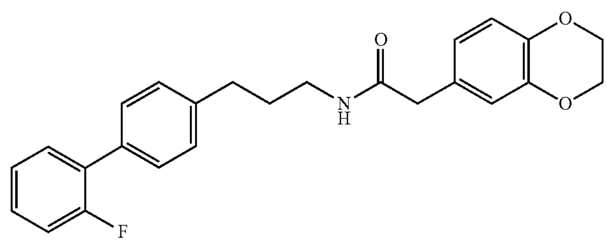 [SMILES: O=C(Cc1ccc2c(c1)OCCO2)NCCCc1ccc(-c2ccccc2F)cc1] |
| 294 | 4-(4-(1-methyl-1H-pyrrolo[2,3-b]pyridin-5-yl)phenyl)-N-(pyridin-3-yl)butanamide | 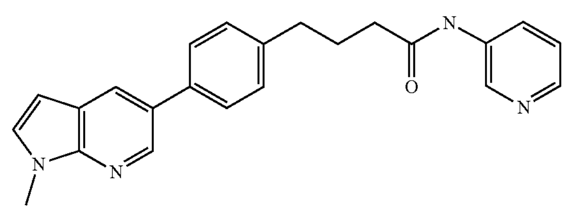 |
| 295 | 4-(4-(1H-pyrrolo[2,3-b]pyridin-3-yl)phenyl)-N-(pyridin-3-yl)butanamide | 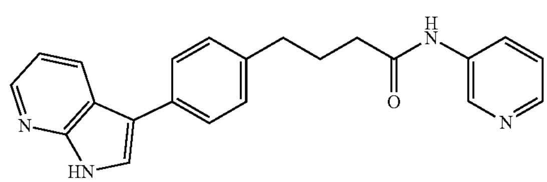 [SMILES: O=C(CCCc1ccc(-c2c[nH]c3ncccc23)cc1)Nc1cccnc1] |
| 296 | 4-(4-(1-methyl-1H-benzo[d]imidazol-5-yl)phenyl)-N-(pyridin-3-yl)butanamide | 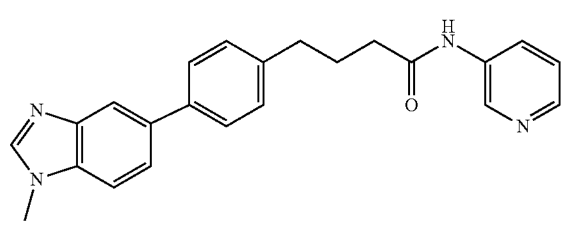 [SMILES: Cn1cnc2cc(-c3ccc(CCCC(=O)Nc4cccnc4)cc3)ccc21] |

TABLE 1-continued

| Compound No. | Name | Structure |
|---|---|---|
| 297 | 4-(4-(1,2-dimethyl-1H-benzo[d]imidazol-5-yl)phenyl)-N-(pyridin-3-yl)butanamide | 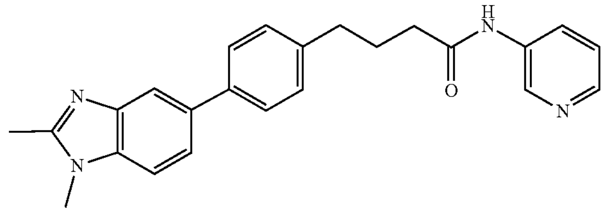 [SMILES: Cc1nc2cc(-c3ccc(CCCC(=O)Nc4cccnc4)cc3)ccc2n1C] |
| 298 | 4-(4-(2-fluorophenoxy)phenyl)-N-(pyridin-3-yl)butanamide | 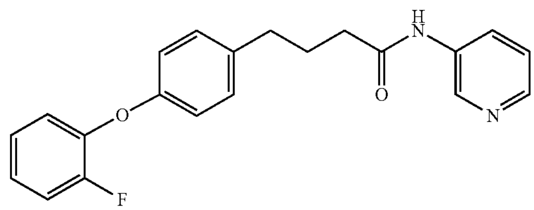 [SMILES: O=C(CCCc1ccc(Oc2ccccc2F)cc1)Nc1cccnc1] |
| 299 | 4-(4-(3-methyl-4-oxo-3,4-dihydroquinazolin-6-yl)phenyl)-N-(pyridin-3-yl)butanamide | 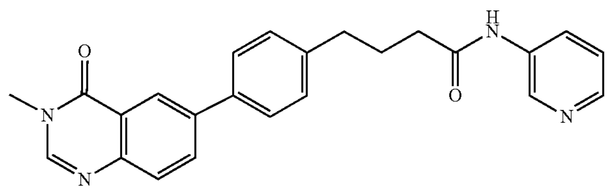 [SMILES: Cn1cnc2ccc(-c3ccc(CCCC(=O)Nc4cccnc4)cc3)cc2c1=O] |
| 300 | 4-(4-(2-oxo-1,2-dihydropyrimidin-5-yl)phenyl)-N-(pyridin-3-yl)butanamide | 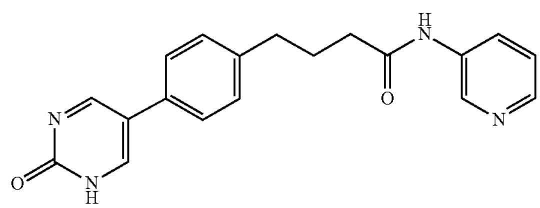 [SMILES: O=C(CCCc1ccc(-c2cnc(=O)[nH]c2)cc1)Nc1cccnc1] |
| 301 | 4-(4-(7-methyl-1H-indazol-5-yl)phenyl)-N-(pyridin-3-yl)butanamide | 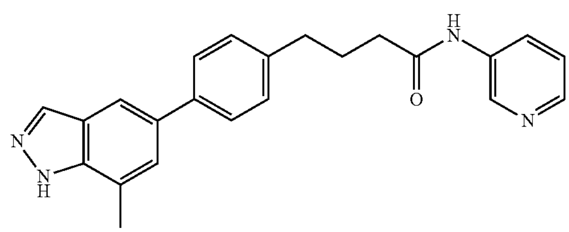 |
| 302 | 4-(4-(6-methyl-1H-indazol-5-yl)phenyl)-N-(pyridin-3-yl)butanamide | 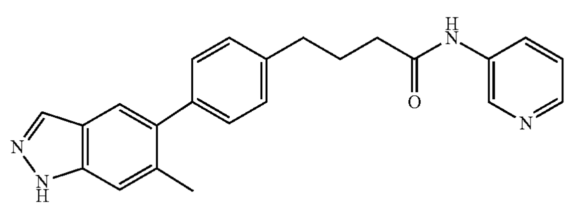 [SMILES: Cc1cc2[nH]ncc2cc1-c1ccc(CCCC(=O)Nc2cccnc2)cc1] |
| 303 | 6-methyl-N-((1-(4-(1-methyl-1H-indazol-5-yl)benzyl)cyclopropyl)methyl)nicotinamide | 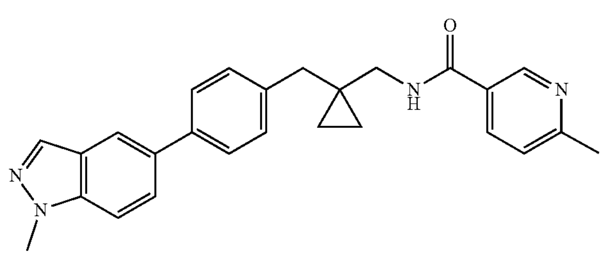 [SMILES: Cc1ccc(C(=O)NCC2(Cc3ccc(-c4ccc5c(cnn5C)c4)cc3)CC2)cn1] |

TABLE 1-continued

| Compound No. | Name | Structure |
|---|---|---|
| 304 | N-(3-(2'-fluoro-3'-methoxy-[1,1'-biphenyl]-4-yl)propyl)-2-methylthiazole-5-carboxamide | 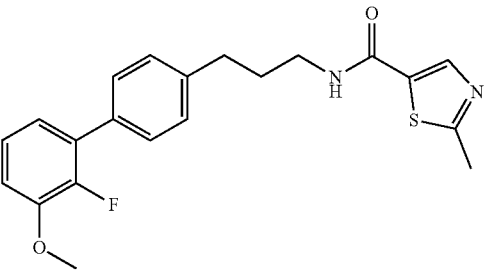 [SMILES: COc1cccc(-c2ccc(CCCNC(=O)c3cnc(C)s3)cc2)c1F] |
| 305 | 2-methyl-N-(3-(4-(1-methyl-1H-indazol-5-yl)phenyl)propyl)thiazole-5-carboxamide | 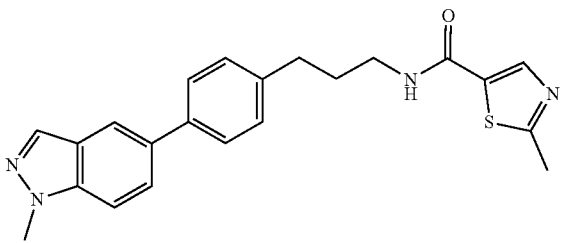 [SMILES: Cc1ncc(C(=O)NCCCc2ccc(-c3ccc4c(cnn4C)c3)cc2)s1] |
| 306 | N-(3-(4-(quinolin-6-yl)phenyl)propyl)pyrimidine-5-carboxamide | 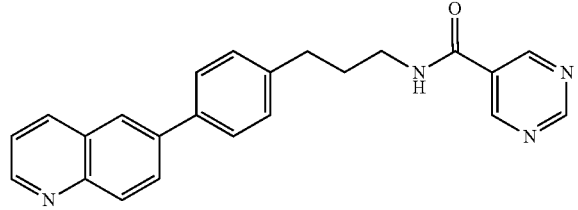 [SMILES: O=C(NCCCc1ccc(-c2ccc3ncccc3c2)cc1)c1cncnc1] |
| 307 | N-(3-(4-(1H-pyrrolo[2,3-b]pyridin-5-yl)phenyl)propyl)pyrimidine-5-carboxamide | 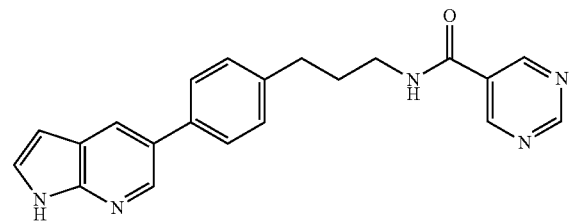 [SMILES: O=C(NCCCc1ccc(-c2cnc3[nH]ccc3c2)cc1)c1cncnc1] |
| 308 | 2-methyl-N-(3-(4-(4-methyl-1H-indazol-5-yl)phenyl)propyl)thiazole-5-carboxamide | 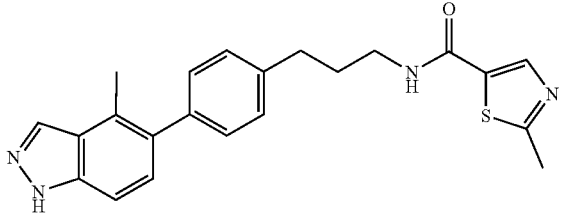 [SMILES: Cc1ncc(C(=O)NCCCc2ccc(-c3ccc4[nH]ncc4c3C)cc2)s1] |
| 309 | N-(3-(4-(1H-pyrrolo[2,3-b]pyridin-5-yl)phenyl)propyl)-2-methylthiazole-5-carboxamide | 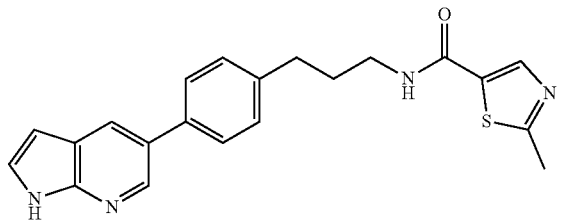 [SMILES: Cc1ncc(C(=O)NCCCc2ccc(-c3cnc4[nH]ccc4c3)cc2)s1] |

TABLE 1-continued

| Compound No. | Name | Structure |
|---|---|---|
| 310 | 2-methyl-N-(3-(4-(4-methyl-1H-indazol-5-yl)phenyl)propyl)nicotinamide | 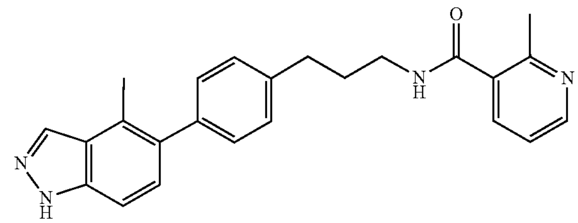 [SMILES: Cc1ncccc1C(=O)NCCCc1ccc(-c2ccc3[nH]ncc3c2C)cc1] |
| 311 | N-(3-(4-(1H-pyrrolo[2,3-b]pyridin-5-yl)phenyl)propyl)-2-methylnicotinamide | 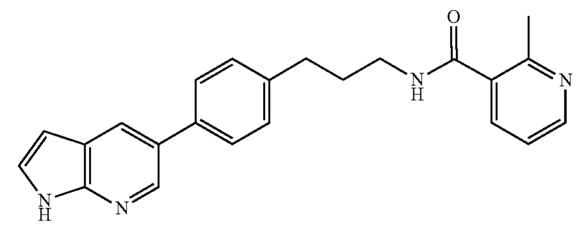 [SMILES: Cc1ncccc1C(=O)NCCCc1ccc(-c2cnc3[nH]ccc3c2)cc1] |
| 312 | 6-methyl-N-(3-(4-(3-oxo-3,4-dihydro-2H-benzo[b][1,4]oxazin-7-yl)phenyl)propyl)nicotinamide | 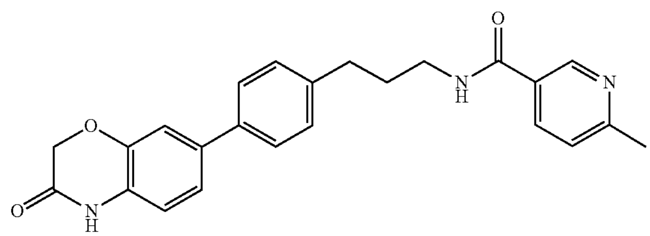 [SMILES: Cc1ccc(C(=O)NCCCc2ccc(-c3ccc4c(c3)OCC(=O)N4)cc2)cn1] |
| 313 | 1,3-dimethyl-N-(3-(4-(3-oxo-3,4-dihydro-2H-benzo[b][1,4]oxazin-7-yl)phenyl)propyl)-1H-pyrazole-5-carboxamide | 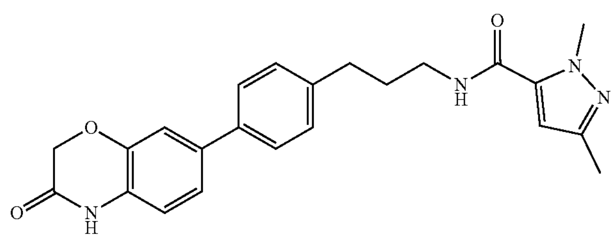 [SMILES: Cc1cc(C(=O)NCCCc2ccc(-c3ccc4c(c3)OCC(=O)N4)cc2)n(C)n1] |
| 314 | 2-methyl-N-(3-(4-(3-oxo-3,4-dihydro-2H-benzo[b][1,4]oxazin-7-yl)phenyl)propyl)nicotinamide | 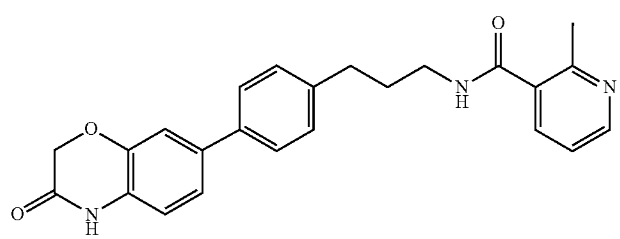 [SMILES: Cc1ncccc1C(=O)NCCCc1ccc(-c2ccc3c(c2)OCC(=O)N3)cc1] |
| 315 | 6-methyl-N-(3-(4-(2-oxo-1,2-dihydroquinolin-6-yl)phenyl)propyl)nicotinamide | 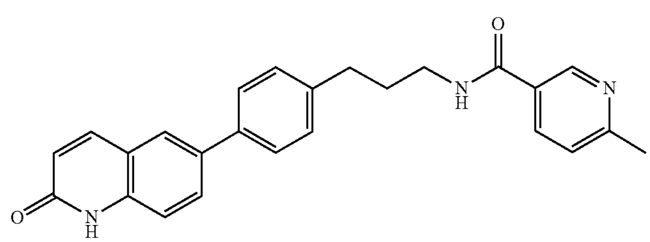 [SMILES: Cc1ccc(C(=O)NCCCc2ccc(-c3ccc4[nH]c(=O)ccc4c3)cc2)cn1] |

TABLE 1-continued

| Compound No. | Name | Structure |
|---|---|---|
| 316 | N-(3-(4-(1H-pyrrolo[2,3-b]pyridin-5-yl)phenyl)propyl)-2-(4-methoxyphenyl)acetamide | 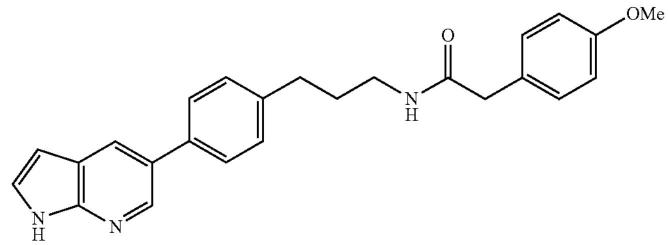 [SMILES: COc1ccc(CC(=O)NCCCc2ccc(-c3cnc4[nH]ccc4c3)cc2)cc1] |
| 317 | N-(3-(2'-fluoro-3'-methoxy-[1,1'-biphenyl]-4-yl)propyl)-2-methylnicotinamide | 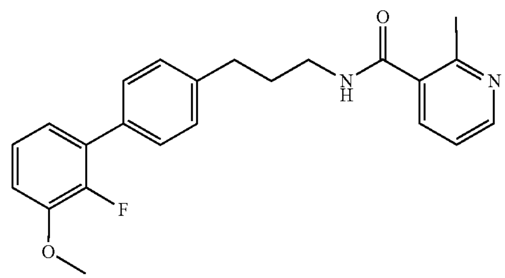 [SMILES: COc1cccc(-c2ccc(CCCNC(=O)c3cccnc3C)cc2)c1F] |
| 318 | 4-(2'-fluoro-[1,1'-biphenyl]-4-yl)-N-4-(3-pholino)phenyl)butanamide | 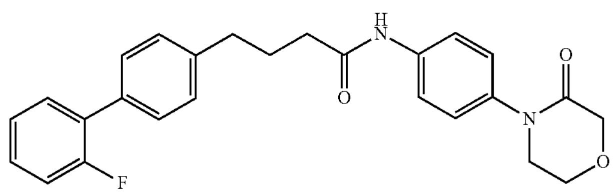 [SMILES: O=C(CCCc1ccc(-c2ccccc2F)cc1)Nc1ccc(N2CCOCC2=O)cc1] |
| 319 | 4-(2'-fluoro-[1,1'-biphenyl]-4-yl)-N-(pyrimidin-5-yl)butanamide | 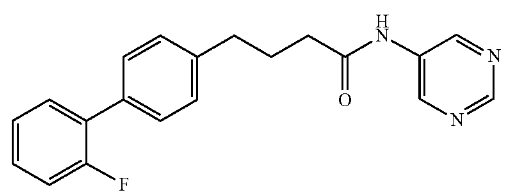 [SMILES: O=C(CCCc1ccc(-c2ccccc2F)cc1)Nc1cncnc1] |
| 320 | 4-(2'-fluoro-[1,1'-biphenyl]-4-yl)-N-(isoquinolin-1-yl)butanamide | 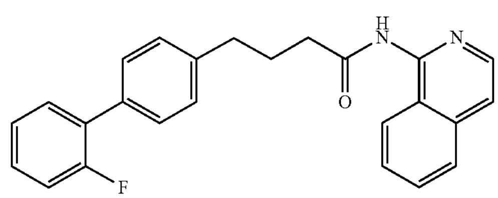 [SMILES: O=C(CCCc1ccc(-c2ccccc2F)cc1)Nc1nccc2ccccc12] |
| 321 | 4-(2'-fluoro-[1,1'-biphenyl]-4-yl)-N-(4-morpholinophenyl)butanamide | 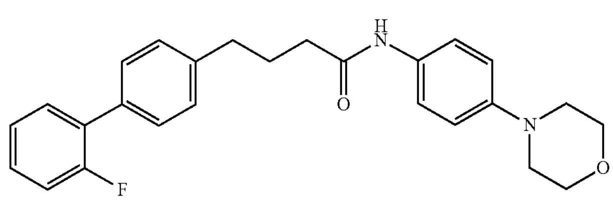 [SMILES: O=C(CCCc1ccc(-c2ccccc2F)cc1)Nc1ccc(N2CCOCC2)cc1] |
| 322 | 4-(2'-fluoro-[1,1'-biphenyl]-4-yl)-N-(6-morpholinopyridin-3-yl)butanamide | 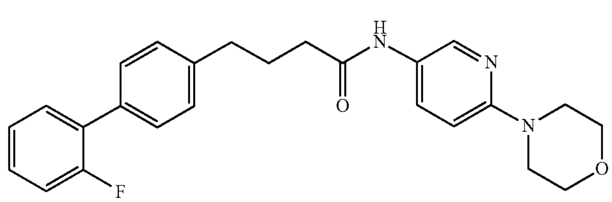 [SMILES: O=C(CCCc1ccc(-c2ccccc2F)cc1)Nc1ccc(N2CCOCC2)nc1] |

TABLE 1-continued

| Compound No. | Name | Structure |
|---|---|---|
| 323 | N-(3-(2'-fluoro-[1,1'-biphenyl]-3-yl)propyl)-6-methylnicotinamide | 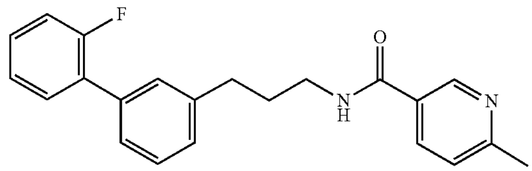 [SMILES: Cc1ccc(C(=O)NCCCc2cccc(-c3ccccc3F)c2)cn1] |
| 324 | 6-methyl-N-(3-(3-(1-methyl-1H-indazol-5-yl)phenyl)propyl)nicotinamide | 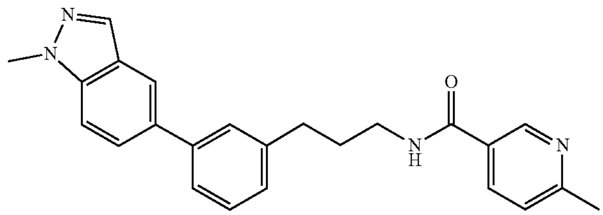 |
| 325 | 6-methyl-N-(3-(3-(pyridin-4-yl)phenyl)propyl)nicotinamide | 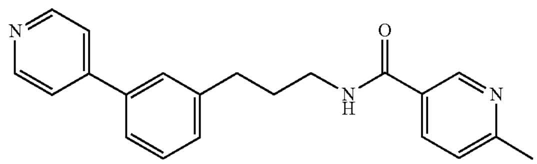 [SMILES: Cc1ccc(C(=O)NCCCc2cccc(-c3ccncc3)c2)cn1] |
| 326 | 6-methyl-N-(3-(3-(pyridin-3-yl)phenyl)propyl)nicotinamide | 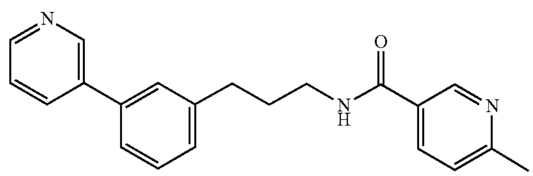 [SMILES: Cc1ccc(C(=O)NCCCc2cccc(-c3cccnc3)c2)cn1] |
| 327 | 6-methyl-N-(3-(3-(6-(trifluoromethyl)pyridin-3-yl)phenyl)propyl)nicotinamide | 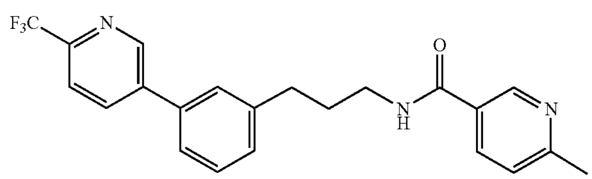 [SMILES: Cc1ccc(C(=O)NCCCc2cccc(-c3ccc(C(F)(F)F)nc3)c2)cn1] |
| 328 | N-(3-(2'-fluoro-5'-methoxy-[1,1'-biphenyl]-3-yl)propyl)-6-methylnicotinamide | 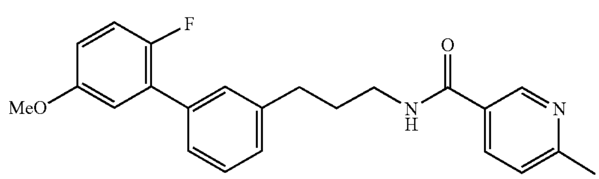 [SMILES: COc1ccc(F)c(-c2cccc(CCCNC(=O)c3ccc(C)nc3)c2)c1] |
| 329 | N-(3-(2'-fluoro-3'-methoxy-[1,1'-biphenyl]-3-yl)propyl)-6-methylnicotinamide | 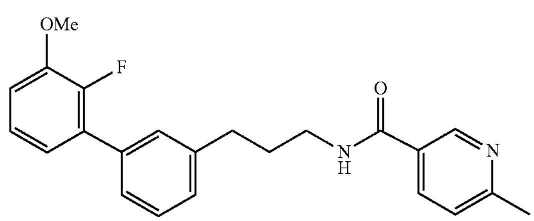 [SMILES: COc1cccc(-c2cccc(CCCNC(=O)c3ccc(C)nc3)c2)c1F] |
| 330 | 6-methyl-N-(3-(3-(quinolin-6-yl)phenyl)propyl)nicotinamide | 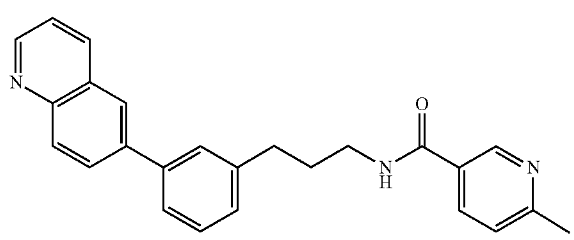 [SMILES: Cc1ccc(C(=O)NCCCc2cccc(-c3ccc4ncccc4c3)c2)cn1] |

TABLE 1-continued

| Compound No. | Name | Structure |
|---|---|---|
| 331 | N-(3-(2'-fluoro-[1,1'-biphenyl]-3-yl)propyl)-1,3-dimethyl-1H-pyrazole-5-carboxamide | 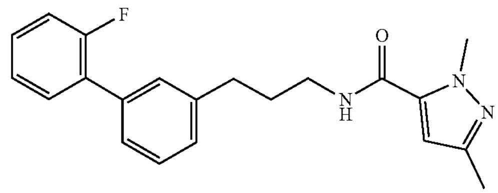 [SMILES: Cc1cc(C(=O)NCCCc2cccc(-c3ccccc3F)c2)n(C)n1] |
| 332 | 1,3-dimethyl-N-(3-(3-(1-methyl-1H-indazol-5-yl)phenyl)propyl)-1H-pyrazole-5-carboxamide | 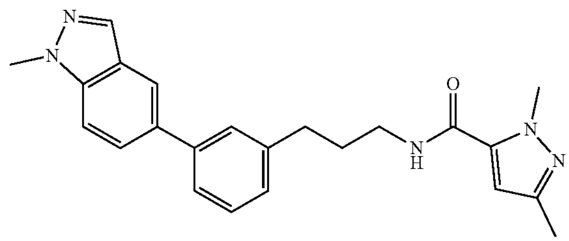 [SMILES: Cc1cc(C(=O)NCCCc2cccc(-c3ccc4c(cnn4C)c3)c2)n(C)n1] |
| 333 | 1,3-dimethyl-N-(3-(3-(pyridin-4-yl)phenyl)propyl)-1H-pyrazole-5-carboxamide | 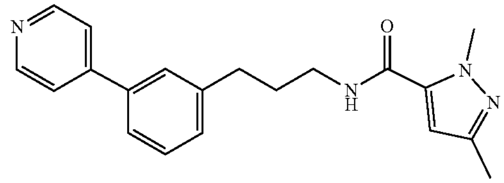 [SMILES: Cc1cc(C(=O)NCCCc2cccc(-c3ccncc3)c2)n(C)n1] |
| 334 | 1,3-dimethyl-N-(3-(3-(pyridin-3-yl)phenyl)propyl)-1H-pyrazole-5-carboxamide | 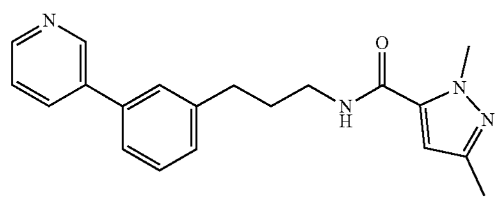 [SMILES: Cc1cc(C(=O)NCCCc2cccc(-c3cccnc3)c2)n(C)n1] |
| 335 | 1,3-dimethyl-N-(3-(3-(6-(trifluoromethyl)pyridin-3-yl)phenyl)propyl)-1H-pyrazole-5-carboxamide | 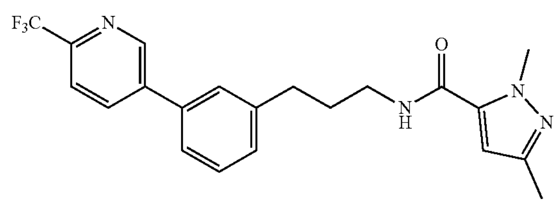 [SMILES: Cc1cc(C(=O)NCCCc2cccc(-c3ccc(C(F)(F)F)nc3)c2)n(C)n1] |
| 336 | N-(3-(2'-fluoro-5'-methoxy-[1,1'-biphenyl]-3-yl)propyl)-1,3-dimethyl-1H-pyrazole-5-carboxamide | 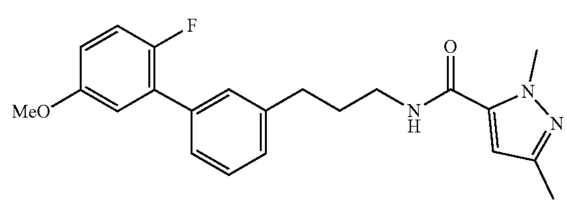 [SMILES: COc1ccc(F)c(-c2cccc(CCCNC(=O)c3cc(C)nn3C)c2)c1] |
| 337 | N-(3-(2'-fluoro-3'-methoxy-[1,1'-biphenyl]-3-yl)propyl)-1,3-dimethyl-1H-pyrazole-5-carboxamide | 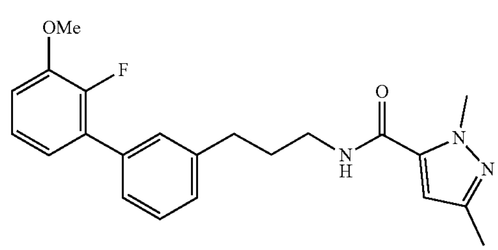 [SMILES: COc1cccc(-c2cccc(CCCNC(=O)c3cc(C)nn3C)c2)c1F] |

TABLE 1-continued

| Compound No. | Name | Structure |
|---|---|---|
| 338 | 1,3-dimethyl-N-(3-(3-(quinolin-6-yl)phenyl)propyl)-1H-pyrazole-5-carboxamide | 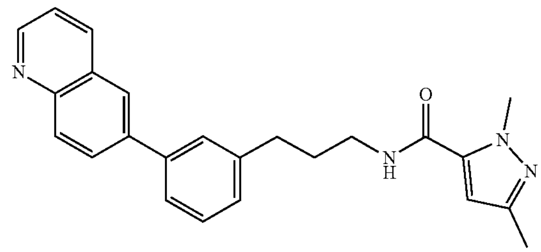 [SMILES: Cc1cc(C(=O)NCCCc2cccc(-c3ccc4ncccc4c3)c2)n(C)n1] |
| 339 | N-(3-(4-(benzo[d][1,3]dioxol-5-yl)phenyl)propyl)-6-methylnicotinamide | 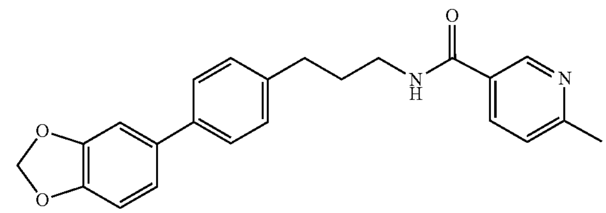 [SMILES: Cc1ccc(C(=O)NCCCc2ccc(-c3ccc4c(c3)OCO4)cc2)cn1] |
| 340 | N-(3-(4-(benzo[b]thiophen-2-yl)phenyl)propyl)-6-methylnicotinamide | 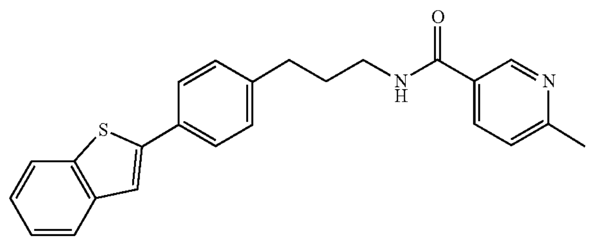 [SMILES: Cc1ccc(C(=O)NCCCc2ccc(-c3cc4ccccc4s3)cc2)cn1] |
| 341 | N-(3-(4'-(N,N-dimethylsulfamoyl)-[1,1'-biphenyl]-4-yl)propyl)-6-methylnicotinamide | 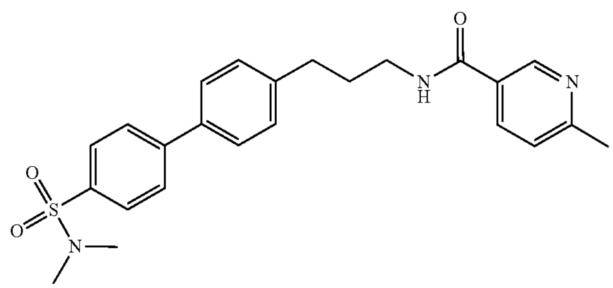 [SMILES: Cc1ccc(C(=O)NCCCc2ccc(-c3ccc(S(=O)(=O)N(C)C)cc3)cc2)cn1] |
| 342 | N-(3-(4-(2-aminopyrimidin-5-yl)phenyl)propyl)-6-methylnicotinamide | 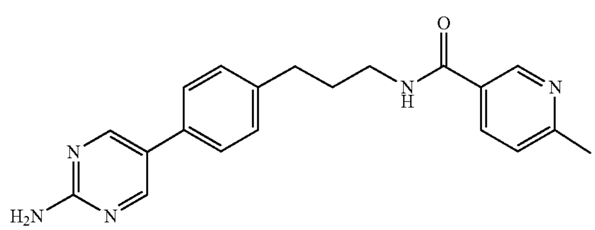 [SMILES: Cc1ccc(C(=O)NCCCc2ccc(-c3cnc(N)nc3)cc2)cn1] |
| 343 | N-(3-(4-(1H-indol-7-yl)phenyl)propyl)-6-methylnicotinamide | 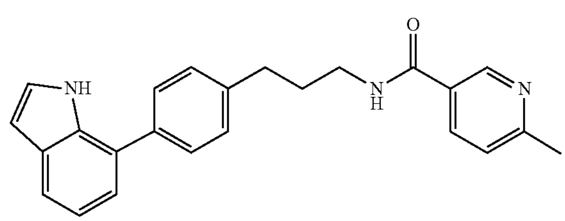 [SMILES: Cc1ccc(C(=O)NCCCc2ccc(-c3cccc4cc[nH]c34)cc2)cn1] |

TABLE 1-continued

| Compound No. | Name |
|---|---|
| 344 | 6-methyl-N-(3-(4'-(methylsulfonamido)-[1,1'-4-yl)propyl)nicotinamide |
| 345 | N-(3-(4-(6-aminopyridin-3-yl)phenyl)propyl)-6-methylnicotinamide |
| 346 | 2-(benzo[d][1,3]dioxol-5-yl)-N-(3-(4-(1-methyl-1H-indazol-5-yl)phenyl)propyl)acetamide |
| 347 | 4-cyano-N-(3-(4-(1-methyl-1H-indazol-5-yl)phenyl)propyl)benzamide |
| 348 | N-(3-(4-(1-methyl-1H-indazol-5-yl)phenyl)propyl)quinoxaline-2-carboxamide |
| 349 | 6-methyl-N-(3-(4-(1-methyl-1H-indazol-5-yl)phenyl)propyl)pyrazine-2-carboxamide |

TABLE 1-continued

| Compound No. | Name | Structure |
|---|---|---|
| 350 | 3,4,5-trimethoxy-N-(3-(4-(1-methyl-1H-indazol-5-yl)phenyl)propyl)benzamide | 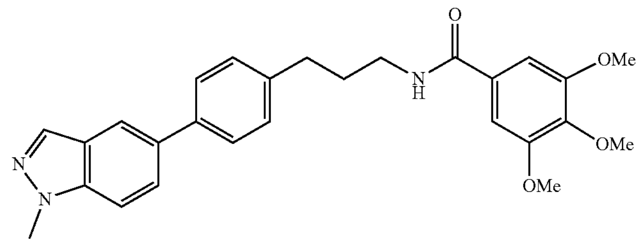 |
| 351 | N-(3-(4-(1-methyl-1H-indazol-5-yl)phenyl)propyl)-4-(pyrrolidin-1-yl)benzamide | 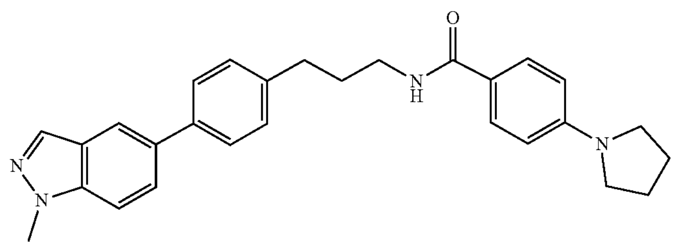 [SMILES: Cn1ncc2cc(-c3ccc(CCCNC(=O)c4ccc(N5CCCC5)cc4)cc3)ccc21] |
| 352 | N-(3-(4-(1-methyl-1H-indazol-5-yl)phenyl)propyl)-4-morpholinobenzamide | 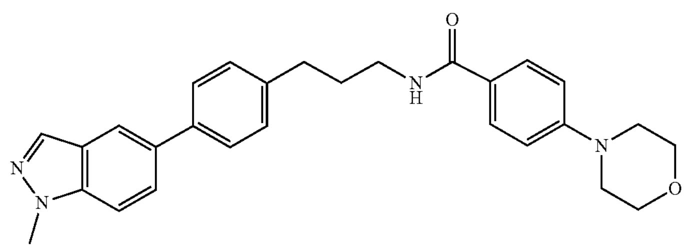 [SMILES: Cn1ncc2cc(-c3ccc(CCCNC(=O)c4ccc(N5CCOCC5)cc4)cc3)ccc21] |
| 353 | N-(3-(4-(1H-indazol-5-yl)phenyl)propyl)-6-methylnicotinamide | 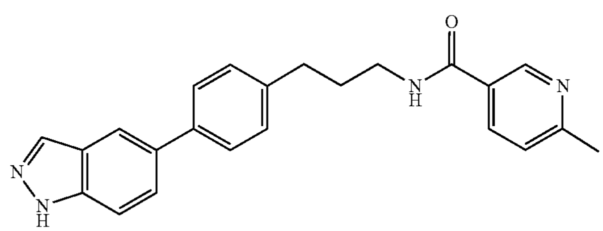 |
| 354 | N-(3-(4-(1H-indazol-5-yl)phenyl)propyl)-1,3-dimethyl-1H-pyrazole-5-carboxamide | 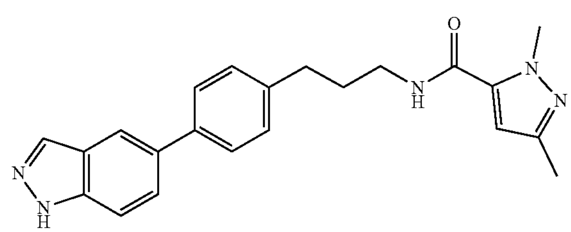 [SMILES: Cc1cc(C(=O)NCCCc2ccc(-c3ccc4[nH]ncc4c3)cc2)n(C)n1] |
| 355 | 2-(4-fluorophenyl)-N-(3-(4-(1-methyl-1H-indazol-5-yl)phenyl)propyl)acetamide | 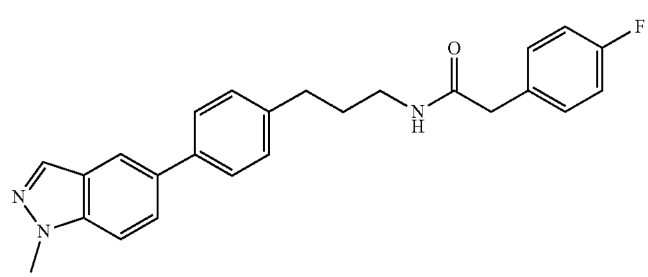 [SMILES: Cn1ncc2cc(-c3ccc(CCCNC(=O)Cc4ccc(F)cc4)cc3)ccc21] |

TABLE 1-continued

| Compound No. | Name | Structure |
|---|---|---|
| 356 | N-(3-(4-(1H-pyrrolo[2,3-b]pyridin-5-yl)phenyl)propyl)-2-(4-fluorophenyl)acetamide | 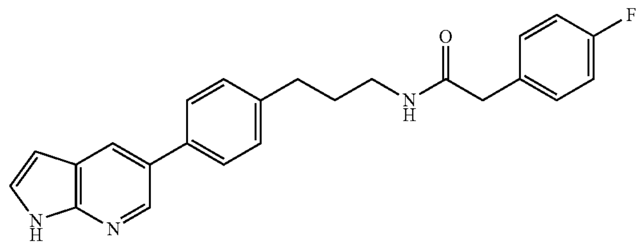 [SMILES: O=C(Cc1ccc(F)cc1)NCCCc1ccc(-c2cnc3[nH]ccc3c2)cc1] |
| 357 | N-(3-(2'-fluoro-3'-methoxy-[1,1'-biphenyl]-4-yl)propyl)-2-(4-fluorophenyl)acetamide | 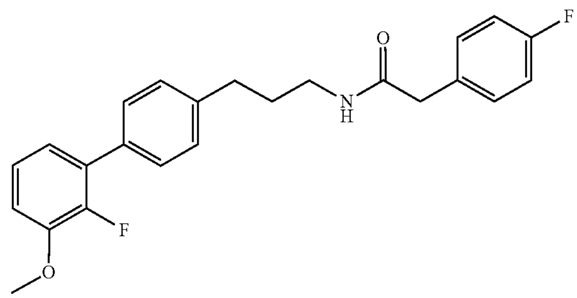 [SMILES: COc1cccc(-c2ccc(CCCNC(=O)Cc3ccc(F)cc3)cc2)c1F] |
| 358 | 6-methyl-N-(3-(4-(7-methyl-1H-indazol-5-yl)phenyl)propyl)nicotinamide | 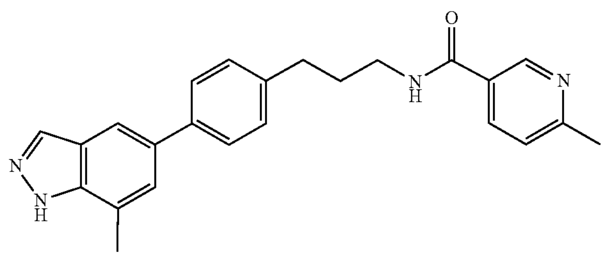 [SMILES: Cc1ccc(C(=O)NCCCc2ccc(-c3cc(C)c4[nH]ncc4c3)cc2)cn1] |
| 359 | 1,3-dimethyl-N-(3-(4-(7-methyl-1H-indazol-5-yl)phenyl)propyl)-1H-pyrazole-5-carboxamide | 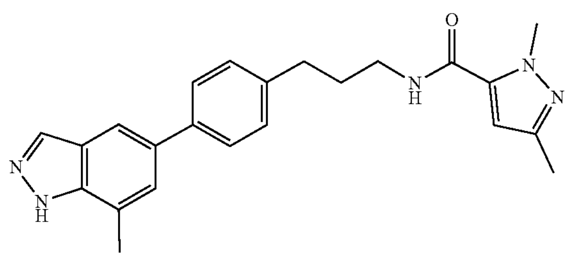 |
| 360 | 2-methyl-N-(3-(4-(1-methyl-1H-indazol-5-yl)phenyl)propyl)pyrazolo[1,5-a]pyrimidine-6-carboxamide | 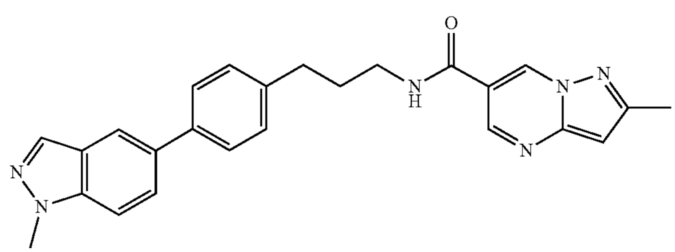 [SMILES: Cc1cc2ncc(C(=O)NCCCc3ccc(-c4ccc5c(cnn5C)c4)cc3)cn2n1] |
| 361 | 2-methyl-N-(3-(4-(4-methyl-1H-indazol-5-yl)phenyl)propyl)pyrazolo[1,5-a]pyrimidine-6-carboxamide | 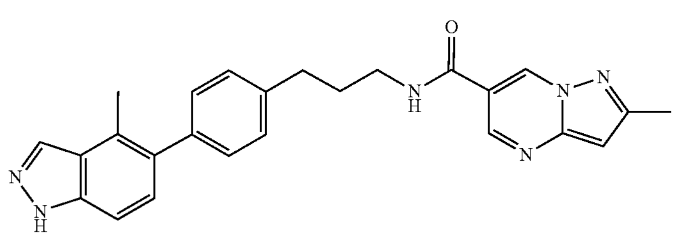 [SMILES: Cc1cc2ncc(C(=O)NCCCc3ccc(-c4ccc5[nH]ncc5c4C)cc3)cn2n1] |

TABLE 1-continued

| Compound No. | Name | Structure |
|---|---|---|
| 362 | N-(3-(2'-fluoro-3'-methoxy-[1,1'-biphenyl]-4-yl)propyl)-2-methylpyrazolo[1,5-a]pyrimidine-6-carboxamide | 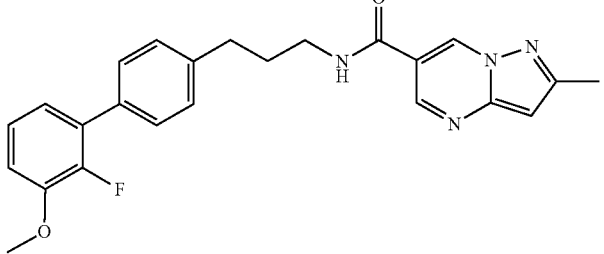 |
| 363 | 6-methyl-N-(3-(4-(2-oxoindolin-5-yl)phenyl)propyl)nicotinamide | 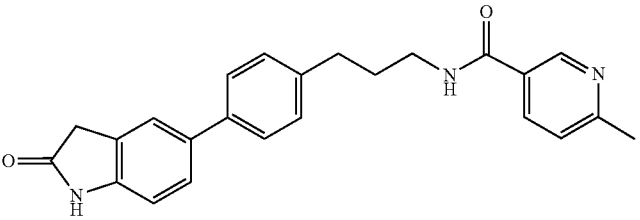 [SMILES: Cc1ccc(C(=O)NCCCc2ccc(-c3ccc4c(c3)CC(=O)N4)cc2)cn1] |
| 364 | 1,3-dimethyl-N-(3-(4-(2-oxoindolin-5-yl)phenyl)propyl)-1H-pyrazole-5-carboxamide | 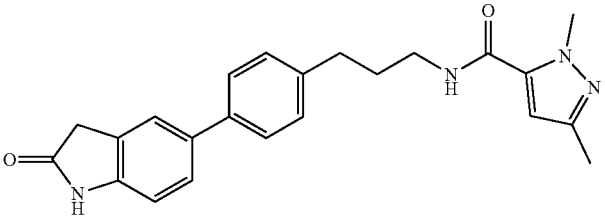 [SMILES: Cc1cc(C(=O)NCCCc2ccc(-c3ccc4c(c3)CC(=O)N4)cc2)n(C)n1] |
| 365 | 2-methyl-N-(3-(4-(4-methyl-1H-indazol-5-yl)phenyl)propyl)pymzolo[1,5-a]pyrimidine-6-carboxamide | 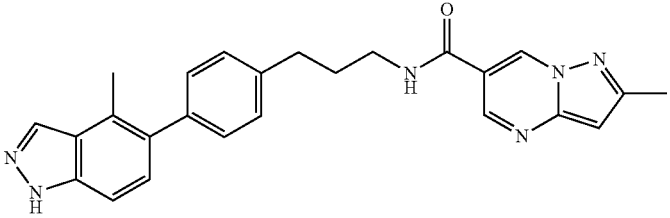 [SMILES: Cc1cc2ncc(C(=O)NCCCc3ccc(-c4ccc5[nH]ncc5c4C)cc3)cn2n1] |
| 366 | N-(3-(4-(1H-pyrrolo[2,3-b]pyridin-5-yl)phenyl)propyl)-2-methylpyrazolo[1,5-a]pyrimidine-6-carboxamide | 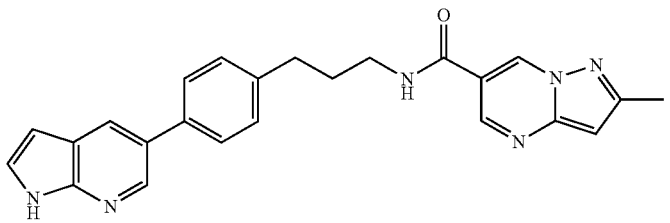 [SMILES: Cc1cc2ncc(C(=O)NCCCc3ccc(-c4cnc5[nH]ccc5c4)cc3)cn2n1] |
| 367 | 1,3-dimethyl-N-(3-(4-(2-oxo-1,2-dihydroquinolin-6-yl)phenyl)propyl)-1H-pyrazole-5-carboxamide | 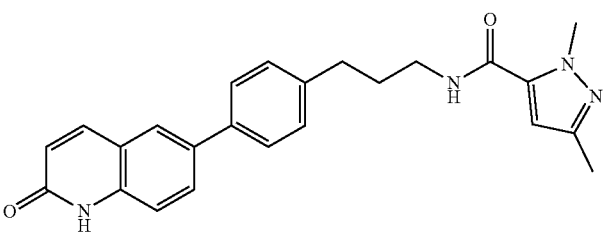 [SMILES: Cc1cc(C(=O)NCCCc2ccc(-c3ccc4[nH]c(=O)ccc4c3)cc2)n(C)n1] |

TABLE 1-continued

| Compound No. | Name | Structure |
|---|---|---|
| 368 | 6-methyl-N-(3-(4-(2-oxo-1,2,3,4-terahydroquinolin-6-yl)phenyl)propyl)nicotinamide | 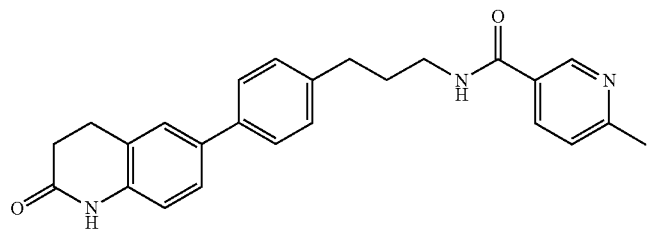 [SMILES: Cc1ccc(C(=O)NCCCc2ccc(-c3ccc4c(c3)CCC(=O)N4)cc2)cn1] |
| 369 | 1,3-dimethyl-N-(3-(4-(2-oxo-1,2,3,4-tetrahydroquinolin-6-yl)phenyl)propyl)-1H-pyrazole-5-carboxamide | 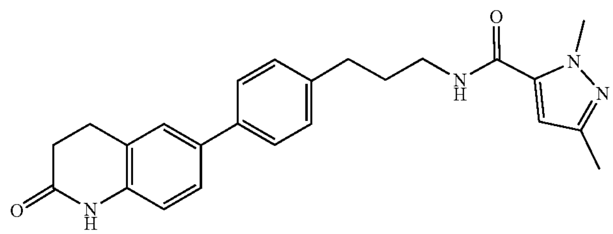 [SMILES: Cc1cc(C(=O)NCCCc2ccc(-c3ccc4c(c3)CCC(=O)N4)cc2)n(C)n1] |
| 370 | 2-methyl-N-(3-(4-(2-oxo-1,2,3,4-terahydroquinolint-6-yl)phenyl)propyl)thiazole-5-carboxamide | 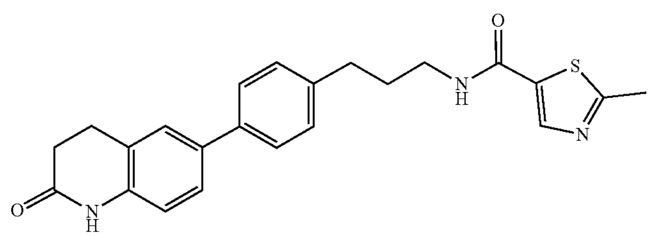 [SMILES: Cc1ncc(C(=O)NCCCc2ccc(-c3ccc4c(c3)CCC(=O)N4)cc2)s1] |
| 371 | N-(3-(4-(1H-indazol-5-yl)phenyl)propyl)-2-methylthiazole-5-carboxamide | 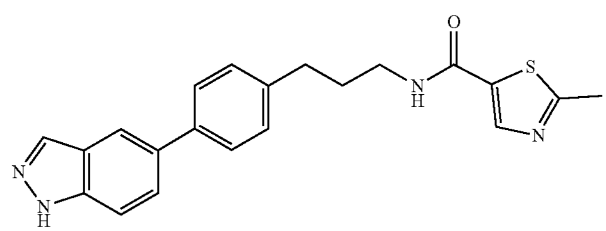 [SMILES: Cc1ncc(C(=O)NCCCc2ccc(-c3ccc4[nH]ncc4c3)cc2)s1] |
| 372 | 2-methyl-N-(3-(4-(2-oxo-1,2-dihydroquinolin-6-yl)phenyl)propyl)thiazole-5-carboxamide | 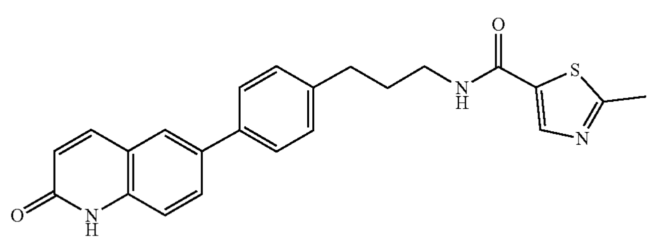 [SMILES: Cc1ncc(C(=O)NCCCc2ccc(-c3ccc4[nH]c(=O)ccc4c3)cc2)s1] |
| 373 | 6-methyl-N-(3-(4-(1-methyl-1H-benzo[d]imidazol-5-yl)phenyl)propyl)nicotinamide | 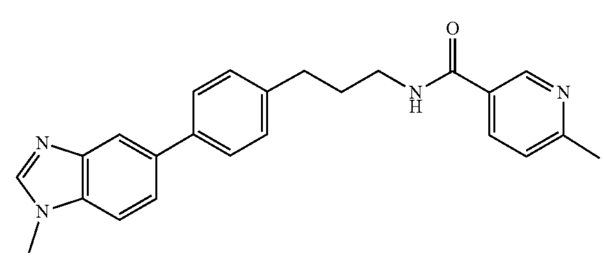 [SMILES: Cc1ccc(C(=O)NCCCc2ccc(-c3ccc4c(c3)ncn4C)cc2)cn1] |

TABLE 1-continued

| Compound No. | Name | Structure |
|---|---|---|
| 374 | 1,3-dimethyl-N-(3-(4-(1-methyl-1H-benzo[d]imidazol-5-yl)phenyl)propyl)-1H-pyrazole-5-carboxamide | 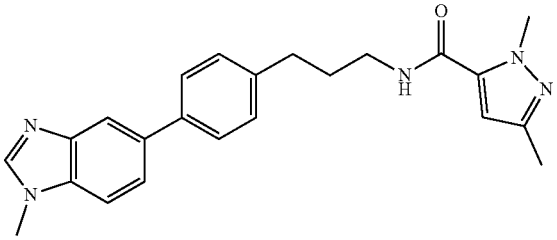 [SMILES: Cc1cc(C(=O)NCCCc2ccc(-c3ccc4c(c3)ncn4C)cc2)n(C)n1] |
| 375 | 2-methyl-N-(3-(4-(1-methyl-1H-benzo[d]imidazol-5-yl)phenyl)propyl)thiazole-5-carboxamide | 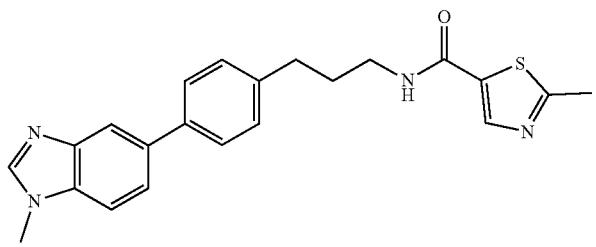 [SMILES: Cc1ncc(C(=O)NCCCc2ccc(-c3ccc4c(c3)ncn4C)cc2)s1] |
| 376 | 2-methyl-N-(3-(4-(7-methyl-1H-indazol-5-yl)phenyl)propyl)thiazole-5-carboxamide | 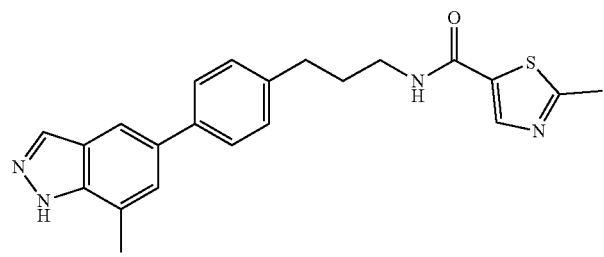 [SMILES: Cc1ncc(C(=O)NCCCc2ccc(-c3cc(C)c4[nH]ncc4c3)cc2)s1] |
| 377 | 2-methyl-N-(3-(4-(2-oxoindolin-5-yl)phenyl)propyl)thiazole-5-carboxamide | 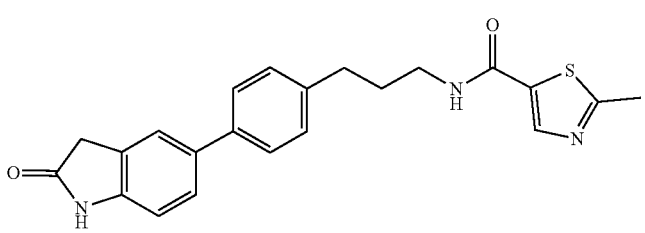 [SMILES: Cc1ncc(C(=O)NCCCc2ccc(-c3ccc4c(c3)CC(=O)N4)cc2)s1] |
| 378 | N-(3-(2'-fluoro-3'-(trifluoromethyl)-[1,1'-biphenyl]-4-yl)propyl)-6-methylnicotinamide | 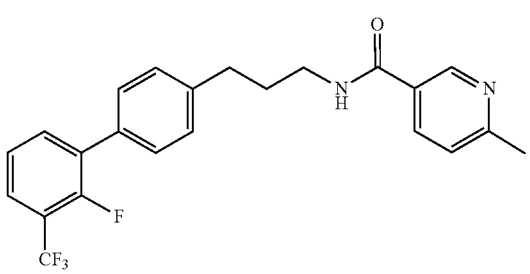 [SMILES: Cc1ccc(C(=O)NCCCc2ccc(-c3cccc(C(F)(F)F)c3F)cc2)cn1] |
| 379 | N-(3-(2'-fluoro-3'-(trifluoromethyl)-[1,1'-biphenyl]-4-yl)propyl)-1,3-dimethyl-1H-pyrazole-5-carboxamide | 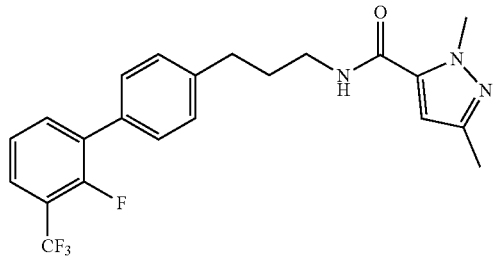 [SMILES: Cc1cc(C(=O)NCCCc2ccc(-c3cccc(C(F)(F)F)c3F)cc2)n(C)n1] |

TABLE 1-continued

| Compound No. | Name | Structure |
|---|---|---|
| 380 | N-(3-(2'-fluoro-3'-(trifluoromethyl)-[1,1'-biphenyl]-4-yl)propyl)-2-methylthiazole-5-carboxamide | 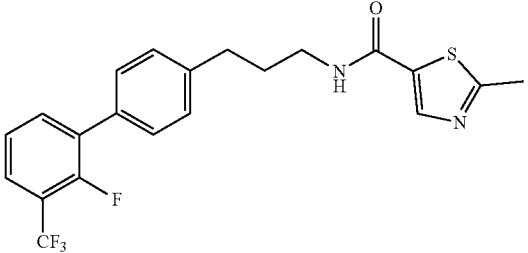 [SMILES: Cc1ncc(C(=O)NCCCc2ccc(-c3cccc(C(F)(F)F)c3F)cc2)s1] |
| 381 | 2-methyl-N-(3-(4-(2-oxo-1,2,3,4-tetrahydroquinolin-6-yl)phenyl)propyl)thiazole-5-carboxamide | 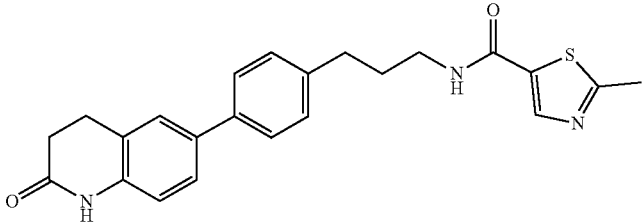 |
| 382 | 2-methyl-N-(3-(4-(3-oxo-3,4-dihydro-2H-benzo[b][1,4]oxazin-7-yl)phenyl)propyl)thiazole-5-carboxamide | 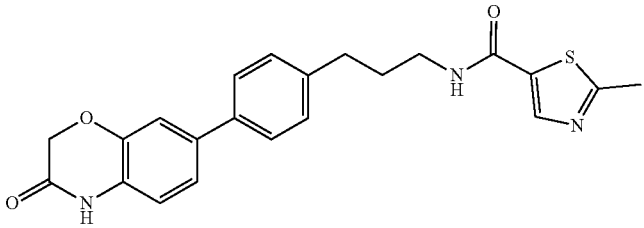 [SMILES: Cc1ncc(C(=O)NCCCc2ccc(-c3ccc4c(c3)CCC(=O)N4)cc2)s1] |
| 383 | N-(3-(4-(1H-pyrazolo[3,4-b]pyridin-5-yl)phenyl)propyl)-6-methylnicotinamide | 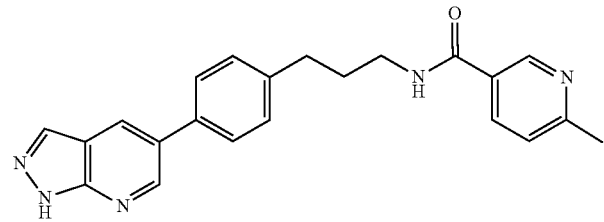 [SMILES: Cc1ccc(C(=O)NCCCc2ccc(-c3cnc4[nH]ncc4c3)cc2)cn1] |
| 384 | N-(3-(4-(1H-pyrazolo[3,4-b]pyridin-5-yl)phenyl)propyl)-1,3-dimethyl-1H-pyrazole-5-carboxamide | 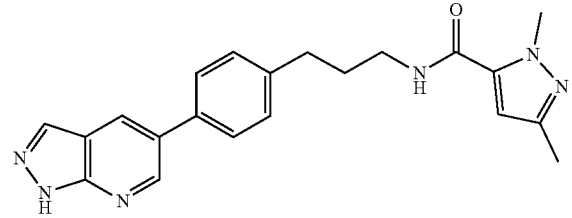 [SMILES: Cc1cc(C(=O)NCCCc2ccc(-c3cnc4[nH]ncc4c3)cc2)n(C)n1] |
| 385 | N-(3-(4-(1H-pyrazolo[3,4-b]pyridin-5-yl)phenyl)propyl)-2-methylthiazole-5-carboxamide | 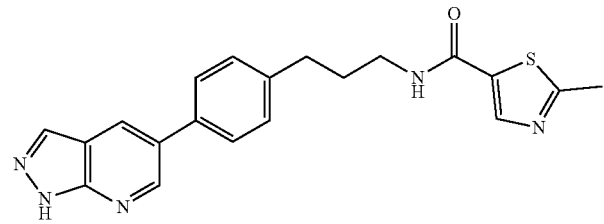 [SMILES: Cc1ncc(C(=O)NCCCc2ccc(-c3cnc4[nH]ncc4c3)cc2)s1] |

TABLE 1-continued
| Compound No. | Name | Structure |
|---|---|---|
| 386 | N-(3-(4-(1H-indazol-5-yl)phenyl)propyl)-2-methylnicotinamide | 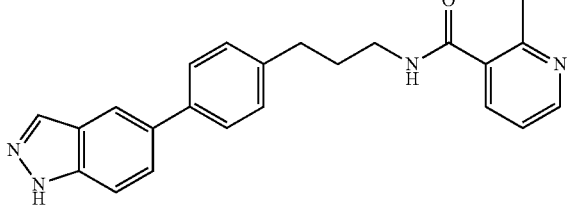 |
| 387 | 2-methyl-N-(3-(4-(7-methyl-1H-indazol-5-yl)phenyl)propyl)nicotinamide | 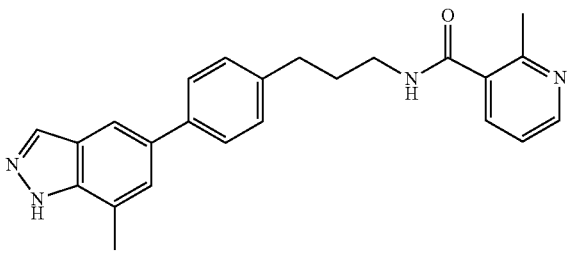 [SMILES: Cc1ncccc1C(=O)NCCCc1ccc(-c2cc(C)c3[nH]ncc3c2)cc1] |
| 388 | N-(3-(4-(1H-indol-5-yl)phenyl)propyl)-6-methylnicotinamide | 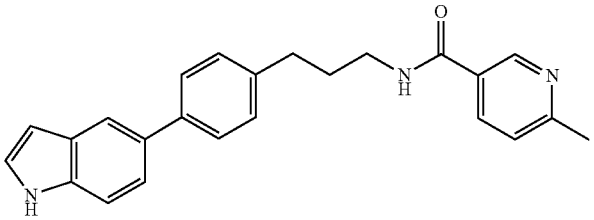 [SMILES: Cc1ccc(C(=O)NCCCc2ccc(-c3ccc4[nH]ccc4c3)cc2)cn1] |
| 389 | N-(3-(4-(1H-indol-5-yl)phenyl)propyl)-1,3-dimethyl-1H-pyrazole-5-carboxamide | 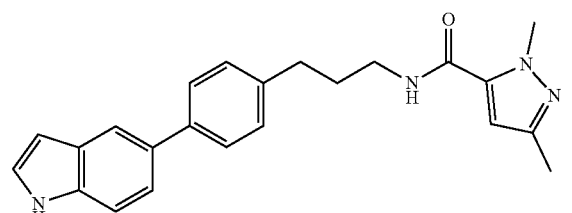 |
| 390 | N-(3-(4-(1H-indol-5-yl)phenyl)propyl)-2-methylthiazole-5-carboxamide | 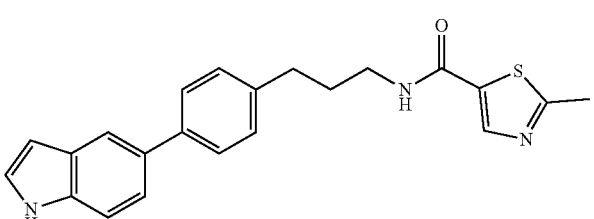 |
| 391 | N-(3-(4-(1H-indol-5-yl)phenyl)propyl)-2-methylnicotinamide | 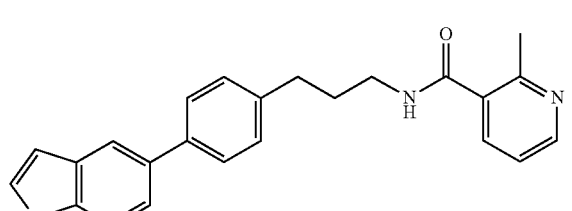 |

TABLE 1-continued

| Compound No. | Name | Structure |
|---|---|---|
| 392 | 2-methyl-N-(3-(4-(2-oxo-1,2-dihydroquinolin-6-yl)phenyl)propyl)nicotinamide | 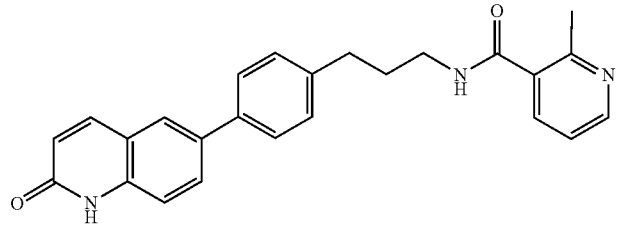 [SMILES: Cc1ncccc1C(=O)NCCCc1ccc(-c2ccc3[nH]c(=O)ccc3c2)cc1] |
| 393 | N-(3-(2'-fluoro-[1,1'-biphenyl]-4-yl)-1H-pyrazol-5-yl)nicotinamidedu | 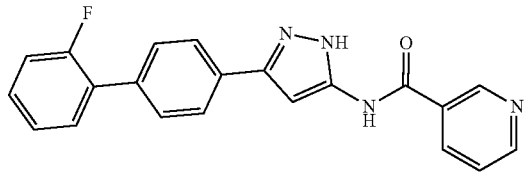 [SMILES: O=C(Nc1cc(-c2ccc(-c3ccccc3F)cc2)n[nH]1)c1cccnc1] |
| 394 | N-(3-(2'-fluoro-[1,1'-biphenyl]-4-yl)isoxazol-5-yl)-6-methylnicotinamide | 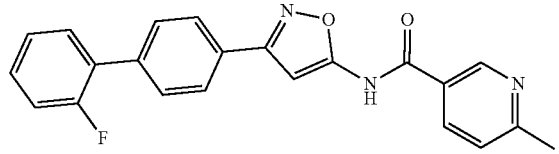 [SMILES: Cc1ccc(C(=O)Nc2cc(-c3ccc(-c4ccccc4F)cc3)no2)cn1] |
| 395 | N-(3,3-difluoro-3-(2'-fluoro-[1,1'-biphenyl]-4-yl)propyl)-6-methylnicotinamide | 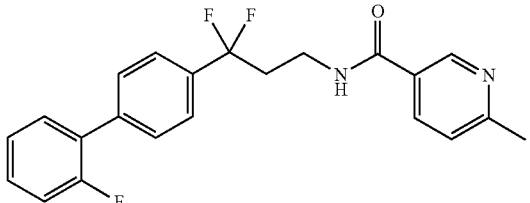 |
| 396 | N-(1-(2'-fluoro-[1,1'-biphenyl]-4-yl)azetidin-3-yl)-6-methylnicotinamide | 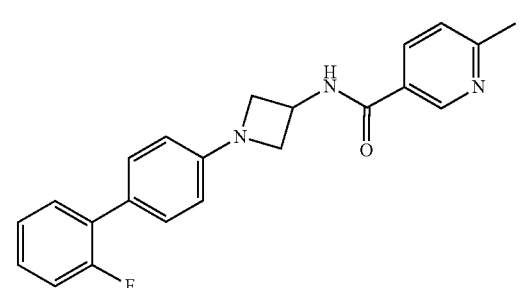 [SMILES: Cc1ccc(NC(=O)N2CC(c3ccc(-c4ccccc4F)cc3)C2)cn1] |
| 397 | 1-(2'-fluoro-[1,1'-biphenyl]-4-yl)-N-(6-methylpyridin-3-yl)azetidine-3-carboxamide | 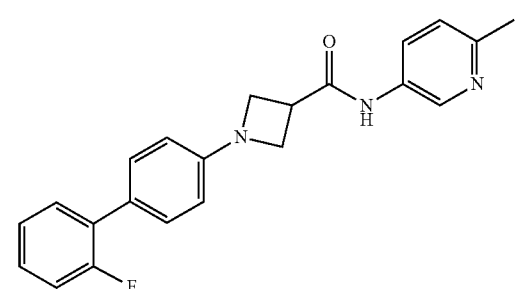 |

TABLE 1-continued

| Compound No. | Name |
|---|---|
| 398 | N-(1-(2'-fluoro-[1,1'-biphenyl]-4-yl)azetidin-3-yl)-1H-indole-5-carboxamide |
| 399 | 1-(2'-fluoro-[1,1'-biphenyl]-4-yl)-N-(1H-indol-5-yl)azetidine-3-carboxamide |
| 400 | N-(2,2-difluoro-3-(2'-fluoro-[1,1'-biphenyl]-4-yl)propyl)-6-methylnicotinamide |
| 401 | 2-(4-(2'-fluoro-[1,1'-biphenyl]-4-yl)piperidin-1-yl)-N-(6-methylpyridin-3-yl)acetamide |
| 402 | 3-(2'-fluoro-[1,1'-biphenyl]-4-yl)-N-(6-methylpyridin-3-yl)azetidine-1-carboxamide |
| 403 | N-(3-(2'-fluoro-[1,1'-biphenyl]-4-yl)-3-hydroxypropyl)-6-methylnicotinamide |

TABLE 1-continued

| Compound No. | Name | Structure |
|---|---|---|
| 404 | N-(4-(2'-fluoro-[1,1'-biphenyl]-4-yl)butan-2-yl)-6-methylnicotinamide | 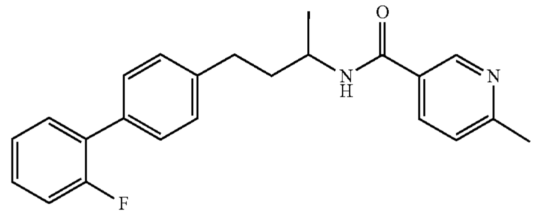 [SMILES: Cc1ccc(C(=O)NC(C)CCc2ccc(-c3ccccc3F)cc2)cn1] |
| 405 | 2-((2'-fluoro-[1,1'-biphenyl]-4-yl)methoxy)-N-(6-methylpyridin-3-yl)acetamide | 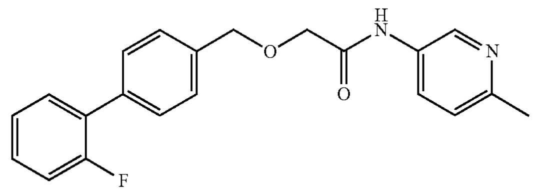 [SMILES: Cc1ccc(NC(=O)COCc2ccc(-c3ccccc3F)cc2)cn1] |
| 406 | 3-(2'-fluoro-[1,1'-biphenyl]-4-yl)-N-(6-methylpyridin-3-yl)cyclobutane-1-carboxamide | 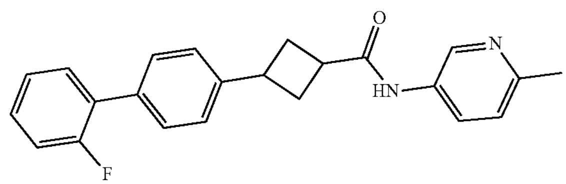 [SMILES: Cc1ccc(NC(=O)C2CC(c3ccc(-c4ccccc4F)cc3)C2)cn1] |

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acres Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CT), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compound described herein is P. H. Stahl & C. G. Wermuth "Handbook of Pharmaceutical Salts", Verlag Helvetica Chimica Acta, Zurich, 2002.

The compounds described herein are prepared using the general methods in the art of organic synthesis, as described in the Examples section. Alternative synthetic methods are also used to generate the compounds described herein.

Methods of Treatment

In certain embodiments, the compounds described herein are used to treat or prevent a disease or condition. The compounds described herein are in some instances p38α (p38 mitogen-activated protein kinase) inhibitors, and are variously used to treat p38α-related diseases or conditions. In some embodiments, the compounds provided herein are MK2 pathway inhibitors. In some instances, the compounds described herein are inhibitors of tubulin polymerization. In some embodiments, the compounds described herein inhibit cell mitosis by binding to the protein tubulin in the mitotic spindle and prevent polymerization or depolymerization into the microtubules. Diseases or conditions treated or prevented by the compounds described herein in some embodiments include proliferative diseases. In some embodiments, a proliferative disease is cancer. Cancers of various organs or tissues such as heart, liver, brain, blood, skin or other types of cancers are in some embodiments treatable or preventable by the compounds described herein. In some embodiments cancers include brain cancer, skin cancer, bladder cancer, lung cancer, prostate cancer, breast cancer, uterine cancer, ovarian cancer, colon cancer, thyroid cancer, or pancreatic cancer. In some embodiments, the cancer is a tumor. In some embodiments, the cancer is metastatic cancer.

In some embodiments cancers include breast, colon, lung, and prostate cancers, cancer of the adrenal cortex, ACTH-producing tumor, bladder cancer, brain cancer, Ewing's sarcoma, head and neck cancer including mouth cancer and larynx cancer, thyroid cancer, trophoblastic neoplasms, Wilms' tumor, kidney cancer including renal cell carcinoma, liver cancer, Kaposi's sarcoma, bone cancer including osteomas and sarcomas such as fibrosarcoma and osteosarcoma, lung cancer including small and non-small cell lung cancers, mesothelioma, malignant peritoneal effusion, malignant pleural effusion, skin cancers (including malignant melanoma, tumor progression of human skin keratinocytes, squamous cell carcinoma, basal cell carcinoma, and hemangiopericytoma), gastrointestinal cancers (including esophageal cancer, stomach cancer, colorectal cancer, polyps associated with colorectal neoplasms, pancreatic cancer and gallbladder cancer), cancers of the female reproductive tract including uterine cancer, endometrial cancer, ovarian cancer, ovarian (germ cell) cancer and solid tumors in the ovarian follicle, vaginal cancer, cancer of the vulva, and cervical cancer, breast cancer (small cell and ductal), male reproductive system (penile cancer, testicular cancer), and retinoblastoma. In some embodiments, cancers spread to other areas of the body to form secondary tumors. In some embodiments, secondary tumors comprise brain tumors or other tumors of the central nervous system.

Cancers in some embodiments including cancers of different outcomes are in some embodiments treated or prevented with the compounds described herein. In some embodiments, cancers are malignant cancers. In some embodiments, cancers are benign. In some embodiments, compounds described herein are used to treat metastatic cancers. In some embodiments the cancer is a primary cancer, originating in a specific tissue. In some embodiments, the cancer spreads from a primary site to a secondary site in a different location, such as a different organ or tissue. In some embodiments, compounds described herein facilitate remission of a previously treated or diagnosed tumor. In some embodiments, the primary cancer is breast cancer. In some embodiments, the primary cancer is lung cancer. In some embodiments, the primary cancer is breast cancer, and the (secondary) metastatic cancer is brain cancer. In some embodiments, the primary cancer is lung cancer, and the (secondary) metastatic cancer is brain cancer.

In various aspects of the invention, compounds described herein often are used in combination with other cancer therapies, such as additional chemotherapy (including immune-stimulating drugs), surgery, radiation treatment, or other treatment used in the art for the treatment or prevention of cancer. In some embodiments, compounds described herein are used to treat secondary metastatic cancers in combination with therapies to treat primary cancers.

In some embodiments the compounds described herein are used to treat or prevent brain cancers, such as central choroid plexus carcinoma, choroid plexus papilloma, choroid plexus tumor, dysembryoplastic neuroepithelial tumor, ependymal tumor, medulloblastoma, giant-cell glioblastoma, trilateral retinoblastoma, glioblastoma multiforme, gliomatosis cerebri, gliosarcoma, medulloepithelioma, meningeal carcinomatosis, neuroblastoma, pinealoblastoma, pleomorphic anaplastic neuroblastoma, pleomorphic xanthoastrocytoma, neurocytoma, pilocytic astrocytoma, astrocytoma, anaplastic astrocytoma, subependymal giant cell astrocytoma, fibrillary astrocytoma, neurocytoma, hemangiopericytoma, oligoastrocytoma, pineocytoma, pediatric ependymoma, primary central nervous system lymphoma, optic nerve sheath meningioma, sphenoid wing meningioma, subependymoma, oligodendroglioma, or diffuse intrinsic pontine glioma. In some embodiments, the brain cancer is metastatic (or secondary). In some embodiments, the cancer is a primary brain cancer. In some embodiments, the brain cancer originates from primary breast cancer. In some embodiments, the brain cancer originates from primary lung cancer.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one compound described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound described herein, or a pharmaceutically acceptable salt thereof, and a pharmaceutically acceptable excipient. In one embodiment, the pharmaceutical compositions are provided in a dosage form for oral administration, which comprise a compound provided herein, and one or more pharmaceutically acceptable excipients or carriers.

In certain embodiments, a compound described herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the pharmaceutical compositions provided herein are formulated for oral administration in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. In some embodiments, physiological saline solution, dextrose or other saccharide solution, or glycols are optionally included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included.

In yet another embodiment, the pharmaceutical compositions are provided in a dosage form for topical administration, which comprise a compound provided herein, and one or more pharmaceutically acceptable excipients or carriers.

Methods of Dosing and Treatment Regimens

The dose of the composition comprising at least one compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, in which the mammal previously experienced at least one symptom of the disease being treated and is currently in remission, a pharmaceutical composition comprising a compound described herein, or a pharmaceutically acceptable salt thereof, in order to prevent a return of the symptoms of the disease or condition.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration as described elsewhere herein.

The following examples are set forth to illustrate more clearly the principle and practice of instances disclosed herein to those skilled in the art and are not to be construed as limiting the scope of any claimed instances. Unless otherwise stated, all parts and percentages are on a weight basis.

EXAMPLES

Example 1: Preparation of N-(1H-benzo[d]imidazol-5-yl)-4-(2'-fluoro-[1,1'-biphenyl]-4-yl)butanamide (Compound 1)

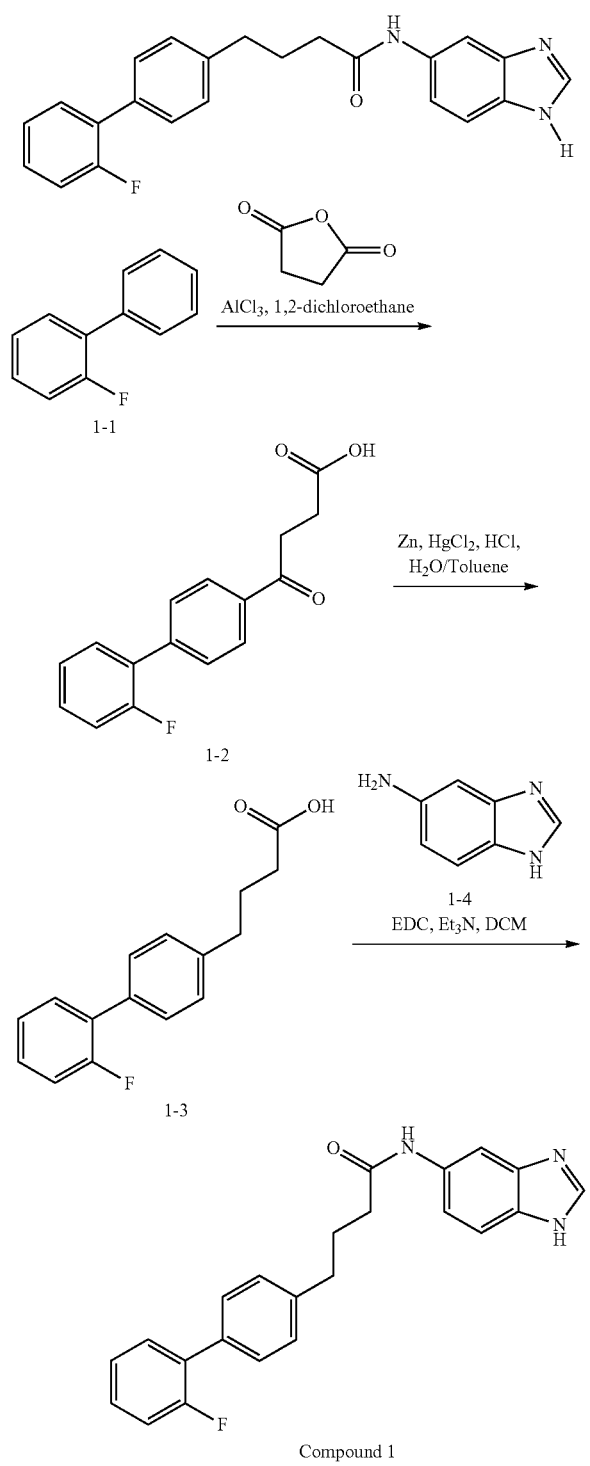

Step 1. 1-1 is reacted with AlCl₃ and succinic anhydride in dry 1,2-dichloroethane to form 1-2.

Step 2. 1-2 is reduced with a Zn-mercury amalgam in the presence of aqueous HCl, by heating the solution under reflux in toluene to provide acid 1-3.

Step 3. 1-3 is coupled with amine 1-4 in the presence of 1-ethyl-3-(3-dimethylaminopropyl) carbodiimide and triethylamine in dichloromethane solvent to provide Compound 1.

Example 2: Preparation of 4-(2'-fluoro-[1,1'-biphenyl]-4-yl)-N-(6-hydroxypyridin-3-yl)butanamide (Compound 8)

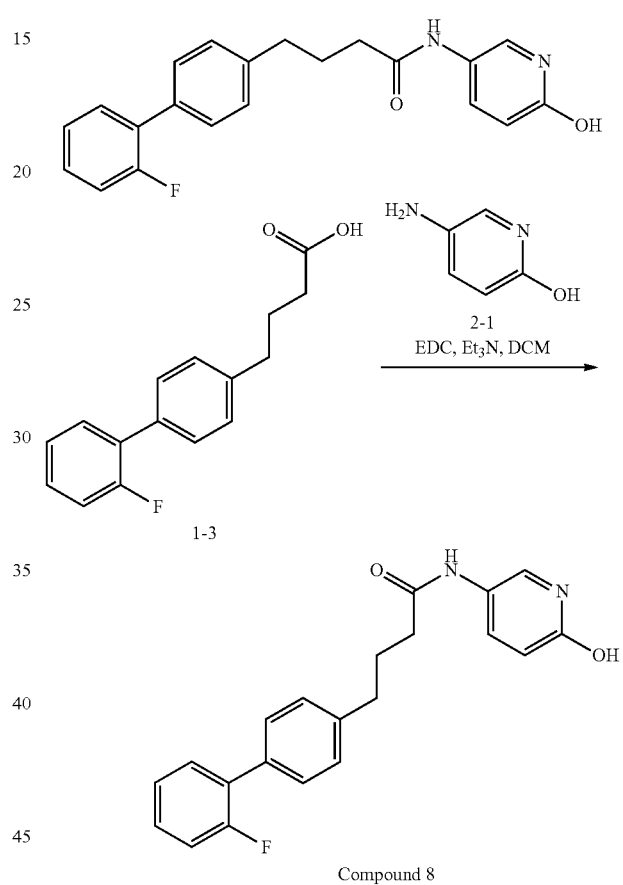

Compound 1-3 was coupled with amine 2-1 in the presence of 1-ethyl-3-(3-dimethylaminopropyl) carbodiimide and triethylamine in dichloromethane solvent to provide Compound 8.

Example 3: Cytotoxicity Assay

U87MG cells were plated at a density of $7 \times 10^3$ cells/well and allowed to seed overnight. Cells were then treated with compounds from Table 1 or CMPD-1 (4-(2'-fluoro-[1,1'-biphenyl]-4-yl)-N-(4-hydroxyphenyl)butanamide as a positive control) were added to cells at a starting concentration of 50 uM, with a 9 point half log dilution, and incubated for 72 hours prior to viability determination. IC50 values were calculated from cell viability as measured using the CellTiter 96® Aqueous MTS reagent from Promega©, and the results are shown in Table 2. When compounds were tested repeatedly, IC50 values represent an average of multiple experiments.

TABLE 2

Exemplary IC50 toxicity activity for compounds described herein.

| Compound No. | Activity (IC50) |
|---|---|
| CMPD-1 | B |
| 1 | D |
| 2 | ND |
| 3 | ND |
| 4 | C |
| 5 | ND |
| 6 | C |
| 7 | ND |
| 8 | D |
| 9 | D |
| 10 | ND |
| 11 | ND |
| 12 | ND |
| 13 | ND |
| 14 | ND |
| 15 | ND |
| 16 | ND |
| 17 | ND |
| 18 | ND |
| 19 | ND |
| 20 | ND |
| 21 | ND |
| 22 | ND |
| 23 | ND |
| 24 | ND |
| 25 | ND |
| 26 | ND |
| 27 | ND |
| 28 | ND |
| 29 | ND |
| 30 | ND |
| 31 | ND |
| 32 | ND |
| 33 | ND |
| 34 | ND |
| 35 | ND |
| 36 | ND |
| 37 | B |
| 38 | D |
| 39 | D |
| 40 | D |
| 41 | D |
| 42 | C |
| 43 | C |
| 44 | B |
| 45 | A |
| 46 | ND |
| 47 | D |
| 48 | C |
| 49 | ND |
| 50 | C |
| 51 | D |
| 52 | D |
| 53 | B |
| 54 | D |
| 55 | C |
| 56 | ND |
| 57 | ND |
| 58 | D |
| 59 | D |
| 60 | ND |
| 61 | ND |
| 62 | D |
| 63 | D |
| 64 | A |
| 65 | D |
| 66 | D |
| 67 | A |
| 68 | ND |
| 69 | ND |
| 70 | D |
| 71 | A |
| 72 | ND |
| 73 | C |
| 74 | B |
| 75 | D |
| 76 | D |
| 77 | D |
| 78 | ND |
| 79 | D |
| 80 | C |
| 81 | A |
| 82 | D |
| 83 | C |
| 84 | D |
| 85 | C |
| 86 | ND |
| 87 | D |
| 88 | D |
| 89 | A |
| 90 | A |
| 91 | D |
| 92 | ND |
| 93 | ND |
| 94 | ND |
| 95 | A |
| 96 | A |
| 97 | ND |
| 98 | ND |
| 99 | C |
| 100 | D |
| 101 | A |
| 102 | D |
| 103 | ND |
| 104 | ND |
| 105 | A |
| 106 | B |
| 107 | ND |
| 108 | A |
| 109 | B |
| 110 | D |
| 111 | D |
| 112 | C |
| 113 | D |
| 114 | D |
| 115 | ND |
| 116 | ND |
| 117 | D |
| 118 | D |
| 119 | ND |
| 120 | B |
| 121 | C |
| 122 | ND |
| 123 | D |
| 124 | D |
| 125 | D |
| 126 | C |
| 127 | D |
| 128 | B |
| 129 | ND |
| 130 | D |
| 131 | D |
| 132 | D |
| 133 | D |
| 134 | C |
| 135 | ND |
| 136 | A |
| 137 | C |
| 138 | A |
| 139 | B |
| 140 | A |
| 141 | D |
| 142 | D |
| 143 | D |
| 144 | D |
| 145 | D |
| 146 | C |
| 147 | ND |
| 148 | A |
| 149 | B |

TABLE 2-continued

Exemplary IC50 toxicity activity for compounds described herein.

| Compound No. | Activity (IC50) |
|---|---|
| 150 | ND |
| 151 | C |
| 152 | D |
| 153 | D |
| 154 | C |
| 155 | B |
| 156 | D |
| 157 | C |
| 158 | D |
| 159 | C |
| 160 | C |
| 161 | D |
| 162 | B |
| 163 | A |
| 164 | B |
| 165 | C |
| 166 | C |
| 167 | D |
| 168 | C |
| 169 | B |
| 170 | ND |
| 171 | ND |
| 172 | ND |
| 173 | B |
| 174 | ND |
| 175 | B |
| 176 | D |
| 177 | B |
| 178 | D |
| 179 | D |
| 180 | A |
| 181 | A |
| 182 | ND |
| 183 | C |
| 184 | A |
| 185 | D |
| 186 | D |
| 187 | ND |
| 188 | ND |
| 189 | C |
| 190 | A |
| 191 | C |
| 192 | C |
| 193 | D |
| 194 | ND |
| 195 | B |
| 196 | A |
| 197 | D |
| 198 | B |
| 199 | B |
| 200 | D |
| 201 | ND |
| 202 | D |
| 203 | D |
| 204 | C |
| 205 | D |
| 206 | A |
| 207 | A |
| 208 | C |
| 209 | A |
| 210 | A |
| 211 | C |
| 212 | ND |
| 213 | A |
| 214 | A |
| 215 | ND |
| 216 | D |
| 217 | D |
| 218 | A |
| 219 | A |
| 220 | A |
| 221 | C |
| 222 | A |
| 223 | D |
| 224 | A |
| 225 | D |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | B |
| 239 | A |
| 240 | B |
| 241 | A |
| 242 | A |
| 243 | A |
| 244 | A |
| 245 | B |
| 246 | A |
| 247 | A |
| 248 | B |
| 249 | ND |
| 250 | ND |
| 251 | ND |
| 252 | ND |
| 253 | ND |
| 254 | ND |
| 255 | ND |
| 256 | ND |
| 257 | ND |
| 258 | ND |
| 259 | ND |
| 260 | ND |
| 261 | ND |
| 262 | C |
| 263 | C |
| 264 | ND |
| 265 | ND |
| 266 | ND |
| 267 | ND |
| 268 | ND |
| 269 | ND |
| 270 | ND |
| 271 | ND |
| 272 | D |
| 273 | D |
| 274 | D |
| 275 | ND |
| 276 | C |
| 277 | B |
| 278 | C |
| 279 | B |
| 280 | A |
| 281 | D |
| 282 | D |
| 283 | ND |
| 284 | A |
| 285 | D |
| 286 | A |
| 287 | ND |
| 288 | ND |
| 289 | ND |
| 290 | D |
| 291 | ND |
| 292 | D |
| 293 | D |
| 294 | B |
| 295 | C |
| 296 | A |
| 297 | A |
| 298 | ND |
| 299 | D |

TABLE 2-continued

Exemplary IC50 toxicity activity for compounds described herein.

| Compound No. | Activity (IC50) |
|---|---|
| 300 | ND |
| 301 | A |
| 302 | C |
| 303 | D |
| 304 | A |
| 305 | A |
| 306 | A |
| 307 | A |
| 308 | A |
| 309 | A |
| 310 | A |
| 311 | A |
| 312 | A |
| 313 | A |
| 314 | A |
| 315 | A |
| 316 | A |
| 317 | A |

A is < 500 nM; B is 501 nM to 1 μM; C is 1.001 μM to 5 μM; D is > 5 μM; ND is not determined.

Example 4. Tubulin Polymerization Assay

Compounds described herein were tested in a tubulin polymerization inhibition assay using the general manufacturer's protocol for inhibitor screening (Cytoskeleton, Inc. BK01 IP). DMSO was used as a negative control, and vinblastine was tested as a positive control. All compounds were tested at a concentration of 3 μM, and incubation was carried out at 37C for 60 minutes. Results were calculated as a percent inhibition (compared to DMSO control) after 60 min of incubation, the results of which are shown in Table 3.

TABLE 3

Exemplary tubulin polymerization activity of compounds described herein.

| Compound | % Tubulin Polymerization at 60 min |
|---|---|
| DMSO | F |
| Vinblastine | A |
| 101 | C |
| 81 | A |
| 136 | A |
| 280 | F |
| 96 | A |
| 138 | A |
| 226 | C |
| 232 | C |
| 207 | D |
| 214 | F |
| 233 | A |
| 243 | A |
| 239 | C |
| 230 | C |

A is < 20%; B is 21-40%, C is 41-60%, D is 61-80%, F is 81-100%

What is claimed is:

1. A compound of Formula (VIIIa), or a pharmaceutically acceptable salt, or stereoisomer thereof:

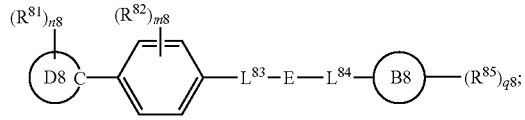

Formula (VIIIa)

wherein:
$L^{83}$ is —C(R$^{83}$)$_2$C(R$^{83}$)$_2$C(R$^{83}$)$_2$—;
E is —C(=O)NR$^{84}$— or —NR$^{84}$C(=O)—;
$L^{84}$ is a bond or —CR$^{86}$R$^{87}$—;
ring D8 is heteroaryl, wherein the heteroaryl is selected from the group consisting of:

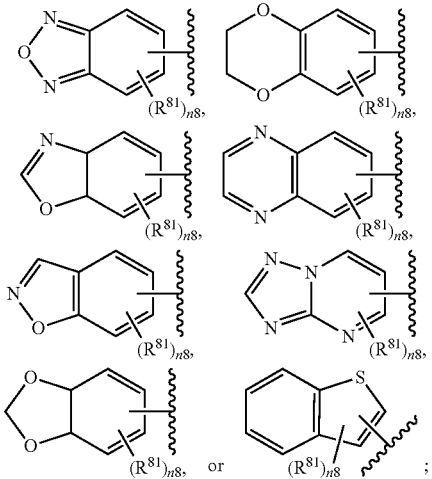

ring B8 is heteroaryl or $C_2$-$C_8$ heterocyclyl;
each $R^{81}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR'R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen or —OR$^a$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
each $R^{82}$ is independently hydrogen, halogen, —CN, —OR$^a$, —SR$^a$, S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$haloalkyl, —$OR^a$, or —$NR^cR^d$;

each $R^{83}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)R^b$, —$NR^aC(=O)OR^a$, (—$NR^aC(=O)NR^cR^d$), $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, or heteroaryl; wherein the alkyl, alkenyl, alkynyl, and heteroalkyl is optionally substituted with one, two, or three of halogen, —$OR^a$, or —$NR^cR^d$; and the cycloalkyl, and heteroaryl is optionally substituted with one, two, or three of halogen, $C_1$-$C_6$ alkyl, $C_1$-$C_6$ haloalkyl-$OR^a$, or $NR^cR^d$;

$R^{84}$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_1$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{85}$ is independently hydrogen, halogen, —CN, —$OR^a$, —$SR^a$, $S(=O)R^b$, (—$S(=O)_2R^d$), —$NO_2$, —$NR^cR^d$, —$NR^aS(=O)_2R^d$, $S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$haloalkyl, —$OR^a$, or —$NR^cR^d$;

or two $R^{85}$ substituents on the same carbon are taken together to form an oxo;

$R^{86}$ and $R^{87}$ are independently hydrogen, halogen, —CN, —$OR^a$, —$SR^a$, —$S(=O)R^b$, —$NO_2$, —$NR^cR^d$, $S(=O)_2R^d$, —$NR^aS(=O)_2R^d$, $S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$haloalkyl, $OR^a$, or $NR^cR^d$, $R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

n8 is 1-5;

m8 is 1-4; and q8 is 1-5.

2. The compound of claim 1, wherein $L^{84}$ is a bond.

3. The compound of claim 1, or a pharmaceutically acceptable salt, or stereoisomer thereof wherein: Ring B8 is $C_3$-$C_9$ heteroaryl.

4. The compound of claim 1, or a pharmaceutically acceptable salt, or stereoisomer thereof wherein:
Ring B8 is $C_3$-$C_9$ fused bicyclic ring.

5. The compound of claim 1, or a pharmaceutically acceptable salt, or stereoisomer thereof wherein: Ring B8 is thiophenyl, furanyl, pyrrolyl, thiazolyl, oxazolyl, isoxazolyl, imidazolyl, pyrazolyl, thiadiazolyl, or oxadiazolyl.

6. The compound of claim 1, or a pharmaceutically acceptable salt, or stereoisomer thereof wherein: each $R^{81}$ is independently halogen, $C_1$-$C_6$ alkyl, or $C_1$-$C_6$ haloalkyl.

7. The compound of claim 1, or a pharmaceutically acceptable salt, or stereoisomer thereof wherein: n8 is 1.

8. The compound of claim 1, or a pharmaceutically acceptable salt, or stereoisomer thereof wherein: each $R^{82}$ is independently hydrogen, halogen, $C_1$-$C_6$ alkyl, or $C_1$-$C_6$ haloalkyl.

9. The compound of claim 1, or a pharmaceutically acceptable salt, or stereoisomer thereof wherein: m8 is 1.

10. The compound of claim 1, or a pharmaceutically acceptable salt, or stereoisomer thereof wherein: each $R^{83}$ is independently hydrogen, halogen, $C_1$-$C_6$ alkyl, or $C_1$-$C_6$ haloalkyl.

11. The compound of claim 1, or a pharmaceutically acceptable salt, or stereoisomer thereof wherein: $R^{84}$ is hydrogen or $C_1$-$C_6$ alkyl.

12. The compound of claim 1, or a pharmaceutically acceptable salt, or stereoisomer thereof wherein: each $R^{85}$ is independently hydrogen, halogen, amino, —$NH_2$, $C_1$-$C_6$ alkyl, or $C_1$-$C_6$ haloalkyl.

13. The compound of claim 1, or a pharmaceutically acceptable salt, or stereoisomer thereof wherein: q8 is 1 or 2.

14. A pharmaceutical composition comprising a compound of claim 1, or a pharmaceutically acceptable salt, or stereoisomer thereof, and a pharmaceutically acceptable excipient.

15. A method of treating a proliferative disease or disorder in a subject in need thereof, the method comprising administering to the subject a compound of claim 1.

16. The method of claim 15, wherein the disease or disorder is brain cancer.

17. The method of claim 15, wherein the disease or disorder is metastatic cancer.

18. The method of claim 17, wherein the metastatic cancer originates from a primary breast or lung cancer.

19. The compound of claim 1, or a pharmaceutically acceptable salt, or stereoisomer thereof wherein:

Ring B8 is $C_2$-$C_8$ heterocyclyl.

20. The compound of claim 1, or a pharmaceutically acceptable salt, or stereoisomer thereof wherein the compound is selected from:

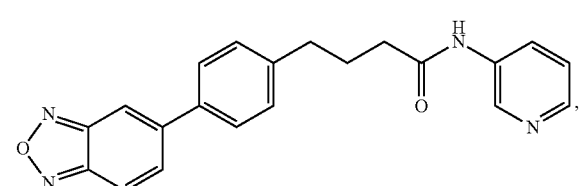

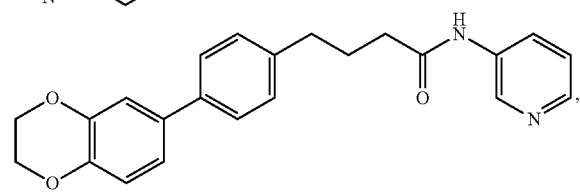

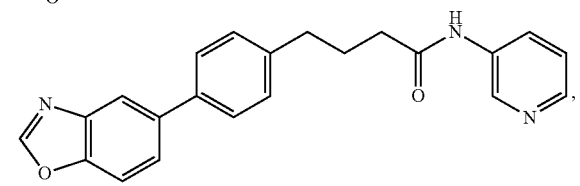

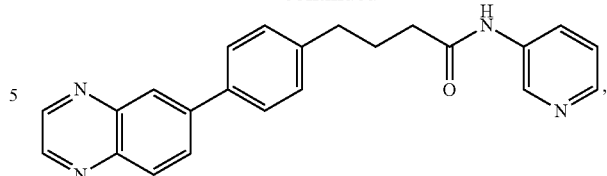

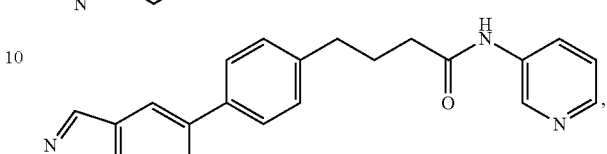

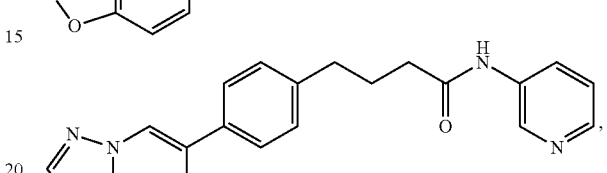

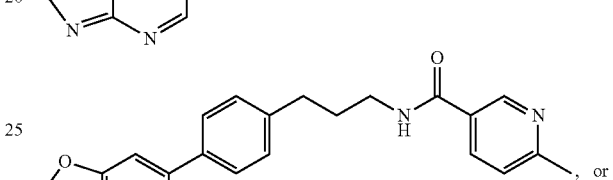

, or

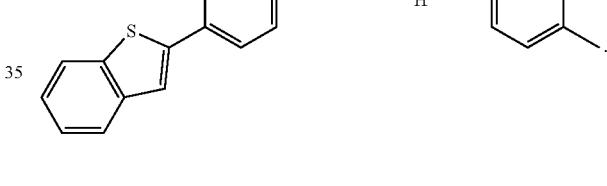

.

* * * * *